United States Patent
Komuro et al.

(10) Patent No.: US 9,063,416 B2
(45) Date of Patent: Jun. 23, 2015

(54) RESIST COMPOSITION, METHOD OF FORMING RESIST PATTERN AND COMPOUND

(71) Applicant: Tokyo Ohka Kogyo Co., Ltd., Kawasaki-shi (JP)

(72) Inventors: Yoshitaka Komuro, Kawasaki (JP); Yoshiyuki Utsumi, Kawasaki (JP); Akiya Kawaue, Kawasaki (JP); Toshiaki Hato, Kawasaki (JP)

(73) Assignee: Tokyo Ohka Kogyo Co., Ltd., Kawasaki-shi (JP)

( * ) Notice: Subject to any disclaimer, the term of this patent is extended or adjusted under 35 U.S.C. 154(b) by 160 days.

(21) Appl. No.: 13/706,771

(22) Filed: Dec. 6, 2012

(65) Prior Publication Data
US 2013/0157197 A1 Jun. 20, 2013

(30) Foreign Application Priority Data
Dec. 14, 2011 (JP) .................................. 2011-273768

(51) Int. Cl.
| | | |
|---|---|---|
| G03F 7/004 | (2006.01) |
| C07C 59/125 | (2006.01) |
| G03F 7/027 | (2006.01) |
| G03F 7/039 | (2006.01) |
| C07D 313/10 | (2006.01) |
| C07D 327/04 | (2006.01) |
| C07D 333/46 | (2006.01) |
| C07D 333/54 | (2006.01) |
| C07D 333/76 | (2006.01) |
| C07D 335/02 | (2006.01) |
| C07D 335/16 | (2006.01) |
| C07C 323/52 | (2006.01) |
| C07C 381/12 | (2006.01) |
| C07D 493/18 | (2006.01) |
| C07D 307/00 | (2006.01) |
| C07D 307/33 | (2006.01) |
| C07C 25/18 | (2006.01) |
| C07C 69/14 | (2006.01) |
| C07C 69/63 | (2006.01) |
| C07C 69/753 | (2006.01) |
| C07C 69/78 | (2006.01) |
| C07C 59/13 | (2006.01) |
| C07C 59/66 | (2006.01) |
| C07C 59/70 | (2006.01) |
| C07C 62/04 | (2006.01) |
| C07D 493/08 | (2006.01) |

(52) U.S. Cl.
CPC .............. *G03F 7/027* (2013.01); *G03F 7/0045* (2013.01); *G03F 7/0397* (2013.01); *C07D 313/10* (2013.01); *C07D 327/04* (2013.01); *C07D 333/46* (2013.01); *C07D 333/54* (2013.01); *C07D 333/76* (2013.01); *C07D 335/02* (2013.01); *C07D 335/16* (2013.01); *C07C 323/52* (2013.01); *C07C 381/12* (2013.01); *C07D 493/18* (2013.01); *C07D 307/00* (2013.01); *C07D 307/33* (2013.01); *C07C 25/18* (2013.01); *C07C 2101/08* (2013.01); *C07C 2103/74* (2013.01); *C07C 69/14* (2013.01); *C07C 69/63* (2013.01); *C07C 69/753* (2013.01); *C07C 69/78* (2013.01); *C07C 59/125* (2013.01); *C07C 59/13* (2013.01); *C07C 59/66* (2013.01); *C07C 59/70* (2013.01); *C07C 62/04* (2013.01); *C07D 493/08* (2013.01)

(58) Field of Classification Search
None
See application file for complete search history.

(56) References Cited

U.S. PATENT DOCUMENTS

| 5,879,856 A | * | 3/1999 | Thackeray et al. | ........ 430/270.1 |
| 5,945,517 A | | 8/1999 | Nitta et al. | |

(Continued)

FOREIGN PATENT DOCUMENTS

| JP | A-06-266100 | 9/1994 |
| JP | A-09-208554 | 8/1997 |

(Continued)

OTHER PUBLICATIONS

Machine translation, JP 2007-178858. Jul. 12, 2007.*

*Primary Examiner* — Cynthia H Kelly
*Assistant Examiner* — Alyssa L Cepluch
(74) *Attorney, Agent, or Firm* — Knobbe Martens Olson & Bear LLP

(57) ABSTRACT

A resist composition comprising: a base component (A) that exhibits changed solubility in a developing solution by the action of acid; a photoreactive quencher (C); and an acid-generator component (B) that generates acid upon exposure, wherein the photoreactive quencher (C) contains a compound represented by general formula (c1) shown below. In the formula, $R^1$ represents a hydrogen atom or a hydrocarbon group of 1 to 20 carbon atoms which may have a substituent; each of $R^2$ and $R^3$ independently represents a hydrogen atom or a hydrocarbon group of 1 to 20 carbon atoms which may have a substituent; at least two of $R^1$ to $R^3$ may be mutually bonded to form a ring; X represents an oxygen atom or a sulfur atom; n represents 0 or 1; and $Z^+$ represents an organic cation.

[Chemical Formula 1]

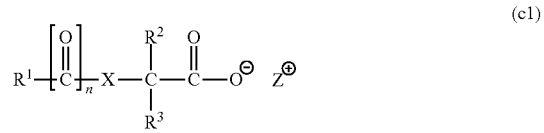

(c1)

8 Claims, No Drawings

(56) References Cited

U.S. PATENT DOCUMENTS

| | | | |
|---|---|---|---|
| 6,153,733 | A | 11/2000 | Yukawa et al. |
| 6,949,325 | B2 | 9/2005 | Li et al. |
| 2001/0049073 | A1 | 12/2001 | Hada et al. |
| 2003/0224285 | A1* | 12/2003 | Nakao et al. ............... 430/270.1 |
| 2004/0009430 | A1* | 1/2004 | Kanna et al. ............... 430/287.1 |
| 2004/0053160 | A1* | 3/2004 | Takahashi et al. ......... 430/270.1 |
| 2004/0110085 | A1 | 6/2004 | Iwai et al. |
| 2006/0166130 | A1* | 7/2006 | Ogata et al. ................ 430/270.1 |
| 2006/0210919 | A1* | 9/2006 | Mizutani et al. ........... 430/270.1 |
| 2008/0187860 | A1 | 8/2008 | Tsubaki et al. |
| 2008/0241736 | A1* | 10/2008 | Kobayashi et al. ........ 430/270.1 |
| 2009/0317743 | A1 | 12/2009 | Shiono et al. |
| 2012/0082936 | A1 | 4/2012 | Serizawa et al. |
| 2012/0288796 | A1* | 11/2012 | Katayama et al. ......... 430/285.1 |

FOREIGN PATENT DOCUMENTS

| | | | |
|---|---|---|---|
| JP | A-11-035551 | | 2/1999 |
| JP | A-11-035552 | | 2/1999 |
| JP | A-11-035573 | | 2/1999 |
| JP | A-11-322707 | | 11/1999 |
| JP | A-2000-206694 | | 7/2000 |
| JP | A-2003-241385 | | 8/2003 |
| JP | A-2005-336452 | | 12/2005 |
| JP | A-2006-259582 | | 9/2006 |
| JP | A-2006-317803 | | 11/2006 |
| JP | 2007178858 A | * | 7/2007 |
| JP | A-2008-292975 | | 12/2008 |
| JP | A-2010-002870 | | 1/2010 |
| WO | WO 2004/074242 A2 | | 9/2004 |
| WO | WO 2010/147079 A1 | | 12/2010 |

\* cited by examiner

RESIST COMPOSITION, METHOD OF FORMING RESIST PATTERN AND COMPOUND

TECHNICAL FIELD

The present invention relates to a resist composition, a method of forming a resist pattern using the same, and a novel compound useful as a photoreactive quencher for a resist composition.

Priority is claimed on Japanese Patent Application No. 2011-273768, filed Dec. 14, 2011, the content of which is incorporated herein by reference.

BACKGROUND ART

In lithography techniques, for example, a resist film composed of a resist material is formed on a substrate, and the resist film is subjected to selective exposure, followed by development, thereby forming a resist pattern having a predetermined shape on the resist film. A resist material in which the exposed portions of the resist film become soluble in a developing solution is called a positive-type, and a resist material in which the exposed portions of the resist film become insoluble in a developing solution is called a negative-type.

In recent years, in the production of semiconductor elements and liquid crystal display elements, advances in lithography techniques have lead to rapid progress in the field of pattern miniaturization. Typically, these miniaturization techniques involve shortening the wavelength (increasing the energy) of the exposure light source. Conventionally, ultraviolet radiation typified by g-line and i-line radiation has been used, but nowadays KrF excimer lasers and ArF excimer lasers are starting to be introduced in mass production. Furthermore, research is also being conducted into lithography techniques that use an exposure light source having a wavelength shorter (energy higher) than these excimer lasers, such as electron beam (EB), extreme ultraviolet radiation (EUV), and X ray.

Resist materials for use with these types of exposure light sources require lithography properties such as a high resolution capable of reproducing patterns of minute dimensions, and a high level of sensitivity to these types of exposure light sources. As a resist material that satisfies these conditions, a chemically amplified composition is used, which includes a base material component that exhibits changed solubility in a developing solution by the action of acid and an acid-generator component that generates acid upon exposure.

On the other hand, as acid generators usable in a chemically amplified resist composition, various types have been proposed including, for example, onium salt acid generators; oxime sulfonate acid generators; diazomethane acid generators; nitrobenzylsulfonate acid generators; iminosulfonate acid generators; and disulfone acid generators.

Conventionally, a resin (base resin) is typically used as the base component of a chemically amplified resist composition.

For example, in the case of alkali developing process in which an alkali developing solution is used as a developing solution, a chemically amplified positive resist composition for forming a positive resist pattern contains an acid generator component and a resin component that exhibits increased solubility in an alkali developing solution by the action of acid is typically used. If the resist film formed using the resist composition is selectively exposed during formation of a resist pattern, then within the exposed portions, acid is generated from the acid-generator component, and the action of this acid causes an increase in the solubility of the resin component in an alkali developing solution, making the exposed portions soluble in the alkali developing solution. Thus, by conducting developing by an alkali developing solution, the unexposed portions remain to form a positive resist pattern.

A resin that exhibits increased polarity by the action of acid is generally used as a resin component. When the polarity of a resin is increased, the solubility in an alkali developing solution is increased. On the other hand, when the polarity of a resin is increased, the solubility in an organic solvent is decreased. Therefore, when such a base resin is applied to a solvent developing process using a developing solution containing an organic solvent (organic developing solution) instead of an alkali developing process, the solubility of the exposed portions in an organic developing solution is decreased. As a result, in the solvent developing process, the unexposed portions of the resist film are dissolved and removed by the organic developing solution, and a negative resist pattern in which the exposed portions are remaining is formed. The solvent developing process by which a negative resist pattern can be formed is frequently referred to as "negative-tone developing process" (for example, see Patent Document 1).

Currently, resins that contain structural units derived from (meth)acrylate esters within the main chain (acrylic resins) are now widely used as base resins for chemically amplified resist compositions that use ArF excimer laser lithography, as they exhibit excellent transparency in the vicinity of 193 nm (for example, see Patent Document 2). Here, the term "(meth)acrylate ester" is a generic term that includes either or both of the acrylate ester having a hydrogen atom bonded to the α-position and the methacrylate ester having a methyl group bonded to the α-position. The term "(meth)acrylate" is a generic term that includes either or both of the acrylate having a hydrogen atom bonded to the α-position and the methacrylate having a methyl group bonded to the α-position. The term "(meth)acrylic acid" is a generic term that includes either or both of acrylic acid having a hydrogen atom bonded to the α-position and methacrylic acid having a methyl group bonded to the α-position.

The base resin contains a plurality of structural units for improving lithography properties and the like. For example, in the case of a resin component which exhibits increased polarity by the action of acid, a base resin containing a structural unit having an acid decomposable group which is decomposed by the action of acid generated from an acid generator component to increase the polarity, a structural unit having a polar group such as a hydroxy group and a structural unit having a lactone structure is typically used.

As a technique for further improving the resolution, a lithography method called liquid immersion lithography (hereafter, frequently referred to as "immersion exposure") is known in which exposure (immersion exposure) is conducted in a state where the region between the lens and the resist layer formed on a wafer is filled with a solvent (a immersion medium) that has a larger refractive index than the refractive index of air.

According to this type of immersion exposure, it is considered that higher resolutions equivalent to those obtained using a shorter wavelength light source or a larger NA lens can be obtained using the same exposure light source wavelength, with no lowering of the depth of focus. Furthermore, immersion exposure can be conducted by applying a conventional exposure apparatus. As a result, it is expected that immersion exposure will enable the formation of resist patterns of higher resolution and superior depth of focus at lower costs. Accordingly, in the production of semiconductor devices, which requires enormous capital investment, immersion exposure is attracting considerable attention as a method that offers significant potential to the semiconductor industry, both in terms of cost and in terms of lithography properties such as resolution.

Immersion lithography is effective in forming patterns having various shapes. Further, immersion exposure is expected to be capable of being used in combination with currently studied super-resolution techniques, such as phase shift method and modified illumination method. Currently, as the immersion exposure technique, technique using an ArF excimer laser as an exposure source is being actively studied. Further, water is mainly used as the immersion medium.

Recently, there have been proposed a photoreactive quencher added to a chemically amplified resist composition (see, for example, see Patent Documents 3 to 4). The photoreactive quencher is a salt of anion moiety with cation moiety. Before exposure, it exhibits quenching effect to trap an acid generated from an acid generator or the like by ion-exchange reaction. After exposure, it is decomposed, and then loses the quenching effect. Therefore, when a resist film formed using a chemically amplified resist composition containing a photoreactive quencher is subjected to exposure, the level of basicity of the photoreactive quencher to trap acid generated from an acid generator or the like is decreased at exposed portions. On the other hand, at unexposed portions, the photoreactive quencher traps acid. As a result, the diffusion of acid from exposed portions to unexposed portions can be suppressed, thereby improving lithography properties.

DOCUMENTS OF RELATED ART

Patent Document

[Patent Document 1] Japanese Unexamined Patent Application, First Publication No. 2008-292975
[Patent Document 2] Japanese Unexamined Patent Application, First Publication No. 2003-241385
[Patent Document 3] Japanese Unexamined Patent Application, First Publication No. Hei 6-266100
[Patent Document 4] WO2010/147079

SUMMARY OF THE INVENTION

As miniaturization of resist patterns progress, improvement will be demanded for resist materials with respect to excellent lithography properties.

A chemically amplified resist composition containing a conventional photoreactive quencher is superior in lithography properties but inferior in storage stability to the resist composition which does not contain a photoreactive quencher. Thus, there is a problem that resist properties such as lithography properties is deteriorated during storage.

The present invention takes the above circumstances into consideration, with an object of providing a resist composition having excellent lithography properties and excellent storage stability, a method of forming a resist pattern using the resist composition, and a new compound useful as a photoreactive quencher for the resist composition.

As a result of further studies of the present inventors, it has been found that stability of the resist composition is dramatically improved by adding a photoreactive quencher which contains an anion moiety having a specific structure. The present invention has been completed based on this finding.

A first aspect of the present invention is a resist composition containing: a base component (A) that exhibits changed solubility in a developing solution by the action of acid; a photoreactive quencher (C); and an acid-generator component (B) which generates acid upon exposure, wherein the photoreactive quencher (C) contains a compound represented by general formula (c1) shown below.

[Chemical Formula 1]

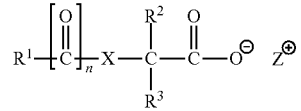

(c1)

In the formula, $R^1$ represents a hydrogen atom or a hydrocarbon group of 1 to 20 carbon atoms which may have a substituent; each of $R^2$ and $R^3$ independently represents a hydrogen atom or a hydrocarbon group of 1 to 20 carbon atoms which may have a substituent; at least two of $R^1$ to $R^3$ may be mutually bonded to form a ring; X represents an oxygen atom or a sulfur atom; n represents 0 or 1; and $Z^+$ represents an organic cation.

A second aspect of the present invention is a method of forming a resist pattern, including: using a resist composition of the first aspect to form a resist film on a substrate; conducting exposure of the resist film; and developing the resist film to form a resist pattern.

A third aspect of the present invention is a compound represented by general formula (c1) shown below.

[Chemical Formula 2]

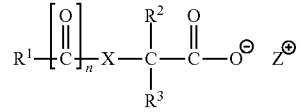

(c1)

In the formula, $R^1$ represents a hydrogen atom or a hydrocarbon group of 1 to 20 carbon atoms which may have a substituent; each of $R^2$ and $R^3$ independently represents a hydrogen atom or a hydrocarbon group of 1 to 20 carbon atoms which may have a substituent; at least two of $R^1$ to $R^3$ may be mutually bonded to form a ring; X represents an oxygen atom or a sulfur atom; n represents 0 or 1; and $Z^+$ represents an organic cation.

In the present description and claims, the term "exposure" is used as a general concept that includes irradiation with any form of radiation.

The term "structural unit" refers to a monomer unit that contributes to the formation of a polymeric compound (resin, polymer, and copolymer).

The term "aliphatic" is a relative concept used in relation to the term "aromatic", and defines a group or compound that has no aromaticity.

The term "alkyl group" includes linear, branched or cyclic, monovalent saturated hydrocarbon, unless otherwise specified. The same applies for the alkyl group within an alkoxy group.

The term "alkylene group" includes linear, branched or cyclic, divalent saturated hydrocarbon, unless otherwise specified.

A "halogenated alkyl group" is a group in which part or all of the hydrogen atoms of an alkyl group are substituted with a halogen atom, and a "halogenated alkylene group" is a group in which part or all of the hydrogen atoms of an alkylene group are substituted with a halogen atom. Examples of the halogen atom include a fluorine atom, a chlorine atom, a bromine atom and an iodine atom.

The fluorinated alkyl group is a group in which part or all of the hydrogen atoms of an alkyl group are substituted with a fluorine atom, and a "fluorinated alkylene group" is a group in which part or all of the hydrogen atoms of an alkylene group is substituted with a fluorine atom.

A "hydroxyalkyl group" is a group in which part or all of the hydrogen atoms within an alkyl group have been substituted with a hydroxyl group.

According to the present invention, there are provided a resist composition having excellent lithography properties and excellent storage stability, a method of forming a resist pattern using the resist composition, and a new compound useful as a photoreactive quencher for the resist composition.

DETAILED DESCRIPTION OF THE INVENTION

Resist Composition

The resist composition according to the present invention includes a base component (A) that exhibits changed solubility in a developing solution by the action of acid (hereafter, referred to as "component (A)"), a photoreactive quencher (C) (hereafter, referred to as "component (C)") and an acid-generator component (B) which generates acid upon exposure (hereafter, referred to as "component (B)").

With respect to a resist film formed using the resist composition, when a selective exposure is conducted during formation of a resist pattern, acid is generated from the component (B), and the generated acid acts on the component (A) to change the solubility of the component (A) in a developing solution. As a result, the solubility of the exposed portions in a developing solution is changed, whereas the solubility of the unexposed portions in a developing solution remains unchanged. Therefore, the exposed portions are dissolved and removed by developing in the case of a positive pattern, whereas unexposed portions are dissolved and removed in the case of a negative pattern, and hence, a resist pattern can be formed.

In the present specification, a resist composition which forms a positive pattern by dissolving and removing the exposed portions is called a positive resist composition, and a resist composition which forms a negative pattern by dissolving and removing the unexposed portions is called a negative resist composition.

The resist composition of the present invention may be either a negative resist composition or a positive resist composition.

Further, in the formation of a resist pattern, the resist composition of the present invention can be applied to an alkali developing process using an alkali developing solution in the developing treatment, or a solvent developing process using a developing solution containing an organic solvent (organic developing solution) in the developing treatment.

<Component (A)>

The component (A) is a base component which exhibits changed solubility in a developing solution under action of acid.

As the component (A), an organic compound typically used as a base component for a chemically amplified resist composition can be used alone, or two or more of such organic compounds can be mixed together.

The term "base component" refers to an organic compound capable of forming a film, and is preferably an organic compound having a molecular weight of 500 or more. When the organic compound has a molecular weight of 500 or more, the film-forming ability is improved, and a resist pattern of nano level can be easily formed.

The "organic compound having a molecular weight of 500 or more" which can be used as a base component is broadly classified into non-polymers and polymers.

In general, as a non-polymer, any of those which have a molecular weight in the range of no less than 500 to less than 4,000 is used. Hereafter, a non-polymer having a molecular weight in the range of 500 to less than 4,000 is referred to as a low molecular weight compound.

As a polymer, any of those which have a molecular weight of 1,000 or more is generally used. Hereafter, a polymer having a molecular weight of 1,000 or more is referred to as a polymeric compound. With respect to a polymeric compound, the "molecular weight" is the weight average molecular weight in terms of the polystyrene equivalent value determined by gel permeation chromatography (GPC). Hereafter, a polymeric compound is frequently referred to simply as a "resin".

As the component (A), a resin component which exhibits changed solubility in a developing solution under action of acid may be used. Alternatively, as the component (A), a low molecular weight material which exhibits changed solubility in a developing solution under action of acid may be used, and a combination of these components may be used.

When the resist composition of the present invention is a resist composition which forms a negative pattern in an alkali developing process, for example, as the component (A), a base component that exhibits solubility in an alkali developing solution is used, and a cross-linking agent is blended in the negative resist composition.

The base component which exhibits solubility in an alkali developing solution contains alkali soluble groups such as a hydroxy group, a carboxy group and a sulfonamide group. The cross-linking agent is a compound containing reactive groups capable of reacting with these alkali soluble groups. In the resist composition, when acid is generated from the component (B) upon exposure, the generated acid causes cross-linking between the base component and the cross-linking agent, and hence, the cross-linked portion becomes insoluble in an alkali developing solution. Therefore, in the formation of a resist pattern, by conducting selective exposure to a resist film formed by applying the resist composition onto a substrate, the exposed portions become insoluble in an alkali developing solution, whereas the unexposed portions remain soluble in an alkali developing solution, and hence, a resist pattern can be formed by alkali developing.

Generally, as the base component that exhibits solubility in an alkali developing solution, a resin that exhibits solubility in an alkali developing solution (hereafter, referred to as "alkali-soluble resin") is used.

Examples of the alkali soluble resin include a resin having a structural unit derived from at least one of α-(hydroxyalkyl) acrylic acid and an alkyl ester of α-(hydroxyalkyl)acrylic acid (preferably an alkyl ester having 1 to 5 carbon atoms), as disclosed in Japanese Unexamined Patent Application, First Publication No. 2000-206694; an acrylic resin which has a sulfonamide group and may have a carbon atom of the α-position having an atom other than a hydrogen atom or a substituent bonded thereto or a polycycloolefin resin having a sulfonamide group, as disclosed in U.S. Pat. No. 6,949,325;

an acrylic resin which may have the carbon atom of the α-position having an atom other than a hydrogen atom or a substituent bonded thereto and which has a fluorinated alcohol, as disclosed in U.S. Pat. No. 6,949,325, Japanese Unexamined Patent Application, First Publication No. 2005-336452 or Japanese Unexamined Patent Application, First Publication No. 2006-317803; and a polycyclolefin resin having a fluorinated alcohol, as disclosed in Japanese Unexamined Patent Application, First Publication No. 2006-259582. These resins are preferable in that a resist pattern can be formed with minimal swelling.

Here, the term "α-(hydroxyalkyl)acrylic acid" refers to one or both of acrylic acid which may has the carbon atom on the α-position having an atom other than a hydrogen atom or a substituent bonded thereto and which has a hydroxy group bonded to a carbon atom on the α-position having the carboxyl group bonded thereto, and α-hydroxyalkylacrylic acid in which a hydroxyalkyl group (preferably a hydroxyalkyl group of 1 to 5 carbon atoms) is bonded to the carbon atom on the α-position.

As the cross-linking agent, typically, an amino-based cross-linking agent such as a glycoluril having a methylol group or alkoxymethyl group, or a melamine-based cross-linking agent is preferable, as it enables formation of a resist pattern with minimal swelling. The amount of the cross-linking agent added is preferably within a range from 1 to 50 parts by weight, relative to 100 parts by weight of the alkali-soluble resin.

In the case where the resist composition of the present invention is a resist composition which forms a positive pattern in an alkali developing process and a negative pattern in a solvent developing process, it is preferable to use a base component (A0) (hereafter, referred to as "component (A0)") which exhibits increased polarity by the action of acid. By using the component (A0), since the polarity of the base component changes prior to and after exposure, an excellent development contrast can be obtained not only in an alkali developing process, but also in a solvent developing process.

More specifically, in the case of applying an alkali developing process, the component (A0) is substantially insoluble in an alkali developing solution prior to exposure, but when acid is generated from the component (B) upon exposure, the acid causes an increase in the polarity of the base component, thereby increasing the solubility of the component (A0) in an alkali developing solution. Therefore, in the formation of a resist pattern, by conducting selective exposure to a resist film formed by applying the resist composition to a substrate, the exposed portions change from an insoluble state to a soluble state in an alkali developing solution, whereas the unexposed portions remain insoluble in an alkali developing solution, and hence, a contrast can be made between the exposed portions and unexposed portions, and a positive resist pattern can be formed by developing using an alkali developing solution.

On the other hand, in the case of a solvent developing process, the component (A0) exhibits high solubility in an organic developing solution prior to exposure, and when acid is generated from the component (B) upon exposure, the polarity of the component (A0) is increased by the action of the generated acid, thereby decreasing the solubility of the component (A0) in an organic developing solution. Therefore, in the formation of a resist pattern, by conducting selective exposure to a resist film formed by applying the resist composition to a substrate, the exposed portions changes from an soluble state to an insoluble state in an organic developing solution, whereas the unexposed portions remain soluble in an organic developing solution. As a result, by conducting development using an organic developing solution, a contrast can be made between the exposed portions and unexposed portions, thereby enabling the formation of a negative resist pattern by developing using an organic developing solution.

In the resist composition of the present invention, the component (A) is preferably a base component which exhibits increased polarity by the action of acid (i.e., a component (A0)). That is, the resist composition of the present invention is preferably a resist composition which becomes a positive type in the case of an alkali developing process, and a negative type in the case of a solvent developing process.

The component (A0) may be a resin component (A1) that exhibits increased polarity by the action of acid (hereafter, frequently referred to as "component (A1)"), a low molecular weight material (A2) that exhibits increased polarity by the action of acid (hereafter, frequently referred to as "component (A2)"), or a mixture thereof.

{Component (A1)}

As the component (A1), a resin component (base resin) typically used as a base component for a chemically amplified resist composition can be used alone, or two or more of such resin components can be mixed together.

The component (A1) preferably has a structural unit (a1) containing an acid decomposable group that exhibits increased polarity by the action of acid.

The component (A1) preferably further includes a structural unit (a2) containing a —$SO_2$-containing cyclic group or a lactone-containing cyclic group, as well as the structural unit (a1).

The component (A1) preferably further includes a structural unit (a3) containing a polar group, as well as the structural unit (a1), or the structural unit (a1) and the structural unit (a2).

[Structural Unit (a1)]

The structural unit (a1) is a structural unit containing an acid decomposable group which exhibits increased polarity by the action of acid.

The term "acid decomposable group" refers to a group in which at least a part of the bond within the structure thereof is cleaved by the action of acid.

Examples of acid decomposable groups which exhibit increased polarity by the action of acid include groups which are decomposed by the action of acid to form a polar group.

Examples of the polar group include a carboxy group, a hydroxy group, an amino group and a sulfo group (—$SO_3H$). Among these, a polar group containing —OH in the structure thereof (hereafter, frequently referred to as "OH-containing polar group") is preferable, a carboxy group or a hydroxy group is more preferable, and a carboxy group is particularly desirable.

Specific examples of an acid decomposable group include a group in which the aforementioned polar group has been protected with an acid dissociable group (such as a group in which the hydrogen atom of the OH-containing polar group has been protected with an acid dissociable group) can be given.

An "acid dissociable group" is a group in which exhibits acid dissociable properties that at least a bond between an acid dissociable group and an atom adjacent to the acid dissociable group is cleaved by the action of acid. It is necessary that the acid dissociable group that constitutes the acid decomposable group is a group which exhibits a lower polarity than the polar group generated by the dissociation of the acid dissociable group. Thus, when the acid dissociable group is dissociated by the action of acid, a polar group exhibiting a higher polarity than that of the acid dissociable group is generated, thereby increasing the polarity. As a result, the polarity of the entire component (A1) is increased. When the polarity of the component (A1) is increased, the solubility in a developing solution is changed relatively. For example, when the developing solution is an alkali developing solution, the solubility of the component (A1) in the developing solution is increased. On the other hand, when the developing solution is an organic developing solution, the solubility of the component (A1) in the developing solution is decreased.

The acid dissociable group is not particularly limited, and any of the groups that have been conventionally proposed as acid dissociable groups for the base resins of chemically amplified resists can be used. Generally, groups that form either a cyclic or chain-like tertiary alkyl ester with the carboxyl group of the (meth)acrylic acid, and acetal-type acid dissociable groups such as alkoxyalkyl groups are widely known.

Here, a tertiary alkyl ester describes a structure in which an ester is formed by substituting the hydrogen atom of a carboxyl group with a chain-like or cyclic tertiary alkyl group, and a tertiary carbon atom within the chain-like or cyclic tertiary alkyl group is bonded to the oxygen atom at the terminal of the carbonyloxy group (—C(=O)—O—). In this tertiary alkyl ester, the action of acid causes cleavage of the bond between the oxygen atom and the tertiary carbon atom, thereby forming a carboxy group.

The chain-like or cyclic alkyl group may have a substituent.

Hereafter, for the sake of simplicity, groups that exhibit acid dissociability as a result of the formation of a tertiary alkyl ester with a carboxyl group are referred to as "tertiary alkyl ester-type acid dissociable groups".

Examples of tertiary alkyl ester-type acid dissociable groups include aliphatic branched, acid dissociable groups and aliphatic cyclic group-containing acid dissociable groups.

The term "aliphatic branched" refers to a branched structure having no aromaticity. The "aliphatic branched, acid dissociable group" is not limited to be constituted of only carbon atoms and hydrogen atoms (not limited to hydrocarbon groups), but is preferably a hydrocarbon group. Further, the "hydrocarbon group" may be either saturated or unsaturated, but is preferably saturated.

As an example of the aliphatic branched, acid dissociable group, for example, a group represented by the formula —C(R$^{71}$)(R$^{72}$)(R$^{73}$) can be given. In the formula, each of R$^7$ to R$^{73}$ independently represents a linear alkyl group of 1 to 5 carbon atoms. The group represented by the formula —C(R$^{71}$)(R$^{72}$)(R$^{73}$) preferably has 4 to 8 carbon atoms, and specific examples include a tert-butyl group, a 2-methyl-2-butyl group, a 2-methyl-2-pentyl group and a 3-methyl-3-pentyl group.

Among these, a tert-butyl group is particularly desirable.

The term "aliphatic cyclic group" refers to a monocyclic group or polycyclic group that has no aromaticity.

In the "aliphatic cyclic group-containing acid dissociable group", the "aliphatic cyclic group" may or may not have a substituent. Examples of the substituent include an alkyl group of 1 to 5 carbon atoms, an alkoxy group of 1 to 5 carbon atoms, a fluorine atom, a fluorinated alkyl group of 1 to 5 carbon atoms, and an oxygen atom (=O).

The basic ring of the "aliphatic cyclic group" exclusive of substituents is not limited to be constituted from only carbon atom and hydrogen atom (not limited to hydrocarbon groups), but is preferably a hydrocarbon group. Further, the "hydrocarbon group" may be either saturated or unsaturated, but is preferably saturated.

The aliphatic cyclic group may be either a monocyclic group or a polycyclic group.

As such aliphatic cyclic groups, groups in which one or more hydrogen atoms have been removed from a monocycloalkane or a polycycloalkane such as a bicycloalkane, tricycloalkane or tetracycloalkane which may or may not be substituted with a lower alkyl group, a fluorine atom or a fluorinated alkyl group, may be used. Specific examples of aliphatic cyclic hydrocarbon groups include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane. In these aliphatic cyclic hydrocarbon groups, part of the carbon atoms constituting the ring may be replaced with an ethereal oxygen atom (—O—).

Examples of aliphatic cyclic group-containing acid dissociable groups include (i) a monovalent aliphatic cyclic group in which a substituent (a group or an atom other than hydrogen) is bonded to the carbon atom on the ring skeleton to which an atom adjacent to the acid dissociable group (e.g., "—O—" within "—C(=O)—O— group") is bonded to form a tertiary carbon atom; and (ii) a group which has a branched alkylene group containing a tertiary carbon atom, and a monovalent aliphatic cyclic group to which the tertiary carbon atom is bonded.

In the group (i), as the substituent bonded to the carbon atom to which an atom adjacent to the acid dissociable group on the ring skeleton of the aliphatic cyclic group is bonded, an alkyl group can be mentioned. Examples of the alkyl group include the same groups as those represented by R$^{14}$ in formulas (1-1) to (1-9) described later.

Specific examples of the group (i) include groups represented by general formulas (1-1) to (1-9) shown below.

Specific examples of the group (ii) include groups represented by general formulas (2-1) to (2-6) shown below.

[Chemical Formula 3]

(1-1)

(1-2)

(1-3)

(1-4)

-continued (1-5) 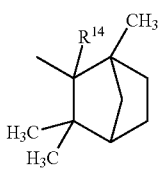

(1-6) 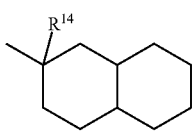

(1-7) 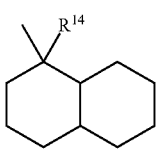

(1-8) 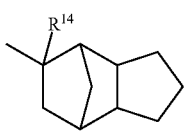

(1-9) 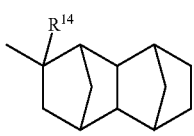

In the formulas above, $R^{14}$ represents an alkyl group; and g represents an integer of 0 to 8.

[Chemical Formula 4]

(2-1) 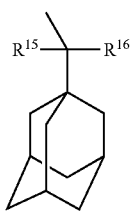

(2-2) 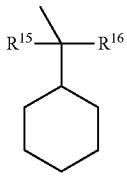

(2-3) 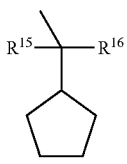

(2-4) 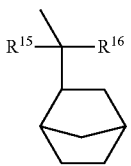

(2-5) 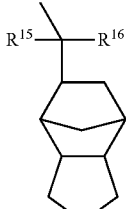

(2-6) 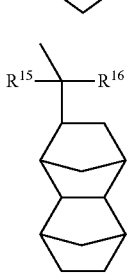

In the formulas above, each of $R^{15}$ and $R^{16}$ independently represents an alkyl group.

In formulas (1-1) to (1-9), the alkyl group for $R^{14}$ may be linear, branched or cyclic, and is preferably linear or branched.

The linear alkyl group preferably has 1 to 5 carbon atoms, more preferably 1 to 4, and still more preferably 1 or 2. Specific examples include a methyl group, an ethyl group, an n-propyl group, an n-butyl group and an n-pentyl group. Among these, a methyl group, an ethyl group or an n-butyl group is preferable, and a methyl group or an ethyl group is more preferable.

The branched alkyl group preferably has 3 to 10 carbon atoms, and more preferably 3 to 5. Specific examples of such branched alkyl groups include an isopropyl group, an isobutyl group, a tert-butyl group, an isopentyl group and a neopentyl group, and an isopropyl group is most desirable.

In general formula (1-2), g is preferably an integer of 0 to 4, more preferably an integer of 1 to 4, and most preferably 1 or 2.

In formulas (2-1) to (2-6), as the alkyl group for $R^{15}$ and $R^{16}$, the same alkyl groups as those for $R^{14}$ can be used.

In formulas (1-1) to (1-9) and (2-1) to (2-6), part of the carbon atoms constituting the ring may be replaced with an ethereal oxygen atom (—O—).

Further, in formulas (1-1) to (1-9) and (2-1) to (2-6), one or more of the hydrogen atoms bonded to the carbon atoms constituting the ring may be substituted with a substituent. Examples of the substituent include an alkyl group of 1 to 5 carbon atoms, a fluorine atom and a fluorinated alkyl group.

An "acetal-type acid dissociable group" generally substitutes a hydrogen atom at the terminal of an OH-containing polar group such as a carboxy group or hydroxy group, so as to be bonded with an oxygen atom. The acid acts to break the bond between the acetal-type acid dissociable group and the oxygen atom to which the acetal-type, acid dissociable group is bonded, thereby forming an OH-containing polar group such as a carboxy group or a hydroxy group.

Examples of acetal-type acid dissociable groups include groups represented by general formula (p1) shown below.

[Chemical Formula 5]

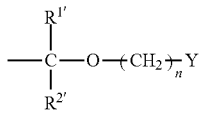

(p1)

In the formula, $R^{1\prime}$ and $R^{2\prime}$ each independently represent a hydrogen atom or an alkyl group of 1 to 5 carbon atoms; n represents an integer of 0 to 3; and Y represents an alkyl group of 1 to 5 carbon atoms or an aliphatic cyclic group.

In general formula (p1), n is preferably an integer of 0 to 2, more preferably 0 or 1, and most preferably 0.

Specific examples of the alkyl groups of 1 to 5 carbon atoms for $R^{1\prime}$ and $R^{2\prime}$ include linear or branched alkyl groups such as a methyl group, an ethyl group, a propyl group, an isopropyl group, an n-butyl group, an isobutyl group, a tert-butyl group, a pentyl group, an isopentyl group and a neopentyl group. Among these examples, a methyl group or an ethyl group is preferable, and a methyl group is particularly desirable.

As the alkyl group of 1 to 5 carbon atoms for Y, the same alkyl groups of 1 to 5 carbon atoms as those above for $R^{1\prime}$ and $R^{2\prime}$ can be used.

As the aliphatic cyclic group for Y, any of the aliphatic monocyclic/polycyclic groups which have been proposed for conventional ArF resists and the like can be appropriately selected for use. For example, the same aliphatic cyclic groups described above in connection with the "acid dissociable group containing an aliphatic cyclic group" can be used.

As the groups represented by the general formula (p1), it is preferable that at least one of $R^1$ and $R^{2\prime}$ be a hydrogen atom. That is, a group represented by general formula (p1-1) is preferable.

[Chemical Formula 6]

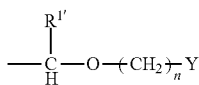

(p1-1)

In the formula, $R^{1\prime}$, n and Y are the same as defined above.

Further, as the acetal-type, acid dissociable group, groups represented by general formula (p2) shown below can also be used.

[Chemical Formula 7]

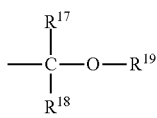

(p2)

In the formula, $R^{17}$ and $R^{18}$ each independently represent a linear or branched alkyl group or a hydrogen atom; and $R^{19}$ represents a linear, branched or cyclic alkyl group; or $R^{17}$ and $R^{19}$ each independently represents a linear or branched alkylene group, and the terminal of $R^{17}$ is bonded to the terminal of $R^{19}$ to form a ring.

In the formula (p2), the alkyl group for $R^{17}$ and $R^{18}$ may be linear, branched or cyclic. The number of carbon atoms within the alkyl group is preferably from 1 to 15. As the alkyl group for $R^{17}$ and $R^{18}$, an ethyl group or a methyl group is preferable, and a methyl group is most preferable.

It is preferable that at least one of $R^{17}$ and $R^{18}$ is a hydrogen atom, and it is particularly preferable that one of $R^{17}$ and $R^{18}$ is a hydrogen atom, and the other be a methyl group.

The alkyl group for $R^{19}$ may be any of linear, branched or cyclic. The number of carbon atoms within the alkyl group is preferably from 1 to 15.

When $R^{19}$ represents a linear or branched alkyl group, it is preferably an alkyl group of 1 to 5 carbon atoms, more preferably an ethyl group or methyl group, and most preferably an ethyl group.

When $R^{19}$ represents a cycloalkyl group, it preferably has 4 to 15 carbon atoms, more preferably 4 to 12 carbon atoms, and most preferably 5 to 10 carbon atoms. As examples of the cycloalkyl group, groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group, may be used. Specific examples include groups in which one or more hydrogen atoms have been removed from a monocycloalkane such as cyclopentane and cyclohexane; and groups in which one or more hydrogen atoms have been removed from a polycycloalkane such as adamantane, norbornane, isobornane, tricyclodecane or tetracyclododecane. Among these, a group in which one or more hydrogen atoms have been removed from adamantane is preferable.

In general formula (p2) above, $R^{17}$ and $R^{19}$ may each independently represent a linear or branched alkylene group (preferably an alkylene group of 1 to 5 carbon atoms), and the terminal of $R^{19}$ may be bonded to the terminal of $R^{17}$.

In such a case, a cyclic group is formed by $R^{17}$, $R^{19}$, the oxygen atom having $R^{19}$ bonded thereto, and the carbon atom having the oxygen atom and $R^{17}$ bonded thereto. Such a cyclic group is preferably a 4 to 7-membered ring, and more preferably a 4 to 6-membered ring. Specific examples of the cyclic group include tetrahydropyranyl group and tetrahydrofuranyl group.

The structural unit (a1) is not particularly limited as long as it has an acid decomposable group, and a structural unit derived from a compound containing an ethylenic double bond is preferred.

Here, the "structural unit derived from a compound containing an ethylenic double bond" refers to a structural unit in which the ethylenic double bond of the compound containing an ethylenic double bond is cleaved to form a single bond.

Examples of the compound containing an ethylenic double bond include an acrylic acid or ester thereof which may have the hydrogen atom bonded to the carbon atom on the α-position substituted with a substituent, an acrylamide or derivative thereof which may have the hydrogen atom bonded to the carbon atom on the α-position substituted with a substituent, a vinyl aromatic compound which may have the hydrogen atom bonded to the carbon atom on the α-position substituted with a substituent, a cycloolefine or derivative thereof, and a vinyl sulfonate ester and the like. Among these, an acrylic acid or ester thereof which may have the hydrogen atom bonded to the carbon atom on the α-position substituted with a substituent, an acrylamide or derivative thereof which may have the hydrogen atom bonded to the carbon atom on the α-position substituted with a substituent, and a vinyl aromatic compound or derivative thereof which may have the hydrogen atom bonded to the carbon atom on the α-position substituted with a substituent are preferable.

An "acrylate ester" refers to a compound in which the terminal hydrogen atom of the carboxy group of acrylic acid ($CH_2$=CH—COOH) has been substituted with an organic group.

In the present specification, an acrylic acid and acrylate ester in which the hydrogen atom bonded to the carbon atom on the α-position has been substituted with a substituent are referred to as an "α-substituted acrylic acid" and an "α-substituted acrylate ester", respectively. Further, acrylic acid and α-substituted acrylic acid are collectively referred to as "(α-substituted) acrylic acid", and acrylate esters and α-substituted acrylate esters are collectively referred to as "(α-substituted) acrylate ester".

Examples of the substituent bonded to the carbon atom on the α-position of the α-substituted acrylate or ester thereof include an alkyl group of 1 to 5 carbon atoms, a halogenated alkyl group of 1 to 5 carbon atoms and a hydroxyalkyl group. With respect to the structural unit derived from an acrylate ester, the α-position (the carbon atom on the α-position) refers to the carbon atom having the carbonyl group bonded thereto, unless specified otherwise.

Examples of the halogen atom as the substituent at the α-position include a fluorine atom, a chlorine atom, a bromine atom and an iodine atom.

Specific examples of the alkyl group of 1 to 5 carbon atoms for the substituent on the α-position include linear or branched alkyl groups such as a methyl group, an ethyl group, a propyl group, an isopropyl group, an n-butyl group, an isobutyl group, a tert-butyl group, a pentyl group, an isopentyl group, and a neopentyl group.

Specific examples of the halogenated alkyl group of 1 to 5 carbon atoms as a substituent on the α-position include groups in which part or all of the hydrogen atoms of the aforementioned alkyl group of 1 to 5 carbon atoms are substituted with halogen atoms. Examples of the halogen atom include a fluorine atom, a chlorine atom, a bromine atom and an iodine atom, and a fluorine atom is particularly preferred.

As the hydroxyalkyl group as a substituent on the α-position, a hydroxyalkyl group of 1 to 5 carbon atoms is preferred. Specific examples include a group in which part or all of the hydrogen atoms of the aforementioned alkyl group of 1 to 5 carbon atoms are substituted with a hydroxy group.

In the present invention, it is preferable that a hydrogen atom, an alkyl group of 1 to 5 carbon atoms or a halogenated alkyl group of 1 to 5 carbon atoms is bonded to the α-position of the (α-substituted) acrylic acid or ester thereof, a hydrogen atom, an alkyl group of 1 to 5 carbon atoms or a fluorinated alkyl group of 1 to 5 carbon atoms is more preferable, and in terms of industrial availability, a hydrogen atom or a methyl group is the most preferred.

The "organic group" refers to a group containing a carbon atom, and may include atoms other than carbon atoms (e.g., a hydrogen atom, an oxygen atom, a nitrogen atom, a sulfur atom, a halogen atom (such as a fluorine atom and a chlorine atom) and the like).

The organic group in (α-substituted) acrylate ester is not particularly limited. Examples thereof include characteristic groups such as an aromatic group described later and an acid decomposable group described above, and a characteristic group-containing group which contains these characteristic groups in the structure thereof. Examples of the characteristic group-containing group include a group in which a divalent linking group is bonded to the characteristic group. Examples of the divalent linking group include the same divalent linking groups as those described later for $Y^2$ in the general formula (a1-3).

Examples of the "acrylamide and derivative thereof" include an acryl amide which may have the hydrogen atom bonded to the carbon atom on the α-position substituted with a substituent (hereafter, frequently referred to as (α-substituted) acrylamide) and a compound in which one or both of hydrogen atoms at the terminal of the amino group within the (α-substituted) acrylamide have been substituted with a substituent.

As the substituent which may be bonded to the carbon atom on the α-position of an acrylamide or derivatives thereof, the same substituents as those described above for the substituent to be bonded to the carbon atom on the α-position of an α-substituted acrylate ester can be mentioned.

As the substituent with which one or both of hydrogen atoms at the terminal of the amino group within (α-substituted) acrylamide is substituted, an organic group is preferable. The organic group is not particularly limited, and examples thereof include the same groups as described for the organic groups within (α-substituted) acrylate ester.

Examples of the compound in which one or both of hydrogen atom at the terminal of amino group within the (α-substituted) acrylamide have been substituted with a substituent include a compound in which —C(=O)—O— bonded to carbon atom on the α-position of the (α-substituted) acrylate ester is replaced by a group —C(=O)—N($R^b$)— [in the formula, $R^b$ represents a hydrogen atom or an alkyl group of 1 to 5 carbon atoms].

In the formula, the alkyl group for $R^b$ is preferably a linear or branched alkyl group.

The "vinyl aromatic compound" is a compound having an aromatic ring and one vinyl group bonded to the aromatic ring, and as the examples thereof, a styrene or derivative thereof and a vinylnaphthalene and derivative thereof can be mentioned.

As the substituent which may be bonded to the carbon atom on the α-position of a vinyl aromatic compound (that is, the carbon atom of the vinyl group, which is bonded to the aromatic ring), the same substituents as those described above for the substituent to be bonded to the carbon atom on the α-position of an α-substituted acrylate ester can be mentioned.

Hereafter, a vinyl aromatic compound in which the hydrogen atom bonded to the carbon atom on the α-position has been substituted with a substituent is frequently referred to as an (α-substituted) vinyl aromatic compound.

Examples of the "styrene and derivative thereof" may include a styrene which have the hydrogen atom bonded to the carbon atom on the α-position substituted with a substituent and may have the hydrogen atom bonded to the benzene ring substituted with a substituent other than the hydroxy group (hereafter, frequently referred to as (α-substituted)styrene), a hydroxystyrene which may have the hydrogen atom bonded to the carbon atom on the α-position substituted with a substituent and may have a hydrogen atom bonded to the benzene ring substituted with a substituent other than a hydroxy group (hereafter, frequently referred to as (α-substituted)hydroxystyrene), a compound in which a hydrogen atom of hydroxy group of (α-substituted)hydroxystyrene is substituted with an organic group, a vinylbenzoic acid which may have the hydrogen atom bonded to the carbon atom on the α-position substituted with a substituent and may have a hydrogen atom bonded to the benzene ring substituted with a substituent other than a hydroxy group or carboxy group (hereafter, frequently referred to as (α-substituted)vinylbenzoic acid), and a compound in which a hydrogen atom of carboxy group of (α-substituted)vinylbenzoic acid is substituted with an organic group.

A hydroxystyrene is a compound which has one vinyl group and at least one hydroxy group bonded to a benzene ring. The number of hydroxy groups bonded to the benzene ring is preferably 1 to 3, and most preferably 1. The bonding position of the hydroxy group on the benzene ring is not particularly limited. When the number of the hydroxy group is 1, para (4th) position against the bonding position of the vinyl group is preferable. When the number of the hydroxy groups is an integer of 2 or more, an arbitrary combination of the bonding positions can be adopted.

The vinylbenzoic acid is a compound in which one vinyl group is bonded to the benzene ring within the benzoic acid.

The bonding position of the vinyl group on the benzene ring is not particularly limited.

The substituent other than a hydroxy group or a carboxy group which may be bonded to the benzene ring of an styrene or derivative thereof is not particularly limited, and examples thereof include a halogen atom, an alkyl group of 1 to 5 carbon atoms and a halogenated alkyl group of 1 to 5 carbon atoms. Examples of the halogen atom include a fluorine atom, a chlorine atom, a bromine atom and an iodine atom, and a fluorine atom is particularly preferred.

The organic group within a compound in which the hydrogen atom of the hydroxy group within the (α-substituted) hydroxystyrene is substituted with an organic group is not particularly limited, and examples thereof include the same groups as described for the organic groups within (α-substituted) acrylate ester.

The organic group within a compound in which the hydrogen atom of the carboxy group within the (α-substituted) vinylbenzoic acid is substituted with an organic group is not particularly limited, and examples thereof include the same organic groups as those described for the organic group within (α-substituted) acrylate ester.

Examples of the "vinylnaphthalene and derivative thereof" include a vinylnaphthalene which may have the hydrogen atom bonded to the carbon atom on the α-position substituted with a substituent and may have the hydrogen atom bonded to the naphthalene ring substituted with a substituent other than the hydroxy group (hereafter, frequently referred to as (α-substituted) vinyl naphthalene), a vinyl (hydroxynaphthalene) which may have the hydrogen atom bonded to the carbon atom on the α-position substituted with a substituent and may have a hydrogen atom bonded to the naphthalene ring substituted with a substituent other than a hydroxy group (hereafter, frequently referred to as (α-substituted) vinyl(hydroxynaphthalene)) and a compound in which a hydrogen atom of the hydroxy group within (α-substituted) vinyl(hydroxynaphthalene) is substituted with a substituent.

A vinyl(hydroxynaphthalene) is a compound which has one vinyl group and at least one hydroxy group bonded to a naphthalene ring. The vinyl group may be bonded to the 1st or 2nd position of the naphthalene ring. The number of hydroxy groups bonded to the naphthalene ring is preferably 1 to 3, and particularly preferably 1. The bonding position of the hydroxy group on the naphthalene ring is not particularly limited. When the vinyl group is bonded to the 1st or 2nd position of the naphthalene ring, the hydroxy group is preferably bonded to either one of the 5th to 8th position of the naphthalene ring. In particular, when the number of hydroxy group is 1, the hydroxy group is preferably bonded to either one of the 5th to 7th position of the naphthalene ring, and more preferably the 5th or 6th position. When the number of the hydroxy groups is an integer of 2 or more, an arbitrary combination of the bonding positions can be adopted.

As the substituent which may be bonded to the naphthalene ring of the vinylnaphthalene or derivative thereof, the same substituents as those described above for the substituent which may be bonded to the benzene ring of the (α-substituted) styrene can be mentioned.

The organic group within a compound in which the hydrogen atom of the hydroxy group within the (α-substituted) vinyl(hydroxystyrene) is substituted with an organic group is not particularly limited, and examples thereof include the same organic groups as those described for the organic group within (α-substituted) acrylate ester.

Examples of the structural unit (a1) include: a structural unit (a11) derived from an acrylate ester which may have the hydrogen atom bonded to the carbon atom on the α-position substituted with a substituent and contains an acid decomposable group; a structural unit (a12) derived from a hydroxystyrene which may have the hydrogen atom bonded to the carbon atom on the α-position substituted with a substituent and may have the hydrogen atom bonded to the benzene ring substituted with a substituent other than a hydroxy group, and which has the hydrogen atom of the hydroxy group substituted with an acid dissociable group or a substituent containing an acid dissociable group; and a structural unit (a13) derived from a vinyl(hydroxynaphthalene) which may have the hydrogen atom bonded to the carbon atom on the α-position substituted with a substituent and may have the hydrogen atom bonded to the naphthalene ring substituted with a substituent other than a hydroxy group, and which has the hydrogen atom of the hydroxy group substituted with an acid dissociable group or a substituent containing an acid dissociable group.

[Structural Unit (a11)]

The structural unit (a11) is a structural unit derived from an acrylate ester which may have the hydrogen atom bonded to the carbon atom on the α-position substituted with a substituent and contains an acid decomposable group.

Examples of the structural unit (a11) include a structural unit represented by general formula (a1-0-1) shown below and a structural unit represented by general formula (a1-0-2) shown below.

[Chemical Formula 8]

(a1-0-1)

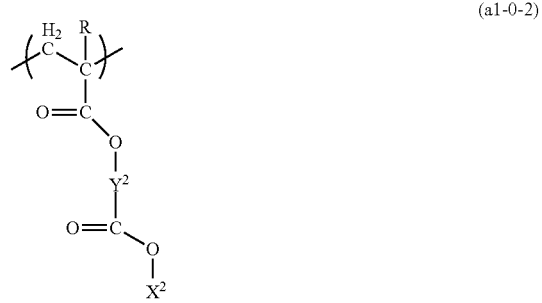

(a1-0-2)

In the formulas, R represents a hydrogen atom, an alkyl group of 1 to 5 carbon atoms or a halogenated alkyl group of 1 to 5 carbon atoms; $X^1$ represents an acid dissociable group; $Y^2$ represents a divalent linking group; and $X^2$ represents an acid dissociable group.

In general formula (a1-0-1), the alkyl group and the halogenated alkyl group for R are respectively the same alkyl group of 1 to 5 carbon atoms and the halogenated alkyl group of 1 to 5 carbon atoms as defined above for a substituent which may be bonded to the carbon atom on the α-position of the aforementioned α-substituted acrylic acid or ester thereof.

R is preferably a hydrogen atom, an alkyl group of 1 to 5 carbon atoms or a fluorinated alkyl group of 1 to 5 carbon atoms, and most preferably a hydrogen atom or a methyl group.

$X^1$ is not particularly limited as long as it is an acid dissociable group. Examples thereof include the aforementioned tertiary alkyl ester-type acid dissociable groups and acetal-type acid dissociable groups, and tertiary alkyl ester-type acid dissociable groups are preferable.

In general formula (a1-0-2), R is the same as defined for R in general formula (a1-0-1).

$X^2$ is the same as defined above for $X^1$ in general formula (a1-0-1).

The divalent linking group for $Y^2$ is not particularly limited, and preferable examples thereof include a divalent hydrocarbon group which may have a substituent and a divalent linking group containing a hetero atom.

(Divalent Hydrocarbon Group which May have a Substituent)

The hydrocarbon group as the divalent linking group may be either an aliphatic hydrocarbon group or an aromatic hydrocarbon group.

An "aliphatic hydrocarbon group" refers to a hydrocarbon group that has no aromaticity. The aliphatic hydrocarbon group may be saturated or unsaturated. In general, the aliphatic hydrocarbon group is preferably saturated.

As specific examples of the aliphatic hydrocarbon group, a linear or branched aliphatic hydrocarbon group, and an aliphatic hydrocarbon group containing a ring in the structure thereof can be given.

The linear or branched aliphatic hydrocarbon group preferably has 1 to 10 carbon atoms, more preferably 1 to 8, and still more preferably 1 to 5.

As the linear aliphatic hydrocarbon group, a linear alkylene group is preferable, and specific examples include a methylene group [—$CH_2$—], an ethylene group [—$(CH_2)_2$—], a trimethylene group [—$(CH_2)_3$—], a tetramethylene group [—$(CH_2)_4$—] and a pentamethylene group [—$(CH_2)_5$—].

As the branched aliphatic hydrocarbon group, a branched alkylene group is preferable, and specific examples include alkylalkylene groups, e.g., alkylmethylene groups such as —CH($CH_3$)—, —CH($CH_2CH_3$)—, —C($CH_3$)$_2$—, —C($CH_3$)($CH_2CH_3$)—, —C($CH_3$)($CH_2CH_2CH_3$)—, and —C($CH_2CH_3$)$_2$—; alkylethylene groups such as —CH($CH_3$)$CH_2$—, —CH($CH_3$)CH($CH_3$)—, —C($CH_3$)$_2CH_2$—, —CH($CH_2CH_3$)$CH_2$—, and —C($CH_2CH_3$)$_2$—$CH_2$—; alkyltrimethylene groups such as —CH($CH_3$)$CH_2CH_2$—, and —$CH_2$CH($CH_3$)$CH_2$—; and alkyltetramethylene groups such as —CH($CH_3$)$CH_2CH_2CH_2$—, and —$CH_2$CH($CH_3$)$CH_2CH_2$—. As the alkyl group within the alkylalkylene group, a linear alkyl group of 1 to 5 carbon atoms is preferable.

The linear or branched aliphatic hydrocarbon group may or may not have a substituent (that is, a group or an atom other than hydrogen atom) which substitutes a hydrogen atom in the cyclic aliphatic hydrocarbon group. Examples of the substituent include a fluorine atom, a fluorinated alkyl group of 1 to 5 carbon atoms, and an oxo group (═O).

As examples of the aliphatic hydrocarbon group containing a ring in the structure thereof, a cyclic aliphatic hydrocarbon group which may have a substituent containing a hetero atom in the ring structure thereof (a group in which two hydrogen atoms have been removed from an aliphatic hydrocarbon ring) and a group in which the cyclic aliphatic hydrocarbon group has been bonded to the terminal of the linear or branched aliphatic hydrocarbon group or interposed within the aforementioned linear or branched aliphatic hydrocarbon group, can be given. Examples of the linear or branched aliphatic hydrocarbon group include the same groups as described above.

The cyclic aliphatic hydrocarbon group preferably has 3 to 20 carbon atoms, and more preferably 3 to 12 carbon atoms.

The cyclic aliphatic hydrocarbon group may be either a polycyclic group or a monocyclic group. As the monocyclic aliphatic hydrocarbon group, a group in which 2 hydrogen atoms have been removed from a monocycloalkane is preferable. The monocycloalkane preferably has 3 to 6 carbon atoms, and specific examples thereof include cyclopentane and cyclohexane. As the polycyclic aliphatic hydrocarbon group, a group in which two hydrogen atoms have been removed from a polycycloalkane is preferable, and the polycyclic group preferably has 7 to 12 carbon atoms. Examples of the polycycloalkane include adamantane, norbornane, isobornane, tricyclodecane and tetracyclododecane.

The cyclic aliphatic hydrocarbon group may or may not have a substituent (that is, a group or an atom other than hydrogen atom) which substitutes a hydrogen atom in the cyclic aliphatic hydrocarbon group. Examples of substituents include an alkyl group, an alkoxy group, a halogen atom, a halogenated alkyl group, a hydroxyl group and an oxo group (═O).

The alkyl group as the substituent is preferably an alkyl group of 1 to 5 carbon atoms, and a methyl group, an ethyl group, a propyl group, an n-butyl group or a tert-butyl group is most desirable.

The alkoxy group as the substituent is preferably an alkoxy group having 1 to 5 carbon atoms, more preferably a methoxy group, an ethoxy group, an n-propoxy group, an iso-propoxy group, an n-butoxy group or a tert-butoxy group, and most preferably a methoxy group or an ethoxy group.

Examples of the halogen atom for the substituent include a fluorine atom, a chlorine atom, a bromine atom and an iodine atom, and a fluorine atom is preferable.

Examples of the halogenated alkyl group for the substituent include groups in which part or all of the hydrogen atoms within the aforementioned alkyl groups has been substituted with the aforementioned halogen atoms.

Further, part of the carbon atoms constituting the cyclic structure of the cyclic aliphatic hydrocarbon group may be substituted with a hetero atom-containing substituent group. The hetero atom-containing substituent group is preferably —O—, —C(═O)—O—, —S—, —S(═O)$_2$— or —S(═O)$_2$—O—.

The aromatic hydrocarbon group as a divalent hydrocarbon group is a divalent hydrocarbon group having at least one aromatic ring, and may have a substituent. The aromatic ring is not particularly limited as long as it is a cyclic conjugation ring having 4n+2 of π electrons, and may be a monocyclic or a polycyclic. The aromatic ring preferably has 5 to 30 carbon atoms, more preferably 5 to 20, still more preferably 6 to 15, and particularly preferably 6 to 12. Here, the number of carbon atoms within a substituent(s) is not included in the number of carbon atoms of the aromatic hydrocarbon group.

Examples of the aromatic ring include aromatic hydrocarbon rings such as benzene, biphenyl, fluorene, naphthalene, anthracene and phenanthrene and aromatic heterocycles in which part of the carbon atoms of the aromatic hydrocarbon ring have been substituted with a hetero atom. Examples of hetero atoms within the aromatic heterocycle include an oxygen atom, a nitrogen atom, and a sulfur atom. Specific examples of aromatic heterocycles include a pyridine ring and a thiophene ring.

Specific examples of the aromatic hydrocarbon group include a group in which two hydrogen atoms have been removed from the aromatic hydrocarbon ring or aromatic heterocycle (arylene group or heteroarylene group); a group in which two hydrogen atoms have been removed from an aromatic compound having two or more aromatic rings (for example, biphenyl or fluorene); a group in which one hydrogen atom has been removed from the aromatic hydrocarbon group or aromatic heterocycle (aryl group or heteroaryl group) and another one hydrogen atom has been substituted with an alkylene group (for example, a group in which one hydrogen atom has been removed from an aryl group of an arylalkyl group such as a benzyl group, a phenethyl group, a 1-naphthylmethyl group, a 2-naphthylmethyl group, a 1-naphthylethyl group, or a 2-naphthylethyl group).

The alkylene group bonded to the aryl group or heteroaryl group preferably has 1 to 4 carbon atom, more preferably 1 or 2, and most preferably 1.

For example, one or more of the hydrogen atoms in the aromatic hydrocarbon group may be substituted with a substituent. For example, the hydrogen atom bonded to the aromatic ring in the aromatic hydrocarbon group may be substituted with a substituent. Examples of substituents include an alkyl group, an alkoxy group, a halogen atom, a halogenated alkyl group, a hydroxyl group and an oxo group (=O).

The alkyl group as the substituent is preferably an alkyl group of 1 to 5 carbon atoms, and a methyl group, an ethyl group, a propyl group, an n-butyl group or a tert-butyl group is most desirable.

The alkoxy group as the substituent is preferably an alkoxy group having 1 to 5 carbon atoms, more preferably a methoxy group, an ethoxy group, an n-propoxy group, an iso-propoxy group, an n-butoxy group or a tert-butoxy group, and most preferably a methoxy group or an ethoxy group.

Examples of the halogen atom for the substituent include a fluorine atom, a chlorine atom, a bromine atom and an iodine atom, and a fluorine atom is preferable.

Examples of the halogenated alkyl group for the substituent include groups in which part or all of the hydrogen atoms within the aforementioned alkyl groups has been substituted with the aforementioned halogen atoms.

(Divalent Linking Group Containing a Hetero Atom)

With respect to a divalent linking group containing a hetero atom, a hetero atom is an atom other than carbon and hydrogen, and examples thereof include an oxygen atom, a nitrogen atom, a sulfur atom and a halogen atom.

Specific examples of the divalent linking group containing a hetero atom include non-hydrocarbon linking groups such as —O—, —C(=O)—, —C(=O)—O—, —O—C(=O)—O—, —S—, —S(=O)$_2$—, —S(=O)$_2$—O—, —NH—, —NH—C(=O)—, —NH—C(=NH)— and =N—; and a combination of any one of these non-hydrocarbon linking groups with a divalent hydrocarbon group. As examples of the divalent hydrocarbon group, the same groups as those described above for the divalent hydrocarbon group which may have a substituent can be given, and a linear or branched aliphatic hydrocarbon group is preferable.

The hydrogen atom included in —NH— within —C(=O)—NH—, —NH— or —NH— within —NH—C(=NH)— may be substituted with a substituent such as an alkyl group or an acyl group. The substituent preferably has 1 to 10 carbon atoms, more preferably 1 to 8 carbon atoms, and most preferably 1 to 5 carbon atoms.

As $Y^2$, a linear or branched alkylene group, a cyclic aliphatic hydrocarbon group or a divalent linking group containing a hetero atom is particularly preferable.

When $Y^2$ represents a linear or branched alkylene group, it preferably has 1 to 10 carbon atoms, more preferably 1 to 6, still more preferably 1 to 4, and most preferably 1 to 3. Specific examples include the same linear alkylene groups and branched alkylene groups as those described above for the linear or branched aliphatic hydrocarbon group in the explanation of the "divalent hydrocarbon group which may have a substituent" as a divalent linking group.

When $Y^2$ represents a cyclic aliphatic hydrocarbon group, as the cyclic aliphatic hydrocarbon group, the same cyclic aliphatic hydrocarbon group as those described above for the "aliphatic hydrocarbon group containing a ring in the structure thereof" explained above in relation to the divalent linking group which may have a substituent.

As the cyclic aliphatic hydrocarbon group, a group in which two or more hydrogen atoms have been removed from cyclopentane, cyclohexane, norbornane, isobornane, adamantane, tricyclodecane or tetracyclododecane is particularly desirable.

When $Y^2$ is a divalent linking group containing a hetero atom, preferable examples of the linking group include —O—, —C(=O)—O—, —C(=O)—, —O—C(=O)—O—, —C(=O)—NH— and —NH— (H may be replaced with a substituent such as an alkyl group, an acyl group or the like), —S—, —S(=O)$_2$—, —S(=O)$_2$—O— and groups represented by general formulas —$Y^{21}$—O—$Y^{22}$—, —[$Y^{21}$—C(=O)—O]$_{m'}$—$Y^{22}$— and —$Y^{21}$—O—C(=O)—$Y^{22}$— and [wherein each of $Y^{21}$ and $Y^{22}$ independently represents a divalent linking group, O represents an oxygen atom; and m' represents an integer of 0 to 3].

When $Y^2$ represents —NH—, H in —NH— may be substituted with a substituent such as an alkyl group, an acyl group or the like. The substituent (an alkyl group, an acyl group or the like) preferably has 1 to 10 carbon atoms, more preferably 1 to 8, and most preferably 1 to 5.

In the formulas, —$Y^{21}$—O—$Y^{22}$—, —[$Y^{21}$—C(=O)—O]$_{m'}$—$Y^{22}$— and —$Y^{21}$—O—C(=O)—$Y^{22}$—, each of $Y^{21}$ and $Y^{22}$ independently represents a divalent hydrocarbon group which may have a substituent. Examples of the divalent hydrocarbon group include the same divalent hydrocarbon group which may have a substituent as described above in the explanation of the divalent linking group.

As $Y^{21}$, a linear aliphatic hydrocarbon group is preferable, more preferably a linear alkylene group, still more preferably a linear alkylene group of 1 to 5 carbon atoms, and a methylene group or an ethylene group is particularly desirable.

As $Y^{22}$, a linear or branched aliphatic hydrocarbon group is preferable, and a methylene group, an ethylene group or an alkylmethylene group is more preferable. The alkyl group within the alkylmethylene group is preferably a linear alkyl group of 1 to 5 carbon atoms, more preferably a linear alkyl group of 1 to 3 carbon atoms, and most preferably a methyl group.

In the group represented by the formula —[$Y^{21}$—C(=O)—O]$_{m'}$—$Y^{22}$—, m' represents an integer of 0 to 3, preferably an integer of 0 to 2, more preferably 0 or 1, and most preferably 1. Namely, it is particularly desirable that the group represented by the formula —[$Y^{21}$—C(=O)—O]$_{m'}$—

$Y^{22}$— is a group represented by the formula —$Y^{21}$—C(=O)—O—$Y^{22}$—. Among these, a group represented by the formula —$(CH_2)_{a'}$—C(=O)—O—$(CH_2)_{b'}$— is preferable. In the formula, a' is an integer of 1 to 10, preferably an integer of 1 to 8, more preferably an integer of 1 to 5, still more preferably 1 or 2, and most preferably 1. b' is an integer of 1 to 10, preferably an integer of 1 to 8, more preferably an integer of 1 to 5, still more preferably 1 or 2, and most preferably 1.

As the divalent linking group containing a hetero atom for $Y^2$, an organic group which is constituted of a combination of at least one of non-hydrocarbon groups and a divalent hydrocarbon group can be mentioned. In particular, as the divalent linking group containing a hetero atom, a linear group containing an oxygen atom as the hetero atom e.g., a group containing an ether bond or an ester bond is preferable, and a group represented by the aforementioned formula —$Y^{21}$—O—$Y^{22}$—, —$[Y^{21}$—C(=O)—O$]_{m'}$—$Y^{22}$— or $Y^{21}$—O—C(=O)—$Y^{22}$— is more preferable, and —$[Y^{21}$—C(=O)—O$]_{m'}$—$Y^{22}$— or —$Y^{21}$—O—C(=O)—$Y^{22}$— is still more preferable.

Among these, as for $Y^2$, a linear or branched alkylene group or a divalent linking group containing a hetero atom is preferable, and a linear or branched alkylene group, a group represented by the formula —$Y^{21}$—O—$Y^{22}$—, a group represented by the formula —$[Y^{21}$—C(=O)—O$]_{m'}$—$Y^{22}$—, or a group represented by the formula —$Y^{21}$—O—C(=O)—$Y^{22}$— is more preferable.

Specific examples of the structural unit (a11) include structural units represented by general formulas (a1-1) to (a1-4) shown below.

[Chemical Formula 9]

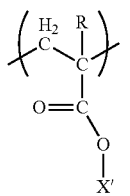

(a1-1)

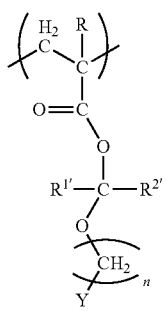

(a1-2)

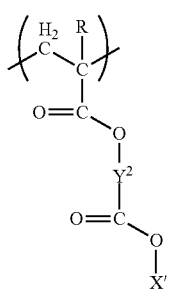

(a1-3)

-continued

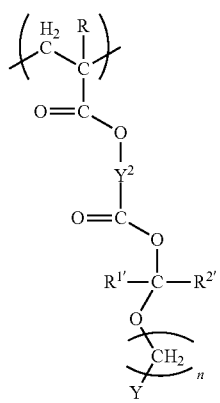

(a1-4)

In the formulas, R, $R^{1'}$, $R^{2'}$, n, Y and $Y^2$ are the same as defined above; and X' represents a tertiary alkyl ester-type acid dissociable group.

In the formulas, R is the same as defined above for R in the formula (a1-0-1).

The tertiary alkyl ester-type acid dissociable group for X' include the same tertiary alkyl ester-type acid dissociable groups as those described above.

As $R^{1'}$, $R^{2'}$, n and Y are respectively the same as defined for $R^{1'}$, $R^{2'}$, n and Y in the general formula (p1) described above in connection with the "acetal-type acid dissociable group".

$Y^2$ is the same as defined for $Y^2$ in general formula (a1-0-2).

Specific examples of structural units represented by general formulas (a1-1) to (a1-4) are shown below.

In the formulas shown below, $R^\alpha$ represents a hydrogen atom, a methyl group or a trifluoromethyl group.

[Chemical Formula 10]

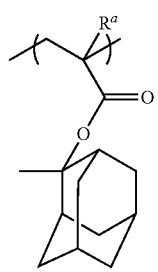

(a1-1-1)

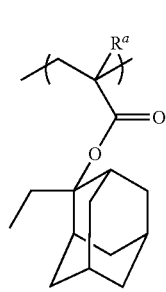

(a1-1-2)

-continued
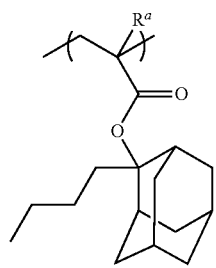 (a1-1-3)
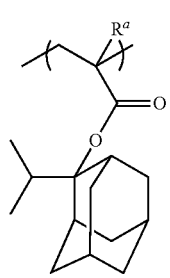 (a1-1-4)
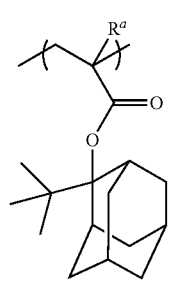 (a1-1-5)
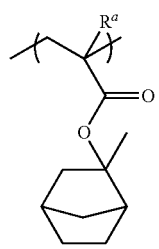 (a1-1-6)
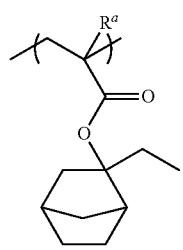 (a11-1-7)
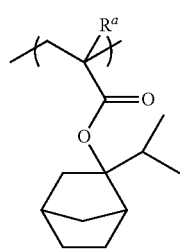 (a1-1-8)
-continued
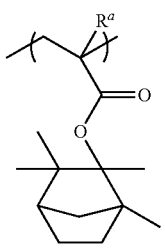 (a1-1-9)
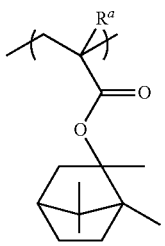 (a1-1-10)
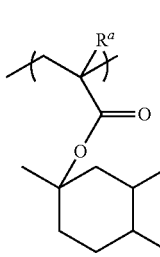 (a1-1-11)
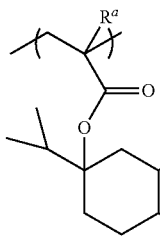 (a1-1-12)
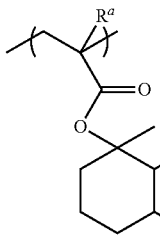 (a1-1-13)
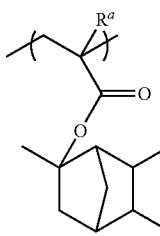 (a1-1-14)

-continued
(a1-1-15) 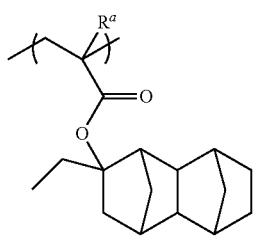
(a1-1-16) 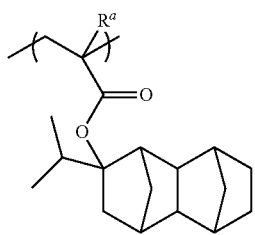
(a1-1-17) 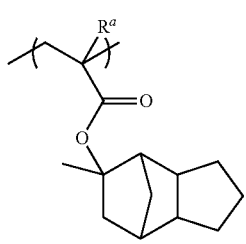
[Chemical Formula 11]
(a1-1-18) 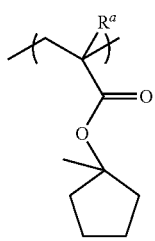
(a1-1-19) 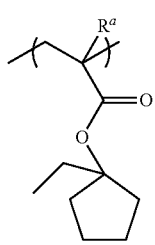
(a1-1-20) 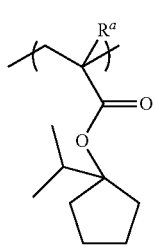
-continued
(a1-1-21) 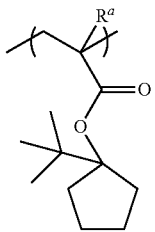
(a1-1-22) 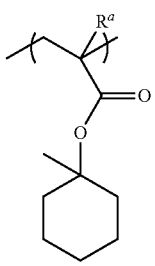
(a1-1-23) 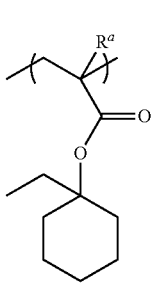
(a1-1-24) 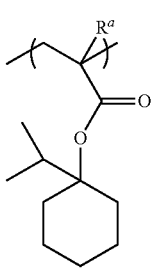
(a1-1-25) 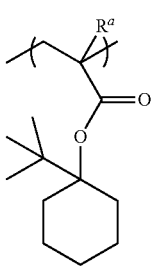
(a1-1-26) 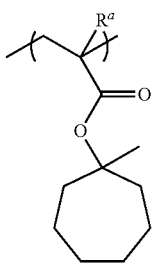

-continued
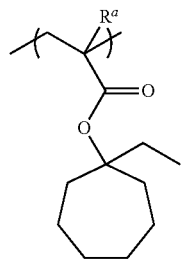 (a1-1-27)
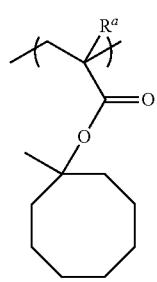 (a1-1-28)
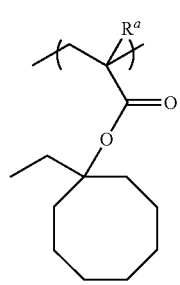 (a1-1-29)
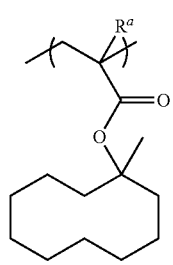 (a1-1-30)
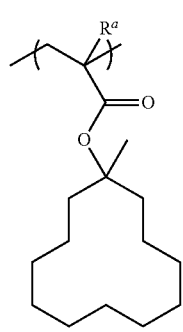 (a1-1-31)
-continued
[Chemical Formula 12]
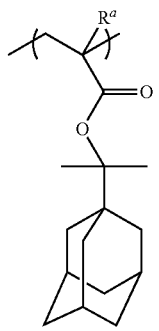 (a1-1-32)
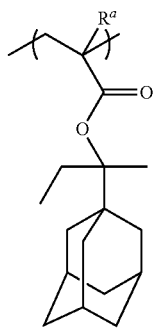 (a1-1-33)
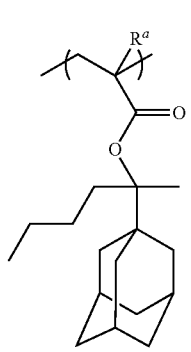 (a1-1-34)
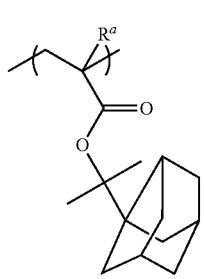 (a1-1-35)
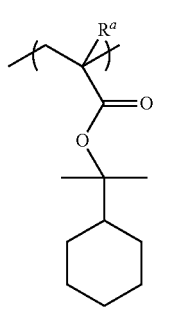 (a1-1-36)

(a1-1-37)
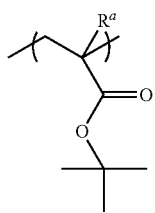
(a1-1-38)
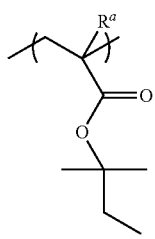
[Chemical Formula 13]
(a1-2-1)
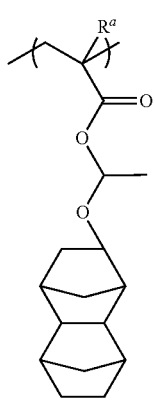
(a1-2-2)
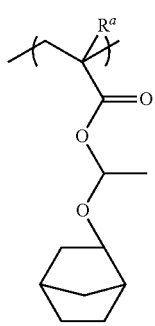
(a1-2-3)
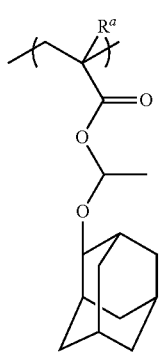
(a1-2-4)
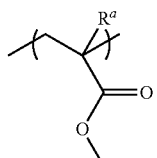
(a1-2-5)
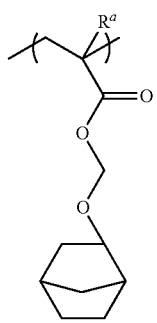
(a1-2-6)
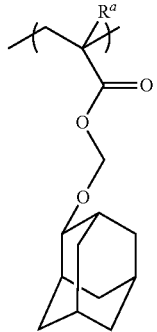
(a1-2-7)
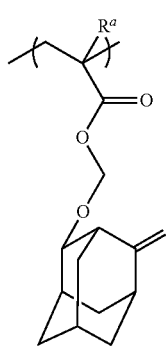

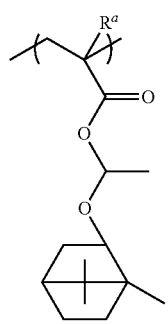 (a1-2-8)
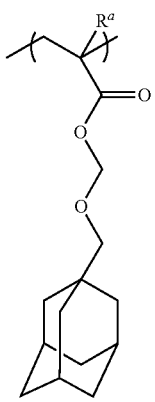 (a1-2-12)
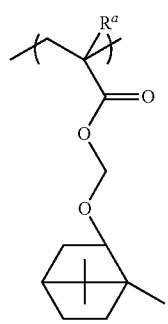 (a1-2-9)
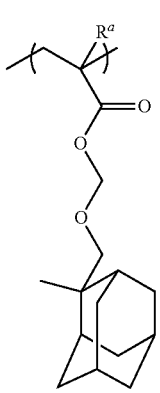 (a1-2-13)
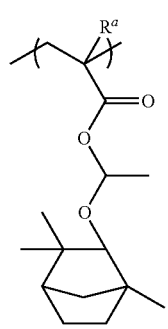 (a1-2-10)
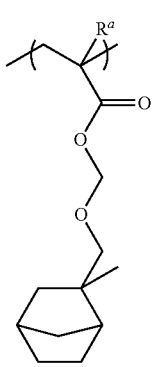 (a1-2-14)
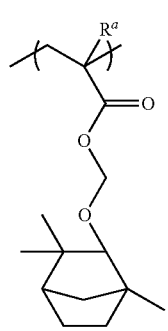 (a1-2-11)
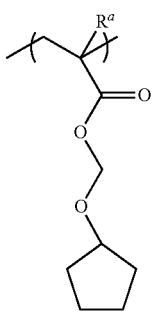 (a1-2-15)

-continued
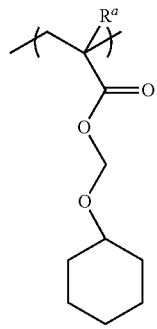
(a1-2-16)
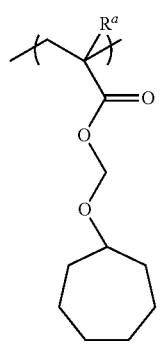
(a1-2-17)
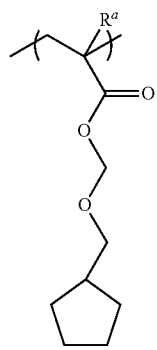
(a1-2-18)
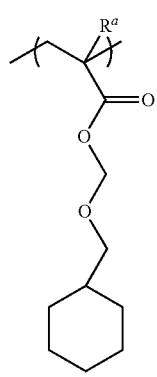
(a1-2-19)
-continued
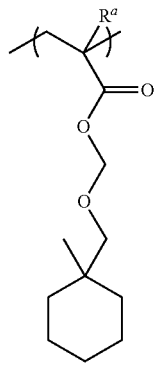
(a1-2-20)
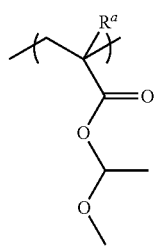
(a1-2-21)
(a1-2-22)
(a1-2-23)
(a1-2-24)
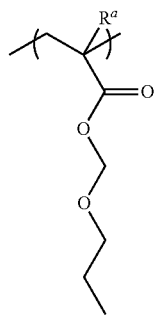

-continued
[Chemical Formula 14]
(a1-3-1) 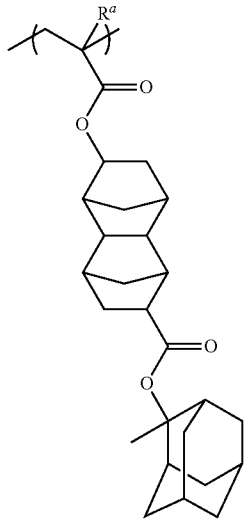
(a1-3-2) 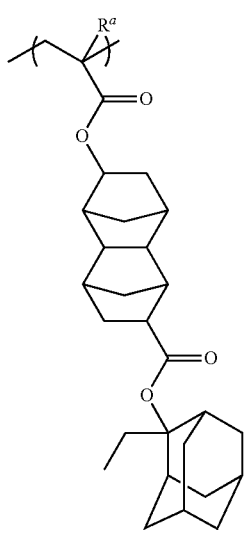
(a1-3-3) 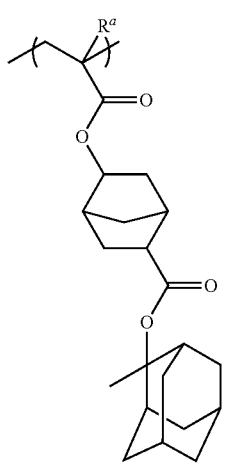
(a1-3-4) 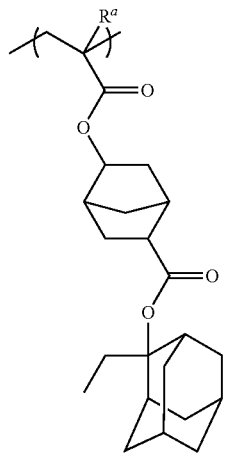
(a1-3-5) 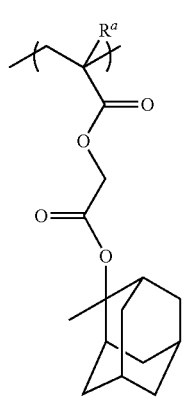
(a1-3-6) 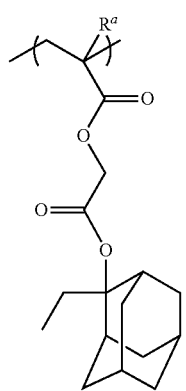
(a1-3-7) 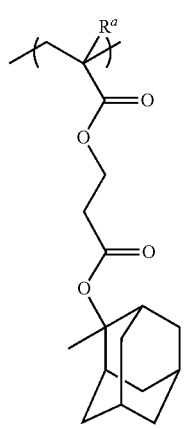

(a1-3-8)
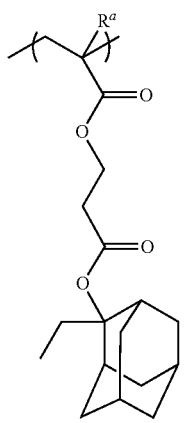
(a1-3-9)
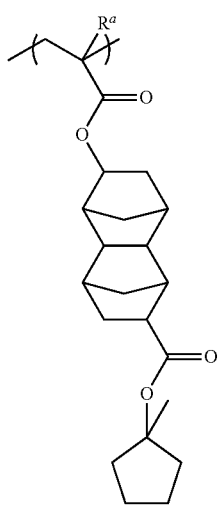
(a1-3-10)
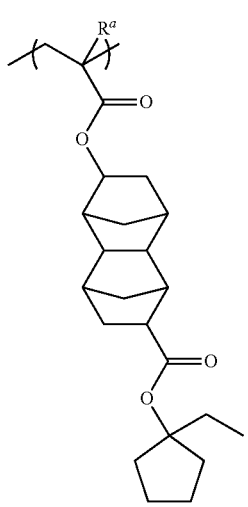
(a1-3-11)
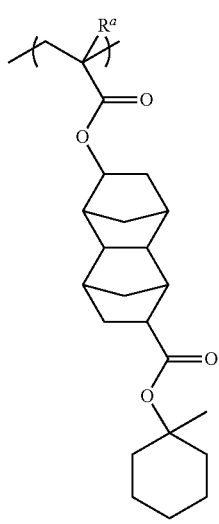
(a1-3-12)
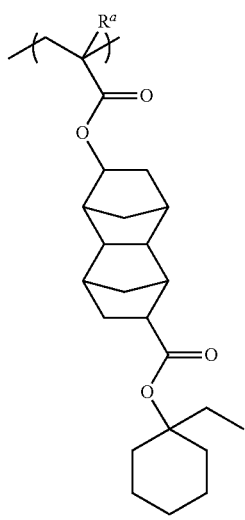
(a1-3-13)
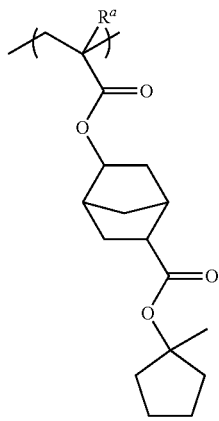

(a1-3-14)
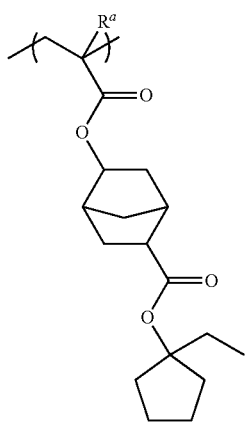
(a1-3-15)
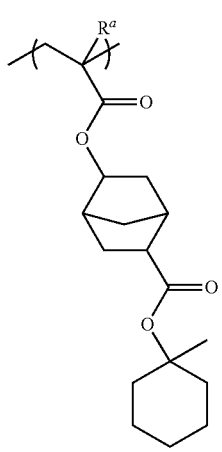
(a1-3-16)
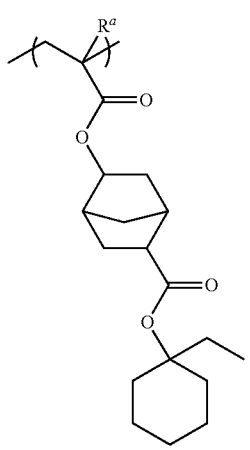
(a1-3-17)
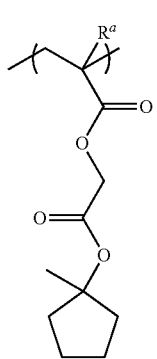
(a1-3-18)
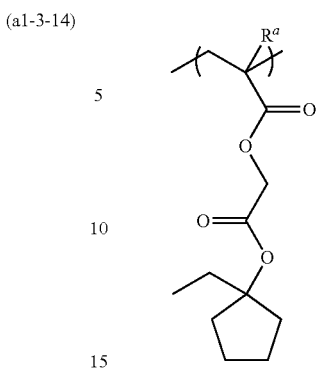
(a1-3-19)
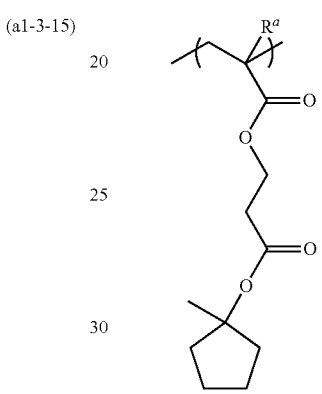
(a1-3-20)
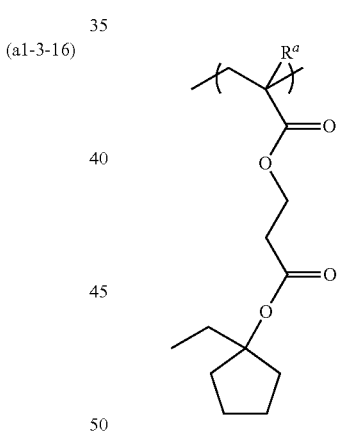
(a1-3-21)
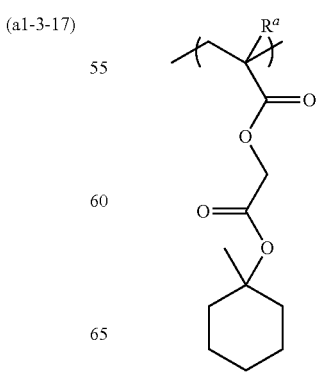

(a1-3-22)
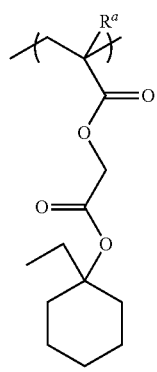
(a1-3-23)
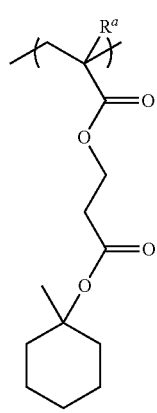
(a1-3-24)
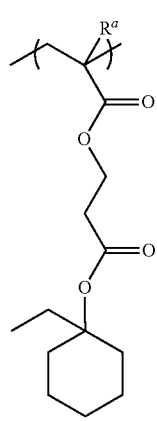
[Chemical Formula 15]
(a1-3-25)
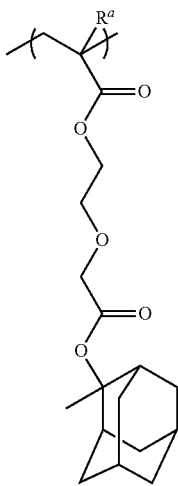
(a1-3-26)
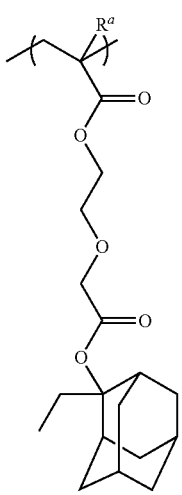
(a1-3-27)
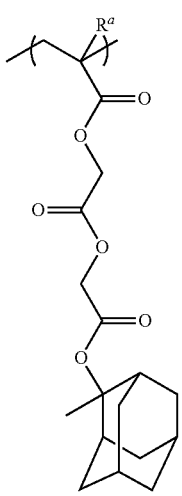

(a1-3-28) 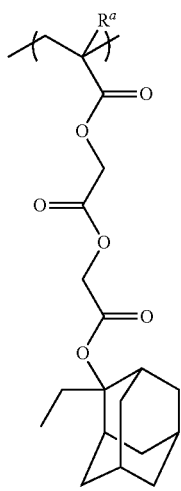
(a1-3-29) 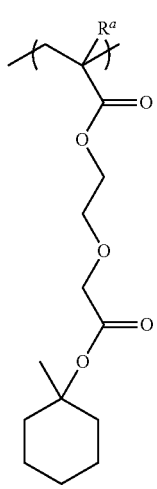
(a1-3-30) 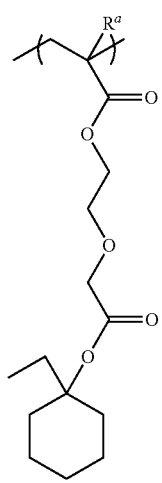
(a1-3-31) 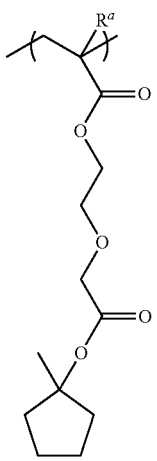
(a1-3-32) 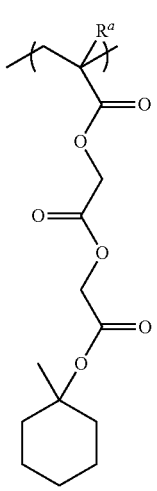
(a1-3-33) 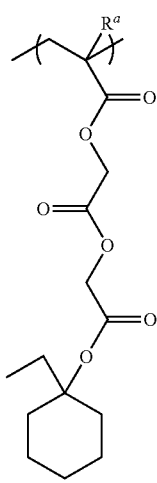

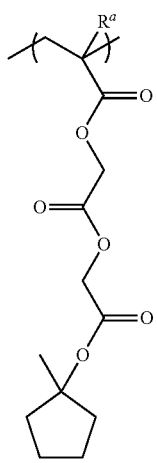
(a1-3-34)
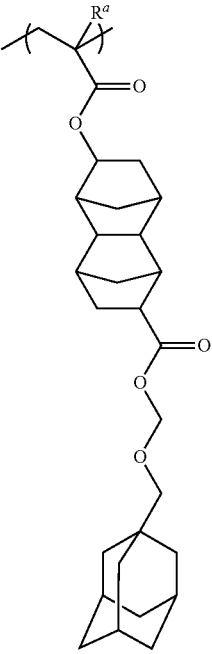
(a1-4-2)
[Chemical Formula 16]
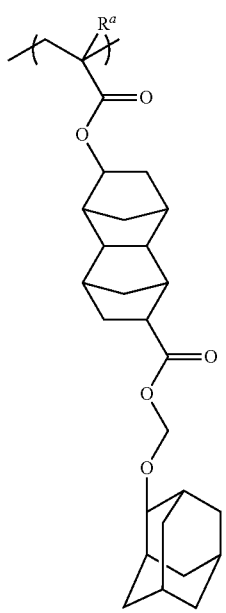
(a1-4-1)
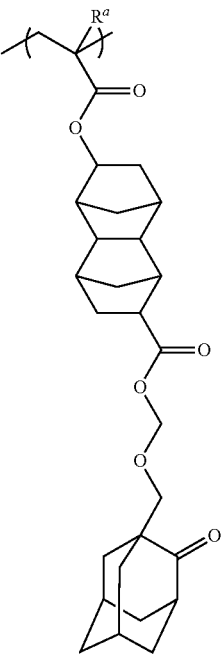
(a1-4-3)

-continued
(a1-4-4)
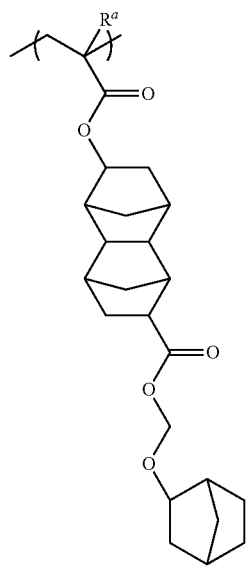
(a1-4-5)
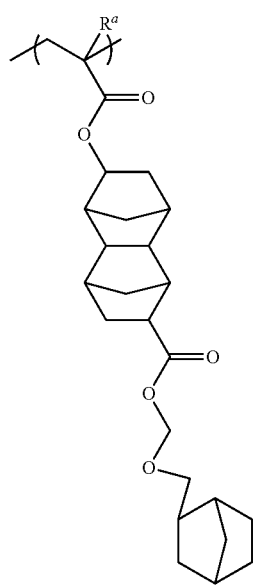
(a1-4-6)
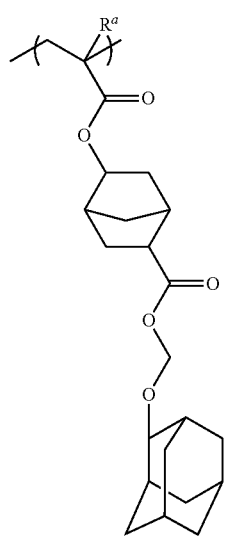
-continued
(a1-4-7)
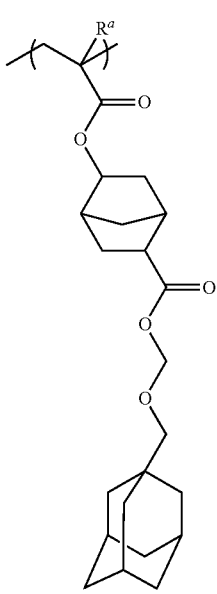
(a1-4-8)
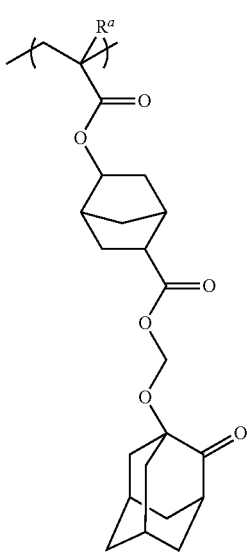
(a1-4-9)
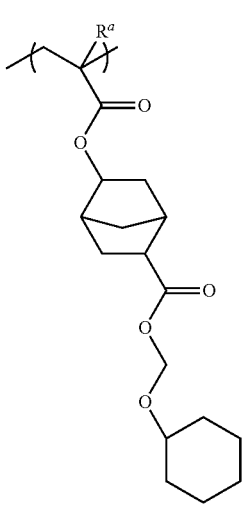

(a1-4-10)
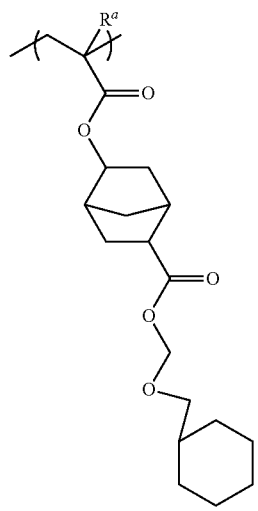
(a1-4-13)
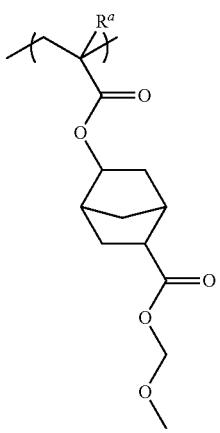
(a1-4-11)
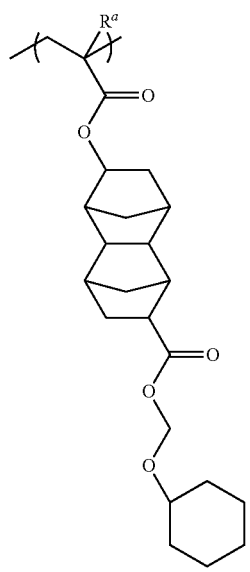
(a1-4-14)
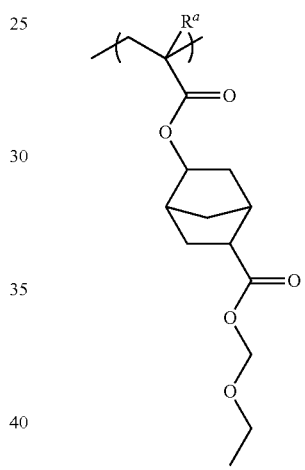
(a1-4-12)
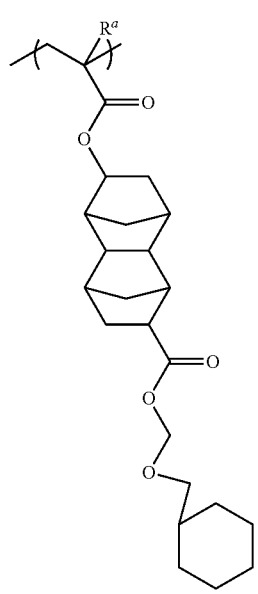
(a1-4-15)
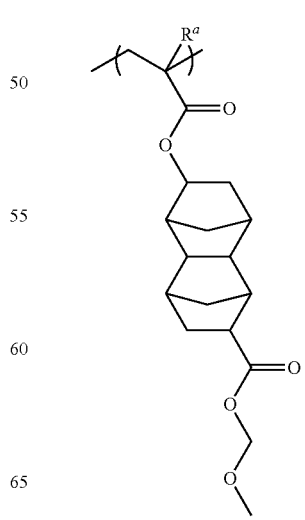

-continued (a1-4-16)

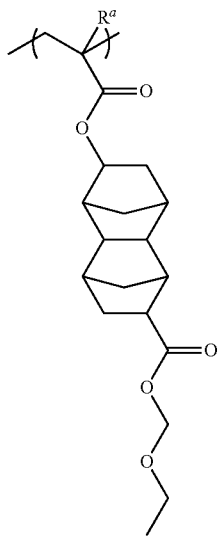

As the structural unit (a11), at least one structural unit selected from the group consisting of a structural unit represented by general formula (a1-0-11) shown below, a structural unit represented by general formula (a1-0-12) shown below, a structural unit represented by general formula (a1-0-13) shown below, a structural unit represented by general formula (a1-0-14) shown below, a structural unit represented by general formula (a1-0-15) shown below and a structural unit represented by general formula (a1-0-2) shown below.

[Chemical Formula 17]

(a1-0-11)

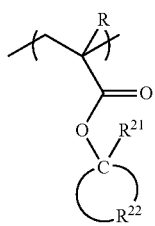

(a1-0-12)

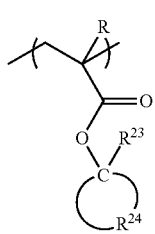

(a1-0-13)

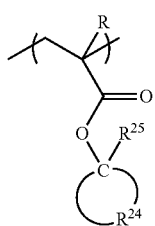

(a1-0-14)

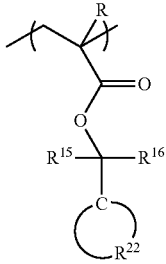

(a1-0-15)

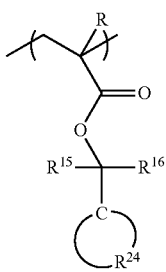

(a1-0-2)

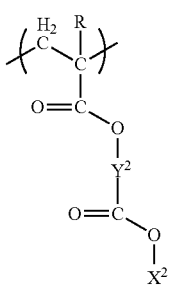

In the formulas, R represents a hydrogen atom, an alkyl group of 1 to 5 carbon atoms or a halogenated alkyl group of 1 to 5 carbon atoms; $R^{21}$ represents an alkyl group; $R^{22}$ represents a group which forms an aliphatic monocyclic group with the carbon atom having $R^{22}$ bonded thereto; $R^{23}$ represents a branched alkyl group; $R^{24}$ represents a group which forms an aliphatic polycyclic group with the carbon atom having $R^{24}$ bonded thereto; $R^{25}$ represents a linear alkyl group of 1 to 5 carbon atoms; each of $R^{15}$ and $R^{16}$ independently represents an alkyl group; $Y^2$ represents a divalent linking group; and $X^2$ represents an acid dissociable group.

In the formulas, R, $Y^2$ and $X^2$ are the same as defined above.

In general formula (a1-0-11), as the alkyl group for $R^{21}$, the same alkyl groups as those described above for $R^{14}$ in the formulas (1-1) to (1-9) can be used, and a methyl group, an ethyl group or an isopropyl group can be preferably used.

As the aliphatic monocyclic group formed by $R^{22}$ and the carbon atoms having $R^{22}$ bonded thereto, the same aliphatic cyclic groups as those described above in relation to the aforementioned tertiary alkyl ester-type acid dissociable group and which are monocyclic can be used. Specific examples include groups in which one or more hydrogen atoms have been removed from a monocycloalkane. The monocycloalkane is preferably a 3- to 11-membered ring, more preferably a 3- to 8-membered ring, still more preferably a 4- to 6-membered ring, and particularly preferably a 5- or 6-membered ring.

The monocycloalkane may or may not have part of the carbon atoms constituting the ring replaced with an ether bond (—O—).

As an examples of $R^{22}$ constituting such an aliphatic monocyclic group, a linear alkylene group which may have an ether bond (—O—) interposed between the carbon atoms can be given.

Further, the aliphatic monocyclic group may have a substituent such as an alkyl group of 1 to 5 carbon atoms, a fluorine atom or a fluorinated alkyl group of 1 to 5 carbon atoms.

Specific examples of structural units represented by general formula (a1-0-11) include structural units represented by the aforementioned formulas (a1-0-18) to (a1-1-31). Among these, a structural unit represented by general formula (a1-0-02) shown below which includes the structural units represented by the aforementioned formulas (a1-1-18) to (a1-1-29) is preferable. Further, a structural unit represented by general formula (a1-1-02') shown below is also preferable.

In the formulas, h represents an integer of 1 to 4, and is preferably 1 or 2.

[Chemical Formula 18]

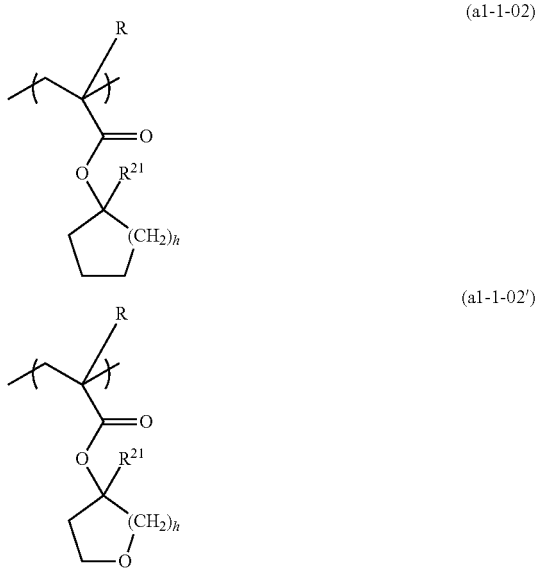

In the formulas, R and $R^{21}$ are the same as defined above; and h represents an integer of 1 to 4.

In general formula (a1-0-12), as the branched alkyl group for $R^{23}$, the same alkyl groups as those described above for $R^{14}$ which are branched in the formulas (1-1) to (1-9) can be used, and an isopropyl group is particularly desirable.

As the aliphatic polycyclic group formed by $R^{24}$ and the carbon atoms having $R^{24}$ bonded thereto, the same aliphatic cyclic groups as those described above in relation to the aforementioned tertiary alkyl ester-type acid dissociable group and which are polycyclic can be used.

Specific examples of structural units represented by general formula (a1-0-12) include structural units represented by the aforementioned formulas (a1-1-4), (a1-1-5), (a1-1-8), (a1-1-12) and (a1-1-16) which were described above as specific examples of the structural unit represented by the general formula (a1-1).

As the structural unit (a1-0-12), a structural unit in which the aliphatic polycyclic group formed by $R^{24}$ and the carbon atom having $R^{24}$ bonded thereto is a 2-adamantyl group is preferable, and a structural unit represented by the aforementioned formula (a1-1-4) is particularly desirable.

In general formula (a1-0-13), $R^{24}$ is the same as defined above.

As the linear alkyl group for $R^{25}$, the same linear alkyl groups as those described above for $R^{14}$ in the aforementioned formulas (1-1) to (1-9) can be mentioned, and a methyl group or an ethyl group is particularly desirable.

Specific examples of structural units represented by general formula (a1-0-13) include structural units represented by the aforementioned formulas (a1-1-1) to (a1-1-3), (a1-1-6), (a1-1-7), (a1-1-9) to (a1-1-11), (a1-1-13) to (a1-1-15) and (a-1-1-17) which were described above as specific examples of the structural unit represented by the general formula (a1-1).

As the structural unit (a1-0-13), a structural unit in which the aliphatic polycyclic group formed by $R^{24}$ and the carbon atom having $R^{24}$ bonded thereto is a 2-adamantyl group is preferable, and a structural unit represented by the aforementioned formula (a1-1-1) or (a1-1-2) is particularly desirable.

In general formula (a1-0-14), $R^{22}$ is the same as defined above.

$R^{15}$ and $R^{16}$ are the same as defined for $R^{15}$ and $R^{16}$ in the general formulas (2-1) to (2-6).

Specific examples of structural units represented by general formula (a1-0-14) include a structural unit represented by the aforementioned formula (a1-1-36) exemplified as specific examples of the structural unit represented by the general formula (a1-1).

In general formula (a1-0-15), $R^{24}$ is the same as defined above.

$R^{15}$ and $R^{16}$ are the same as defined for $R^{15}$ and $R^{16}$ in the general formulas (2-1) to (2-6).

Specific examples of structural units represented by general formula (a1-0-15) include structural units represented by the aforementioned formulas (a1-1-32) to (a1-1-36) exemplified as specific examples of the structural unit represented by the general formula (a1-1).

Examples of structural units represented by general formula (a1-0-2) include structural units represented by the aforementioned formulas (a1-3) and (a1-4), and the structural unit represented by the formula (a1-3) is particularly preferable.

As the structural unit represented by general formula (a1-0-2), a structural unit in which $Y^2$ is a group represented by the aforementioned formula —$Y^{21}$—O—$Y^{22}$— or —$Y^{21}$—O—C(=O)—$Y^{22}$— is particularly desirable.

Preferable examples of such structural units include a structural unit represented by general formula (a1-3-01) shown below, a structural unit represented by general formula (a1-3-02) shown below, and a structural unit represented by general formula (a1-3-03) shown below.

[Chemical Formula 19]

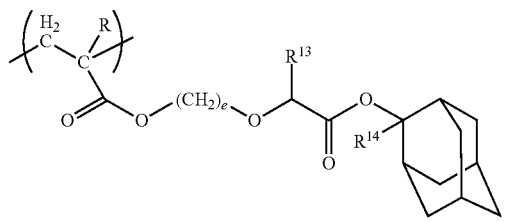

(a1-3-02)

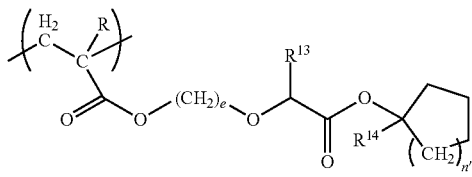

In the formulas, R is the same as defined above; $R^{13}$ represents a hydrogen atom or a methyl group; $R^{14}$ represents an alkyl group; e represents an integer of 1 to 10; and n' represents an integer of 0 to 4.

[Chemical Formula 20]

(a1-3-03)

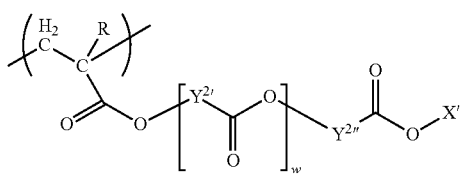

In the formula, R is as defined above; each of $Y^{2\prime}$ and $Y^{2\prime\prime}$ independently represents a divalent linking group; X' represents an acid dissociable group; and w represents an integer of 0 to 3.

In general formulas (a1-3-01) and (a1-3-02), $R^{13}$ is preferably a hydrogen atom.

$R^{14}$ is the same as defined for $R^{14}$ in the aforementioned formulas (1-1) to (1-9).

e is preferably an integer of 1 to 8, more preferably 1 to 5, and most preferably 1 or 2.

n' is preferably 1 or 2, and most preferably 2.

Specific examples of structural units represented by general formula (a1-3-01) include structural units represented by the aforementioned formulas (a1-3-25) and (a1-3-26).

Specific examples of structural units represented by general formula (a1-3-02) include structural units represented by the aforementioned formulas (a1-3-29) to (a1-3-31).

In general formula (a1-3-03), as the divalent linking group for $Y^{2\prime}$ and $Y^{2\prime\prime}$, the same groups as those described above for $Y^2$ in the general formula (a1-3) can be used.

As $Y^{2\prime}$, a divalent hydrocarbon group which may have a substituent is preferable, a linear aliphatic hydrocarbon group is more preferable, and a linear alkylene group is still more preferable. Among linear alkylene groups, a linear alkylene group of 1 to 5 carbon atoms is preferable, and a methylene group or an ethylene group is particularly desirable.

As $Y^{2\prime\prime}$, a divalent hydrocarbon group which may have a substituent is preferable, a linear aliphatic hydrocarbon group is more preferable, and a linear alkylene group is still more preferable. Among linear alkylene groups, a linear alkylene group of 1 to 5 carbon atoms is preferable, and a methylene group or an ethylene group is particularly desirable.

As the acid dissociable group for X', the same groups as those described above can be used. X' is preferably a tertiary alkyl ester-type acid dissociable group, more preferably the aforementioned group (i) in which a substituent is bonded to the carbon atom to which an atom adjacent to the acid dissociable group is bonded, on the ring skeleton to form a tertiary carbon atom. Among these, a group represented by the aforementioned general formula (1-1) is particularly desirable.

w represents an integer of 0 to 3, preferably an integer of 0 to 2, more preferably 0 or 1, and most preferably 1.

As the structural unit represented by general formula (a1-3-03), a structural unit represented by general formula (a1-3-03-1) or (a1-3-03-2) shown below is preferable, and a structural unit represented by general formula (a1-3-03-1) is particularly desirable.

[Chemical Formula 21]

(a1-3-03-1)

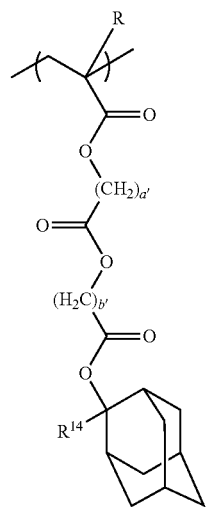

(a1-3-03-2)

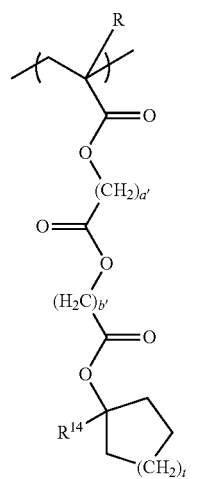

In the formulas, R and $R^{14}$ are the same as defined above; a' represents an integer of 1 to 10; b' represents an integer of 1 to 10; and t represents an integer of 0 to 4.

In the formulas (a1-3-03-1) and (a1-3-03-2), each of a' and b' represents the same groups as those described above for a' and b' in the group represented by the general formula —$(CH_2)a'$—C(=O)—O—$(CH_2)b'$— exemplified as a preferable example of the group represented by the formula —[$Y^{21}$—C(=O)—O]m'-$Y^{22}$ in relation to the divalent linking group for $Y^2$.

a' is preferably an integer of 1 to 8, more preferably 1 to 5, and still more preferably 1 or 2.

b' is preferably an integer of 1 to 8, more preferably 1 to 5, and still more preferably 1 or 2.

t is preferably an integer of 1 to 4, and particularly preferably 1 or 2.

Specific examples of structural units represented by general formula (a1-3-03-1) or (a1-3-03-2) include structural units represented by the aforementioned formulas (a1-3-27), (a1-3-28) and (a1-3-32) to (a1-3-34).

[Structural Unit (a12)]

The structural unit (a12) is a structural unit derived from a hydroxystyrene which may have the hydrogen atom bonded to the carbon atom on the α-position substituted with a substituent and may have the hydrogen atom bonded to the benzene ring substituted with a substituent other than a hydroxy group, and which has the hydrogen atom of the hydroxy group substituted with an acid dissociable group or a substituent containing an acid dissociable group.

As the acid dissociable group for substituting the hydrogen atom of the hydroxy group, the aforementioned tertiary alkyl ester-type acid dissociable groups and acetal-type acid dissociable groups are preferable, and acetal-type acid dissociable groups are more preferable.

As the substituent containing an acid dissociable group, a group constituted of an acid dissociable group and a divalent linking group. As the divalent linking group, the same divalent linking group as those described for $Y^2$ in the formula (a1-3), and a group having a carbonyloxy group at the terminal of an acid dissociable group is particularly preferable. In this case, it is preferable that the acid dissociable group be bonded to the oxygen atom (—O—) in the carbonyloxy group.

As the substituent containing an acid dissociable group, a group represented by formula $R^{11'}$—O—C(=O)— and a group represented by formula $R^{11'}$—O—C(=O)—$R^{12'}$—. In the formula, $R^{11}$ represents an acid dissociable group, and $R^{12'}$ represents a linear or branched alkylene group.

As the acid dissociable group for $R^{11'}$, the aforementioned tertiary alkyl ester-type acid dissociable groups and acetal-type acid dissociable groups are preferable, and tertiary alkyl ester-type acid dissociable groups are more preferable. Examples of the tertiary alkyl ester-type acid dissociable groups, aliphatic branched, acid dissociable groups represented by formula —C($R^{71}$)($R^{72}$)($R^{73}$) and groups represented by formula (1-1) to (1-9) and groups represented by formulas (2-1) to (2-6).

Examples of the alkylene group for $R^{12'}$ include a methylene group, an ethylene group, a trimethylene group, a tetramethylene group and a 1,1-dimethylethylene group. As $R^{12'}$, a linear alkylene group is preferable.

The "substituent other than a hydroxy group" which may be bonded to the benzene ring is not particularly limited, and examples thereof include a halogen atom, an alkyl group of 1 to 5 carbon atoms, a halogenated alkyl group of 1 to 5 carbon atoms and a carboxy group. Examples of the halogen atom include a fluorine atom, a chlorine atom, a bromine atom and an iodine atom, and a fluorine atom is particularly preferred.

Among these, as the structural unit (a12), a structural unit represented by general formula (a12-1) shown below is preferable.

[Chemical Formula 22]

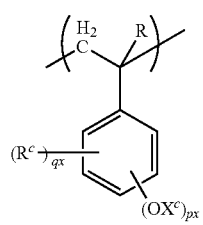

(a12-1)

In the formulas, R represents a hydrogen atom, an alkyl group of 1 to 5 carbon atoms or a halogenated alkyl group of 1 to 5 carbon atoms; px represents an integer of 1 to 3, and qx represents an integer of 0 to 4, provided that px+qx=1 to 5; $X^c$ each independently represents a hydrogen atom, an acid dissociable group or a substituent containing an acid dissociable group, and at least one of $X^c$ contains an acid dissociable group or a substituent containing an acid dissociable group; and $R^c$ each independently represents a halogen atom, an alkyl group of 1 to 5 carbon atoms or a halogenated alkyl group of 1 to 5 carbon atoms.

In genera formula (a12-1), R is the same as defined above.

As the acid dissociable group or substituent containing an acid dissociable group for $X^c$, the same groups as those described above can be given.

px represents 1 to 3, and most preferably 1.

When px is 2 or 3, the plurality of $X^c$ group may be the same or different from each other. For example, one of $X^c$ may be a group containing an acid dissociable group or a substituent containing an acid dissociable group, and the other one or two of $X^c$ may be a hydrogen atom. When qx is 2 to 4, the plurality of $R^c$ group may be the same or different from each other.

The bonding position of $OX^c$ on the benzene ring is not particularly limited. When px is 1, para (4th) position against the position to which the carbon atom on the α-position (carbon atom having R bonded thereto) is bonded is preferable. When px is an integer of 2 or more, an arbitrary combination of the bonding positions can be adopted.

Examples of the halogen atom for $R^c$ include a fluorine atom, a chlorine atom, a bromine atom and an iodine atom, and a fluorine atom is particularly preferred.

As the alkyl group and the halogenated alkyl group for $R^c$, the same alkyl groups and halogenated alkyl groups as those described above for R can be mentioned.

[Structural Unit (a13)]

The structural unit (a13) is a structural unit derived from a vinyl(hydroxynaphthalene) which may have the hydrogen atom bonded to the carbon atom on the α-position substituted with a substituent and may have the hydrogen atom bonded to the naphthalene ring substituted with a substituent other than a hydroxy group, and which has the hydrogen atom of the hydroxy group substituted with an acid dissociable group or a substituent containing an acid dissociable group.

In the structural unit (a13), examples of the an acid dissociable group or substituent containing an acid dissociable group for substituting the hydrogen atom of the hydroxy group include the same groups as those described above in relation to the structural unit (a12).

The "substituent other than a hydroxy group" with which the hydrogen atom bonded to the naphthalene ring may be substituted is not particularly limited, and examples thereof include a halogen atom, an alkyl group of 1 to 5 carbon atoms, a halogenated alkyl group of 1 to 5 carbon atoms and a carboxy group. Examples of the halogen atom include a fluorine atom, a chlorine atom, a bromine atom and an iodine atom, and a fluorine atom is particularly preferred.

Among these, as the structural unit (a13), a structural unit represented by general formula (a13-1) shown below is preferable.

[Chemical Formula 23]

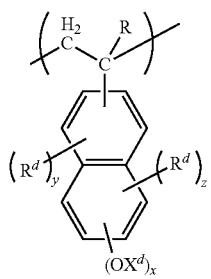

(a13-1)

In the formula, R represents a hydrogen atom, an alkyl group of 1 to 5 carbon atoms or a halogenated alkyl group of 1 to 5 carbon atoms; x represents an integer of 1 to 3; y represents an integer of 0 to 3; and z represents an integer of 0 to 3, provided that x+y+z=1 to 7; $X^d$ each independently represents a hydrogen atom, an acid dissociable group or a substituent containing an acid dissociable group, and at least one of $X^d$ contains an acid dissociable group or a substituent containing an acid dissociable group; and $R^d$ each independently represents a halogen atom, an alkyl group of 1 to 5 carbon atoms or a halogenated alkyl group of 1 to 5 carbon atoms.

In genera formula (a13-1), R is the same as defined above.

As the acid dissociable group or substituent containing an acid dissociable group for $X^d$, the same groups as those described above can be given.

x represents 1 to 3, and most preferably 1.

When x is 2 or 3, the plurality of $X^d$ group may be the same or different from each other. For example, one of $X^d$ may be an acid dissociable group or a substituent containing an acid dissociable group, and the other one or two of substituents may be a hydrogen atom. When x+y=2 to 6, the plurality of $R^d$ group may be the same or different from each other.

In the formula, the carbon atom of the α-position (i.e., the carbon atom having R bonded thereto) may be bonded 1st or 2nd position of the naphthalene ring.

The bonding position of $OX^d$ on the naphthalene ring is not particularly limited. When the carbon atom of the α-position is bonded to the 1st or 2nd position of the naphthalene ring, the carbon atom is preferably bonded to either one of the 5th to 8th position of the naphthalene ring. In particular, when the number of $OX^d$ group is 1, $OX^d$ is preferably bonded to either one of the 5th to 7th position of the naphthalene ring, and more preferably the 5th or 6th position. When the number of the $OX^d$ groups is an integer of 2 or more, an arbitrary combination of the bonding positions can be adopted.

As the halogen atom, alkyl group and halogenated alkyl group for $R^c$, the same halogen atoms, alkyl groups and halogenated alkyl groups as those described above for $R^c$ can be mentioned.

As the structural unit (a1) contained in the component (A1), 1 type of structural unit may be used, or 2 or more types may be used.

Among these, as the structural unit (a1), a structural unit (a11) is preferred.

In the component (A1), the amount of the structural unit (a1) based on the combined total of all structural units constituting the component (A1) is preferably 15 to 70 mol %, more preferably 15 to 60 mol %, and still more preferably 20 to 55 mol %. When the amount of the structural unit (a1) is at least as large as the lower limit of the above-mentioned range, a pattern can be easily formed using a resist composition prepared from the component (A1), and various lithography properties such as sensitivity, resolution, pattern shape and the like are improved. On the other hand, when the amount of the structural unit (a1) is no more than the upper limit of the above-mentioned range, a good balance can be achieved with the other structural units.

[Structural Unit (a2)]

It is preferable that the component (A1) include a structural unit (a2) containing a —$SO_2$-containing cyclic group or a lactone-containing cyclic group, as well as the structural unit (a1).

When the component (A1) is used for forming a resist film, the —$SO_2$-containing cyclic group or the lactone-containing cyclic group in the structural unit (a2) is effective in improving the adhesion between the resist film and the substrate. Furthermore, in the case of alkali developing process, it is effective in increasing the compatibility with the developing solution containing water such as an alkali developing solution.

In the case where the structural unit (a1) contains a —$SO_2$-containing cyclic group or a lactone-containing cyclic group in the structure thereof, the structural unit also falls under the definition of the structural unit (a2). However, the structural unit is regarded as a structural unit (a1), and is not regarded as a structural unit (a2).

Here, an "—$SO_2$— containing cyclic group" refers to a cyclic group having a ring containing —$SO_2$— within the ring skeleton thereof, i.e., a cyclic group in which the sulfur atom (S) within —$SO_2$— forms part of the ring skeleton of the cyclic group. The ring containing —$SO_2$— within the ring skeleton thereof is counted as the first ring. A cyclic group in which the only ring structure is the ring that contains —$SO_2$— in the ring skeleton thereof is referred to as a monocyclic group, and a group containing other ring structures is described as a polycyclic group regardless of the structure of the other rings. The —$SO_2$— containing cyclic group may be either a monocyclic group or a polycyclic group.

As the —$SO_2$— containing cyclic group, a cyclic group containing —O—$SO_2$— within the ring skeleton thereof, i.e., a cyclic group containing a sultone ring in which —O—S— within the —O—$SO_2$— group forms part of the ring skeleton thereof is particularly desirable.

The —$SO_2$— containing cyclic group preferably has 3 to 30 carbon atoms, more preferably 4 to 20, still more preferably 4 to 15, and particularly preferably 4 to 12. Herein, the number of carbon atoms refers to the number of carbon atoms constituting the ring skeleton, excluding the number of carbon atoms within a substituent.

The —$SO_2$— containing cyclic group may be either a —$SO_2$— containing aliphatic cyclic group or a —$SO_2$— containing aromatic cyclic group. A —$SO_2$— containing aliphatic cyclic group is preferable.

Examples of the —$SO_2$— containing aliphatic cyclic group include aliphatic cyclic groups in which part of the carbon atoms constituting the ring skeleton has been substituted with a —$SO_2$— group or a —O—$SO_2$— group and has at least one hydrogen atom removed from the aliphatic hydrocarbon ring. Specific examples include an aliphatic hydrocarbon ring in which a —$CH_2$— group constituting the ring skeleton thereof has been substituted with a —$SO_2$— group and has at least one hydrogen atom removed therefrom; and an aliphatic hydrocarbon ring in which a —$CH_2$—$CH_2$— group constituting the ring skeleton has been substituted with a —O—$SO_2$— group and has at least one hydrogen atom removed therefrom.

The alicyclic hydrocarbon ring preferably has 3 to 20 carbon atoms, and more preferably 3 to 12 carbon atoms.

The alicyclic hydrocarbon ring may be either a monocyclic group or a polycyclic group. As the monocyclic group, a group in which two hydrogen atoms have been removed from a monocycloalkane of 3 to 6 carbon atoms is preferable. Examples of the monocycloalkane include cyclopentane and cyclohexane. As the polycyclic alicyclic hydrocarbon group, a group in which two hydrogen atoms have been removed from a polycycloalkane of 7 to 12 carbon atoms is preferable. Examples of the polycycloalkane include adamantane, norbornane, isobornane, tricyclodecane and tetracyclododecane.

The —$SO_2$— containing cyclic group may have a substituent. Examples of substituents include an alkyl group, an alkoxy group, a halogen atom, a halogenated alkyl group, a hydroxy group, an oxygen atom (═O), —OC(═O)R″, a hydroxyalkyl group and a cyano group.

The alkyl group as a the substituent is preferably an alkyl group of 1 to 6 carbon atoms. Further, the alkyl group is preferably a linear alkyl group or a branched alkyl group. Specific examples include a methyl group, ethyl group, propyl group, isopropyl group, n-butyl group, isobutyl group, tert-butyl group, pentyl group, isopentyl group, neopentyl group and hexyl group. Among these examples, a methyl group or an ethyl group is preferable, and a methyl group is particularly desirable.

As the alkoxy group as a the substituent, an alkoxy group of 1 to 6 carbon atoms is preferable. Further, the alkoxy group is preferably a linear alkoxy group or a branched alkoxy group. Specific examples of the alkoxy groups include the aforementioned alkyl groups for the substituent having an oxygen atom (—O—) bonded thereto.

Examples of the halogen atom as a substituent include a fluorine atom, a chlorine atom, a bromine atom and an iodine atom, and a fluorine atom is preferable.

Examples of the halogenated alkyl group as a substituent include groups in which part or all of the hydrogen atoms within the aforementioned alkyl groups has been substituted with the aforementioned halogen atoms.

As examples of the halogenated alkyl group as a substituent, groups in which part or all of the hydrogen atoms of the aforementioned alkyl groups as a substituent have been substituted with the aforementioned halogen atoms can be given. As the halogenated alkyl group, a fluorinated alkyl group is preferable, and a perfluoroalkyl group is particularly desirable.

In the —COOR″ group and the —OC(═O)R″ group, R″ represents a hydrogen atom or a linear, branched or cyclic alkyl group of 1 to 15 carbon atoms.

When R″ represents a linear or branched alkyl group, it is preferably an alkyl group of 1 to 10 carbon atoms, more preferably an alkyl group of 1 to 5 carbon atoms, and most preferably a methyl group or an ethyl group.

When R″ is a cyclic alkyl group (cycloalkyl group), it preferably has 3 to 15 carbon atoms, more preferably 4 to 12 carbon atoms, and most preferably 5 to 10 carbon atoms. As examples of the cycloalkyl group, groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group, may be used. Specific examples include groups in which one or more hydrogen atoms have been removed from a monocycloalkane such as cyclopentane and cyclohexane; and groups in which one or more hydrogen atoms have been removed from a polycycloalkane such as adamantane, norbornane, isobornane, tricyclodecane or tetracyclododecane.

The hydroxyalkyl group as a substituent preferably has 1 to 6 carbon atoms, and specific examples thereof include the aforementioned alkyl groups as a substituent in which at least one hydrogen atom has been substituted with a hydroxy group.

More specific examples of the —$SO_2$— containing cyclic group include groups represented by general formulas (3-1) to (3-4) shown below.

[Chemical Formula 24]

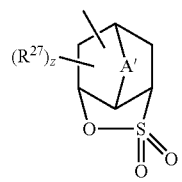
(3-1)

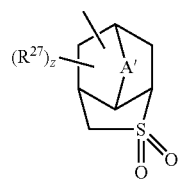
(3-2)

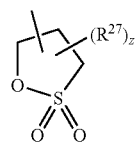
(3-3)

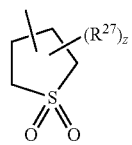
(3-4)

In the formulas, A′ represents an oxygen atom, a sulfur atom or an alkylene group of 1 to 5 carbon atoms which may contain an oxygen atom or a sulfur atom; z represents an integer of 0 to 2; and $R^{27}$ represents an alkyl group, an alkoxy group, a halogenated alkyl group, a hydroxyl group, —COOR″, —OC(═O)R″, a hydroxyalkyl group or a cyano group, wherein R″ represents a hydrogen atom or an alkyl group.

In general formulas (3-1) to (3-4) above, A′ represents an oxygen atom (—O—), a sulfur atom (—S—) or an alkylene group of 1 to 5 carbon atoms which may contain an oxygen atom or a sulfur atom.

As the alkylene group of 1 to 5 carbon atoms for A′, a linear or branched alkylene group is preferable, and examples thereof include a methylene group, an ethylene group, an n-propylene group and an isopropylene group.

Examples of alkylene groups that contain an oxygen atom or a sulfur atom include the aforementioned alkylene groups in which —O— or —S— is bonded to the terminal of the alkylene group or interposed within the alkylene group. Specific examples of such alkylene groups include —O—$CH_2$—, —$CH_2$—O—$CH_2$—, —S—$CH_2$— and —$CH_2$—S—$CH_2$—.

As A′, an alkylene group of 1 to 5 carbon atoms or —O— is preferable, more preferably an alkylene group of 1 to 5 carbon atoms, and most preferably a methylene group.

z represents an integer of 0 to 2, and is most preferably 0.

If there are two of the $R^{27}$ groups, as indicated by the value z, then the two of the $R^{27}$ groups may be the same or different from each other.

As the alkyl group, alkoxy group, halogenated alkyl group, —COOR″, —OC(=O)R″ and hydroxyalkyl group for $R^{27}$, the same alkyl groups, alkoxy groups, halogenated alkyl groups, —COOR″, —OC(=O)R″ and hydroxyalkyl groups as those described above as the substituent which the —SO$_2$— containing cyclic group may have, can be mentioned.

Specific examples of the cyclic groups represented by general formulas (3-1) to (3-4) are shown below. In the formulas shown below, "Ac" represents an acetyl group.

[Chemical Formula 25]

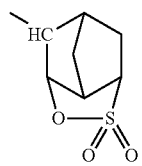 (3-1-1)

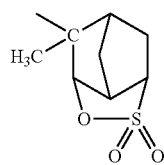 (3-1-2)

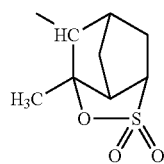 (3-1-3)

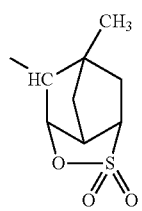 (3-1-4)

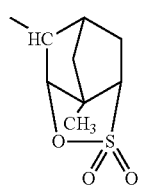 (3-1-5)

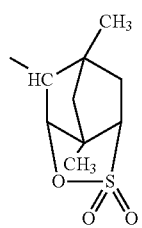 (3-1-6)

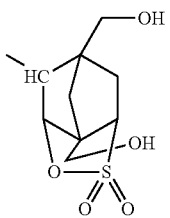 (3-1-7)

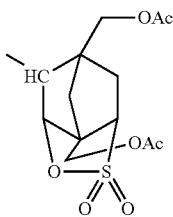 (3-1-8)

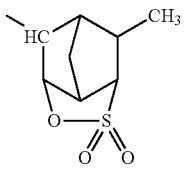 (3-1-9)

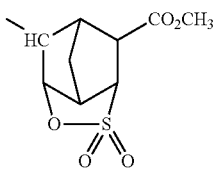 (3-1-10)

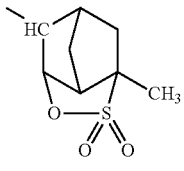 (3-1-11)

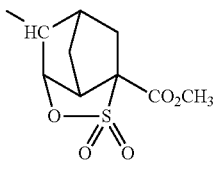 (3-1-12)

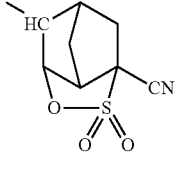 (3-1-13)

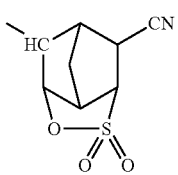 (3-1-14)

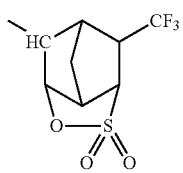
(3-1-15)
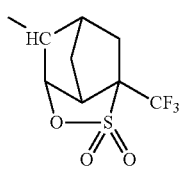
(3-1-16)
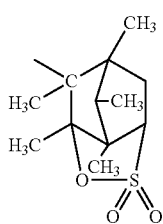
(3-1-17)
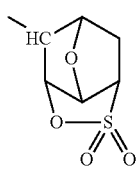
(3-1-18)
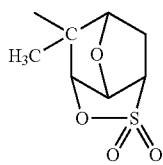
(3-1-19)
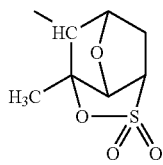
(3-1-20)
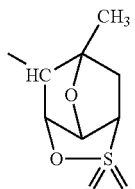
(3-1-21)
[Chemical Formula 26]
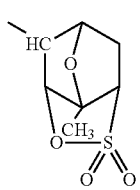
(3-1-22)
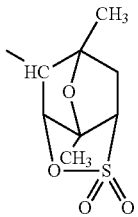
(3-1-23)
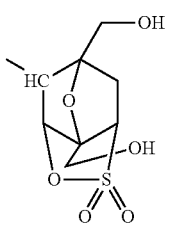
(3-1-24)
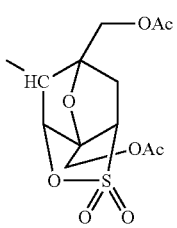
(3-1-25)
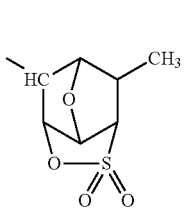
(3-1-26)
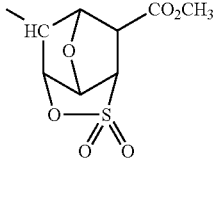
(3-1-27)
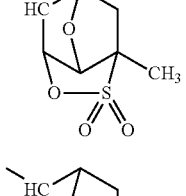
(3-1-28)
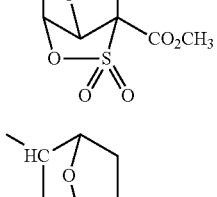
(3-1-29)
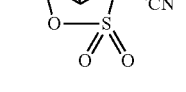
(3-1-30)

-continued (3-1-31)
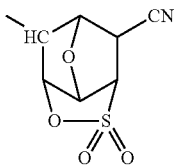

(3-1-32)
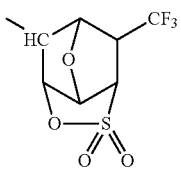

(3-1-33)
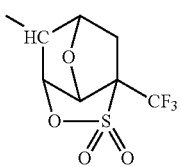

[Chemical Formula 27]

(3-2-1)
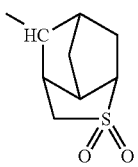

(3-2-2)
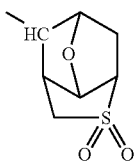

(3-3-1)
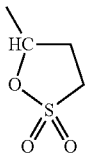

(3-4-1)
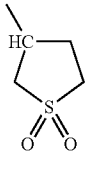

As the —$SO_2$— containing cyclic group, a group represented by the aforementioned general formula (3-1) is preferable, at least one member selected from the group consisting of groups represented by the aforementioned chemical formulas (3-1-1), (3-1-18), (3-3-1) and (3-4-1) is more preferable, and a group represented by the chemical formula (3-1-1) is most preferable.

The term "lactone-containing cyclic group" refers to a cyclic group including a ring containing a —O—C(=O)— structure (lactone ring). The term "lactone ring" refers to a single ring containing a —O—C(=O)— structure, and this ring is counted as the first ring. A lactone-containing cyclic group in which the only ring structure is the lactone ring is referred to as a monocyclic group, and groups containing other ring structures are described as polycyclic groups regardless of the structure of the other rings. The lactone-containing cyclic group may be either a monocyclic group or a polycyclic group.

The lactone-containing cyclic group for the structural unit (a2) is not particularly limited, and an arbitrary structural unit may be used. Specific examples of lactone-containing monocyclic groups include a group in which one hydrogen atom has been removed from a 4- to 6-membered lactone ring, such as a group in which one hydrogen atom has been removed from β-propionolatone, a group in which one hydrogen atom has been removed from γ-butyrolactone, and a group in which one hydrogen atom has been removed from δ-valerolactone. Further, specific examples of lactone-containing polycyclic groups include groups in which one hydrogen atom has been removed from a lactone ring-containing bicycloalkane, tricycloalkane or tetracycloalkane.

With respect to the structural unit (a2), the partial structure other than the —$SO_2$-containing cyclic group or a lactone-containing cyclic group is not particularly limited as long as the structural unit (a2) having an —$SO_2$— containing cyclic group or a lactone-containing cyclic group. The structural unit (a2) is preferably at least one structural unit selected from the group consisting of a structural unit derived from an acrylate ester which may have the hydrogen atom bonded to the carbon atom on the α-position substituted with a substituent and contains an —$SO_2$— containing cyclic group (hereafter, referred to as "structural unit ($a2^S$)"), and a structural unit derived from an acrylate ester which may have the hydrogen atom bonded to the carbon atom on the α-position substituted with a substituent and contains a lactone-containing cyclic group (hereafter, referred to as "structural unit ($a2^L$)").

—Structural Unit ($a2^S$):

More specific examples of the structural unit ($a2^S$) include structural units represented by general formula (a2-0) shown below.

[Chemical Formula 28]

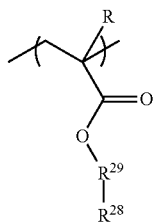

(a2-0)

In the formula, R represents a hydrogen atom, an alkyl group of 1 to 5 carbon atoms or a halogenated alkyl group of 1 to 5 carbon atoms; $R^{28}$ represents a —$SO_2$-containing cyclic group; and $R^{29}$ represents a single bond or a divalent linking group.

In genera formula (a2-0), R is the same as defined above.

$R^{28}$ is the same as defined for the aforementioned —$SO_2$— containing group.

$R^{29}$ may be either a single bond or a divalent linking group. In terms of the effects of the present invention, a divalent linking group is preferable.

The divalent linking group for $R^{29}$ is not particularly limited, and examples thereof include the same divalent linking groups as those described above for $Y^2$ in the aforementioned formula (a1-3). Among these, an alkylene group or a divalent linking group containing an ester bond (—C(=O)—O—) is preferable.

As the alkylene group, a linear or branched alkylene group is preferable. Specific examples include the same linear alkylene groups and branched alkylene groups as those described above in relation to the aliphatic hydrocarbon group for $Y^2$.

As the divalent linking group containing an ester bond, a group represented by general formula: —$R^{30}$—C(=O)—O— (in the formula, $R^{30}$ represents a divalent linking group) is particularly desirable. That is, the structural unit ($a2^S$) is preferably a structural unit represented by general formula (a2-0-1) shown below.

[Chemical Formulla 29]

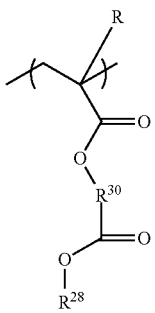

(a2-0-1)

In the formula, R and $R^{28}$ are the same as defined above; and $R^{30}$ represents a divalent linking group.

$R^{30}$ is not particularly limited, and examples thereof include the same divalent linking groups as those described above for $Y^2$ in the aforementioned formula (a1-3).

As the divalent linking group for $R^{30}$, a linear or branched alkylene group, an aliphatic hydrocarbon group containing a ring in the structure thereof or a divalent linking group containing a hetero atom is preferable, and a linear or branched alkylene group or a divalent linking group containing an oxygen atom as a hetero atom is more preferable.

As the linear alkylene group, a methylene group or an ethylene group is preferable, and a methylene group is particularly desirable.

As the branched alkylene group, an alkylmethylene group or an alkylethylene group is preferable, and —CH(CH$_3$)—, —C(CH$_3$)$_2$— or —C(CH$_3$)$_2$CH$_2$— is particularly desirable.

As the divalent linking group containing an oxygen atom, a divalent linking group containing an ether bond or an ester bond is preferable, and a group represented by the aforementioned formulas —$Y^{21}$—O—$Y^{22}$—, —[$Y^{21}$—C(=O)—O]$_{m'}$—$Y^{22}$— and —$Y^{21}$—O—C(=O)—$Y^{22}$— is more preferable. Each of $Y^{21}$ and $Y^{22}$ independently represents a divalent hydrocarbon group which may have a substituent and m' represents an integer of 0 to 3. Among these, a group represented by formula —$Y^{21}$—O—C(=O)—$Y^{22}$— is preferable, and a group represented by formula —(CH$_2$)$_c$—O—C(=O)—(CH$_2$)$_d$— is particularly preferable. c represents an integer of 1 to 5, and preferably 1 or 2. d represents an integer of 1 to 5, and preferably 1 or 2.

In particular, as the structural unit ($a2^S$), a structural unit represented by general formula (a2-0-11) or (a2-0-12) shown below is preferable, and a structural unit represented by general formula (a2-0-12) shown below is more preferable.

[Chemical Formula 30]

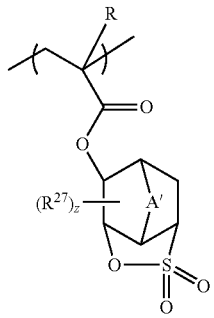

(a2-0-11)

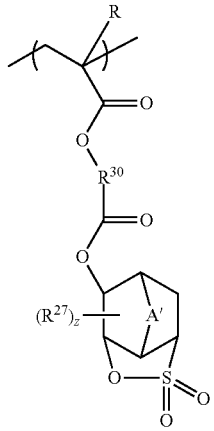

(a2-0-12)

In the formulas, R, A', $R^{27}$, z and $R^{30}$ are the same as defined above.

In general formula (a2-0-11), A' is preferably a methylene group, an oxygen atom (—O—) or a sulfur atom (—S—).

As $R^{30}$ a linear or branched alkylene group or a divalent linking group containing an oxygen atom is preferable. As the linear or branched alkylene group and the divalent linking group containing an oxygen atom for $R^{30}$, the same linear or branched alkylene groups and the divalent linking groups containing an oxygen atom as those described above can be mentioned.

As the structural unit represented by general formula (a2-0-12), a structural unit represented by general formula (a2-0-12a) or (a2-0-12b) shown below is particularly desirable.

[Chemical Formula 31]

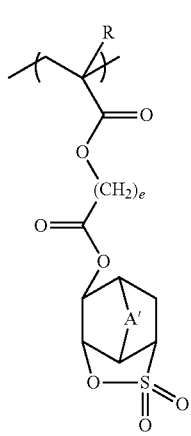

(a2-0-12a)

-continued (a2-0-12b)

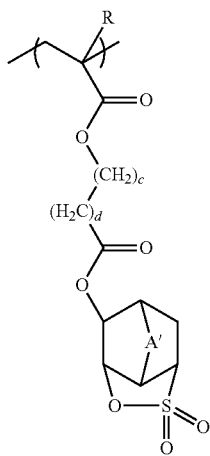

In the formulas, R and A' are the same as defined above; and each of c to e independently represents an integer of 1 to 3.

—Structural Unit (a2$^L$):

Examples of the structural unit (a2$^L$) include structural units represented by the aforementioned general formula (a2-0) in which the R$^{28}$ group has been substituted with a lactone-containing cyclic group. Specific examples include structural units represented by general formulas (a2-1) to (a2-5) shown below.

[Chemical Formula 32]

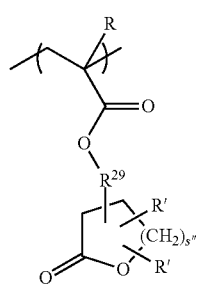

(a2-1)

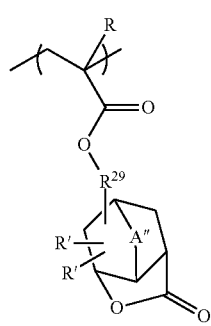

(a2-2)

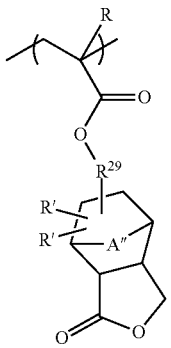

(a2-3)

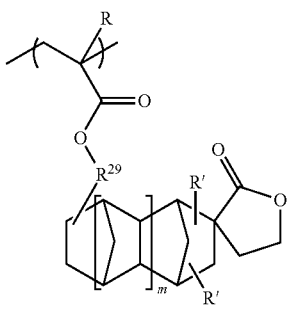

(a2-4)

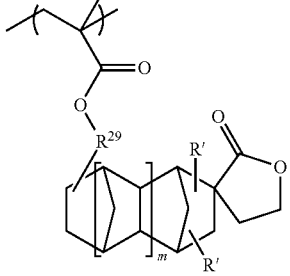

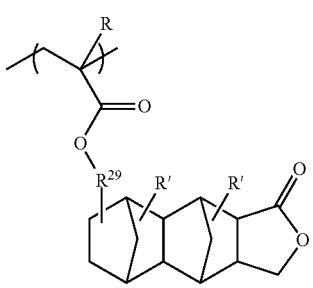

(a2-5)

In the formulas, R represents a hydrogen atom, an alkyl group of 1 to 5 carbon atoms or a halogenated alkyl group of 1 to 5 carbon atoms; each R' independently represents a hydrogen atom, an alkyl group, an alkoxy group, a halogenated alkyl group, a hydroxy group, —COOR", —OC(=O)R", a hydroxyalkyl group, or a cyano group, wherein R" represents a hydrogen atom or an alkyl group; R$^{29}$ represents a single bond or a divalent linking group; s" represents an integer of 0 to 2; A" represents an oxygen atom, a sulfur atom or an alkylene group of 1 to 5 carbon atoms which may contain an oxygen atom or a sulfur atom; and m represents 0 or 1.

In general formulas (a2-1) to (a2-5), R is the same as defined above.

As the alkyl group, alkoxy group, halogenated alkyl group, —COOR", —OC(=O)R" and hydroxyalkyl group for R', the same alkyl groups, alkoxy groups, halogenated alkyl groups, —COOR", —OC(=O)R" and hydroxyalkyl groups as those described above as the substituent which a —SO$_2$— containing cyclic group may have, can be mentioned.

In terms of industrial availability, R' is preferably a hydrogen atom.

The alkyl group for R" may be any of linear, branched or cyclic.

When R" is a linear or branched alkyl group, it preferably has 1 to 10 carbon atoms, more preferably 1 to 5 carbon atoms.

When R" is a cyclic alkyl group (cycloalkyl group), it preferably has 3 to 15 carbon atoms, more preferably 4 to 12 carbon atoms, and most preferably 5 to 10 carbon atoms. As examples of the cycloalkyl group, groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group, may be used. Examples of such groups include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane.

As examples of A", the same groups as those described above for A' in general formula (3-1) can be given. A" is preferably an alkylene group of 1 to 5 carbon atoms, an oxygen atom (—O—) or a sulfur atom (—S—), and more preferably an alkylene group of 1 to 5 carbon atoms or —O—. As the alkylene group of 1 to 5 carbon atoms, a methylene group or a dimethylethylene group is preferable, and a methylene group is particularly desirable.

$R^{29}$ is the same as defined for $R^{29}$ in the aforementioned general formula (a2-0).

In formula (a2-1), s" is preferably 1 or 2.

Specific examples of structural units represented by general formulas (a2-1) to (a2-5) are shown below. In the formulas shown below, $R^\alpha$ represents a hydrogen atom, a methyl group or a trifluoromethyl group.

[Chemical Formula 33]

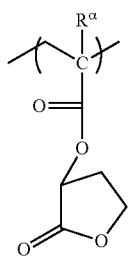
(a2-1-1)

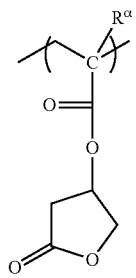
(a2-1-2)

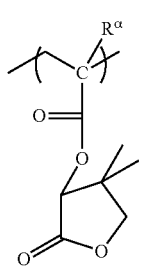
(a2-1-3)

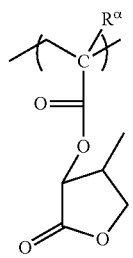
(a2-1-4)

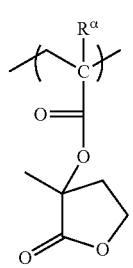
(a2-1-5)

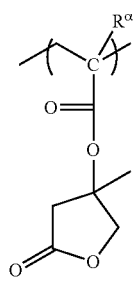
(a2-1-6)

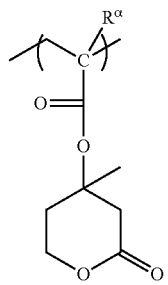
(a2-1-7)

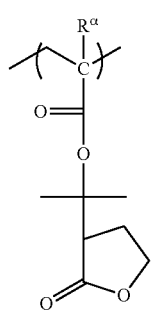
(a2-1-8)

(a2-1-9) 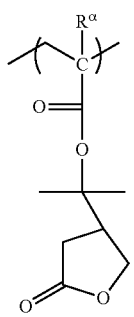
(a2-1-10) 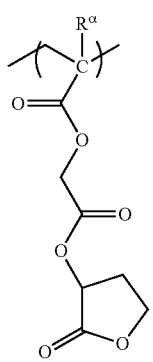
(a2-1-11) 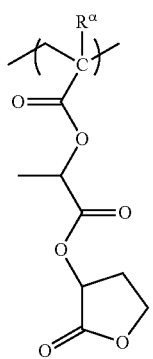
(a2-1-12) 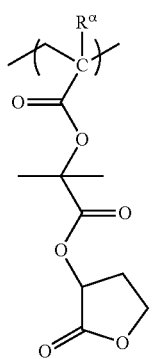
(a2-1-13) 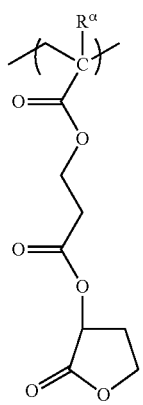
[Chemical Formula 34]
(a2-2-1) 
(a2-2-2) 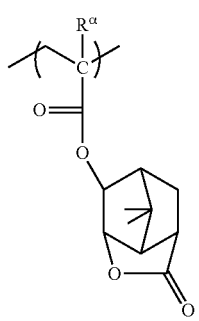
(a2-2-3) 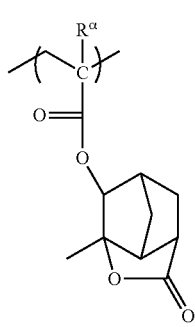

(a2-2-4)
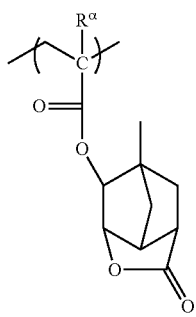
(a2-2-5)
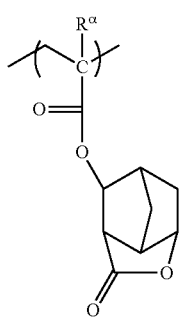
(a2-2-6)
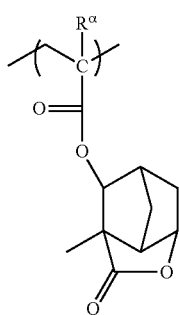
(a2-2-7)
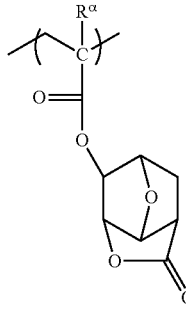
(a2-2-8)
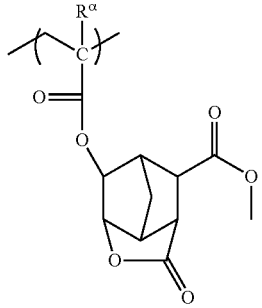
(a2-2-9)
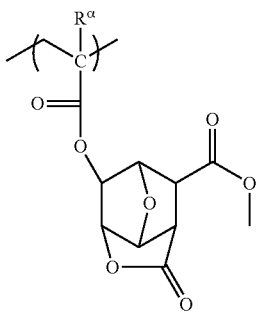
(a2-2-10)
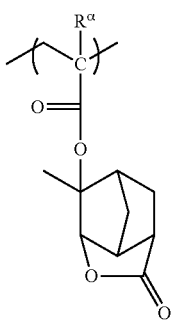
(a2-2-11)
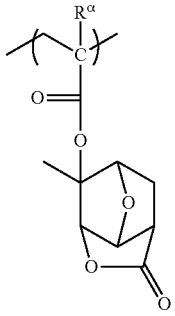
(a2-2-12)
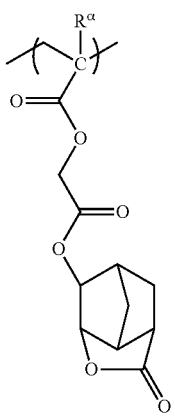

-continued
(a2-2-13)
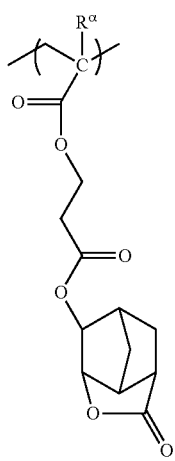
(a2-2-14)
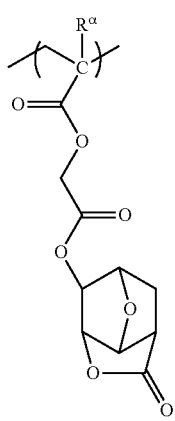
(a2-2-15)
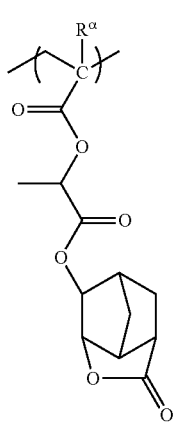
-continued
(a2-2-16)
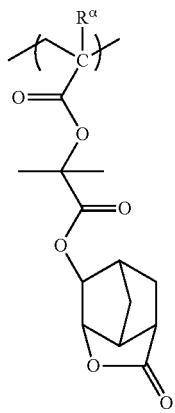
(a2-2-17)
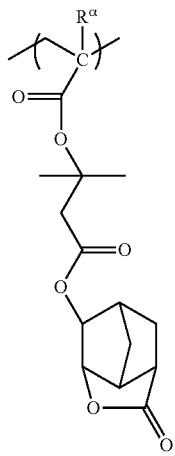
[Chemical Formula 35]
(a2-3-1)
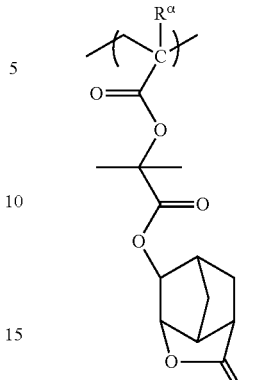
(a2-3-2)
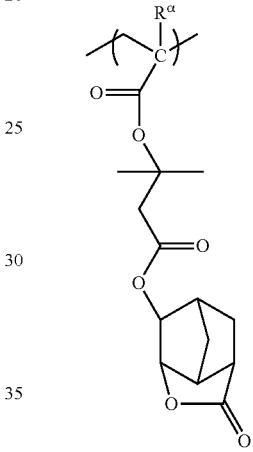

(a2-3-3)
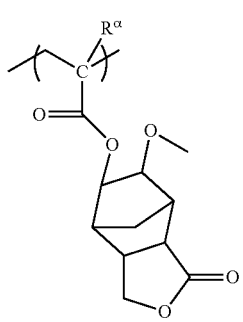
(a2-3-4)
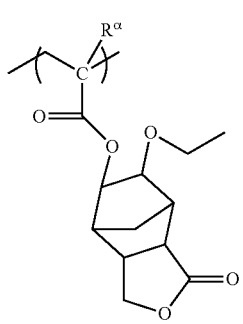
(a2-3-5)
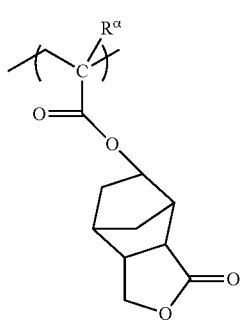
[Chemical Formula 36]
(a2-4-1)
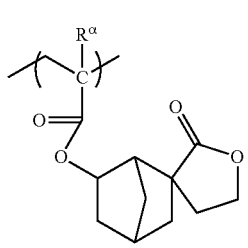
(a2-4-2)
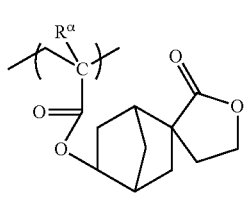
(a2-4-3)
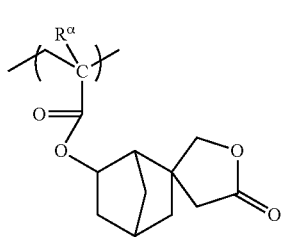
(a2-4-4)
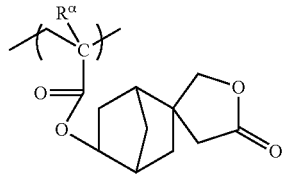
(a2-4-5)
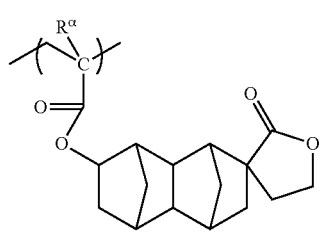
(a2-4-6)
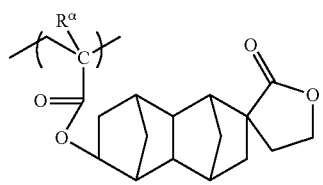
(a2-4-7)
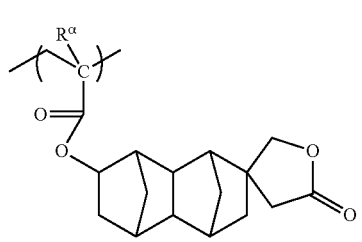
(a2-4-8)
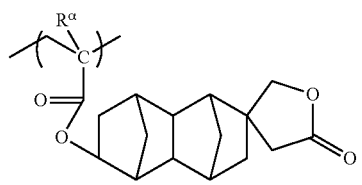
(a2-4-9)
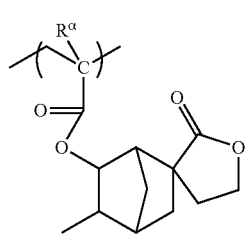
(a2-4-10)
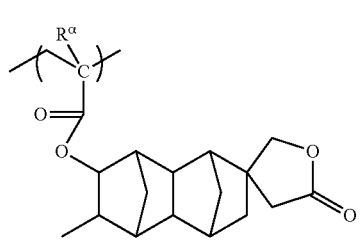

(a2-4-11)
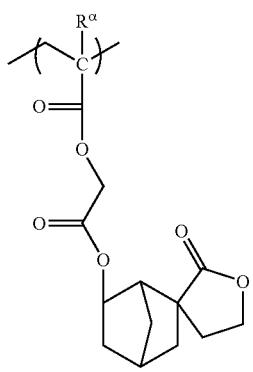
(a2-4-12)
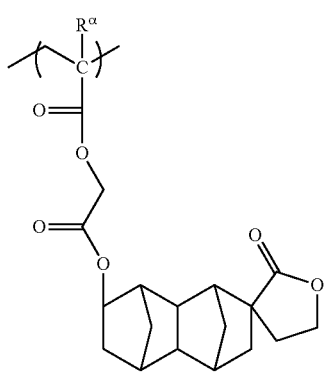
[Chemical Formula 37]
(a2-5-1)
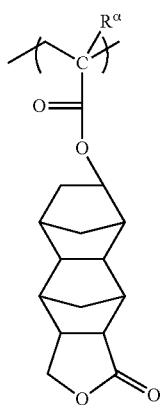
(a2-5-2)
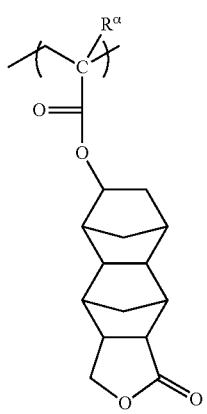
(a2-5-3)
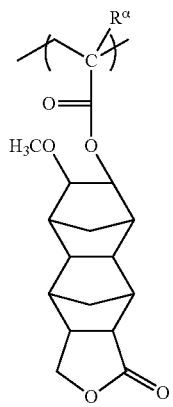
(a2-5-4)
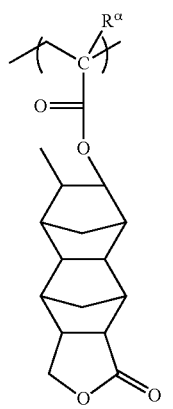
(a2-5-5)
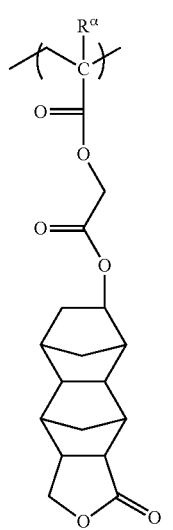

(a2-5-6)

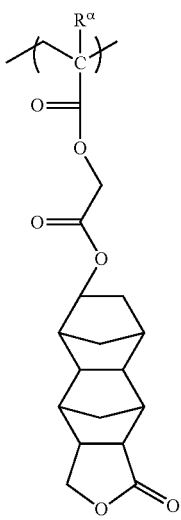

As the structural unit (a2$^L$), it is preferable to include at least one structural unit selected from the group consisting of structural units represented by the aforementioned general formulas (a2-1) to (a2-5), more preferably at least one structural unit selected from the group consisting of structural units represented by the aforementioned general formulas (a2-1) to (a2-3), and particularly preferably at least one structural unit selected from the group consisting of structural units represented by the aforementioned general formulas (a2-1) and (a2-3).

Specifically, it is preferable to use at least one structural unit selected from the group consisting of formulas (a2-1-1), (a2-1-2), (a2-2-1), (a2-2-7), (a2-2-12), (a2-2-14), (a2-3-1) and (a2-3-5).

Furthermore, as the structural unit (a2$^L$), structural units represented by general formulas (a2-6) and (a2-7) are also preferable.

[Chemical Formula 38]

(a2-6)

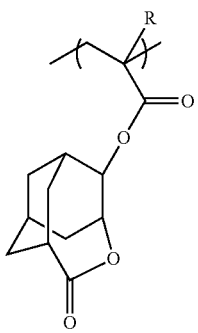

(a2-7)

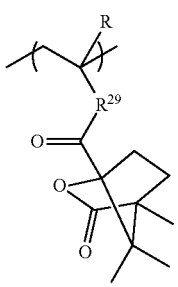

In the formula, R$^{29}$ is the same as those defined above.

As the structural unit (a2) contained in the component (A1), 1 type of structural unit may be used, or 2 or more types may be used. For example, as the structural unit (a2), a structural unit (a2$^S$) may be used alone, or a structural unit (a2$^L$), or a combination of these structural units may be used. Further, as the structural unit (a2$^S$) or the structural unit (a2$^L$), either a single type of structural unit may be used, or two or more types may be used in combination.

In the component (A1), the amount of the structural unit (a2) based on the combined total of all structural units constituting the component (A1) is preferably 1 to 80 mol %, more preferably 10 to 70 mol %, still more preferably 10 to 65 mol %, and most preferably 10 to 60 mol %. When the amount of the structural unit (a2) is at least as large as the lower limit of the above-mentioned range, the effect of using the structural unit (a2) can be satisfactorily achieved. On the other hand, when the amount of the structural unit (a2) is no more than the upper limit of the above-mentioned range, a good balance can be achieved with the other structural units, and various lithography properties such as DOF and CDU and pattern shape can be improved.

[Structural Unit (a3)]

The component (A1) may include a structural unit (a3) containing a polar group, as well as the structural unit (a1), or the structural units (a1) and (a2). When the component (A1) includes the structural unit (a3), the polarity of the component (A1) after exposure is enhanced. In the case of alkali development process, a high polarity contributes to improving resolution and the like.

Examples of the polar group include —OH, —COOH, —CN, —SO$_2$NH$_2$— and —CONH$_2$. As the structural unit containing —COOH, a structural unit derived from the (α-substituted) acrylic acid.

The structural unit (a3) is a structural unit containing a hydrocarbon group in which part of the hydrogen atoms within the hydrocarbon group is substituted with the polar group. The hydrocarbon group may be either an aliphatic hydrocarbon group or an aromatic hydrocarbon group. Among these, the hydrocarbon group is preferably an aliphatic hydrocarbon group.

Examples of the aliphatic hydrocarbon group in the hydrocarbon group include linear or branched hydrocarbon groups (preferably alkylene groups) of 1 to 10 carbon atoms, and aliphatic cyclic groups (monocyclic groups and polycyclic groups).

These aliphatic cyclic groups (monocyclic groups and polycyclic groups) can be selected appropriately from the multitude of groups that have been proposed for the resins of resist compositions designed for use with ArF excimer lasers. The aliphatic cyclic group preferably has 3 to 30 carbon atoms, more preferably 5 to 30, still more preferably 5 to 20, particularly preferably 6 to 15, and most preferably 6 to 12. As the aliphatic cyclic group, a group in which two or more hydrogen atoms have been removed from a monocycloalkane or a polycycloalkane such as a bicycloalkane, tricycloalkane or tetracycloalkane can be used. Specific examples include groups in which two or more hydrogen atoms have been removed from a monocycloalkane such as cyclopentane or cyclohexane; and groups in which two or more hydrogen atoms have been removed from a polycycloalkane such as adamantane, norbornane, isobornane, tricyclodecane or tetracyclododecane. The aliphatic cyclic group may or may not have a substituent. Examples of the substituent include an alkyl group of 1 to 5 carbon atoms, a fluorine atom and a fluorinated alkyl group of 1 to 5 carbon atoms.

The aromatic hydrocarbon group in the hydrocarbon group is a hydrocarbon group having at least one aromatic ring.

The aromatic ring is not particularly limited as long as it is a cyclic conjugation ring having 4n+2 of π electrons, and may be a monocyclic or a polycyclic. The aromatic ring preferably has 5 to 30 carbon atoms, more preferably 5 to 20, still more preferably 6 to 15, and particularly preferably 6 to 12. Here, the number of carbon atoms within a substituent(s) is not included in the number of carbon atoms of the aromatic hydrocarbon group. Examples of the aromatic ring include aromatic hydrocarbon rings such as benzene, biphenyl, fluorene, naphthalene, anthracene and phenanthrene and aromatic heterocycles in which part of the carbon atoms of the aromatic hydrocarbon ring have been substituted with a hetero atom. Examples of hetero atoms within the aromatic heterocycle include an oxygen atom, a nitrogen atom, and a sulfur atom. Specific examples of aromatic heterocycles include a pyridine ring and a thiophene ring.

Specific examples of the aromatic hydrocarbon group as a divalent hydrocarbon group include a group in which two hydrogen atoms have been removed from the aromatic hydrocarbon ring or aromatic heterocycle (arylene group or heteroarylene group); a group in which two hydrogen atoms have been removed from an aromatic compound having two or more aromatic rings (for example, biphenyl or fluorene); and a group in which one hydrogen atom has been removed from the aromatic ring within an aryl alkyl group or a heteroaryl alkyl group in which one hydrogen atom of the aromatic ring has been substituted with an alkylene group (for example, a benzyl group, a phenethyl group, a 1-naphthylmethyl group, a 2-naphthylmethyl group, a 1-naphthylethyl group, or a 2-naphthylethyl group). The alkylene group with which a hydrogen atom of the aromatic hydrocarbon ring or aromatic heterocycles has been substituted, preferably has 1 to 4 carbon atom, more preferably 1 or 2, and most preferably 1.

The aromatic hydrocarbon group may have a substituent. For example, the hydrogen atom bonded to the aromatic ring within the aromatic hydrocarbon group may be substituted with a substituent. Examples of substituents include an alkyl group, an alkoxy group, a halogen atom, a halogenated alkyl group, a hydroxy group and an oxygen atom (=O).

The alkyl group as a substituent is preferably an alkyl group of 1 to 5 carbon atoms, and a methyl group, an ethyl group, a propyl group, an n-butyl group or a tert-butyl group is most desirable.

Examples of the halogen atom as a substituent for the aromatic hydrocarbon group include a fluorine atom, a chlorine atom, a bromine atom and an iodine atom, and a fluorine atom is preferable.

Examples of the halogenated alkyl group as a substituent include groups in which part or all of the hydrogen atoms within the aforementioned alkyl groups has been substituted with the aforementioned halogen atoms.

Among these, as the structural unit (a3), a structural unit represented by general formula (a3-1) is preferable.

[Chemical Formula 39]

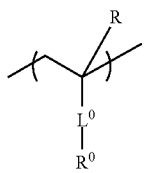

(a3-1)

In the formula, R represents a hydrogen atom, an alkyl group of 1 to 5 carbon atoms or a halogenated alkyl group of 1 to 5 carbon atoms; $L^0$ represents —C(=O)—O—, —C(=O)—NR″— (wherein R″ represents a hydrogen atom or an alkyl group of 1 to 5 carbon atoms) or a single bond; and $R^0$ represents a hydrocarbon group containing at least one group selected from the group consisting of —OH, —COOH, —CN, —SO$_2$NH$_2$ and —CONH$_2$, and may contain an oxygen atom or a sulfur atom at an arbitrary position.

As the alkyl group for R in the formula (a3-1), a linear or branched alkyl group is preferable, and specific examples include a methyl group, an ethyl group, a propyl group, an isopropyl group, an n-butyl group, an isobutyl group, a tert-butyl group, a pentyl group, an isopentyl group and a neopentyl group.

Examples of the halogenated alkyl group for R include groups in which part or all of the hydrogen atoms within the aforementioned alkyl groups for R. Examples of the halogen atom include a fluorine atom, a chlorine atom, a bromine atom and an iodine atom, and a fluorine atom is particularly preferred.

As R, a hydrogen atom, an alkyl group of 1 to 5 carbon atoms or a fluorinated alkyl group of 1 to 5 carbon atoms is preferable, and a hydrogen atom or a methyl group is particularly desirable.

In the formula (a3-1), $L^0$ represents —C(=O)—O—, —C(=O)—NR″— (wherein R″ represents a hydrogen atom or an alkyl group of 1 to 5 carbon atoms) or a single bond. As the alkyl group for R″, the same alkyl groups as those described above for R can be used.

In the formula (a3-1), $R^0$ is a hydrocarbon group having at least one of the group consisting of —OH, —COOH, —CN, —SO$_2$NH$_2$ and —CONH$_2$ as a substituent, and may have an oxygen atom or a sulfur atom at an arbitrary position.

A "hydrocarbon group which have a substituent" means a group in which part or all of the hydrogen atoms within the hydrocarbon group is substituted with a substituent.

The hydrocarbon group for $R^0$ may be either an aliphatic hydrocarbon group, or an aromatic hydrocarbon group.

Examples of the aliphatic hydrocarbon group for $R^0$ include linear or branched hydrocarbon groups (preferably alkylene groups) of 1 to 10 carbon atoms, and aliphatic cyclic groups (monocyclic groups and polycyclic groups), and these definitions are the same as those described above.

The aromatic hydrocarbon group for $R^0$ is a hydrocarbon group having an aromatic ring, and these definitions are the same as those described above.

$R^0$ may include an oxygen atom or a sulfur atom at an arbitrary position. The group "may includes an oxygen atom or a sulfur atom at an arbitrary position" means that a group in which part of the carbon atom constituting the hydrocarbon group or hydrocarbon group containing a substituent may be substituted with an oxygen atom or a sulfur atom, or a group in which a hydrogen atom bonded to the hydrocarbon group may be substituted with an oxygen atom or a sulfur atom.

Examples of $R^0$ containing an oxygen atom at an arbitrary position are shown below.

[Chemical Formula 40]

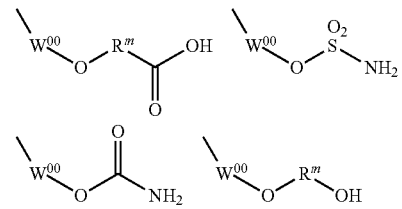

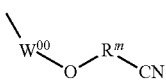

In the formulas, $W^{00}$ represents a hydrocarbon group; and $R^{00}$ represents an alkylene group of 1 to 5 carbon atoms.

In the formula, $W^{00}$ represents a hydrocarbon group, and the same hydrocarbon group as those described for $R^0$ in the formula (a3-1). $W^{00}$ is preferably an aliphatic hydrocarbon group, more preferably an aliphatic cyclic group (monocyclic group and polycyclic group).

$R^m$ is preferably a linear or branched group, preferably an alkylene group of 1 to 3 carbon atoms, and more preferably a methylene group or an ethylene group.

Specific examples of the structural unit (a3) include structural units derived from (α-substituted) acrylic acid and structural units represented by general formulas (a3-11) to (a3-13) shown below.

Specific examples of the structural unit derived from the (α-substituted) acrylic acid include a structural unit represented by the general formula (a3-1) in which $L^0$ is a single bond and $R^0$ is —COOH.

[Chemical Formula 41]

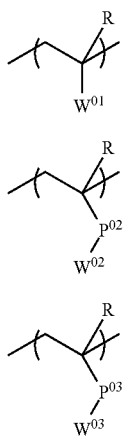

In the formulas, R represents a hydrogen atom, an alkyl group of 1 to 5 carbon atoms or a halogenated alkyl group of 1 to 5 carbon atoms; $W^{01}$ is an aromatic hydrocarbon group containing at least one group selected from the group consisting of —OH, —COOH, —CN, —SO$_2$NH$_2$ and —CONH$_2$ as a substituent; each of $P^{02}$ and $P^{03}$ represents —C(=O)—O— or —C(=O)—NR"— (wherein R" represents a hydrogen atom or an alkyl group of 1 to 5 carbon atoms); $W^{02}$ is a cyclic hydrocarbon group containing at least one group selected from the group consisting of —OH, —COOH, —CN, —SO$_2$NH$_2$ and —CONH$_2$ as a substituent and which may have an oxygen atom or a sulfur atom at an arbitrary position; and $W^{03}$ is a linear hydrocarbon group containing at least one group selected from the group consisting of —OH, —COOH, —CN, —SO$_2$NH$_2$ and —CONH$_2$ as a substituent.

[Structural Unit Represented by General Formula (a3-11)]

In general formula (a3-11), R is the same as defined for R in general formula (a3-1).

The aromatic hydrocarbon group for $W^{01}$ is the same as defined for the aromatic hydrocarbon group for $R^0$ in general formula (a3-1).

The aromatic hydrocarbon group for $W^{01}$ may have a substituent other than at least one group selected from the group consisting of —OH, —COOH, —CN, —SO$_2$NH$_2$ and —CONH$_2$. Examples of the substituent include a halogen atom, an alkyl group of 1 to 5 carbon atoms and a halogenated alkyl group of 1 to 5 carbon atoms. Among these, a halogen atom is preferable, and a fluorine atom is particularly desirable.

Specific examples of structural units represented by general formula (a3-11) are shown below. In the formulas shown below, $R^\alpha$ represents a hydrogen atom, a methyl group or a trifluoromethyl group.

[Chemical Formula 42]

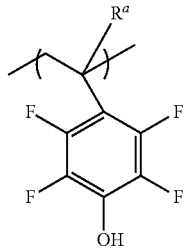

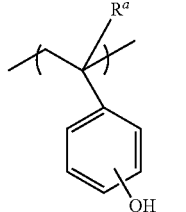

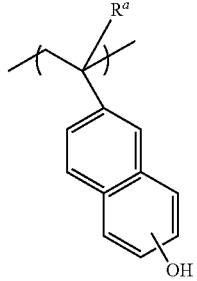

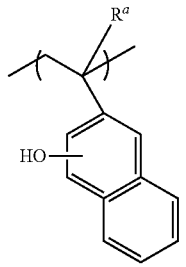

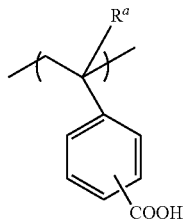

[Structural Unit Represented by General Formula (a3-12)]

In general formula (a3-12), R is the same as defined for R in general formula (a3-1).

$P^{02}$ represents —C(=O)—O— or —C(=O)—NR″— (wherein R″ represents a hydrogen atom or an alkyl group of 1 to 5 carbon atoms), and preferably —C(=O)—O—. The alkyl group for R″ is the same alkyl group as described above for R.

The cyclic hydrocarbon group for $W^{02}$ is the same aliphatic cyclic group (monocyclic group and polycyclic group) and aromatic hydrocarbon group for $R^0$ in general formula (a3-1).

$W^{02}$ may include an oxygen atom or a sulfur atom at an arbitrary position, and the definition is the same as defined for $R^0$ in the formula (a3-1).

Specific examples of structural units represented by general formula (a3-12) are shown below. In the formulas shown below, $R^\alpha$ represents a hydrogen atom, a methyl group or a trifluoromethyl group.

[Chemical Formula 43]

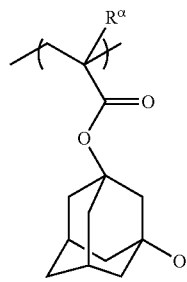
(a3-12-1)

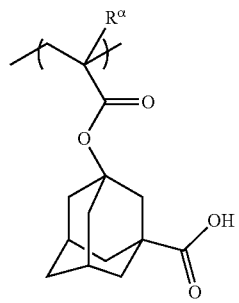
(a3-12-2)

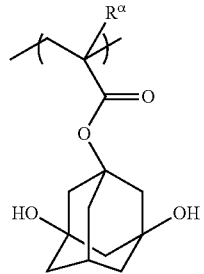
(a3-12-3)

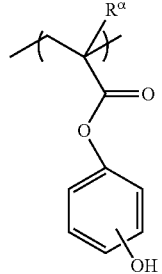
(a3-12-4)

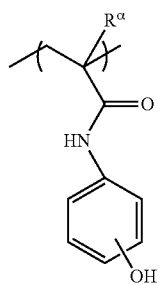
(a3-12-5)

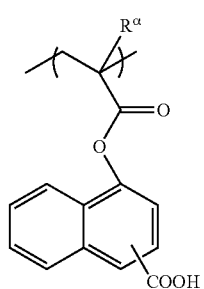
(a3-12-6)

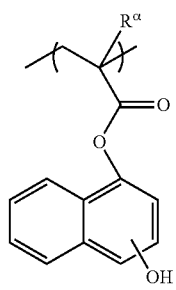
(a3-12-7)

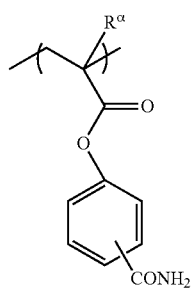
(a3-12-8)

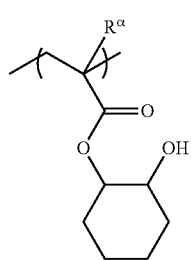
(a3-12-9)

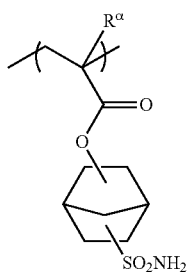
(a3-12-10)

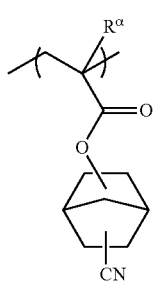
(a3-12-11)

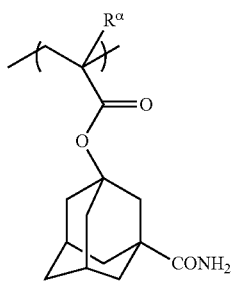
(a3-12-12)

[Chemical Formula 44]

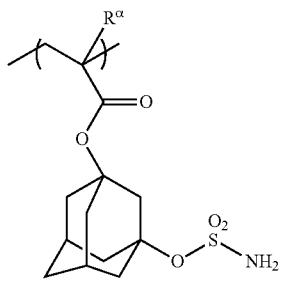
(a3-12-13)

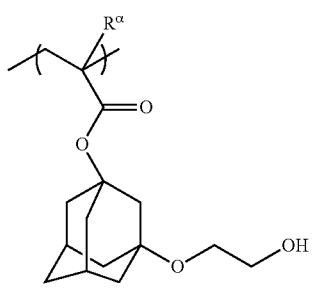
(a3-12-14)

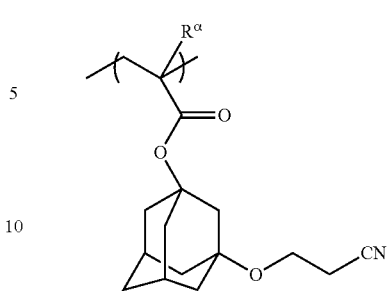
(a3-12-15)

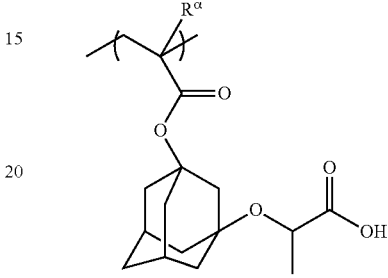
(a3-12-16)

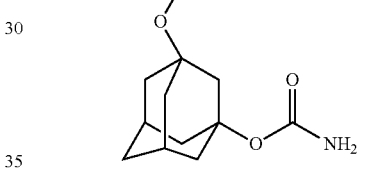
(a3-12-17)

[Structural Unit Represented by General Formula (a3-13)]

In general formula (a3-13), R is the same as defined for R in general formula (a3-1).

$P^{03}$ represents —C(=O)—O— or —C(=O)—NR″— (wherein R″ represents a hydrogen atom or an alkyl group of 1 to 5 carbon atoms), and preferably —C(=O)—O—. The alkyl group for R″ is the same alkyl group as described above for R.

The linear hydrocarbon group for $W^{03}$ preferably has 1 to 10 carbon atoms, more preferably 1 to 5 carbon atoms, and still more preferably 1 or 3 carbon atoms.

The linear hydrocarbon group for $W^{03}$ may have a substituent (a) other than —OH, —COOH, —CN, —SO₂NH₂ and —CONH₂. Examples of the substituent (a) include an alkyl group of 1 to 5 carbon atoms, an aliphatic cyclic group (monocyclic group and polycyclic group), a fluorine atom and a fluorinated alkyl group of 1 to 5 carbon atoms. The aliphatic cyclic group for the substituent (a) preferably has 3 to 30 carbon atoms, more preferably 5 to 30, still more preferably 5 to 20, particularly more preferably 6 to 15, and most preferably 6 to 12. As the aliphatic cyclic group, a group in which two or more hydrogen atoms have been removed from a monocycloalkane or a polycycloalkane such as a bicycloalkane, tricycloalkane or tetracycloalkane can be used. Specific examples include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane.

In addition, the linear hydrocarbon group for $W^{o3}$ may have a plurality of substituents (a), and the plurality of substituents (a) may be mutually bonded to form a ring, as in the case with the structural unit represented by the general formula (a3-13-a) shown below.

[Chemical Formula 45]

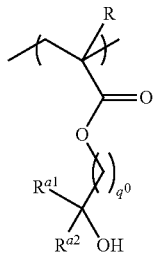

(a3-13-a)

In the formula, R represents a hydrogen atom, an alkyl group of 1 to 5 carbon atoms or a halogenated alkyl group of 1 to 5 carbon atoms; each of $R^{a1}$ and $R^{a2}$ independently represents an alkyl group of 1 to 5 carbon atom, an aliphatic cyclic group (monocyclic group and polycyclic group), a fluorine atom or a fluorinated alkyl group of 1 to 5 carbon atoms, provided that $R^{a1}$ and $R^{a2}$ may be mutually bonded to form a ring; and $q^0$ represents an integer of 1 to 4.

In general formula (a3-13-a), R is the same as defined for R in general formula (a3-1).

The aliphatic cyclic group for $R^{a1}$ and $R^{a2}$ is the same aliphatic cyclic group (monocyclic group and polycyclic group) for substituent (a) as described above.

$R^{a1}$ and $R^{a2}$ may be mutually bonded to form a ring. In such a case, a cyclic group is formed by $R^{a1}$, $R^{a2}$ and the carbon atom having $R^{a1}$ and $R^{a2}$ bonded thereto. The cyclic group may be either a monocyclic group or a polycyclic group. Specific examples include groups in which one or more hydrogen atoms have been removed from a monocycloalkane or polycycloalkane which is exemplified in the explanation of the aliphatic cyclic group (monocyclic group and polycyclic group) for the substituent (a).

$q^0$ is preferably 1 or 2, and more preferably 1.

Specific examples of structural units represented by general formula (a3-13) are shown below. In the formulas shown below, $R^\alpha$ represents a hydrogen atom, a methyl group or a trifluoromethyl group.

[Chemical Formula 46]

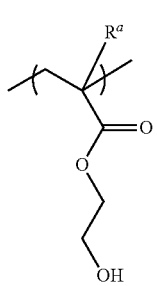

(a3-13-1)

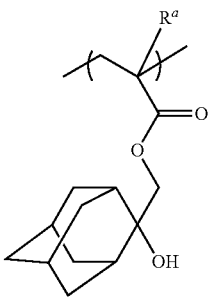

(a3-13-2)

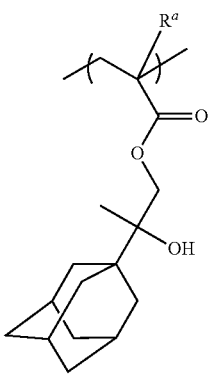

(a3-13-3)

As the structural unit (a3) contained in the component (A1), one type of structural unit may be used, or two or more types may be used.

In the component (A1), the amount of the structural unit (a3) based on the combined total of all structural units constituting the component (A1) is preferably 0 to 85 mol %, and more preferably 0 to 80 mol %. When the amount of the structural unit (a3) is at least as large as the lower limit of the above-mentioned range, the effect of using the structural unit (a3) (such as improvement effect in resolution, lithography properties and pattern shape) can be satisfactorily achieved. On the other hand, when the amount of the structural unit (a3) is no more than the upper limit of the above-mentioned range, a good balance can be achieved with the other structural units.

[Structural Unit (a4)]

The component (A1) may further include a structural unit (a4) containing an acid non-dissociable cyclic group as necessary. When the component (A1) includes the structural unit (a4), the dry etching resistance of the resist pattern to be formed can be improved. The hydrophobicity of the component (A1) is enhanced.

In particular, in the case of conducting the development using a developing solution containing an organic solvent, improvement of hydrophobicity of the polymer contributes to improve resolution, resist pattern shape, and the like.

In the structural unit (a4), an "acid non-dissociable cyclic group" refers to a cyclic group which is not dissociated by the action of the acid generated from the component (B) upon exposure, and remains in the structural unit.

Specific examples of the structural unit (a4) include a structural unit in which an acid dissociable group in the structural unit (a1) has been substituted with an acid non-dissociable cyclic group. Among these, a structural unit (a41) derived from an acrylate ester which may have the hydrogen atom bonded to the carbon atom on the α-position substituted with a substituent and contains a non-acid-dissociable aliphatic polycyclic group, a structural unit (a42) derived from a styrene which may have the hydrogen atom bonded to the carbon atom on the α-position substituted with a substituent, and a structural unit (a43) derived from a vinylnaphthalene which may have the hydrogen atom bonded to the carbon atom on the α-position substituted with a substituent.

In the structural unit (a41), specific examples of the acid non-dissociable aliphatic cyclic group include monovalent aliphatic cyclic groups in which the carbon atom having an atom adjacent to the aliphatic cyclic group (e.g., —O— within —C(=O)—O—) bonded thereto has no substituent (a group or an atom other than hydrogen) and groups in which one hydrogen atom of a primary or secondary alkyl group has been substituted with a monovalent aliphatic cyclic group.

The monovalent aliphatic cyclic group is not particularly limited as long as it is acid non-dissociable, and any of the multitude of conventional polycyclic groups used within the resin component of resist compositions for ArF excimer lasers or KrF excimer lasers (and particularly for ArF excimer lasers) can be used. The aliphatic cyclic group may be either saturated or unsaturated, preferably saturated.

The aliphatic cyclic group may or may not have a substituent. Examples of the substituent include an alkyl group of 1 to 5 carbon atoms, an alkoxyl group of 1 to 5 carbon atoms, a fluorine atom, a fluorinated alkyl group of 1 to 5 carbon atoms, and an oxygen atom (=O).

The basic ring of the "aliphatic cyclic group" exclusive of substituents is not limited to be constituted from only carbon atom and hydrogen atom (not limited to hydrocarbon groups), but is preferably a hydrocarbon group. Further, the "hydrocarbon group" may be either saturated or unsaturated, but is preferably saturated.

The aliphatic cyclic group preferably has 3 to 30 carbon atoms, more preferably 5 to 30, still more preferably 5 to 20, particularly preferably 6 to 15, and most preferably 6 to 12.

The aliphatic cyclic group may be either a monocyclic group or a polycyclic group. As the monocyclic aliphatic cyclic group, a group in which one or more hydrogen atoms have been removed from a monocycloalkane is preferable. The monocycloalkane preferably has 3 to 6 carbon atoms, and specific examples thereof include cyclobutane, cyclopentane and cyclohexane. As the polycyclic aliphatic cyclic group, a group in which one or more hydrogen atoms have been removed from a polycycloalkane is preferable, and the polycyclic group preferably has 7 to 12 carbon atoms. Examples of the polycycloalkane include adamantane, norbornane, isobornane, tricyclodecane and tetracyclododecane. In these aliphatic cyclic groups, part of the carbon atoms constituting the ring may be replaced with an ethereal oxygen atom (—O—).

In terms of the aforementioned effects, as the aliphatic cyclic group, a polycyclic group is preferable. In particular, a bi-, tri- or tetracyclic group is preferable. In consideration of industrial availability and the like, at least one polycyclic group selected from amongst a tricyclodecyl group, an adamantyl group, a tetracyclododecyl group, an isobornyl group and a norbornyl group is particularly desirable.

Specific examples of the monovalent aliphatic cyclic group as an acid non-dissociable aliphatic cyclic group include monovalent aliphatic cyclic groups in which the carbon atom having an atom adjacent to the aliphatic cyclic group (e.g., —O— within —C(=O)—O—) bonded thereto has no substituent (a group or an atom other than hydrogen). More specific examples include groups represented by general formulas (1-1) to (1-9) explained above in relation to the acid dissociable group, in which the $R^{14}$ group has been substituted with a hydrogen atom; and a cycloalkane having a tertiary carbon atom constituting the ring skeleton and having one hydrogen atom removed from.

As the groups in which one hydrogen atom of a primary or secondary alkyl group has been substituted with a monovalent aliphatic cyclic group, a group represented by the formulas (2-1) to (2-6) explained above in relation to the acid dissociable group, in which at least one of $R^{15}$ and $R^{16}$ represents a hydrogen atom, can be mentioned.

As the structural unit (a41), a structural unit in which the acid dissociable group in the structural unit (a11) has been replaced with an acid non-dissociable group can be mentioned, and a structural unit represented by the general formula (a1-0-1) in which $X^1$ is replaced with an acid non-dissociable, aliphatic polycyclic group and a structural unit represented by general formula (a4-0) shown below are preferable, and structural units represented by general formulas (a4-1) and (a4-5) shown below are particularly preferable.

[Chemical Formula 47]

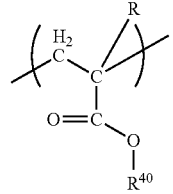

(a4-0)

In the formula, R is the same as defined above; and $R^{40}$ represents an acid non-dissociable, aliphatic polycyclic group.

[Chemical Formula 48]

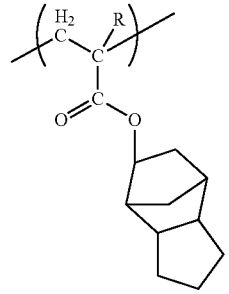

(a4-1)

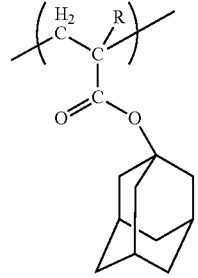

(a4-2)

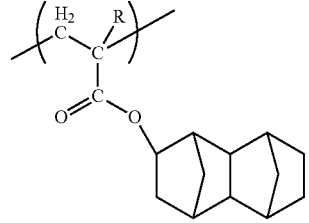

(a4-3)

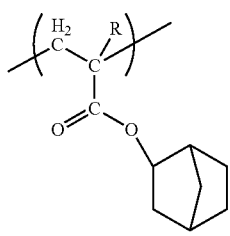

(a4-4)

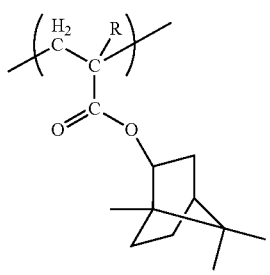

(a4-5)

In the formulas, R is the same as defined above.

Specific examples of the structural unit (a42) includes structural units (a12) represented by the general formula (a12-1) in which px indicating the number of —$OX^c$ bonded to the benzene ring is 0 and qx indicating the number of arbitrary substituent $R^c$ is an integer of 0 to 5.

Specific examples of the structural unit (a43) include a structural unit represented by the general formula (a13-1) in which x indicating the number of —$OX^d$ bonded to the naphthalene ring is 0 and the number of arbitrary substituent $R^d$ is y+z=an integer of 0 to 7.

As the structural unit (a4) contained in the component (A1), 1 type of structural unit may be used, or 2 or more types may be used.

When the component (A1) contains the structural unit (a4), the amount of the structural unit (a4) based on the combined total of all structural units constituting the component (A1) is preferably 1 to 30 mol %, more preferably 1 to 20 mol %, and still more preferably 5 to 20 mol %. When the amount of the structural unit (a4) is at least as large as the lower limit of the above-mentioned range, the effect of using the structural unit (a4) can be satisfactorily achieved. On the other hand, when the amount of the structural unit (a4) is no more than the upper limit of the above-mentioned range, a good balance can be achieved with the other structural units.

The component (A1) may also have a structural unit other than the above-mentioned structural units (a1) to (a4), as long as the effects of the present invention are not impaired.

As such a structural unit, any other structural unit which cannot be classified as one of the above structural units (a1) to (a4) can be used without any particular limitation, and any of the multitude of conventional structural units used within resist resins for ArF excimer lasers, KrF excimer lasers, EB or EUV can be used.

The component (A1) is preferably a polymer containing the structural units (a1), and more preferably a copolymer containing at least one structural unit selected from the structural units (a2) and (a3), as well as the structural unit (a1). Among these, a copolymer containing the structural unit (a1) and the structural unit (a2) is preferable, and a copolymer containing the structural unit (a1), the structural unit (a2) and the structural unit (a3) is particularly preferable.

Examples of the polymers or copolymers include a copolymer consisting of the structural units (a1)) and (a2), a copolymer consisting of the structural units (a1) and (a3), a copolymer consisting of the structural units (a1), (a2) and (a3), and a copolymer consisting of the structural units (a1), (a2), (a3) and (a4).

As the structural unit (a1), structural unit (a2), structural unit (a3) and structural unit (a4) contained in the polymer or copolymer, 1 type of structural unit may be used, or 2 or more types may be used, respectively.

The weight average molecular weight (Mw) (the polystyrene equivalent value determined by gel permeation chromatography) of the component (A1) is not particularly limited, but is preferably 1,000 to 50,000, more preferably 1,500 to 30,000, and most preferably 2,000 to 20,000. When the weight average molecular weight of the component (A1) is no more than the upper limit of the above-mentioned range, the resist composition exhibits a satisfactory solubility in a resist solvent. On the other hand, when the weight average molecular weight is at least as large as the lower limit of the above-mentioned range, the dry etching resistance and the cross-sectional shape of the resist pattern becomes satisfactory.

Further, the dispersity (Mw/Mn) is not particularly limited, but is preferably 1.0 to 5.0, more preferably 1.0 to 3.0, and most preferably 1.2 to 2.5. Here, Mn is the number average molecular weight.

As the component (A1), one type of resin may be used, or two or more types of resins may be used in combination.

The component (A1) can be obtained, for example, by a conventional radical polymerization or the like of the monomers corresponding to each of the structural units, using a radical polymerization initiator such as azobisisobutyronitrile (AIBN).

Furthermore, in the component (A1), by using a chain transfer agent such as HS—$CH_2$—$CH_2$—$CH_2$—$C(CF_3)_2$—OH, a —$C(CF_3)_2$—OH group can be introduced at the terminals of the component (A1). Such a copolymer having introduced a hydroxyalkyl group in which some of the hydrogen atoms of the alkyl group are substituted with fluorine atoms is effective in reducing developing defects and LER (line edge roughness: unevenness of the side walls of a line pattern).

As the monomers for deriving the corresponding structural units, commercially available monomers may be used, or the monomers may be synthesized by a conventional method.

[Component (A2)]

As the component (A2), it is preferable to use a compound that has a molecular weight of at least 500 and less than 4,000, contains a hydrophilic group, and also contains an acid dissociable group described above in connection with the component (A1).

Specific examples include compounds containing a plurality of phenol skeletons in which a part of the hydrogen atoms within hydroxy groups have been substituted with the aforementioned acid dissociable groups.

Examples of the component (A2) include low molecular weight phenolic compounds in which a portion of the hydroxy group hydrogen atoms have been substituted with an aforementioned acid dissociable group, and these types of compounds are known, for example, as sensitizers or heat resistance improvers for use in non-chemically amplified g-line or i-line resists.

Examples of these low molecular weight phenol compounds include bis(4-hydroxyphenyl)methane, bis(2,3,4-trihydroxyphenyl)methane, 2-(4-hydroxyphenyl)-2-(4'-hydroxyphenyl)propane, 2-(2,3,4-trihydroxyphenyl)-2-(2',3', 4'-trihydroxyphenyl)propane, tris(4-hydroxyphenyl) methane, bis(4-hydroxy-3,5-dimethylphenyl)-2-hydroxyphenylmethane, bis(4-hydroxy-2,5-dimethylphenyl)-2-hydroxyphenylmethane, bis(4-hydroxy- 3,5-dimethylphenyl)-3,4-dihydroxyphenylmethane, bis(4-hydroxy-2,5-dimethylphenyl)-3,4-dihydroxyphenylmethane, bis(4-hydroxy-3-methylphenyl)-3,4-dihydroxyphenylmethane, bis(3-cyclohexyl-4-hydroxy-6-methylphenyl)-4-hydroxyphenylmethane, bis(3-cyclohexyl-4-hydroxy-6-methylphenyl)-3,4-dihydroxyphenylmethane, 1-[1-(4-hydroxyphenyl)isopropyl]-4-[1,1-bis(4-hydroxyphenyl)ethyl]benzene, and dimers, trimers, tetramers, pentamers and hexamers of formalin condensation products of phenols such as phenol, m-cresol, p-cresol and xylenol. Needless to say, the low molecular weight phenol compound is not limited to these examples.

In particular, as the low molecular weight phenol compound, a phenol compound having 2 to 6 triphenylmethane skeletons is preferable in terms of resolution and LWR.

The acid decomposable group is not particularly limited, and the same acid decomposable groups as those described above in relation to the component (A1) can be mentioned.

As the component (A2), one type of resin may be used, or two or more types of resins may be used in combination.

In the resist composition of the present invention, as the component (A), one type may be used, or two or more types of compounds may be used in combination.

Of these, the component (A) preferably includes the component (A1).

In the component (A), the amount of the component (A1) based on the total weight of the component (A) is preferably 25% by weight or more, more preferably 50% by weight or more, still more preferably 75% by weight or more, and may be even 100% by weight. When the amount of the component (A1) is 25% by weight or more, various lithography properties such as mask error factor (MEF), circularity and reducing roughness are improved.

In the resist composition according to the present invention, the amount of the component (A) can be appropriately adjusted depending on the thickness of the resist film to be formed, and the like.

<Component (C)>

The component (C) is a photoreactive quencher.

The "quencher" is an acid diffusion control agent which traps acid generated from the component (B) or the like upon exposure.

The "photoreactive quencher" acts as an quencher prior to exposure (at exposed portions), and does not act as a quencher after exposure (after irradiation of radiation such as EB and EUV).

The resist composition according to present invention includes at least one compound represented by general formula (1) (hereafter, referred to as component (C1)) shown below as a component (C). Therefore, the resist composition containing the component (C1) is superior in storage stability to the resist composition containing a conventional photoreactive quencher.

[Chemical Formula 49]

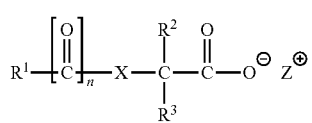

(c1)

wherein $R^1$ represents a hydrogen atom or a hydrocarbon group of 1 to 20 carbon atoms which may have a substituent; each of $R^2$ and $R^3$ independently represents a hydrogen atom or a hydrocarbon group of 1 to 20 carbon atoms which may have a substituent; at least two of $R^1$ to $R^3$ may be mutually bonded to form a ring; X represents an oxygen atom or a sulfur atom; n represents 0 or 1; and $Z^+$ represents an organic cation.

In formula (c1), $R^1$ represents a hydrocarbon group of 1 to 20 carbon atoms which may have a substituent, A hydrocarbon group for $R^1$ "may have a substituent" means that part of the carbon atoms constituting the hydrocarbon group may be substituted with a substituent group containing a hetero atom, or part or all of the hydrogen atoms constituting the hydrocarbon group may be substituted with a substituent group.

The hydrocarbon group for $R^1$ may be either an aromatic hydrocarbon group or an aliphatic hydrocarbon group.

The aromatic hydrocarbon group is a hydrocarbon group having at least one aromatic ring.

The aromatic ring is not particularly limited as long as it is a cyclic conjugation ring having 4n+2 of π electrons, and may be a monocyclic or a polycyclic. The number of the atom constituting the ring skeleton of the aromatic ring is preferably 5 to 20 carbon atoms, more preferably 5 to 15, still more preferably 6 to 15, and particularly preferably 6 to 12. Examples of the aromatic ring include aromatic hydrocarbon rings such as benzene, biphenyl, fluorene, naphthalene, anthracene and phenanthrene and aromatic heterocycles in which part of the carbon atoms of the aromatic hydrocarbon ring have been substituted with a hetero atom. Examples of hetero atoms within the aromatic heterocycle include an oxygen atom, a nitrogen atom, and a sulfur atom. Specific examples of aromatic heterocycles include a pyridine ring and a thiophene ring.

Specific examples of the aromatic hydrocarbon group for $R^1$ include a group in which two hydrogen atoms have been removed from the aromatic hydrocarbon ring or aromatic heterocycle (aryl group or heteroaryl group); a group in which two hydrogen atoms have been removed from an aromatic compound having two or more aromatic rings (for example, biphenyl or fluorene); and a group in which one hydrogen atom of the aromatic hydrocarbon ring or aromatic heterocycle has been substituted with an alkylene group (arylalkyl groups such as a benzyl group, a phenethyl group, a 1-naphthylmethyl group, a 2-naphthylmethyl group, a 1-naphthylethyl group and a 2-naphthylethyl group and heteroarylalkyl groups). The alkylene group with which a hydrogen atom of the aromatic hydrocarbon ring or aromatic heterocycles has been substituted, preferably has 1 to 4 carbon atom, more preferably 1 or 2, and most preferably 1.

The aromatic hydrocarbon group for $R^1$ preferably has 5 to 20 carbon atoms, more preferably 5 to 15, still more preferably 6 to 15, and particularly preferably 6 to 12. Herein, when the aromatic hydrocarbon group has part or all of hydrogen atoms have been substituted with a substituent, the number of carbon atoms refers to the number of carbon atoms constituting the ring skeleton, excluding the number of carbon atoms within a substituent.

The aromatic hydrocarbon group may have part or all of the hydrogen atoms constituting the aromatic hydrocarbon group substituted with a substituent. For example, the hydrogen atom bonded to the aromatic ring in the aromatic hydrocarbon group may be substituted with a substituent.

Specific examples thereof include an alkyl group, an alkoxy group, a halogen atom, a halogenated alkyl group, a hydroxy group, an oxo group (=O), a cyano group, an aryl group, an alkoxyalkyloxy group, an alkoxycarbonylalkyloxy group, a carboxy group, —COO⁻Z⁺ (wherein Z⁺ is the same as defined above), —C(=O)—O—$R^{6'}$, —O—C(=O)—$R^{7'}$ and —O—$R^{8'}$. Each of $R^{6'}$, $R^{7'}$ and $R^{8'}$ independently represents a linear or branched saturated hydrocarbon group of 1 to 25 atoms, a cyclic saturated hydrocarbon group of 3 to 20 carbon atoms or a linear or branched, aliphatic unsaturated hydrocarbon group of 2 to 5 carbon atoms.

The alkyl group as a substituent for the aromatic hydrocarbon group is preferably an alkyl group of 1 to 5 carbon atoms, and a methyl group, an ethyl group, a propyl group, an n-butyl group or a tert-butyl group is most desirable.

The alkoxy group as a substituent for the aromatic hydrocarbon group is preferably an alkoxy group having 1 to 5 carbon atoms, more preferably a methoxy group, an ethoxy group, an n-propoxy group, an iso-propoxy group, an n-butoxy group or a tert-butoxy group, and most preferably a methoxy group or an ethoxy group.

Examples of the halogen atom as a substituent for the aromatic hydrocarbon group include a fluorine atom, a chlorine atom, a bromine atom and an iodine atom, and a fluorine atom is preferable.

Example of the halogenated alkyl group as a substituent for the aromatic hydrocarbon group includes a group in which part or all of the hydrogen atoms within the aforementioned alkyl group have been substituted with the aforementioned halogen atoms.

As the aryl group as a substituent for the aromatic hydrocarbon group, a group in which one hydrogen atom has been removed from the aromatic hydrocarbon ring can be mentioned. Among these, an aryl group of 6 to 12 carbon atoms is preferable, and a phenyl group or a naphthyl group is more desirable.

Examples of the alkoxyalkyloxy group as a substituent for the aromatic hydrocarbon group includes:

a group represented by general formula —O—C($R^{47}$)($R^{48}$)—O—$R^{49}$ [in the formula, each of $R^{47}$ and $R^{48}$ independently represents a hydrogen atom or a linear or branched alkyl group; and $R^{49}$ represents an alkyl group].

The alkyl group for $R^{47}$ and $R^{48}$ preferably has 1 to 5 carbon atoms, and may be either linear or branched, and is preferably an ethyl group or a methyl group, and most preferably a methyl group.

It is preferable that at least one of $R^{47}$ and $R^{48}$ be a hydrogen atom. It is particularly desirable that at least one of $R^{47}$ and $R^{48}$ be a hydrogen atom, and the other be a hydrogen atom or a methyl group.

The alkyl group for $R^{49}$ preferably has 1 to 15 carbon atoms, and may be linear, branched or cyclic.

The linear or branched alkyl group for $R^{49}$ preferably has 1 to 5 carbon atoms. Examples thereof include a methyl group, an ethyl group, a propyl group, an n-butyl group and a tert-butyl group.

The cyclic alkyl group for $R^{49}$ preferably has 4 to 15 carbon atoms, more preferably 4 to 12, and most preferably 5 to 10. Specific examples thereof include groups in which one or more hydrogen atoms have been removed from a monocycloalkane or a polycycloalkane such as a bicycloalkane, tricycloalkane or tetracycloalkane, and which may or may not be substituted with an alkyl group of 1 to 5 carbon atoms, a fluorine atom or a fluorinated alkyl group. Examples of the monocycloalkane include cyclopentane and cyclohexane. Examples of polycycloalkanes include adamantane, norbornane, isobornane, tricyclodecane and tetracyclododecane. Among these, a group in which one or more hydrogen atoms have been removed from adamantane is preferable.

Examples of the alkoxycarbonylalkyloxy group as a substituent for the aromatic hydrocarbon group includes:

a group represented by general formula —O—$R^{50}$—C(=O)—O—$R^{56}$ [in the formula, $R^{50}$ represents a linear or branched alkylene group; and $R^{56}$ represents a tert-alkyl group].

The linear or branched alkylene group for $R^{50}$ preferably has 1 to 5 carbon atoms, and examples thereof include a methylene group, an ethylene group, a trimethylene group, a tetramethylene group and a 1,1-dimethylethylene group.

The alkyl group for $R^{56}$ is a tertiary alkyl group, and examples thereof include a 2-methyl-2-adamantyl group, a 2-ethyl-2-adamantyl group, a 1-methyl-1-cyclopentyl group, a 1-ethyl-1-cyclopentyl group, a 1-methyl-1-cyclohexyl group, a 1-ethyl-1-cyclohexyl group, a 1-(1-adamantyl)-1-methylethyl group, a 1-(1-adamantyl)-1-methylpropyl group, a 1-(1-adamantyl)-1-methylbutyl group, a 1-(1-adamantyl)-1-methylpentyl group, a 1-(1-cyclopentyl)-1-methylethyl group, a 1-(1-cyclopentyl)-1-methylpropyl group, a 1-(1-cyclopentyl)-1-methylbutyl group, a 1-(1-cyclopentyl)-1-methylpentyl group, a 1-(1-cyclohexyl)-1-methylethyl group, a 1-(1-cyclohexyl)-1-methylpropyl group, a 1-(1-cyclohexyl)-1-methylbutyl group, a 1-(1-cyclohexyl)-1-methylpentyl group, a tert-butyl group, a tert-pentyl group and a tert-hexyl group.

Further, a group in which $R^{56}$ in the group represented by the aforementioned general formula: —O—$R^{50}$—C(=O)—O—$R^{56}$ has been substituted with $R^{56'}$ can also be mentioned. $R^{56'}$ represents a hydrogen atom, an alkyl group, a fluorinated alkyl group or an aliphatic cyclic group which may contain a hetero atom.

The alkyl group for $R^{56'}$ is the same as defined for the alkyl group for the aforementioned $R^{49}$.

Examples of the fluorinated alkyl group for $R^{56'}$ include groups in which part or all of the hydrogen atoms within the alkyl group for $R^{49}$ has been substituted with a fluorine atom.

Examples of the aliphatic cyclic group for $R^{56'}$ which may contain a hetero atom include an aliphatic cyclic group which does not contain a hetero atom, an aliphatic cyclic group containing a hetero atom in the ring structure, and an aliphatic cyclic group in which a hydrogen atom has been substituted with a hetero atom.

As an aliphatic cyclic group for $R^{56'}$ which does not contain a hetero atom, a group in which one or more hydrogen atoms have been removed from a monocycloalkane or a polycycloalkane such as a bicycloalkane, a tricycloalkane or a tetracycloalkane can be mentioned. Examples of the monocycloalkane include cyclopentane and cyclohexane. Examples of polycycloalkanes include adamantane, norbornane, isobornane, tricyclodecane and tetracyclododecane. Among these, a group in which one or more hydrogen atoms have been removed from adamantane is preferable.

Specific examples of the aliphatic cyclic group for $R^{56'}$ containing a hetero atom in the ring structure include groups represented by formulas (L1) to (L7) and (S1) to (S4) described later in the explanation of the aliphatic hydrocarbon group for $R^1$.

As the aliphatic cyclic group for $R^{56'}$ in which a hydrogen atom has been substituted with a hetero atom, an aliphatic cyclic group in which a hydrogen atom has been substituted with an oxygen atom (=O) can be mentioned.

In the groups —C(=O)—O—$R^{6'}$, —O—C(=O)—$R^{7'}$ and —O—$R^{8'}$, each of $R^{6'}$, $R^{7'}$ and $R^{8'}$ independently represents a linear or branched saturated hydrocarbon group of 1 to 25 atoms, a cyclic saturated hydrocarbon group of 3 to 20 carbon atoms or a linear or branched, aliphatic unsaturated hydrocarbon group of 2 to 5 carbon atoms.

The linear or branched, saturated hydrocarbon group preferably has 1 to 25 carbon atoms, more preferably 1 to 15, and still more preferably 4 to 10.

Examples of the linear, saturated hydrocarbon group include a methyl group, an ethyl group, a propyl group, a butyl group, a pentyl group, a hexyl group, a heptyl group, an octyl group, a nonyl group and a decyl group.

Examples of the branched, saturated hydrocarbon group include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group and a 4-methylpentyl group, but excluding tertiary alkyl groups.

The linear or branched, saturated hydrocarbon group may have a substituent. Examples of the substituent include an alkoxy group, a halogen atom, a halogenated alkyl group, a hydroxyl group, an oxygen atom (=O), a cyano group and a carboxy group.

The alkoxy group as a substituent for the linear or branched saturated hydrocarbon group is preferably an alkoxy group having 1 to 5 carbon atoms, more preferably a methoxy group, an ethoxy group, an n-propoxy group, an iso-propoxy group, an n-butoxy group or a tert-butoxy group, and most preferably a methoxy group or an ethoxy group.

Examples of the halogen atom as a substituent for the linear or branched, saturated alkyl group include a fluorine atom, a chlorine atom, a bromine atom and an iodine atom, and a fluorine atom is preferable.

Example of the halogenated alkyl group as a substituent for the linear or branched, saturated hydrocarbon group includes a group in which part or all of the hydrogen atoms within the aforementioned linear or branched, saturated hydrocarbon group have been substituted with the aforementioned halogen atoms.

The cyclic saturated hydrocarbon group of 3 to 20 carbon atoms for $R^{6'}$, $R^{7'}$ and $R^{8'}$ may be either a polycyclic group or a monocyclic group, and examples thereof include groups in which one hydrogen atom has been removed from a monocycloalkane, and groups in which one hydrogen atom has been removed from a polycycloalkane (e.g., a bicycloalkane, a tricycloalkane or a tetracycloalkane). More specific examples include groups in which one hydrogen atom has been removed from a monocycloalkane such as cyclopentane, cyclohexane, cycloheptane or cyclooctane; and groups in which one or more hydrogen atoms have been removed from a polycycloalkane such as adamantane, norbornane, isobornane, tricyclodecane or tetracyclododecane.

The cyclic, saturated hydrocarbon group may have a substituent. For example, part of the carbon atoms constituting the ring within the cyclic alkyl group may be substituted with a hetero atom, or a hydrogen atom bonded to the ring within the cyclic alkyl group may be substituted with a substituent.

In the former example, a heterocycloalkane in which part of the carbon atoms constituting the ring within the aforementioned monocycloalkane or polycycloalkane has been substituted with a hetero atom such as an oxygen atom, a sulfur atom or a nitrogen atom, and one hydrogen atom has been removed therefrom, can be used. Further, the ring may contain an ester bond (—C(=O)—O—) in the ring structure thereof. More specific examples include a lactone-containing monocyclic group, such as a group in which one hydrogen atom has been removed from γ-butyrolactone; and a lactone-containing polycyclic group, such as a group in which one hydrogen atom has been removed from a bicycloalkane, tricycloalkane or tetracycloalkane containing a lactone ring.

In the latter example, as the substituent, the same substituent groups as those for the aforementioned linear or branched alkyl group, or an alkyl group of 1 to 5 carbon atoms can be used.

Alternatively, $R^{6'}$, $R^{7'}$ and $R^{8'}$ may be a combination of a linear or branched alkyl group and a cyclic group.

Examples of the combination of a linear or branched alkyl group with a cyclic alkyl group include groups in which a cyclic alkyl group as a substituent is bonded to a linear or branched alkyl group, and groups in which a linear or branched alkyl group as a substituent is bonded to a cyclic alkyl group.

Examples of the linear aliphatic unsaturated hydrocarbon group for $R^{6'}$, $R^{7'}$ and $R^{8'}$ include a vinyl group, a propenyl group (an allyl group) and a butynyl group.

Examples of the branched aliphatic unsaturated hydrocarbon group for $R^{6'}$, $R^{7'}$ and $R^{8'}$ include a 1-methylpropenyl group and a 2-methylpropenyl group.

The aforementioned linear or branched, aliphatic unsaturated hydrocarbon group may have a substituent. Examples of substituents include the same substituents as those which the aforementioned linear or branched alkyl group may have.

Among the aforementioned examples, as $R^{7'}$ and $R^{8'}$, in terms of improvement in lithography properties and shape of the resist pattern, a linear or branched, saturated hydrocarbon group of 1 to 15 carbon atoms or a cyclic saturated hydrocarbon group of 3 to 20 carbon atoms is preferable.

The aliphatic hydrocarbon group for $R^1$ may be either a saturated hydrocarbon group (that is, alkyl group), or an unsaturated aliphatic hydrocarbon group. Further, the aliphatic hydrocarbon group may be chain-like or cyclic. The chain-like aliphatic hydrocarbon group may be linear or branched. The cyclic aliphatic hydrocarbon group may be either a polycyclic group or a monocyclic group.

In the aliphatic hydrocarbon group, part of the carbon atoms constituting the aliphatic hydrocarbon group may be substituted with a substituent group containing a hetero atom, or part or all of the hydrogen atoms constituting the aliphatic hydrocarbon group may be substituted with a substituent.

With respect to the substituent containing a hetero atom for substituting part of the carbon atom constituting the aliphatic hydrocarbon group, a hetero atom is an atom other than carbon and hydrogen, and examples thereof include an oxygen atom, a nitrogen atom, a sulfur atom and a halogen atom. Examples of the halogen atom include a fluorine atom, a chlorine atom, an iodine atom and a bromine atom.

The substituent group containing a hetero atom may be a group consisting of a hetero atom, or may be a group containing a group or atom other than a hetero atom.

Specific examples of the substituent group for substituting part of the carbon atoms include —O—, —C(=O)—O—, —C(=O)—, —O—C(=O)—O—, —C(=O)—NH—, —NH— (wherein the H may be substituted with a substituent such as an alkyl group or an acyl group), —S—, —S(=O)$_2$— and —S(=O)$_2$—O—. When the aliphatic hydrocarbon group is cyclic, the aliphatic hydrocarbon group may contain any of these substituent groups in the ring structure.

Specific examples of the substituent for substituting part of the hydrogen atom constituting the aliphatic hydrocarbon group, include an alkoxy group, a halogen atom, a halogenated alkyl group, a hydroxy group, an oxo group (=O), a cyano group, an aryl group, an alkoxyalkyloxy group, an alkoxycarbonylalkyloxy group, a carboxy group, —COO$^-$Z$^+$ (wherein Z$^+$ is the same as defined above), —C(=O)—O—R$^{6'}$, —O—C(=O)—R$^{7'}$ and —O—R$^{8'}$. Each of R$^{6'}$, R$^{7'}$ and R$^{8'}$ independently represents a linear or branched saturated hydrocarbon group of 1 to 25 atoms, a cyclic saturated hydrocarbon group of 3 to 20 carbon atoms or a linear or branched, aliphatic unsaturated hydrocarbon group of 2 to 5 carbon atoms. When the aliphatic hydrocarbon group is cyclic, the aliphatic hydrocarbon group may have an alkyl group as a substituent. As these substituents, the same groups as those described above for the substituent of the aforementioned aromatic hydrocarbon groups can be mentioned.

As the aliphatic hydrocarbon group for $R^1$, a chain-like alkyl group or a chain-like unsubstituted hydrocarbon group is preferable.

The chain-like alkyl group has 1 to 20 carbon atoms, preferably 1 to 15, more preferably 1 to 10, and still more preferably 1 to 5.

The chain-like alkyl group may be linear or branched.

Specific examples of linear alkyl group include a methyl group, an ethyl group, a propyl group, a butyl group, a pentyl group, a hexyl group, a heptyl group, an octyl group, a nonyl group, a decanyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecyl group and an icosyl group.

Specific examples of branched alkyl groups include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group and a 4-methylpentyl group.

The chain-like alkyl groups may have part or all of the hydrogen atoms constituting the alkyl group substituted with a substituent. Examples of the substituent include the same substituents as those described above for substituting part or all of the hydrogen atoms constituting the aliphatic hydrocarbon group.

Among these, as the substituent, a halogen atom is preferable, and a fluorine atom is particularly desirable.

The chain-like, unsaturated hydrocarbon group has 2 to 20 carbon atoms, preferably 2 to 10 carbon atoms, more preferably 2 to 5 carbon atoms, still more preferably 2 to 4 carbon atoms, and particularly preferably 3.

The chain-like unsaturated hydrocarbon group may be linear or branched.

Examples of linear unsaturated hydrocarbon groups include a vinyl group, a propenyl group (i.e., allyl group) and a butynyl group.

Examples of branched unsaturated hydrocarbon groups include a 1-methylpropenyl group and a 2-methylpropenyl group.

Among the above-mentioned examples, as the chain-like unsaturated hydrocarbon group, a propenyl group (i.e., allyl group) is particularly desirable.

The chain-like alkyl groups may have part or all of the hydrogen atoms constituting the alkyl group substituted with a substituent. Examples of the substituent include the same substituents as those described above for substituting part or all of the hydrogen atoms constituting the aliphatic hydrocarbon group.

Among these, as the substituent, a halogen atom is preferable, and a fluorine atom is particularly desirable.

The number of carbon atoms within the cyclic alkyl group is 3 to 20, preferably 5 to 20, and more preferably 5 to 10.

The cyclic alkyl group may be either a polycyclic group or a monocyclic group.

Examples of the aliphatic monocyclic groups include groups in which one or more hydrogen atoms have been removed from a monocycloalkane. The monocycloalkane preferably has 5 to 6 carbon atoms, and specific examples thereof include cyclopentane and cyclohexane.

As an example of an polycyclic alkyl group, a group in which one or more hydrogen atoms have been removed from a polycycloalkane such as a bicycloalkane, tricycloalkane or tetracycloalkane can be given. The polycycloalkane preferably has 7 to 12 carbon atoms, and examples thereof include adamantane, norbornane, isobornane, tricyclodecane and tetracyclododecane.

In the cyclic alkyl group, part or all of the hydrogen atoms bonded to the carbon atoms constituting the ring structure may be substituted with a substituent. Examples of the substituent include the same substituents as those described above for substituting part or all of the hydrogen atoms constituting the aliphatic hydrocarbon group.

Further, part of the carbon atoms constituting the cyclic alkyl group may be substituted with a substituent containing a hetero atom. Examples of the substituent include the same substituents as those described above for substituting part of the carbon atoms constituting the aliphatic hydrocarbon group. Among these, —O—, —C(=O)—O—, —S—, —S(=O)$_2$— and —S(=O)$_2$—O— are preferable.

Preferable examples of cyclic alkyl groups in which part of the carbon atoms has been substituted with a substituent containing a hetero atom include cyclic groups represented by formulas (L1) to (L7) and (S1) to (S4) shown below.

[Chemical Formula 50]

(L1)

(L2)

(L3)

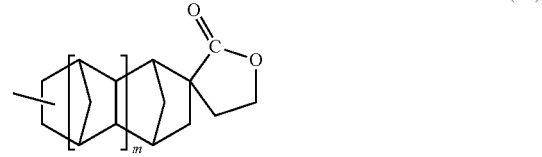
(L4)

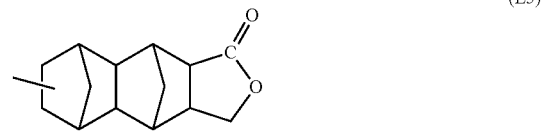
(L5)

(L6)
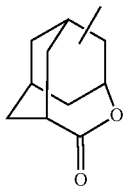

(L7)
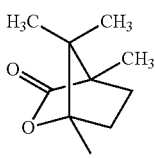

(S1)
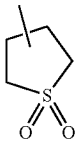

(S2)
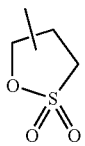

(S3)
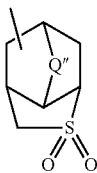

(S4)
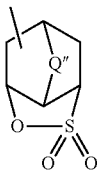

In the formulas, Q" represents an alkylene group of 1 to 5 carbon atoms, —O—, —S—, —O—R$^{94'}$— or —S—R$^{95'}$—, and R$^{94'}$ and R$^{95'}$ each independently represent an alkylene group of 1 to 5 carbon atoms; and m represents an integer of 0 or 1.

In the formulas, the alkylene group for Q", R$^{94'}$ or R$^{95'}$ is preferably a linear or branched alkylene group, and preferably has 1 to 12 carbon atoms, more preferably 1 to 5, and still more preferably 1 to 3.

Specific examples of the alkylene group include a methylene group [—CH$_2$—]; alkylmethylene groups such as —CH(CH$_3$)—, —CH(CH$_2$CH$_3$)—, —C(CH$_3$)$_2$—, —C(CH$_3$)(CH$_2$CH$_3$)—, —C(CH$_3$)(CH$_2$CH$_2$CH$_3$)— and —C(CH$_2$CH$_3$)$_2$—; an ethylene group [—CH$_2$CH$_2$—]; alkylethylene groups such as —CH(CH$_3$)CH$_2$—, —CH(CH$_3$)CH(CH$_3$)—, —C(CH$_3$)$_2$CH$_2$— and —CH(CH$_2$CH$_3$)CH$_2$—; a trimethylene group (n-propylene group) [—CH$_2$CH$_2$CH$_2$—]; alkyltrimethylene groups such as —CH(CH$_3$)CH$_2$CH$_2$— and —CH$_2$CH(CH$_3$)CH$_2$—; a tetramethylene group [—CH$_2$CH$_2$CH$_2$CH$_2$—]; alkyltetramethylene groups such as —CH(CH$_3$)CH$_2$CH$_2$CH$_2$— and —CH$_2$CH(CH$_3$)CH$_2$CH$_2$—; and a pentamethylene group [—CH$_2$CH$_2$CH$_2$CH$_2$CH$_2$—]. Among these examples, a methylene group or an alkylmethylene group is preferable, and a methylene group is particularly desirable.

In these cyclic groups, part of the hydrogen atoms bonded to the carbon atoms constituting the ring structure may be substituted with a substituent. Examples of the substituent include the same substituents as those described above for substituting part or all of the hydrogen atoms bonded to the carbon atom constituting the ring structure within the cyclic alkyl group.

As R$^1$, a hydrogen atom, a chain-like alkyl group of 1 to 15 carbon atoms which may have a substituent, a cyclic alkyl group of 3 to 20 carbon atoms which may have a substituent or an aromatic hydrocarbon group of 5 to 20 carbon atoms which may have a substituent is preferable, and a chain-like alkyl group of 1 to 15 carbon atoms which may have a substituent, a cyclic alkyl group or 3 to 20 carbon atoms which may have a substituent or an aromatic hydrocarbon group of 5 to 20 carbon atoms which may have a substituent is more preferable.

Among these, when n in the formula (c1) is 0, a chain-like alkyl group or 1 to 15 carbon atoms which may have a substituent or an aromatic hydrocarbon group of 5 to 20 carbon atoms which may have a substituent is preferable, and a methyl group which may have the hydrogen atom substituted with a fluorine atom, an ethyl group which may have the hydrogen atom substituted with a fluorine atom or a phenyl group which may have the hydrogen atom substituted with a fluorine atom is most preferable.

When n in the formula (c1) is 1, a cyclic alkyl group of 3 to 20 carbon atoms which may have a substituent is preferable, and a polycyclic alkyl group is particularly preferable.

As the polycyclic alkyl group, a group in which one or more hydrogen atoms have been removed from a polycycloalkane which may have a hydrogen atom substituted with a fluorine atom, and groups represented by the formulas (L2) to (L7), (S3) and (S4) are preferable.

Examples of the polycycloalkane include the same polycycloalkanes as described above. Examples of the group in which one hydrogen atom has been removed from a polycycloalkane include an adamantyl group, a norbornyl group, an isobornyl group, a tricyclodecyl group, a tetracyclododecyl group and the like, and these groups may have a hydrogen atom substituted with a fluorine atom.

As the polycyclic alkyl group, an adamantyl group which may have a hydrogen atom substituted with a fluorine atom or a cyclic group represented by the formula (L7) is most preferable.

Examples of the hydrocarbon group of 1 to 20 carbon atoms which may have a substituent for R$^2$ and R$^3$, the same hydrocarbon group of 1 to 20 carbon atoms which may have a substituent for R$^1$.

In the present invention, as R$^2$ and R$^3$, a hydrogen atom or an alkyl group of 1 to 5 carbon atom is preferable, and a hydrogen atom is most preferable.

In the formula (c1), two or three of R$^1$ to R$^3$ may be mutually bonded to form a ring. For example, R$^2$ and R$^3$ may be mutually bonded to form a ring, R$^1$ and R$^3$ may be mutually bonded to form a ring, and all of R$^1$ to R$^3$ may be mutually bonded to form a ring. Among these, it is preferable that R$^2$ and R$^3$ are mutually bonded or all of R$^1$ to R$^3$ are mutually bonded.

When R$^2$ and R$^3$ are mutually bonded to form a ring, the ring to be formed may be either saturated or unsaturated, preferably saturated. Further, the ring may be monocyclic or polycyclic. For example, in the case where one or both of R$^2$ and R$^3$ contain a ring structure (i.e., for example, in the case where at least one or both of these groups represent a cyclic alkyl group or aromatic hydrocarbon group), when these groups are mutually bonded, a polycyclic ring (fused ring) is formed.

Specific examples of the rings which formed by $R^2$ and $R^3$ mutually bonded include a groups in which at least two hydrogen atoms bonded to the same carbon atom have been removed from a monocycloalkane described above in relation to the cyclic alkyl group, and groups in which two hydrogen atoms bonded to the same carbon atom have been removed from a polycycloalkane.

When $R^2$ and $R^3$ are mutually bonded to form a ring, preferable examples of the component (C1) include a compound represented by general formula (c1-01) shown below.

[Chemical Formula 51]

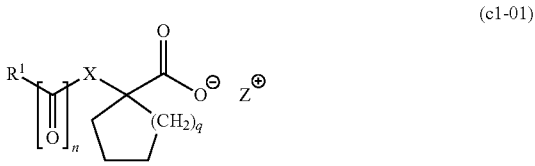

(c1-01)

In the formula, $R^1$, n, X and $Z^+$ are the same as those defined above; and q represents an integer of 0 to 2.

When all of $R^1$ to $R^3$ are mutually bonded to form a ring, the ring to be formed may be either saturated or unsaturated, preferably saturated. The ring is typically a polycyclic ring.

Specific examples of the rings which formed by all of $R^1$ to $R^3$ mutually bonded include groups in which the hydrogen atom on the tertiary-carbon atom have been removed from a polycycloalkane which is described above in relation to the cyclic alkyl group and which has a tertiary-carbon atom bonded to three carbon atoms constituting the ring skeleton and the carbon atom adjacent to the tertiary-carbon atom has been substituted with an oxygen atom or a sulfur atom. In the groups, one of the carbon atoms bonded to the oxygen atom in the ring skeleton other than the tertiary-carbon atom may be substituted with an oxo group (=O).

Specific examples of the groups include a group in which the hydrogen atom have been removed from the tertiary-carbon atom in the lactone-ring which has a tertiary-carbon atom adjacent to the oxygen atom in the ring structure (e.g. a groups in which a binding portion of the groups represented by the formula (L2) and (L5) to (L7) is bonded to the tertiary-carbon atom adjacent to the oxygen atom (—O—).

X may be either an oxygen atom or a sulfur atom.

In terms of ease of synthesis, when n is 1, X is preferably an oxygen atom.

n represents either 0 or 1. It is preferable that n is 1 (i.e., —[C(=O)]n-X— forms an ester bond), because a pKa value of the conjugate acid corresponding to the anion moiety of the component (C1) becomes low as compared to a pKa value of the conjugated acid when n is 0 (i.e., —[C(=O)]$_n$—X— forms an ether bond), and thereby increasing the stability of the resist component.

When n is 0, $R^1$ is preferably an aromatic hydrocarbon group, an aliphatic hydrocarbon group which has the hydrogen atom substituted with a fluorine atom and an aliphatic hydrocarbon group of 2 or more carbon atoms.

It is preferable that $R^1$ is an aromatic hydrocarbon group or an aliphatic hydrocarbon group which has the hydrogen atom substituted with a fluorine atom, because the pKa value of the component (C1) becomes low. It is preferable that $R^1$ is an aliphatic hydrocarbon group of 2 or more carbon atoms, because the compatibility of the component (C1) with the component (A) is improved. The aliphatic hydrocarbon group of 2 or more carbon atoms is preferably the aforementioned cyclic alkyl group.

$Z^+$ represents an organic cation.

The organic cation for $Z^+$ is not particularly limited, and an organic cation conventionally known as the cation moiety of a photo-decomposable base (photoreactive quencher) used as a quencher for a resist composition or the cation moiety of an onium salt (onium salt acid generator) used as an acid generator component can be used. Examples of the organic cation include a cation moiety represented by general formula (ca-1) or (ca-2) shown below. Among these, a cation moiety represented by the formula (ca-1) is preferable.

[Chemical Formula 52]

(ca-1)

(ca-2)

In formulas, each of $R^{1"}$ to $R^{3"}$ and $R^{5"}$ to $R^{6"}$ independently represents an aryl group, alkyl group or alkenyl group which may have a substituent; in formula (ca-1), two of $R^{1"}$ to $R^{3"}$ may be bonded to each other to form a ring with the sulfur atom.

$R^{1"}$ to $R^{3"}$ in the formula (ca-1) and $R^{5"}$ to $R^{6"}$ in the formula (ca-2) are each the same as defined for $R^{1"}$ to $R^{3"}$ in the formula (b-1) and $R^{5"}$ to $R^{6"}$ in the formula (b-2).

More specific examples of the component (C1) include compounds represented by general formulas (c1-1), (c1-2) and (3-4) shown below.

The compound represented by the formula (c1-1) or (c1-2) corresponds to the compound represented by the formula (c1) in which n is 0, and a compound represented by the formula (c1-3) corresponds to the compound represented by the formula (c1) in which n is 1.

[Chemical Formula 53]

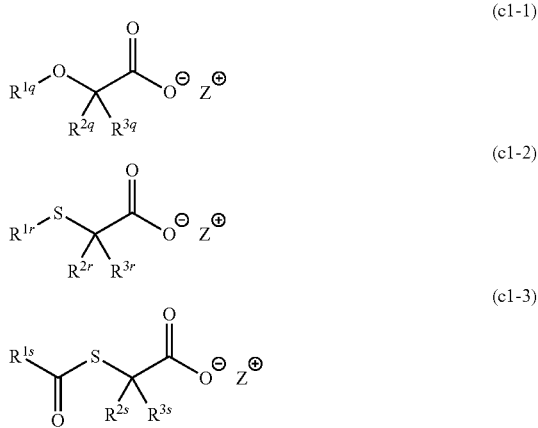

(c1-1)

(c1-2)

(c1-3)

In the formulas, $Z^+$ is the same as defined above; $R^{1q}$ is a hydrogen atom or a hydrocarbon group of 1 to 20 carbon atoms which may have a substituent; each of $R^{2q}$ and $R^{3q}$ independently represents a hydrogen atom, or a hydrocarbon group of 1 to 20 carbon atoms which may have a substituent, $R^{2q}$ and $R^{3q}$ may be mutually bonded to form a ring; $R^{1r}$ represents a hydrogen atom, or a hydrocarbon group of 1 to 20 carbon atoms which may have a substituent; each of $R^{2r}$ and $R^{3r}$ independently represents a hydrogen atom or a hydrocarbon group of 1 to 20 carbon atoms which may have a substituent, $R^{2r}$ and $R^{3r}$ may be mutually bonded to form a ring; and $R^{1s}$ represents a hydrogen atom, or a hydrocarbon group of 1 to 20 carbon atoms which may have a substituent; each of $R^{2s}$ and $R^{3s}$ independently represents a hydrogen atom or a hydrocarbon group of 1 to 20 carbon atoms which may have a substituent, $R^{2s}$ and $R^{3s}$ may be mutually bonded to form a ring.

In the formula (c1-1), $Z^+$ is the same as defined for $Z^+$ in the general formula (c1).

In the (c1-1), $R^{1q}$, $R^{2q}$ and $R^{3q}$ are the same groups as those described above for $R^1$, $R^2$ and $R^3$ in the general formula (c1).

As $R^1$, a hydrogen atom, a chain-like alkyl group of 1 to 15 carbon atoms which may have a substituent, a cyclic alkyl group of 3 to 20 carbon atoms which may have a substituent or an aromatic hydrocarbon group of 5 to 20 carbon atoms which may have a substituent is preferable, and a chain-like alkyl group of 1 to 15 carbon atoms which may have a substituent or an aromatic hydrocarbon group of 5 to 20 carbon atoms which may have a substituent is particularly preferable.

It is preferable that both of $R^{2q}$ and $R^{3q}$ represent hydrogen atoms, and it is preferable that $R^{2q}$ and $R^{3q}$ are mutually bonded to form a ring, and it is most preferable that both of $R^{2q}$ and $R^{3q}$ are hydrogen atoms.

$Z^+$, $R^{1r}$, $R^{2r}$ and $R^{3r}$ in the formula (c1-2) are the same as defined for $Z^+$, $R^{1q}$, $R^{2q}$ and $R^{3q}$ in the general formula (c1-1).

$R^{1s}$, $R^{2s}$ and $R^{3s}$ in the formula (c1-3) are the same as defined for $R^1$, $R^2$ and $R^3$ in the formula (c1).

As $R^{1s}$, a hydrogen atom, a chain-like alkyl group of 1 to 15 carbon atoms which may have a substituent, a cyclic alkyl group of 3 to 20 carbon atoms which may have a substituent or an aromatic hydrocarbon group of 5 to 20 carbon atoms which may have a substituent is preferable, a cyclic alkyl group or 3 to 20 carbon atoms which may have a substituent is more preferable, and a polycyclic alkyl group is particularly preferable.

It is preferable that both of $R^{2s}$ and $R^{3s}$ represent hydrogen atoms, and it is preferable that $R^{2s}$ and $R^{3s}$ are mutually bonded to form a ring, and it is most preferable that both of $R^{2s}$ and $R^{3s}$ are hydrogen atom.

Specific examples of the component (C1) are shown below. In the formulas, $Z^+$ is the same as defined above.

[Chemical Formula 54]

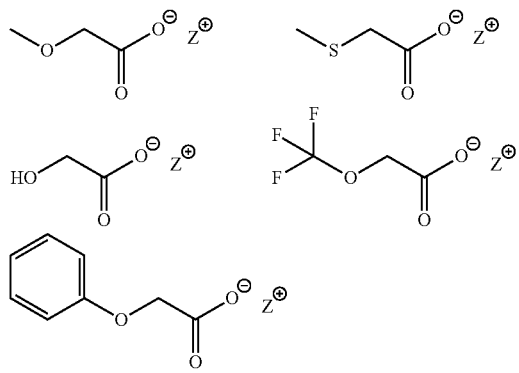

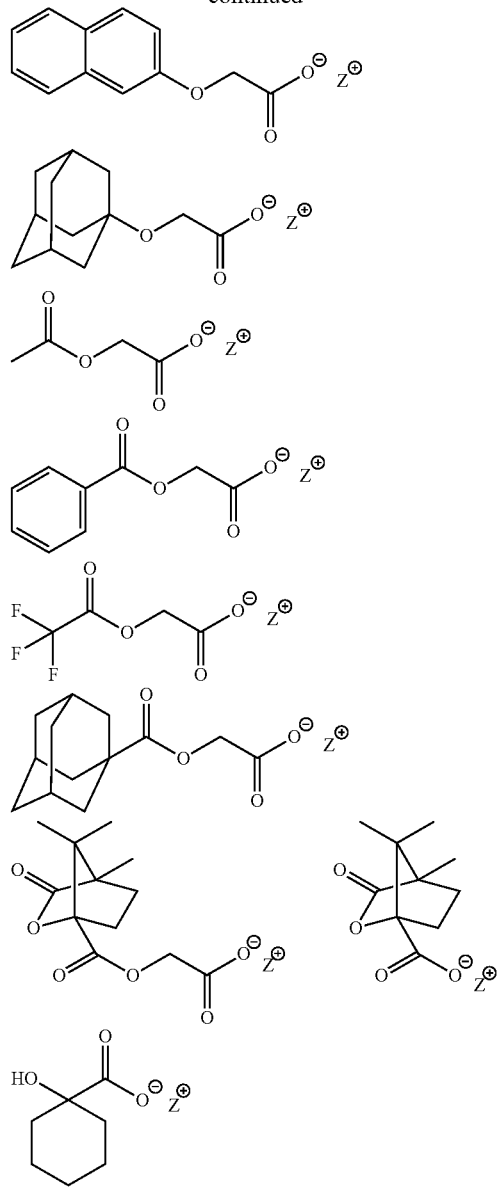

As the component (C1), one type of compound may be used, or two or more types of compounds may be used in combination.

The amount of the component (C1) within the component (C) is preferably 80% by weight or more, and may be even 100% by weight.

The component (C1) can be produced by a conventional method.

For example, the component (C1) can be obtained by a salt exchange reaction of the acid corresponding to the anion moiety of the component (C1) ($R^1$—[C(=O)]n-X—C($R^2$)($R^3$)—COOH) with a salt having a predetermined cation moiety $Z^+$.

The acid ($R^1$—[C(=O)]n-X—C($R^2$)($R^3$)—COOH) used in the salt exchange reaction can be produced by a conventional method. For example, the acid represented by the formula ($R^1$—[C(=O)]n-X—C($R^2$)($R^3$)—COOH) in which n is 1 can be produced in the same manner as in the production method of the compound represented by the formula (g1-1) in the explanation of the component (G) described later.

In the resist composition of the present invention, a photoreactive quencher other than the component (C1) (hereafter, referred to as "component (C2)") may further be added.

The component (C2) is not particularly limited as long as it acts as a photoreactive quencher, and for example, any of the known photoreactive quencher used in conventional resist compositions can be used.

Specific examples of the component (C2) include a basic compound consisting of an anion other than the anion represented by the formula $(R^1—[C(=O)]n-X—C(R^2)(R^3)—C(=O)—O^−)$ in the general formula (c1) and a cation moiety (e.g., carboxylic acid onium salts, alkylsulfonic acid onium salts, arylsulfonic acid onium salts, sulfonylamide acid onium salts and sulfonylimide acid onium salt). These basic compound traps acid (strong acid) generated from the component (B) by a salt-exchange reaction.

In the present invention, a "basic compound" refers to a compound which is basic relative to the component (B).

In the resist composition, the amount of the component (C) relative to 100 parts by weight of the component (A) is preferably within a range from 0.5 to 10.0 parts by weight, more preferably from 0.5 to 8.0 parts by weight, still more preferably from 1.0 to 8.0 parts by weight, and particularly preferably from 1.5 to 5.5 parts by weight. When the amount of the component (C) is at least as large as the lower limit of the above-mentioned range, various lithography properties such as resolution, roughness and exposure latitude are improved. Further, a resist pattern having an excellent shape can be obtained. On the other hand, in the case where the amount of the component (C) is no more than the upper limit of the above-mentioned range, sensitivity can be maintained at a satisfactory level, and throughput becomes excellent.

<Component (B)>

The component (B) is an acid generator component which generates acid upon exposure.

As the component (B), there is no particular limitation, and any of the known acid generators used in conventional chemically amplified resist compositions can be used. Examples of these acid generators are numerous, and include onium salt acid generators such as iodonium salts and sulfonium salts; oxime sulfonate acid generators; diazomethane acid generators such as bisalkyl or bisaryl sulfonyl diazomethanes and poly(bis-sulfonyl)diazomethanes; nitrobenzylsulfonate acid generators; iminosulfonate acid generators; and disulfone acid generators.

As an onium salt acid generator, a compound represented by general formula (b-1) or (b-2) shown below can be used.

[Chemical Formula 55]

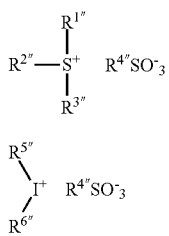

In formulas, each of $R^{1\prime\prime\prime}$ to $R^{3\prime\prime\prime}$, and $R^{5\prime\prime\prime}$ to $R^{6\prime\prime\prime}$ independently represents an aryl group, alkyl group or alkenyl group which may have a substituent. In formula (b-1), two of $R^{1\prime\prime\prime}$ to $R^{3\prime\prime\prime}$ may be bonded to each other to form a ring with the sulfur atom. $R^{4\prime\prime\prime}$ represents an alkyl group, a halogenated alkyl group, an aryl group or an alkenyl group which may have a substituent.

Examples of the aryl group which may have a substituent for $R^{1\prime\prime\prime}$ to $R^{3\prime\prime\prime}$ include an unsubstituted aryl group of 6 to 20 carbon atoms, a substituted aryl group in which part or all of hydrogen atoms of the unsubstituted aryl group have been substituted by a substituent.

As the of unsubstituted aryl group, an aryl groups of 6 to 10 carbon atoms is preferable. Specific examples thereof include a phenyl group and a naphthyl group.

Examples of the substituent of the substituted alkyl group include an alkyl group, an alkoxy group, a halogen atom, a halogenated alkyl group, a hydroxy group, an oxo group (=O), a cyano group, an aryl group, an alkoxyalkyloxy group, an alkoxycarbonylalkyloxy group, —C(=O)—O—$R^{6\prime}$, —O—C(=O)—$R^{7\prime}$, —O—$R^{8\prime}$, —O—$R^{9\prime}$, a halogenated alkylsulfonyloxy group and —O-$Q^1$-[O—$R^{11\prime\prime\prime}$—$S^+(R^{21\prime\prime\prime})(R^{31\prime\prime\prime})]_x$. Each of $R^{6\prime}$, $R^{7\prime}$ and $R^{8\prime}$ independently represents a linear or branched saturated hydrocarbon group of 1 to 25 atoms, a cyclic saturated hydrocarbon group of 3 to 20 carbon atoms or a linear or branched, aliphatic unsaturated hydrocarbon group of 2 to 5 carbon atoms. $R^{9\prime}$ represents a nitrogen-containing hydrocarbon group. $R^{11\prime\prime\prime}$ represents an arylene group, an alkylene group or an alkenylene which may have a substituent. Each of $R^{21\prime\prime\prime}$ and $R^{31\prime\prime\prime}$ independently represents an aryl group, an alkyl group or an alkenylene group which may have a substituent, and $R^{21\prime\prime\prime}$ and $R^{31\prime\prime\prime}$ may be mutually bonded with the sulfur atom to form a ring. x represents 1 or 2, and $Q^1$ represents a (x+1)-valent linking group.

Among these, as the alkyl group, alkoxy group, halogen atom, halogenated alkyl group, aryl group, alkoxyalkyloxy group, alkoxycarbonylalkyloxy group, —C(=O)—O—$R^{6\prime}$, —O—C(=O)—$R^{7\prime}$ and —O—$R^{8\prime}$, the same groups as those described above as substituent with which the aromatic hydrocarbon group for $R^1$ in the general formula (c1) may be substituted, can be mentioned.

As the nitrogen-containing hydrocarbon group for $R^{9\prime}$, a group in which part of the carbon atom in the aromatic hydrocarbon group or aliphatic hydrocarbon group has been substituted with a nitrogen atom. Preferable examples thereof include a mono- or di-alkylaminoalkyl group in which one or two hydrogen atoms bonded to the nitrogen atom in the linear or branched aminoalkyl group of 1 to 10 carbon atoms have been substituted with alkyl groups of 1 to 10 carbon atoms.

Examples of the halogenated alkyl group in the halogenated alkylsulfonyloxy group include the same halogenated alkyl group as those described above as a substituent, and a trifluoromethyl group is particularly preferable.

With respect to —O-$Q^1$-(O—$R^{11\prime\prime\prime}$—$S^+(R^{21\prime\prime\prime})(R^{31\prime\prime\prime}))_x$, as the arylene group, alkylene group or alkenylene group which may have a substituent for $R^{11\prime\prime\prime}$, a group in which one hydrogen atom has been removed from the aryl group, alkyl group or alkenyl group which may have a substituent for $R^{1\prime\prime\prime}$ can be mentioned.

As examples of $R^{21\prime\prime\prime}$ and $R^{31\prime\prime\prime}$, the same groups as those described above for $R^{2\prime\prime\prime}$ and $R^{3\prime\prime\prime}$ in the formula (b-1) can be given, respectively.

x represents 1 or 2.

$Q^1$ represents a (x+1)-valent linking group, that is, divalent or trivalent linking group.

Examples of the divalent linking group for $Q^1$ include the same divalent linking groups as those described above for $Y^2$. The divalent linking group may be linear, branched or cyclic, but is preferably cyclic. Among these, an arylene group having two carbonyl groups, each bonded to the terminal thereof is preferable. Specific examples of the arylene groups include a phenylene group and a naphthylene group. Of these, a phenylene group is particularly desirable.

Examples of the trivalent linking group for $Q^1$ include a group in which one hydrogen atom has been removed from the divalent linking group, or a group in which one divalent linking group has been bonded to another divalent linking group. Examples of the divalent linking group include the same divalent linking groups as those described above for $Y^2$. The trivalent linking group for $Q^1$ is preferably an arylene group combined with three carbonyl groups.

When the aryl group has a group represented by the formula $-O-Q^1-[O-R^{11''}-S^+(R^{21''})(R^{31''})]_x$ as a substituent, it is preferable that $R^{1''}$ to $R^{3''}$ has single group represented by formula $-O-Q^1-[O-R^{11''}-S^+(R^{21''})(R^{31''})]_x$ in total.

Specific examples of the cation moiety having a group represented by formula $-O-Q^1-[O-R^{11''}-S^+(R^{21''})(R^{31''})]_x$ as a substituent include the anion moiety represented by general formula (ca-0) shown below.

[Chemical Formula 56]

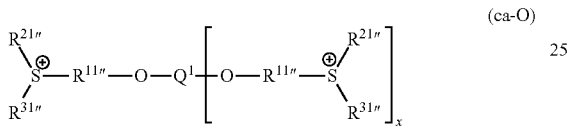

(ca-O)

In the formula, $R^{11''}$ represents an arylene group, an alkylene group or an alkenylene group which may have a substituent; each of $R^{21''}$ and $R^{31''}$ independently represents an aryl group, an alkyl group or an alkenyl group which may have a substituent, and $R^{21''}$ and $R^{31''}$ may be mutually bonded with the sulfur atom to form a ring; x represents 1 or 2; and $Q^1$ represents a (x+1)-valent linking group.

Examples of the alkyl group which may have a substituent for $R^{1''}$ to $R^{3''}$ include a substituted alkyl group in which part or all of hydrogen atoms of the unsubstituted alkyl group have been substituted with a substituent.

The unsubstituted alkyl group may be any of linear, branched or cyclic. In terms of achieving excellent resolution, an alkyl group of 1 to 10 carbon atoms is preferable, and an alkyl group of 1 to 5 carbon atoms. Specific examples include a methyl group, an ethyl group, an n-propyl group, an isopropyl group, an n-butyl group, an isobutyl group, an n-pentyl group, a cyclopentyl group, a hexyl group, a cyclohexyl group, a nonyl group and a decyl group.

Examples of the substituent of the substituted alkyl group include an alkoxy group, a halogen atom, a halogenated alkyl group, a hydroxy group, an oxo group (=O), a cyano group, an aryl group, an alkoxyalkyloxy group, an alkoxycarbonylalkyloxy group, $-C(=O)-O-R^{6'}$, $-O-C(=O)-R^{7'}$, $-O-R^{8'}$, $-O-R^{9'}$, a halogenated alkylsulfonyloxy group and $-O-Q^1-[O-R^{11''}-S^+(R^{21''})(R^{31''})]_x$.

[13]Examples of these substituents include an alkoxy group, a halogen atom, a halogenated alkyl group, a hydroxy group, an oxo group (=O), a cyano group, an aryl group, an alkoxyalkyloxy group, an alkoxycarbonylalkyloxy group, $-C(=O)-O-R^{6'}$, $-O-C(=O)-R^{7'}$, $-O-R^{8'}$, $-O-R^{9'}$, a halogenated alkylsulfonyloxy group and $-O-Q^1-[O-R^{11''}-S^+(R^{21''})(R^{31''})]_x$ which are the same groups as those described above for substituent which the substituted aryl group for $R^{1''}$ to $R^{3''}$ may have.

Examples of the alkenyl group which may have a substituent for substituting $R^{1''}$ to $R^{3''}$ include an unsubstituted alkenyl group and a substituted alkenyl group in which part or all of hydrogen atoms of the unsubstituted alkenyl group have been substituted by a substituent.

The unsubstituted alkylene group is preferably linear or branched. Further, the unsubstituted alkylene group preferably has 2 to 10 carbon atoms, more preferably 2 to 5, and still more preferably 2 to 4. Specific examples thereof include a vinyl group, a propenyl group (an allyl group), a butynyl group, a 1-methylpropenyl group and a 2-methylpropenyl group.

Examples of the substituent for the substituted alkenyl group include the same groups as those described above as the substituent which the substituted alkyl group represented by $R^{1''}$ to $R^{3''}$ may have.

In the formula (b-1), preferable examples of the cation moiety represented by formula $(S^+(R^{1''})(R^{2''})(R^{3''}))$ in which each of $R^{1''}$ to $R^{3''}$ independently represents an aryl group, an alkyl group or an alkenyl group which may have a substituent include cation moieties represented by formula (ca-1-1) to (ca-1-46) shown below.

[Chemical Formula 57]

(ca-1-1)

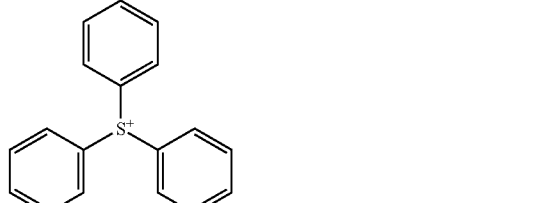

(ca-1-2)

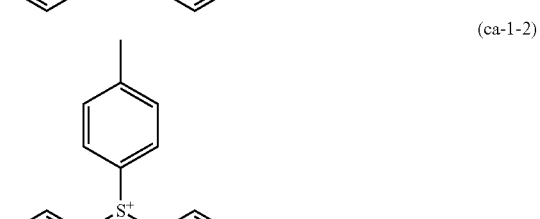

(ca-1-3)

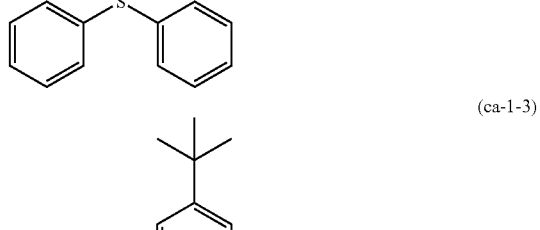

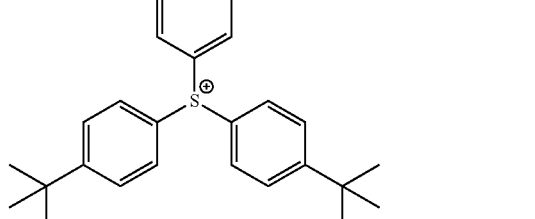

(ca-1-4)

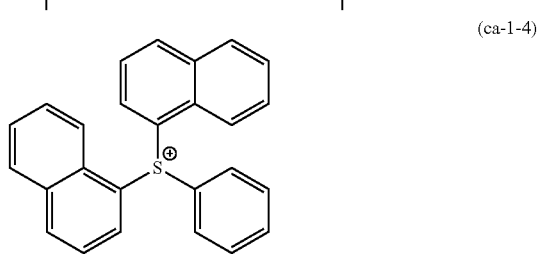

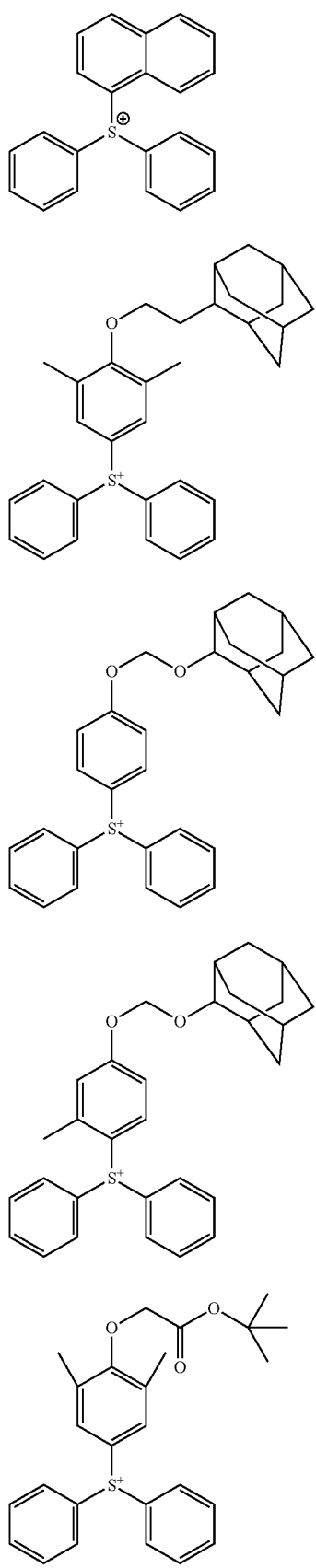
(ca-1-5)
(ca-1-6)
(ca-1-7)
(ca-1-8)
(ca-1-9)
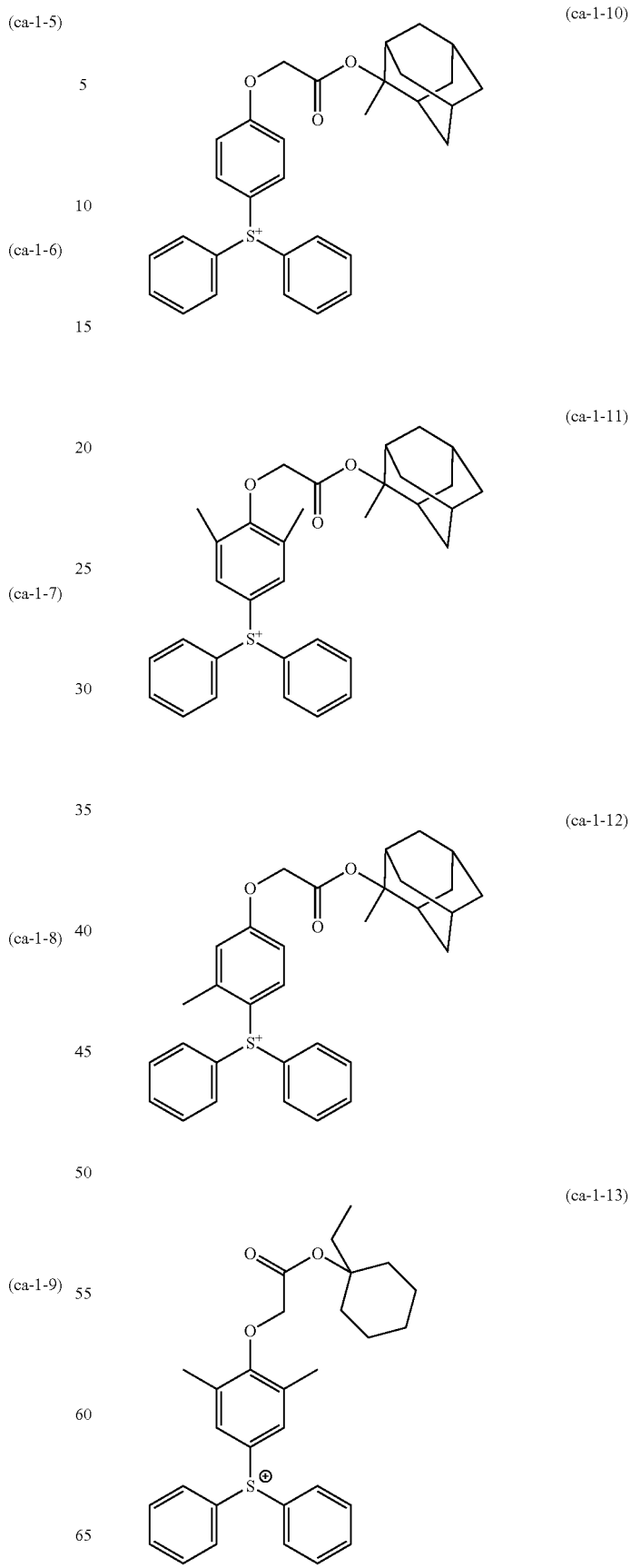
(ca-1-10)
(ca-1-11)
(ca-1-12)
(ca-1-13)

(ca-1-14)
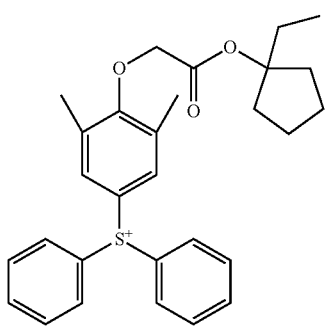
(ca-1-15)
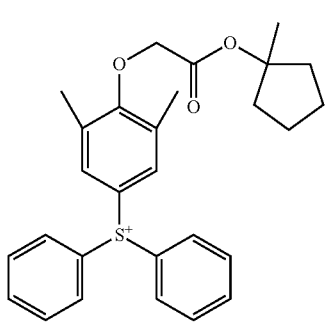
(ca-1-16)
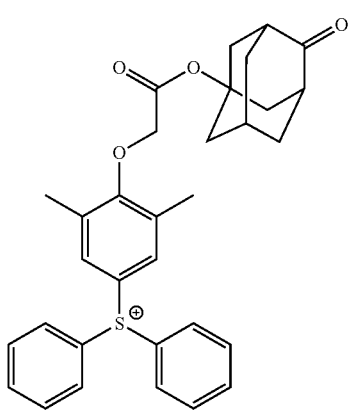
(ca-1-17)
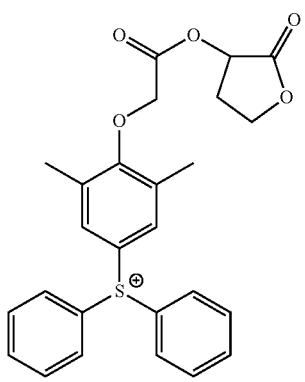
[Chemical Formula 58]
(ca-1-18)
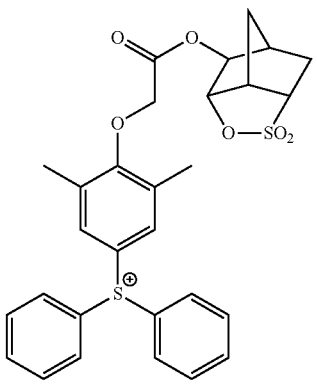
(ca-1-19)
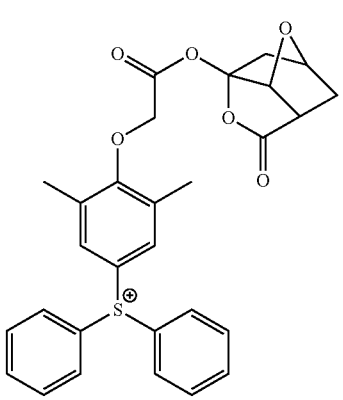
(ca-1-20)
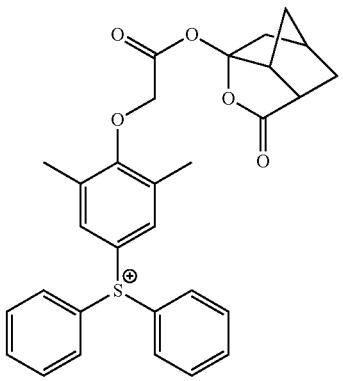
(ca-1-21)
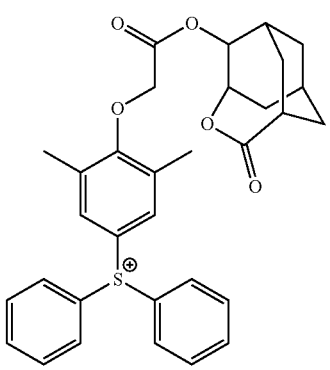

(ca-1-22) 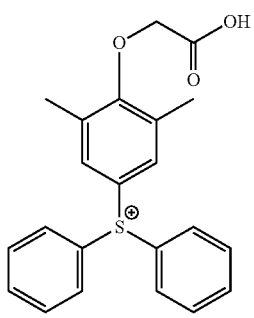
(ca-1-23) 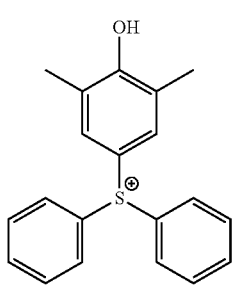
(ca-1-24) 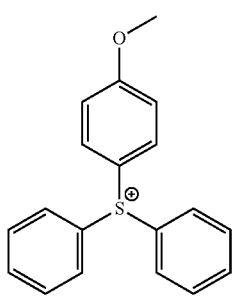
(ca-1-25) 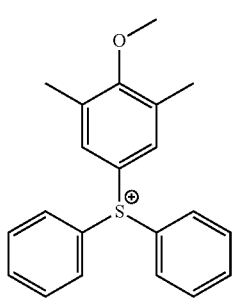
(ca-1-26) 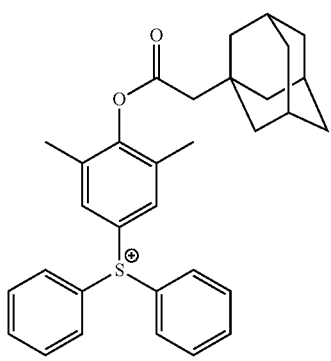
(ca-1-27) 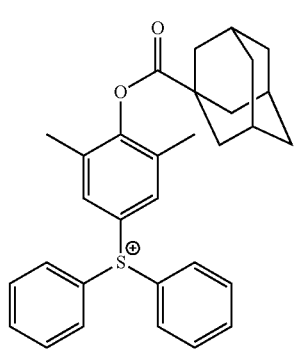
(ca-1-28) 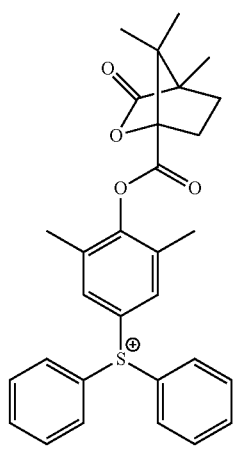
(ca-1-29) 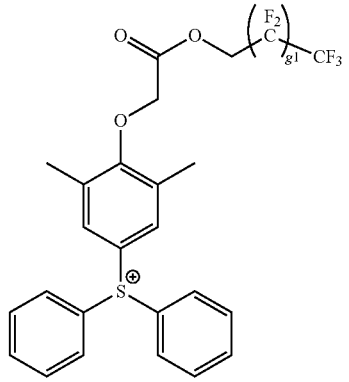
(ca-1-30) 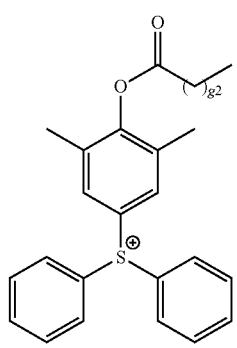

(ca-1-31)
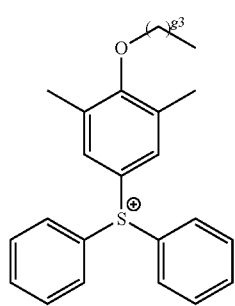
(ca-1-32)
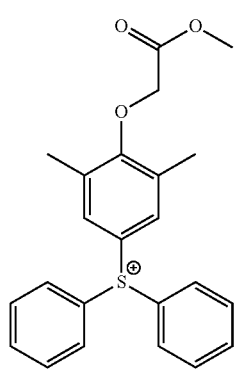
(ca-1-33)
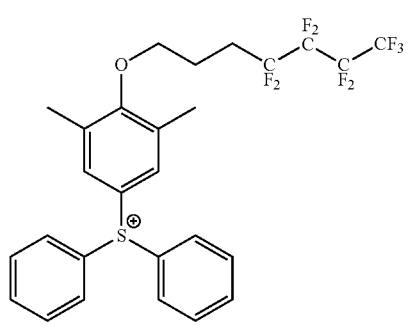
In the formulas, g1, g2 and g3 represent recurring numbers, wherein g1 is an integer of 1 to 5, g2 is an integer of 0 to 20, and g3 is an integer of 0 to 20.
[Chemical Formula 59]
(ca-1-34)
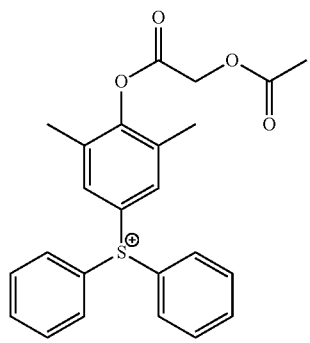
(ca-1-35)
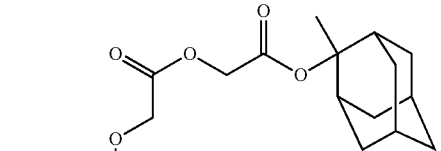
(ca-1-37)
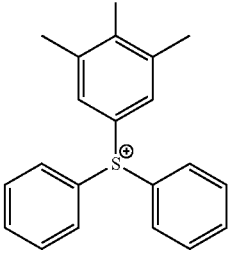
(ca-1-38)
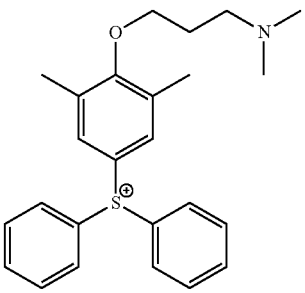
(ca-1-39)
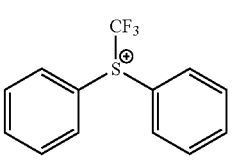
(ca-1-40)
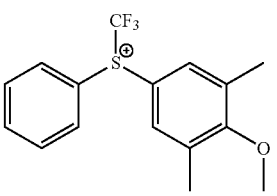

(ca-1-41)
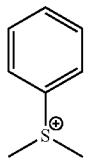

(ca-1-42)

(ca-1-43)
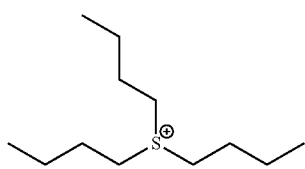

(ca-1-44)
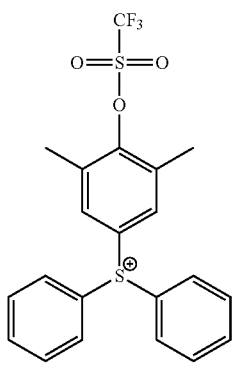

(ca-1-45)
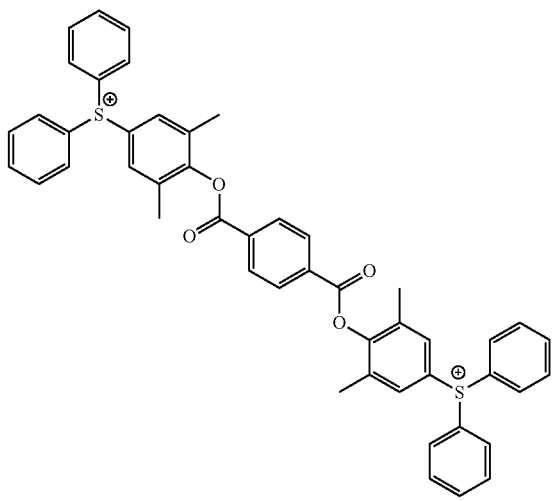

(ca-1-46)
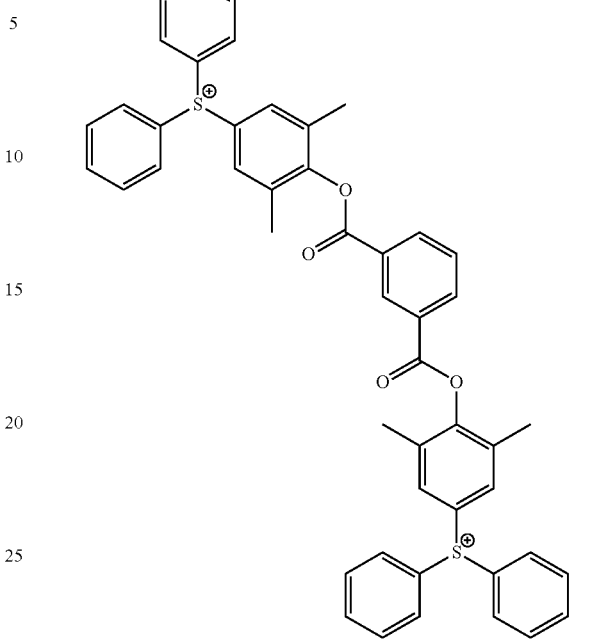

In formula (b-1), two of $R^{1\prime\prime}$ to $R^{3\prime\prime}$ may be bonded to each other to form a ring with the sulfur atom. The ring may be saturated or unsaturated. Further, the ring may be monocyclic or polycyclic. For example, in the case where either one or both of the two of $R^{1\prime\prime}$ to $R^3$ represent a cyclic group (i.e., a cyclic alkyl group or an aryl group), when the two groups are bonded, a polycyclic ring (fused ring) is formed.

As the ring to be formed, the ring containing the sulfur atom in the skeleton thereof is preferably a 3 to 10-membered ring, and most preferably a 5 to 7-membered ring.

The ring may have a hetero atom as an atom constituting the ring skeleton other than the sulfur atom having $R^{1\prime\prime}$ to $R^{3\prime\prime}$ bonded thereto. Examples of hetero atoms include an oxygen atom, a nitrogen atom, and a sulfur atom.

Specific examples of the rings to be formed include a thiophene ring, a thiazole ring, a benzothiophene ring, a thianthrene ring, a benzothiophene ring, a dibenzothiophene ring, a 9H-thioxanthene ring, a thioxanthone ring, a thianthrene ring, a phenoxathiin ring, a tetrahydrothiophenium ring and tetrahydrothiopyranium ring.

In the formula (b-1), preferable examples of the cation moiety represented by formula $(S^+(R^{1\prime\prime})(R^{2\prime\prime})(R^{3\prime\prime}))$ in which two of $R^{1\prime\prime}$ to $R^{3\prime\prime}$ are mutually bonded with the sulfur atom to form a ring include cation moieties represented by formula (ca-12) to (ca-15) shown below.

[Chemical Formula 60]

(ca-12)
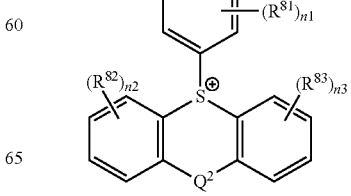

(ca-13)

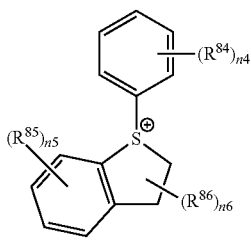

In the formulas, $Q^2$ represents a single bond, a methylene group, a sulfur atom, an oxygen atom, a nitrogen atom, a carbonyl group, —SO—, —SO$_2$—, —SO$_3$—, —COO—, —CONH— or —N(R$_N$)— (R$_N$ represents an alkyl group of 1 to 5 carbon atoms); each of $R^{81}$ to $R^{86}$ independently represents an alkyl group, an acetyl group, an alkoxy group, a carboxy group, a hydroxy group or a hydroxyalkyl group; each of $n_1$ to $n_5$ independently represents an integer of 0 to 3; and $n_6$ represents an integer of 0 to 2.

[Chemical Formula 61]

(ca-14)

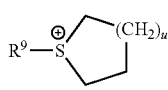

(ca-15)

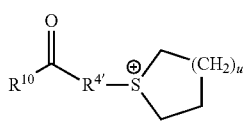

In the formulas, u represents an integer of 1 to 3; $R^9$ represents a phenyl group, a naphthyl group or an alkyl group which may have a substituent; $R^{10}$ represents a hydroxy group, a phenyl group, a naphthyl group, an alkyl group or an alkoxy group which may have a substituent; and $R^{4'}$ represents an alkylene group which may have a substituent.

In the formulas (ca-12) and (ca-13), the alkyl group for $R^{81}$ to $R^{86}$ is preferably an alkyl group of 1 to 5 carbon atoms, more preferably a linear or branched alkyl group, and particularly preferably a methyl group, an ethyl group, a propyl group, an isopropyl group, an n-butyl group or a tert-butyl group.

The alkoxy group is preferably an alkoxy group of 1 to 5 carbon atoms, more preferably a linear or branched alkoxy group, and most preferably a methoxy group or an ethoxy group.

The hydroxyalkyl group is preferably a group in which one or more hydrogen atoms in the aforementioned alkyl group have been substituted with hydroxy groups, and examples thereof include a hydroxymethyl group, a hydroxyethyl group and a hydroxypropyl group.

If there are two or more of an individual $R^{81}$ to $R^{86}$ group, as indicated by the corresponding value of $n_1$ to $n_6$ then the two or more of the individual $R^{81}$ to $R^{86}$ group may be the same or different from each other.

$n_1$ is preferably 0 to 2, more preferably 0 or 1, and still more preferably 0.

It is preferable that each of $n_2$ and $n_3$ independently represent 0 or 1, and more preferably 0.

$n_4$ is preferably 0 to 2, and more preferably 0 or 1.

$n_5$ is preferably 0 or 1, and more preferably 0.

$n_6$ is preferably 0 or 1, and more preferably 1.

Preferable examples of the cation represented by formula (ca-12) or (ca-13) are shown below.

[Chemical Formula 62]

(ca-12-1)

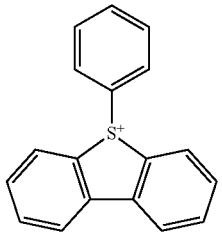

(ca-12-2)

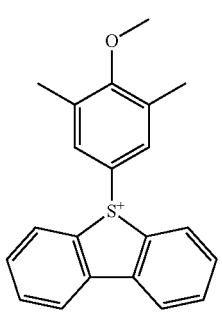

(ca-12-3)

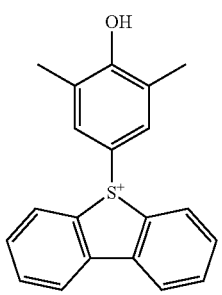

(ca-12-4)

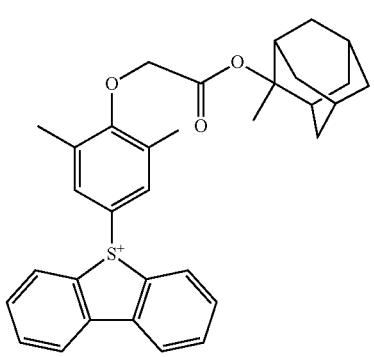

(ca-12-5)

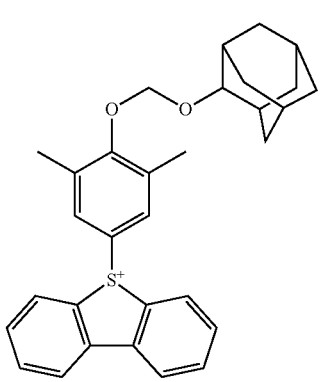

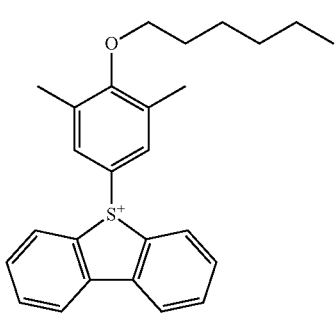
(ca-12-6)

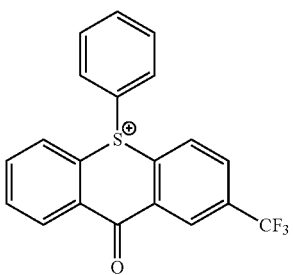
(ca-12-7)

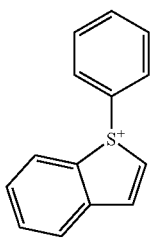
(ca-13-1)

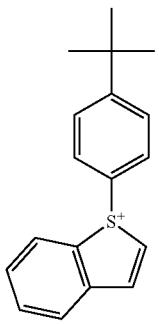
(ca-13-2)

In the formulas (ca-14) and (ca-15), u is an integer of 1 to 3, and most preferably 1 or 2.

$R^9$ represents a phenyl group, a naphthyl group or an alkyl group which may have a substituent.

Further, examples of the substituent for the phenyl group or naphthyl group represented by $R^9$ include the same groups as those described above for substituents which the substituted aryl group represented by $R^{1\prime\prime\prime}$ to $R^{3\prime\prime\prime}$ may have. Specific examples thereof include an alkyl group, an alkoxy group, a halogen atom, a halogenated alkyl group, a hydroxy group, an oxo group (=O), a cyano group, an aryl group, an alkoxyalkyloxy group, an alkoxycarbonylalkyloxy group, —C(=O)—O—$R^{6\prime}$, —O—C(=O)—$R^{7\prime}$, —O—$R^{8\prime}$, —O—$R^{9\prime}$, a halogenated alkylsulfonyoxy group and —O-$Q^1$-[O—$R^{11\prime\prime\prime}$—$S^+$($R^{21\prime\prime\prime}$)($R^{31\prime\prime\prime}$)]$_x$.

As the alkyl group which may have a substituent for $R^9$, the same alkyl group which may have a substituent as those described above for $R^{1\prime\prime\prime}$ to $R^{3\prime\prime\prime}$.

$R^{10}$ represents a phenyl group, a naphthyl group, an alkyl group and an alkoxy group which may have a substituent.

Examples of the substituent for the phenyl group or naphthyl group represented by $R^{10}$ include the same groups as those described above for substituents which the phenyl group or naphthyl group represented by $R^9$ may have.

As the alkyl group in the alkyl group and alkoxy group which may have a substituent for $R^{10}$, the same alkyl group as those described above for $R^{1\prime\prime\prime}$ to $R^{3\prime\prime\prime}$ can be mentioned.

As the alkylene group for $R^{4\prime}$, a linear or branched alkylene group is preferable. The alkylene group preferably has 1 to 12 carbon atoms, more preferably 1 to 5 carbon atoms, and most preferably 1 to 3 carbon atoms.

Further, examples of the substituent which the alkylene group represented by $R^{4\prime}$ may have include the same groups as those described above for substituents which the substituted alkyl group represented by $R^{1\prime\prime\prime}$ to $R^{3\prime\prime\prime}$ may have. Specific examples thereof include an alkoxy group, a halogen atom, a halogenated alkyl group, a hydroxy group, an oxo group (=O), a cyano group, an aryl group, an alkoxyalkyloxy group, an alkoxycarbonylalkyloxy group, —C(=O)—O—$R^{6\prime}$, —O—C(=O)—$R^{7\prime}$, —O—$R^{8\prime}$, —O—$R^{9\prime}$, a halogenated alkylsulfonyoxy group and —O-$Q^1$-[O—$R^{11\prime\prime\prime}$—$S^+$($R^{21\prime\prime\prime}$)($R^{31\prime\prime\prime}$)]$_x$.

Preferable examples of the cation represented by the formula (ca-14) or (ca-15) are shown below.

[Chemical Formula 63]

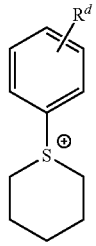
(ca-14-1)

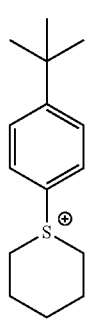
(ca-14-2)

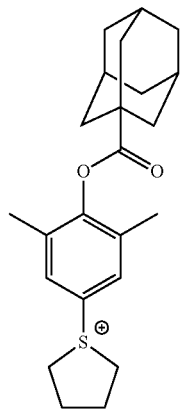
(ca-14-3)

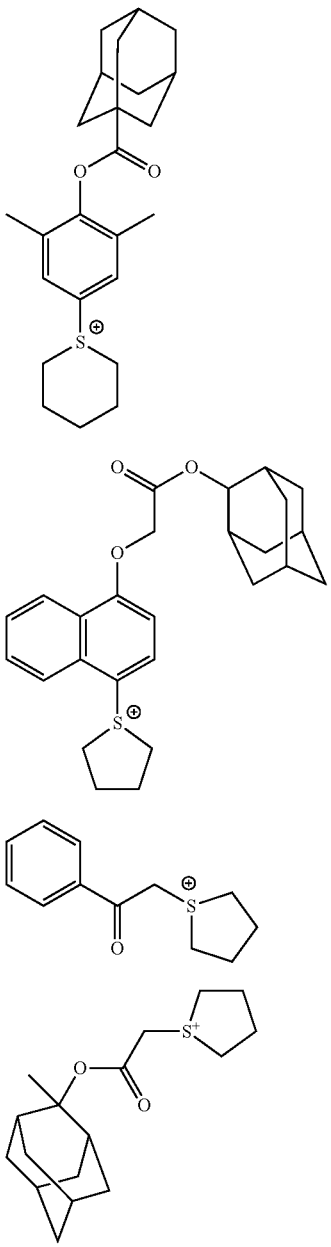

(ca-14-4)

(ca-14-5)

(ca-15-1)

(ca-15-2)

In formula (ca-1), $R^d$ represents a substituent. Examples of substituents include the same groups as those described above for substituents which the phenyl group or naphthyl group for $R^9$ may have. Specific examples thereof include an alkyl group, an alkoxy group, a halogen atom, a halogenated alkyl group, a hydroxy group, an oxo group (=O), a cyano group, an aryl group, an alkoxyalkyloxy group, an alkoxycarbonylalkyloxy group, —C(=O)—O—$R^{6\prime}$, —O—C(=O)—$R^{7\prime}$, —O—$R^{8\prime}$, —O—$R^{9\prime}$, a halogenated alkylsulfonyoxy group and —O-$Q^1$-[O—$R^{11\prime\prime\prime}$—$S^+(R^{21\prime\prime\prime})(R^{31\prime\prime\prime})]_x$. Each of $R^{7\prime}$, $R^{8\prime}$ and $R^{9\prime}$ independently represents a hydrogen atom or a hydrocarbon group.

As the aryl group, alkyl group or alkenyl group which may have a substituent for $R^{5\prime\prime\prime}$ and $R^{6\prime\prime\prime}$ in the formula (b-2), the same aryl group, alkyl group or alkenyl group which may have a substituent as those described above for $R^{1\prime\prime\prime}$ to $R^{3\prime\prime\prime}$.

It is preferable that at least one of $R^{5\prime\prime\prime}$ and $R^{6\prime\prime\prime}$ represents an aryl group which may have a substituent, and it is more preferable that both of $R^{5\prime\prime\prime}$ and $R^{6\prime\prime\prime}$ represent an aryl group which may have a substituent.

Specific examples of the cation moiety ($I^+(R^{5\prime\prime\prime})(R^{6\prime\prime\prime})$) in the formula (b-2) include diphenyliodonium and bis(4-tert-butylphenyl)iodonium.

In formulas (b-1) and (b-2), $R^{4\prime\prime\prime}$ represents an alkyl group, a halogenated alkyl group, an aryl group or an alkenyl group which may have a substituent.

The alkyl group for $R^{4\prime\prime\prime}$ may be any of linear, branched or cyclic.

The linear or branched alkyl group for $R^{4\prime\prime\prime}$ preferably has 1 to 10 carbon atoms, more preferably 1 to 8 carbon atoms, and most preferably 1 to 4 carbon atoms.

The cyclic alkyl group for $R^{4\prime\prime\prime}$ preferably has 4 to 15 carbon atoms, more preferably 4 to 10, and most preferably 6 to 10.

When $R^{4\prime\prime\prime}$ represents an alkyl group, examples of "$R^{4\prime\prime\prime}SO_3^-$" includes alkylsulfonates such as methanesulfonate, n-propanesulfonate, n-butanesulfonate, n-octanesulfonate, 1-adamantanesulfonate, 2-norbornanesulfonate, d-camphor-10-sulfonate.

The halogenated alkyl group for $R^{4\prime\prime\prime}$ is a group in which part of all of the hydrogen atoms in the alkyl group have been substituted with a halogen atom. As the alkyl group, an alkyl group of 1 to 5 carbon atoms is preferred. Among these, a linear or branched alkyl group is preferred, and more preferably a methyl group, an ethyl group, a propyl group, an isopropyl group, an n-butyl group, a tert-butyl group, a tert-pentyl group or an isopentyl group. Examples of the halogen atom which substitutes the hydrogen atoms include a fluorine atom, a chlorine atom, an iodine atom and a bromine atom.

With respect to the halogenated alkyl group, 50 to 100% of the hydrogen atoms in the alkyl group (alkyl group before halogenation) are preferably substituted with the halogen atoms, and all of the hydrogen atoms are more preferably substituted with the halogen atoms.

As the halogenated alkyl group, a fluorinated alkyl group is desirable. The fluorinated alkyl group preferably has 1 to 10 carbon atoms, more preferably 1 to 8 carbon atoms, and most preferably 1 to 4 carbon atoms.

Further, the fluorination ratio of the fluorinated alkyl group is preferably from 10 to 100%, more preferably from 50 to 100%, and it is most preferable that all hydrogen atoms are substituted with fluorine atoms because the acid strength increases.

Specific examples of the fluorinated alkyl group include a trifluoromethyl group, a heptafluoro-n-propyl group and a nonafluoro-n-butyl group.

As examples of the aryl group for $R^{4\prime\prime\prime}$, the same aryl groups as those described above for $R^{1\prime\prime\prime}$ to $R^{3\prime\prime\prime}$, $R^{5\prime\prime\prime}$ and $R^{6\prime\prime\prime}$ can be used. Among these, the substituent is preferably an aryl group of 6 to 20 carbon atoms.

As examples of the alkenyl group for $R^{4\prime\prime\prime}$, the same aryl groups as those described above for $R^{1\prime\prime\prime}$ to $R^{3\prime\prime\prime}$, $R^{5\prime\prime\prime}$ and $R^{6\prime\prime\prime}$ can be used. Among these, an alkenyl group of 2 to 10 carbon atoms is preferable.

The alkyl group, halogenated alkyl group, aryl group or alkenyl group for $R^{4\prime\prime\prime}$ may have a substituent.

The expression "may have a substituent" means that part of or all of the hydrogen atoms within the aforementioned linear, branched or cyclic alkyl group, halogenated alkyl group, aryl group or alkenyl group may be substituted with substituents (atoms other than hydrogen atoms, or groups).

$R^{4\prime\prime\prime}$ may have one substituent, or two or more substituents.

Examples of the substituent include a halogen atom, a hetero atom, an alkyl group, and a group represented by the formula $X^3$-Q'- (in the formula, Q' represents a divalent linking group containing an oxygen atom; and $X^3$ represents a hydrocarbon group of 3 to 30 carbon atoms which may have a substituent).

Examples of halogen atoms and alkyl groups include the same halogen atoms and alkyl groups as those described above with respect to the halogenated alkyl group for $R^{4'''}$.

Examples of hetero atoms include an oxygen atom, a nitrogen atom, and a sulfur atom.

In the group represented by formula $X^3$-Q'-, Q' represents a divalent linking group containing an oxygen atom.

Q' may contain an atom other than an oxygen atom. Examples of atoms other than oxygen include a carbon atom, a hydrogen atom, a sulfur atom and a nitrogen atom.

Examples of divalent linkage groups containing an oxygen atom include non-hydrocarbon, oxygen atom-containing linkage groups such as an oxygen atom (an ether bond; —O—), an ester bond (—C(=O)—O—), an amide bond (—C(=O)—NH—), a carbonyl group (—C(=O)—) and a carbonate group (—O—C(=O)—O—); and a combination of any of the aforementioned non-hydrocarbon, oxygen atom-containing linkage groups with an alkylene group. To the combination, a sulfonyl group (—$SO_2$—) may further be linked.

Specific examples of the combinations of the aforementioned non-hydrocarbon, oxygen atom-containing linkage groups with alkylene groups include —$R^{91}$—O—, —$R^{92}$—O—C(=O)—, —C(=O)—O—$R^{93}$—O—C(=O)—, —$SO_2$—O—$R^{94}$—O—C(=O)— and —$R^{95}$—$SO_2$—O—$R^{94}$—O—C(=O)— (in the formulas, $R^{91}$ to $R^{95}$ each independently represent an alkylene group.)

The alkylene group for $R^{91}$ to $R^{95}$ is preferably a linear or branched alkylene group, and preferably has 1 to 12 carbon atoms, more preferably 1 to 5, and most preferably 1 to 3.

Specific examples of the alkylene group include a methylene group [—$CH_2$—]; alkylmethylene groups such as —CH($CH_3$)—, —CH($CH_2CH_3$)—, —C($CH_3$)$_2$—, —C($CH_3$)($CH_2CH_3$)—, —C($CH_3$)($CH_2CH_2CH_3$)— and —C($CH_2CH_3$)$_2$—; an ethylene group [—$CH_2CH_2$—]; alkylethylene groups such as —CH($CH_3$)$CH_2$—, —CH($CH_3$)CH($CH_3$)—, —C($CH_3$)$_2CH_2$— and —CH($CH_2CH_3$)$CH_2$—; a trimethylene group (n-propylene group) [—$CH_2CH_2CH_2$—]; alkyltrimethylene groups such as —CH($CH_3$)$CH_2CH_2$— and —$CH_2$CH($CH_3$)$CH_2$—; a tetramethylene group [—$CH_2CH_2CH_2CH_2$—]; alkyltetramethylene groups such as —CH($CH_3$)$CH_2CH_2CH_2$— and —$CH_2$CH($CH_3$)$CH_2CH_2$—; and a pentamethylene group [—$CH_2CH_2CH_2CH_2CH_2$—].

Q' is preferably a divalent linking group containing an ester bond or ether bond, and more preferably a group of —$R^{91}$—O—, —$R^{92}$—O—C(=O)— or —C(=O)—O—$R^{93}$—O—C(=O)—.

In the group represented by the formula $X^3$-Q'-, $X^3$ represents a hydrocarbon group of 1 to 30 carbon atoms which may have a substituent.

The hydrocarbon group for $X^3$ may be either an aromatic hydrocarbon group or an aliphatic hydrocarbon group. Examples of the aromatic hydrocarbon groups and aliphatic hydrocarbon groups for $X^3$ include the same aromatic hydrocarbon groups and aliphatic hydrocarbon groups as those described above for $R^1$ in the general formula (c1).

As $X^3$, a cyclic group which may have a substituent is preferable. The cyclic group may be either an aromatic hydrocarbon group which may have a substituent, or a cyclic alkyl group which may have a substituent, and an aliphatic cyclic group which may have a substituent is preferable.

As the aromatic hydrocarbon group, a phenyl group which may have a substituent or a naphthyl group which may have a substituent is preferable. As the substituent, a fluorine atom is preferable.

As the cyclic alkyl group which may have a substituent, a polycyclic alkyl group which may have a substituent is preferable. As the polycyclic alkyl group, the aforementioned group in which one or more hydrogen atoms have been removed from a polycycloalkane, and groups represented by formulas (L2) to (L7), (S3) and (S4) are preferable.

Among the above, as $R^{4'''}$, a halogenated alkyl group or a group having $X^3$-Q'- as a substituent is preferable.

When the $R^{4'''}$ group has $X^3$-Q'- as a substituent, as $R^{4'''}$, a group represented by the formula: $X^3$-Q'-$Y^5$— (in the formula, Q' and $X^3$ are the same as defined above, and $Y^5$ represents an alkylene group of 1 to 4 carbon atoms which may have a substituent or a fluorinated alkylene group of 1 to 4 carbon atoms which may have a substituent is preferable.

In the group represented by the formula $X^3$-Q'-$Y^5$—, as the alkylene group for $Y^5$, the same alkylene group as those described above for Q' in which the number of carbon atoms is 1 to 4 can be used.

As the fluorinated alkylene group, the aforementioned alkylene group in which part or all of the hydrogen atoms has been substituted with fluorine atoms can be used.

Specific examples of $Y^5$ include —$CF_2$—, —$CF_2CF_2$—, —$CF_2CF_2CF_2$—, —CF($CF_3$)$CF_2$—, —CF($CF_2CF_3$)—, —C($CF_3$)$_2$—, —$CF_2CF_2CF_2CF_2$—, —CF($CF_3$)$CF_2CF_2$—, —$CF_2$CF($CF_3$)$CF_2$—, —CF($CF_3$)CF($CF_3$)—, —C($CF_3$)$_2CF_2$—, —CF($CF_2CF_3$)$CF_2$—, —CF($CF_2CF_2CF_3$)—, —C($CF_3$)($CF_2CF_3$)—, —CHF—, —$CH_2CF_2$—, —$CH_2CH_2CF_2$—, —$CH_2CF_2CF_2$—, —CH($CF_3$)$CH_2$—, —CH($CF_2CF_3$)—, —C($CH_3$)($CF_3$)—, —$CH_2CH_2CH_2CF_2$—, —$CH_2CH_2CF_2CF_2$—, —CH($CF_3$)$CH_2CH_2$—, —$CH_2$CH($CF_3$)$CH_2$—, —CH($CF_3$)CH($CF_3$)—, —C($CF_3$)$_2CH_2$—, —$CH_2$—, —$CH_2CH_2$—, —$CH_2CH_2CH_2$—, —CH($CH_3$)$CH_2$—, —CH($CH_2CH_3$)—, —C($CH_3$)$_2$—, —$CH_2CH_2CH_2CH_2$—, —CH($CH_3$)$CH_2CH_2$—, —$CH_2$CH($CH_3$)$CH_2$—, —CH($CH_3$)CH($CH_3$)—, —C($CH_3$)$_2CH_2$—, —CH($CH_2CH_3$)$CH_2$—, —CH($CH_2CH_2CH_3$)— and —C($CH_3$)($CH_2CH_3$)—.

As $Y^5$, a fluorinated alkylene group is preferable, and a fluorinated alkylene group in which the carbon atom bonded to the adjacent sulfur atom is fluorinated is particularly desirable. Examples of such fluorinated alkylene groups include —$CF_2$—, —$CF_2CF_2$—, —$CF_2CF_2CF_2$—, —CF($CF_3$)$CF_2$—, —$CF_2CF_2CF_2CF_2$—, —CF($CF_3$)$CF_2CF_2$—, —$CF_2$CF($CF_3$)$CF_2$—, —CF($CF_3$)CF($CF_3$)—, —C($CF_3$)$_2CF_2$—, —CF($CF_2CF_3$)$CF_2$—, —$CH_2CF_2$—, —$CH_2CH_2CF_2$—, —$CH_2CF_2CF_2$—, —$CH_2CH_2CH_2CF_2$—, —$CH_2CH_2CF_2CF_2$— and —$CH_2CF_2CF_2CF_2$—.

Of these, —$CF_2$—, —$CF_2CF_2$—, —$CF_2CF_2CF_2$— or $CH_2CF_2CF_2$— is preferable, —$CF_2$—, —$CF_2CF_2$— or —$CF_2CF_2CF_2$— is more preferable, and —$CF_2$— is particularly desirable.

The alkylene group or fluorinated alkylene group may have a substituent. The alkylene group or fluorinated alkylene group "has a substituent" means that part or all of the hydrogen atoms or fluorine atoms in the alkylene group or fluorinated alkylene group has been substituted with groups or atoms other than hydrogen atoms and fluorine atoms.

Examples of substituents which the alkylene group or fluorinated alkylene group may have include an alkyl group of 1 to 4 carbon atoms, an alkoxy group of 1 to 4 carbon atoms, and a hydroxy group.

Specific examples of groups represented by formula $R^{4''}SO_3-$ in which $R^{4''}$ represents $X^3-Q'-Y^5-$ include anions represented by the following formulae (b1) to (b9).

[Chemical Formula 64]

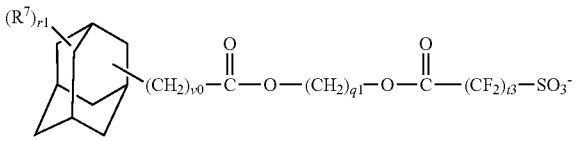
(b1)

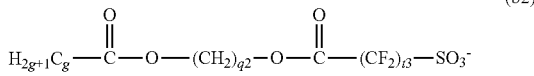
(b2)

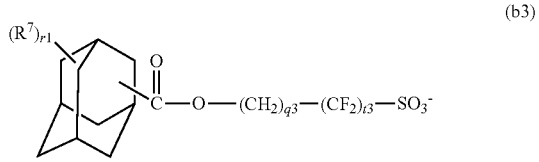
(b3)

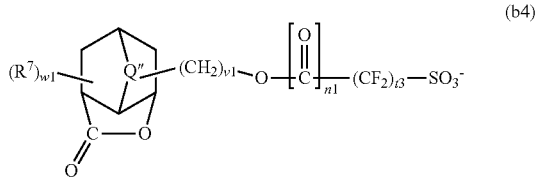
(b4)

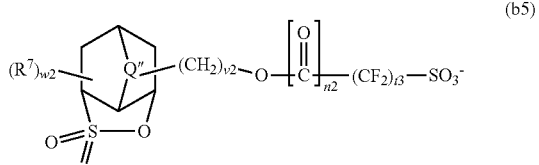
(b5)

[Chemical Formula 65]

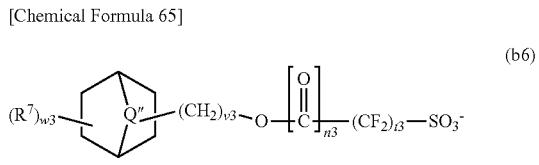
(b6)

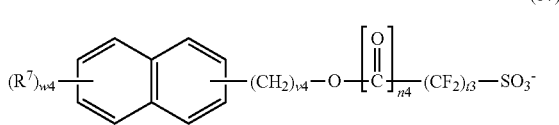
(b7)

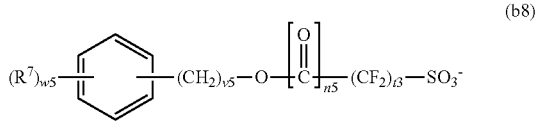
(b8)

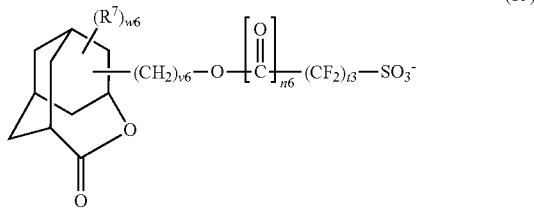
(b9)

In the formulas, each of q1 and q2 independently represents an integer of 1 to 5; q3 represents an integer of 1 to 12; t3 represents an integer of 1 to 3; each of r1 and r2 independently represents an integer of 0 to 3; g represents an integer of 1 to 20; $R^7$ represents a substituent; each of n1 to n6 independently represents 0 or 1; each of v0 to v6 independently represents an integer of 0 to 3; each of w1 to w6 independently represents an integer of 0 to 3; and Q'' is the same as defined above.

Examples of the substituent for substituting $R^7$ include the same substituents as those described above for the substituent in the explanation of $R^1$ in the general formula (c1), which may substitute a part of the hydrogen atom bonded to the carbon atom constituting the ring structure within the cyclic alkyl group, and the substituent which may substitute the hydrogen atom bonded to the aromatic ring within the aromatic hydrocarbon group.

If there are two or more of the $R^7$ group, as indicated by the values r1, r2, and w1 to w6 then the two or more of the $R^7$ groups may be the same or different from each other.

Further, onium salt-based acid generators in which the anion moiety ($R^{4'''}SO_3^-$) in the general formula (b-1) or (b-2) is replaced by an anion moiety represented by general formula (b-3) or (b-4) shown below (the cation moiety is the same as (b-1) or (b-2)) may be used.

[Chemical Formula 66]

(b-3)

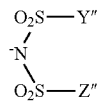
(b-4)

In the formulas, X'' represents an alkylene group of 2 to 6 carbon atoms in which at least one hydrogen atom has been substituted with a fluorine atom; and Y'' and Z'' each independently represents an alkyl group of 1 to 10 carbon atoms in which at least one hydrogen atom has been substituted with a fluorine atom.

In the formula (b-3), X'' represents a linear or branched alkylene group in which at least one hydrogen atom has been substituted with a fluorine atom, and the alkylene group has 2 to 6 carbon atoms, preferably 3 to 5 carbon atoms, and most preferably 3 carbon atoms.

In the formula (b-4), each of Y'' and Z'' independently represents a linear or branched alkyl group in which at least one hydrogen atom has been substituted with a fluorine atom, and the alkyl group has 1 to 10 carbon atoms, preferably 1 to 7 carbon atoms, and most preferably 1 to 3 carbon atoms.

The smaller the number of carbon atoms of the alkylene group for X'' or those of the alkyl group for Y'' and Z'' within the above-mentioned range of the number of carbon atoms, the more the solubility in a resist solvent is improved.

Further, in the alkylene group for X'' or the alkyl group for Y'' and Z'', it is preferable that the number of hydrogen atoms substituted with fluorine atoms is as large as possible because the acid strength increases and the transparency to high energy radiation of 200 nm or less or electron beam is improved.

The amount of fluorine atoms within the alkylene group or alkyl group, i.e., fluorination ratio, is preferably from 70 to 100%, more preferably from 90 to 100%, and it is particularly desirable that the alkylene group or alkyl group be a perfluoroalkylene or perfluoroalkyl group in which all hydrogen atoms are substituted with fluorine atoms.

In the present description, an oximesulfonate-based acid generator is a compound having at least one group represented by general formula (B-1) shown below, and has a feature of generating acid by irradiation. Such oxime sulfonate acid generators are widely used for a chemically amplified resist composition, and can be appropriately selected.

[Chemical Formula 67]

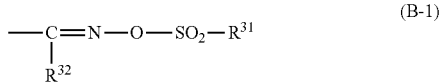

(B-1)

In the formula, $R^{31}$ and $R^{32}$ each independently represent an organic group.

The organic group for $R^{31}$ and $R^{32}$ refers to a group containing a carbon atom, and may include atoms other than carbon atoms (e.g., a hydrogen atom, an oxygen atom, a nitrogen atom, a sulfur atom, a halogen atom (such as a fluorine atom and a chlorine atom) and the like).

As the organic group for $R^{31}$, a linear, branched, or cyclic alkyl group or aryl group is preferable. The alkyl group or the aryl group may have a substituent. The substituent is not particularly limited, and examples thereof include a fluorine atom and a linear, branched, or cyclic alkyl group having 1 to 6 carbon atoms. The alkyl group or the aryl group "has a substituent" means that part or all of the hydrogen atoms of the alkyl group or the aryl group is substituted with a substituent.

The alkyl group preferably has 1 to 20 carbon atoms, more preferably 1 to 10 carbon atoms, still more preferably 1 to 8 carbon atoms, particularly preferably 1 to 6 carbon atoms, and most preferably 1 to 4 carbon atoms. As the alkyl group, a partially or completely halogenated alkyl group (hereinafter, sometimes referred to as a "halogenated alkyl group") is particularly desirable. The "partially halogenated alkyl group" refers to an alkyl group in which part of the hydrogen atoms are substituted with halogen atoms and the "completely halogenated alkyl group" refers to an alkyl group in which all of the hydrogen atoms are substituted with halogen atoms. Examples of the halogen atom include a fluorine atom, a chlorine atom, a bromine atom and an iodine atom, and a fluorine atom is particularly preferred. In other words, the halogenated alkyl group is preferably a fluorinated alkyl group.

The aryl group preferably has 4 to 20 carbon atoms, more preferably 4 to 10 carbon atoms, and most preferably 6 to 10 carbon atoms. As the aryl group, partially or completely halogenated aryl group is particularly desirable. The "partially halogenated aryl group" refers to an aryl group in which part of the hydrogen atoms are substituted with halogen atoms, and the "completely halogenated aryl group" refers to an aryl group in which all of hydrogen atoms are substituted with halogen atoms.

As $R^{31}$, an alkyl group of 1 to 4 carbon atoms which has no substituent or a fluorinated alkyl group of 1 to 4 carbon atoms is particularly desirable.

As the organic group for $R^{32}$, a linear, branched, or cyclic alkyl group, aryl group, or cyano group is preferable. As the alkyl group or aryl group for $R^{32}$, the same alkyl groups or aryl groups as those described above for $R^{31}$ can be used.

As $R^{32}$, a cyano group, an alkyl group of 1 to 8 carbon atoms having no substituent or a fluorinated alkyl group of 1 to 8 carbon atoms is particularly desirable.

Preferable examples of the oxime sulfonate-based acid generator include compounds represented by general formula (B-2) or (B-3) shown below.

[Chemical Formula 68]

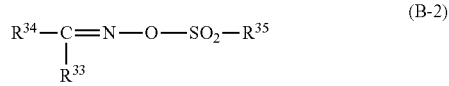

(B-2)

In the formula, $R^{33}$ represents a cyano group, an alkyl group having no substituent or a halogenated alkyl group; $R^{34}$ represents an aryl group; and $R^{35}$ represents an alkyl group having no substituent or a halogenated alkyl group.

[Chemical Formula 69]

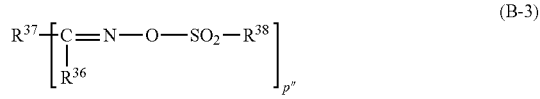

(B-3)

In the formula (B-3), $R^{36}$ represents a cyano group, an alkyl group having no substituent or a halogenated alkyl group; $R^{37}$ represents a divalent or trivalent aromatic hydrocarbon group; $R^{38}$ represents an alkyl group having no substituent or a halogenated alkyl group; and p" represents 2 or 3.

In general formula (B-2), the alkyl group having no substituent or the halogenated alkyl group for $R^{33}$ preferably has 1 to 10 carbon atoms, more preferably 1 to 8 carbon atoms, and most preferably 1 to 6 carbon atoms.

As $R^{33}$, a halogenated alkyl group is preferable, and a fluorinated alkyl group is more preferable.

The fluorinated alkyl group for $R^{33}$ preferably has 50% or more of the hydrogen atoms thereof fluorinated, more preferably 70% or more, and most preferably 90% or more.

Examples of the aryl group for $R^{34}$ include groups in which one hydrogen atom has been removed from an aromatic hydrocarbon ring, such as a phenyl group, a biphenyl group, a fluorenyl group, a naphthyl group, an anthryl group, and a phenantryl group, and heteroaryl groups in which some of the carbon atoms constituting the ring(s) of these groups are substituted with hetero atoms such as an oxygen atom, a sulfur atom, and a nitrogen atom. Of these, a fluorenyl group is preferable.

The aryl group for $R^{34}$ may have a substituent such as an alkyl group of 1 to 10 carbon atoms, a halogenated alkyl group, or an alkoxy group. The alkyl group and halogenated alkyl group as the substituent preferably has 1 to 8 carbon atoms, and more preferably 1 to 4 carbon atoms. Further, the halogenated alkyl group is preferably a fluorinated alkyl group.

The alkyl group having no substituent or the halogenated alkyl group for $R^{35}$ preferably has 1 to 10 carbon atoms, more preferably 1 to 8 carbon atoms, and most preferably 1 to 6 carbon atoms.

As $R^{35}$, a halogenated alkyl group is preferable, and a fluorinated alkyl group is more preferable.

In terms of enhancing the strength of the acid generated, the fluorinated alkyl group for $R^{35}$ preferably has 50% or more of the hydrogen atoms fluorinated, more preferably 70% or more, still more preferably 90% or more. A completely fluorinated alkyl group in which 100% of the hydrogen atoms are substituted with fluorine atoms is particularly desirable.

In general formula (B-3), as the alkyl group having no substituent and the halogenated alkyl group for $R^{36}$, the same alkyl group having no substituent and the halogenated alkyl group described above for $R^{33}$ can be used.

Examples of the divalent or trivalent aromatic hydrocarbon group for $R^{37}$ include groups in which one or two hydrogen atoms have been removed from the aryl group for $R^{34}$.

As the alkyl group having no substituent or the halogenated alkyl group for $R^{38}$, the same one as the alkyl group having no substituent or the halogenated alkyl group for $R^{35}$ can be used.

p" is preferably 2.

Specific examples of suitable oxime sulfonate acid generators include α-(p-toluenesulfonyloxyimino)-benzyl cyanide, α-(p-chlorobenzenesulfonyloxyimino)-benzyl cyanide, α-(4-nitrobenzenesulfonyloxyimino)-benzyl cyanide, α-(4-nitro-2-trifluoromethylbenzenesulfonyloxyimino)-benzyl cyanide, α-(benzenesulfonyloxyimino)-4-chlorobenzyl cyanide, α-(benzenesulfonyloxyimino)-2,4-dichlorobenzyl cyanide, α-(benzenesulfonyloxyimino)-2,6-dichlorobenzyl cyanide, α-(benzenesulfonyloxyimino)-4-methoxybenzyl cyanide, α-(2-chlorobenzenesulfonyloxyimino)-4-methoxybenzyl cyanide, α-(benzenesulfonyloxyimino)-thien-2-yl acetonitrile, α-(4-dodecylbenzenesulfonyloxyimino)benzyl cyanide, α-[(p-toluenesulfonyloxyimino)-4-methoxyphenyl]acetonitrile, α-[(dodecylbenzenesulfonyloxyimino)-4-methoxyphenyl]acetonitrile, α-(tosyloxyimino)-4-thienyl cyanide, α-(methylsulfonyloxyimino)-1-cyclopentenyl acetonitrile, α-(methylsulfonyloxyimino)-1-cyclohexenyl acetonitrile, α-(methyl sulfonyloxyimino)-1-cycloheptenyl acetonitrile, α-(methylsulfonyloxyimino)-1-cyclooctenyl acetonitrile, α-(trifluoromethylsulfonyloxyimino)-1-cyclopentenyl acetonitrile, α-(trifluoromethylsulfonyloxyimino)-cyclohexyl acetonitrile, α-(ethylsulfonyloxyimino)-ethyl acetonitrile, α-(propylsulfonyloxyimino)-propyl acetonitrile, α-(cyclohexyl sulfonyloxyimino)-cyclopentyl acetonitrile, α-(cyclohexylsulfonyloxyimino)-cyclohexyl acetonitrile, α-(cyclohexylsulfonyloxyimino)-1-cyclopentenyl acetonitrile, α-(ethylsulfonyloxyimino)-1-cyclopentenyl acetonitrile, α-(isopropylsulfonyloxyimino)-1-cyclopentenyl acetonitrile, α-(n-butylsulfonyloxyimino)-1-cyclopentenyl acetonitrile, α-(ethylsulfonyloxyimino)-1-cyclohexenyl acetonitrile, α-(isopropylsulfonyloxyimino)-1-cyclohexenyl acetonitrile, α-(n-butylsulfonyloxyimino)-1-cyclohexenyl acetonitrile, α-(methylsulfonyloxyimino)-phenyl acetonitrile, α-(methylsulfonyloxyimino)-p-methoxyphenyl acetonitrile, α-(trifluoromethylsulfonyloxyimino)-phenyl acetonitrile, α-(trifluoromethylsulfonyloxyimino)-p-methoxyphenyl acetonitrile, α-(ethylsulfonyloxyimino)-p-methoxyphenyl acetonitrile, α-(propylsulfonyloxyimino)-p-methylphenyl acetonitrile, and α-(methylsulfonyloxyimino)-p-bromophenyl acetonitrile.

Further, oxime sulfonate-based acid generators disclosed in Japanese Unexamined Patent Application, First Publication No. Hei 9-208554 (Chemical Formulas 18 and 19 shown in paragraphs [0012] to [0014]) and oxime sulfonate-based acid generators disclosed in WO 2004/074242A2 (Examples 1 to 40 described at pages 65 to 86) may be preferably used.

Furthermore, as preferable examples, the following can be used.

[Chemical Formula 70]

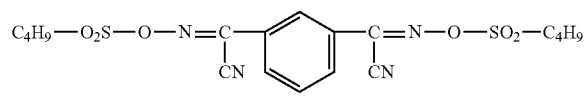

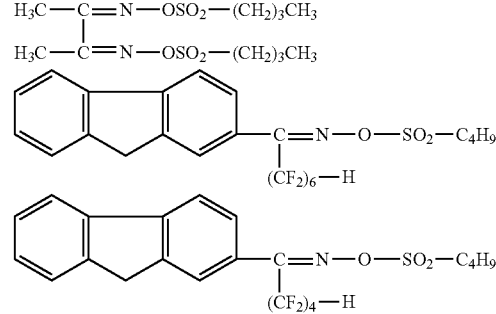

Of the aforementioned diazomethane-based acid generators, specific examples of suitable bisalkyl or bisaryl sulfonyl diazomethanes include bis(isopropylsulfonyl)diazomethane, bis(p-toluenesulfonyl)diazomethane, bis(1,1-dimethylethylsulfonyl)diazomethane, bis(cyclohexylsulfonyl)diazomethane, and bis(2,4-dimethylphenylsulfonyl)diazomethane.

Further, diazomethane-based acid generators disclosed in Japanese Unexamined Patent Application, First Publication No. Hei 11-035551, Japanese Unexamined Patent Application, First Publication No. Hei 11-035552 and Japanese Unexamined Patent Application, First Publication No. Hei 11-035573 may be preferably used.

Furthermore, as poly(bis-sulfonyl)diazomethanes, those disclosed in Japanese Unexamined Patent Application, First Publication No. Hei 11-322707, including 1,3-bis(phenylsulfonyldiazomethylsulfonyl)propane, 1,4-bis(phenylsulfonyldiazomethylsulfonyl)butane, 1,6-bis(phenylsulfonyldiazomethylsulfonyl)hexane, 1,10-bis(phenylsulfonyldiazomethylsulfonyl)decane, 1,2-bis(cyclohexylsulfonyldiazomethylsulfonyl)ethane, 1,3-bis(cyclohexylsulfonyldiazomethylsulfonyl)propane, 1,6-bis(cyclohexylsulfonyldiazomethylsulfonyl)hexane, and 1,10-bis(cyclohexylsulfonyldiazomethylsulfonyl)decane, may be mentioned.

As the component (B), one type of these acid generators may be used alone, or two or more types may be used in combination.

In the resist composition, the amount of the component (B), relative to 100 parts by weight of the component (A) is preferably from 0.5 to 60 parts by weight, more preferably from 1 to 50 parts by weight, and most preferably from 1 to 40 parts by weight. When the amount of the component (B) is within the above-mentioned range, formation of a resist pattern can be satisfactorily performed. Further, when these components of the resist composition are dissolved in the organic solvent, a uniform solution can be obtained and the storage stability becomes satisfactory.

<Component (G)>

It is preferable that the resist composition of the present invention further includes an acid (G) (hereafter referred to as "component (G)"). By blending a component (G), the storage stability of the resist composition can be improved.

As the component (G), a carboxylic acid, an alkylsulfonic acid, an arylsulfonic acid, a sulfonylamide acid, an sulfonylimide acid, a phosphorus oxo acid or derivatives thereof can be given.

Examples of the carboxylic acids include compounds (G1) represented by general formula (g1) shown below.

[Chemical Formula 71]

$$R^{g11}-\overset{O}{\underset{\|}{C}}-OH \quad (g1)$$

In the formula, $R^{g11}$ represents a hydrocarbon group which may have a substituent.

In the general formula (g1), $R^{g11}$ may be either an aliphatic hydrocarbon group which may have a substituent or an aromatic hydrocarbon group which may have a substituent, and the same aliphatic hydrocarbon groups and aromatic hydrocarbon groups as those described above for $R^1$ in the general formula (c1) can be mentioned.

Further, $R^{g11}$ may be the same groups as those represented by formula $R^1-[C(=O)]_n-X-C(R^2)(R^3)-$ for the general formula (c1).

Specific examples of the compound (G1) include compounds in which "—COO⁻Z⁺" within the compound described above as a specific example of the component (C1) is replaced with "—COOH", an other aliphatic monocarboxylic acid and aromatic monocarboxylic acid. The specific examples are shown below. Also, polycarboxylic acids having two or more carboxy groups such as malonic acid, citric acid, malic acid, succinic acid and the like can be mentioned.

[Chemical Formula 72]

[Chemical Formula 73]

As the compound (G1), commercially available compounds may be used, or the compounds may be synthesized by a conventional method.

With respect to the compound (G1), a compound having a group represented by formula $R^1-[C(=O)]_n-X-C(R^2)(R^3)-$, for example, a compound represented by general formula (g1-1) shown below can be produced by reacting a compound (i-1) with a compound (i-2) as shown below.

[Chemical Formula 74]

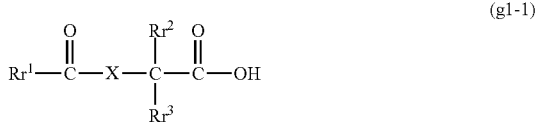

(g1-1)

In the formula, $Rr^1$ represents a hydrogen atom or a hydrocarbon group of 1 to 20 carbon atoms which may have a substituent; each of $Rr^2$ and $Rr^3$ independently represents a hydrogen atom or a hydrocarbon group of 1 to 20 carbon atoms which may have a substituent; at least two of $Rr^1$ to $Rr^3$ may be mutually bonded to form a ring; and X represents an oxygen atom or a sulfur atom.

In the formula (g1-1), $Rr^1$, $Rr^2$, $Rr^3$, X and n are the same as defined for $R^1$, $R^2$, $R^3$, X and n in the general formula (c1).

[Chemical Formula 75]

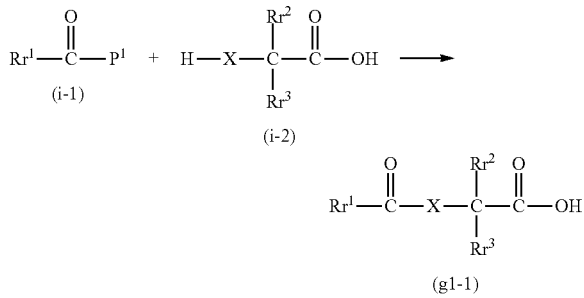

In the formulas, $Rr^1$, $Rr^2$, $Rr^3$, X and n are the same as defined above; $P^1$ represents a halogen atom (preferably a chlorine atom or bromine atom).

As the sulfonic acids, a compound (G2) represented by general formula (g2) shown below is preferred.

[Chemical Formula 76]

$R^{g12}$—$SO_3H$ (g2)

In the formula, $R^{g12}$ represents a hydrocarbon group of 1 to 30 carbon atoms which may have a substituent, provided that the carbon atom adjacent to the sulfur atom has no fluorine atom as a substituent.

In the general formula (g2), as the hydrocarbon group of 1 to 30 carbon atoms for $R^{g12}$ which may have a substituent may be either an aliphatic hydrocarbon group or an aromatic hydrocarbon group, and the same aliphatic hydrocarbon groups and aromatic hydrocarbon groups as those described above for $R^1$ in the general formula (c1) can be mentioned.

Among these, as the hydrocarbon group for $R^{g12}$ which may have a substituent, an aliphatic cyclic group which may have a substituent is preferable, and a group in which one or more hydrogen atoms have been removed from adamantane, norbornane, isobornane, tricyclodecane, tetracyclododecane or camphor (which may have a substituent) is more preferable.

Examples of the substituent which the hydrocarbon group for $R^{g12}$ may have include the same groups as those described above for substituents which $R^{4'''}$ in the general formula (b-1) or (b-2) may have in relation to the component (B). Specific examples of the substituents include a halogen atom, a hetero atom, an alkyl group, and a group represented by the formula $X^3$-Q'- (in the formula, Q' represents a divalent linking group containing an oxygen atom; and $X^3$ represents a hydrocarbon group of 3 to 30 carbon atoms which may have a substituent). Provided that, in $R^{g12}$, the carbon atom adjacent to the sulfur atom within $SO_3^-$ has no fluorine atom as a substituent.

Specific examples of the compound (G2) include compounds shown below.

[Chemical Formula 77]

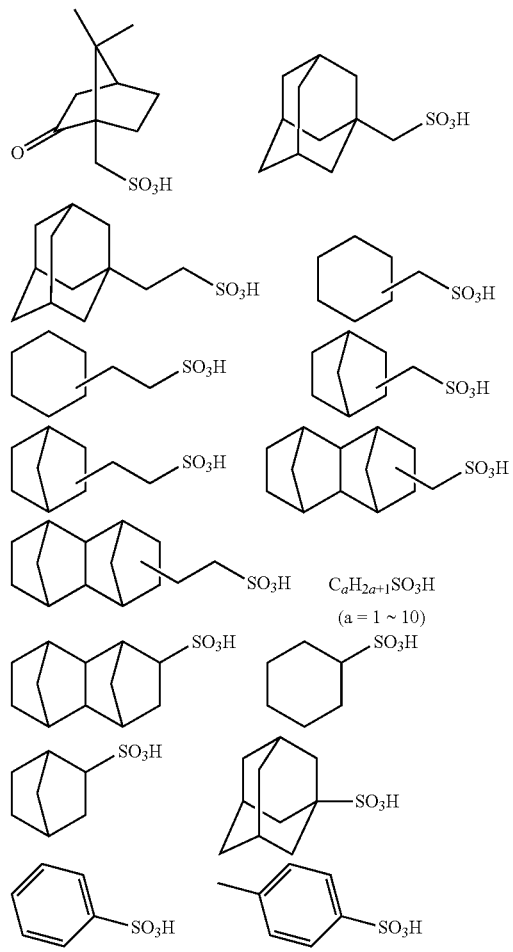

As the sulfonylamide compounds, a compound (G3) represented by general formula (g3) shown below is preferred.

[Chemical Formula 78]

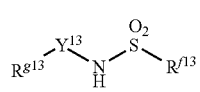

(g-3)

In the formula, $R^{g13}$ is an organic group; $Y^{13}$ represents a linear, branched or cyclic alkylene group or arylene group; and $R^{f13}$ represents a hydrocarbon group containing a fluorine atom.

In the general formula (g3), the organic group for $R^{g13}$ is not particularly limited, and preferable examples thereof include an alkyl group, an alkoxy group, —O—C(=O)—C(R$^{C2}$)=CH$_2$ (wherein R$^{C2}$ represents a hydrogen atom, an alkyl group of 1 to 5 carbon atoms or a halogenated alkyl group of 1 to 5 carbon atoms) and —O—C(=O)—R$^{C3}$ (wherein, R$^{C3}$ represents a hydrocarbon group).

The alkyl group for R$^{g13}$ is preferably a linear or branched alkyl group of 1 to 5 carbon atoms, and specific examples include a methyl group, an ethyl group, a propyl group, an isopropyl group, an n-butyl group, an isobutyl group, a tert-butyl group, a pentyl group, an isopentyl group, and a neopentyl group. Part of the hydrogen atoms within the alkyl group for R$^2$ may be substituted with a hydroxy group, a cyano group or the like.

The alkoxy group for R$^{g13}$ is preferably an alkoxy group of 1 to 5 carbon atoms, and specific examples thereof include a methoxy group, an ethoxy group, an n-propoxy group, an iso-propoxy group, an n-butoxy group and a tert-butoxy group. Among these, a methoxy group and an ethoxy group are particularly desirable.

In —O—C(=O)—C(R$^{C2}$)=CH$_2$, R$^{C2}$ represents a hydrogen atom, an alkyl group of 1 to 5 carbon atoms or a halogenated alkyl group of 1 to 5 carbon atoms.

The alkyl group of 1 to 5 carbon atoms for R$^{C2}$ is preferably a linear or branched alkyl group of 1 to 5 carbon atoms, and specific examples thereof include a methyl group, an ethyl group, a propyl group, an isopropyl group, an n-butyl group, an isobutyl group, a tert-butyl group, a pentyl group, an isopentyl group and a neopentyl group.

The halogenated alkyl group for R$^{C2}$ is a group in which part or all of the hydrogen atoms of the aforementioned alkyl group of 1 to 5 carbon atoms has been substituted with halogen atoms. Examples of the halogen atom include a fluorine atom, a chlorine atom, a bromine atom and an iodine atom, and a fluorine atom is particularly preferred.

As R$^{C2}$, a hydrogen atom, an alkyl group of 1 to 3 carbon atoms or a fluorinated alkyl group of 1 to 3 carbon atoms is preferable, and a hydrogen atom or a methyl group is particularly desirable in terms of industrial availability.

In the formula —O—C(=O)—R$^{C3}$, R$^{C3}$ represents a hydrocarbon group.

The hydrocarbon group for R$^{C3}$ may be either an aromatic hydrocarbon group or an aliphatic hydrocarbon group. Examples of the hydrocarbon groups for R$^{C3}$ include the same aliphatic hydrocarbon groups or aromatic hydrocarbon groups as those described above for R$^1$ in the general formula (c1).

Among these, as the hydrocarbon group for R$^{C3}$, an alicyclic group (e.g., a group in which one or more hydrogen atoms have been removed from a cycloalkane such as cyclopentane, cyclohexane, adamantane, norbornane, isobornane, tricyclodecane or tetracyclododecane) or an aromatic group (e.g., a phenyl group or a naphthyl group) is preferable. When R$^{C3}$ is an alicyclic group, the resist composition can be satisfactorily dissolved in an organic solvent, thereby improving the lithography properties.

Among these, as R$^{3c}$, —O—C(=O)—C(R$^{C2}$)=CH$_2$ or —O—C(=O)—R$^{C3}$ is preferable. Among these, —O—C(=O)—C(R$^{C2'}$)=CH$_2$ (wherein R$^{C2'}$ represents a hydrogen atom or a methyl group) or —O—C(=O)—R$^{C3'}$ (wherein R$^{C3'}$ represents an aliphatic cyclic group) is preferable.

Y$^{13}$ represents a linear, branched or cyclic alkylene group or an arylene group.

Examples of the linear or branched alkylene group for Y$^{13}$ include the same "linear or branched aliphatic hydrocarbon group" described above as the divalent linking group for Y$^2$ in the formula (a1-3).

Examples of the cyclic alkylene group for Y$^{13}$ include the same "cyclic aliphatic hydrocarbon group" described above as the divalent linking group for Y$^2$ in the formula (a1-3).

Examples of the arylene group for Y$^{13}$ include the same "aromatic hydrocarbon group" described above as the divalent linking group for Y$^2$ in the formula (a1-3).

Among these, as Y$^{13}$, an alkylene group is preferable, a linear or branched alkylene group is more preferable, and a methylene group or an ethylene group is still more preferable.

Specific examples of the compound (G3) include compounds shown below.

[Chemical Formula 79]

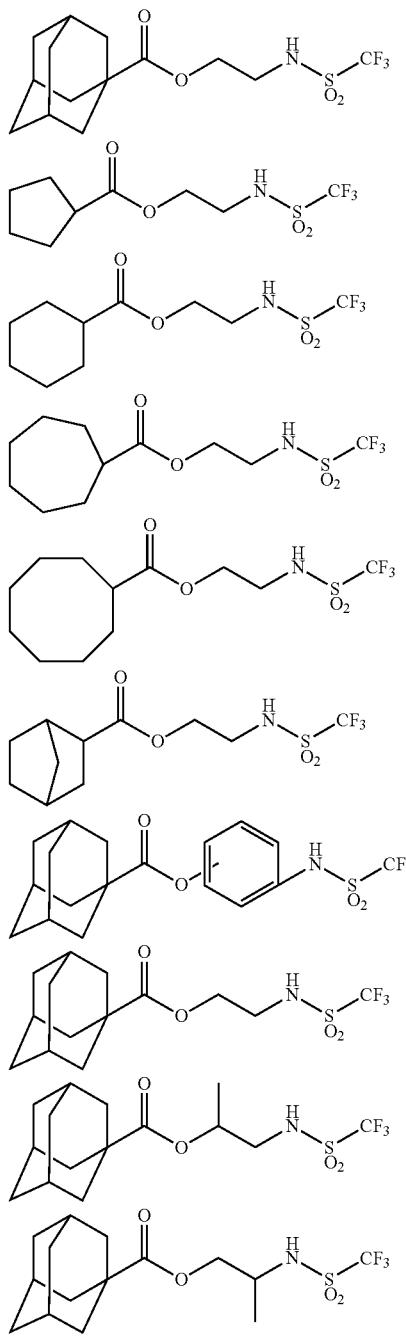

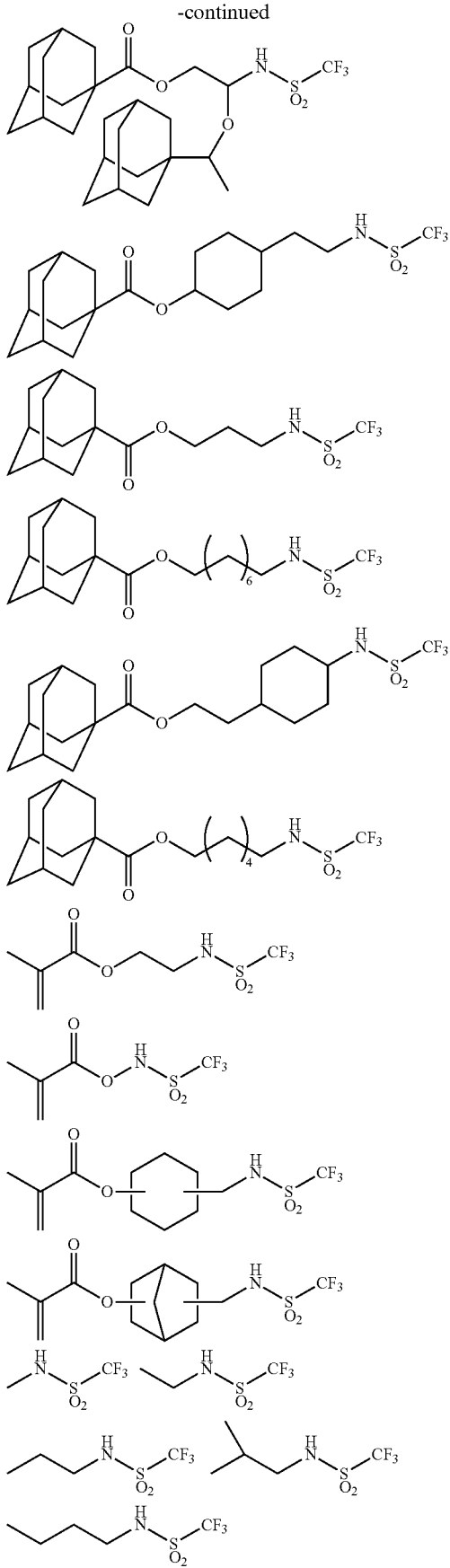

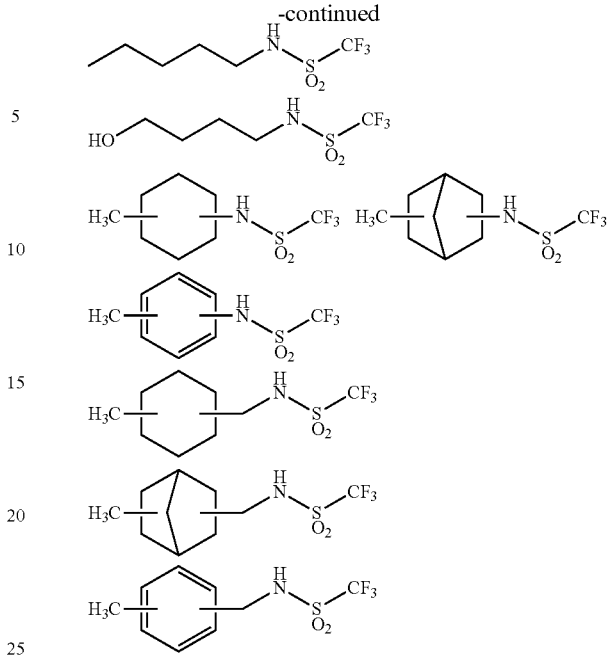

Examples of the sulfonylimide acid include bis(alkylsulfonyl)imide, and the alkyl group in the bis(alkylsulfonyl) imide referable has no electron withdrawing group.

Examples of phosphorus oxo acids include phosphoric acid, phosphoric acid and phosphoric acid.

Examples of phosphorus oxo acid derivatives include esters in which a hydrogen atom within the above-mentioned oxo acids is substituted with a hydrocarbon group.

Examples of the hydrocarbon group include an alkyl group of 1 to 5 carbon atoms and an aryl group of 6 to 15 carbon atoms.

Examples of phosphoric acid derivatives include phosphoric acid esters such as di-n-butyl phosphate and diphenyl phosphate.

Examples of phosphoric acid derivatives include phosphoric acid esters such as dimethyl phosphonate, di-n-butyl phosphonate, phenyl phosphonate, diphenyl phosphonate and dibenzyl phosphonate.

Examples of phosphoric acid derivatives include phosphoric acid esters and phenylphosphinic acid.

As the component (G), one type of compound may be used alone, or two or more types of compounds may be used in combination.

Among these, a component (G) preferably contains a carboxylic acid, and more preferably contains a compound (G1).

When the resist composition includes the component (G), the amount of the component (G) in the resist composition, relative to 100 parts by weight of the component (A) is preferably from 0.01 to 5 parts by weight, and more preferably from 0.5 to 3 parts by weight. When the amount of the component (G) is at least as large as the lower limit of the above-mentioned range, the storage stability effect of the resist composition can be improved. On the other hand, when the amount of the component (G) is no more than the upper limit of the above-mentioned range, excellent lithography properties (e.g., sensitivity) can be obtained.

<Other Optional Components>

[Component (D)]

The resist composition of the present invention may also contain, a basic compound which does not fall under the definition of the aforementioned component (C) (hereafter, referred to as "component (D)") as an arbitrary component.

The component (D) is not particularly limited, as long as it is a compound which is basic relative to the component (B), so as to function as an acid diffusion inhibitor, that is, a quencher which traps acid generated from the component (A) or (B) upon exposure, and does not fall under the definition of the component (C). As the component (D), any of the conventionally known compounds may be selected for use. Examples thereof include an aliphatic amine and an aromatic amine. Among these, an aliphatic amine is preferable, and a secondary aliphatic amine or tertiary aliphatic amine is particularly desirable.

An aliphatic amine is an amine having one or more aliphatic groups, and the aliphatic groups preferably have 1 to 12 carbon atoms.

Examples of these aliphatic amines include amines in which at least one hydrogen atom of ammonia ($NH_3$) has been substituted with an alkyl group or hydroxyalkyl group of no more than 20 carbon atoms (i.e., alkylamines or alkylalcoholamines), cyclic amines and other aliphatic amines.

The alkyl group in the alkylamine may be any of linear, branched or cyclic.

When the alkyl group is linear or branched, the number of carbon atoms thereof is preferably 2 to 20, and more preferably 2 to 8.

When the alkyl group is cyclic (i.e., a cycloalkyl group), the number of carbon atoms is preferably 3 to 30, more preferably 3 to 20, still more preferably 3 to 15, still more preferably 4 to 12, and most preferably 5 to 10. The alkyl group may be monocyclic or polycyclic. Examples thereof include groups in which one or more of the hydrogen atoms have been removed from a monocycloalkane; and groups in which one or more of the hydrogen atoms have been removed from a polycycloalkane such as a bicycloalkane, a tricycloalkane, or a tetracycloalkane. Specific examples of the monocycloalkane include cyclopentane and cyclohexane. Specific examples of the polycycloalkane include adamantane, norbornane, isobornane, tricyclodecane and tetracyclododecane.

As the alkyl group in the hydroxyalkyl group in the alkylalcoholamine, the same alkyl group as those in the alkylamine can be mentioned.

Specific examples of the alkylamines include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; and trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decanylamine, and tri-n-dodecylamine.

Specific examples of the alkylalcoholamines include diethanolamine, triethanolamine, diisopropanolamine, triisopropanolamine, di-n-octanolamine, tri-n-octanolamine, stearyldiethanolamine and lauryldiethanolamine.

Among these, trialkylamines of 5 to 10 carbon atoms are preferable, and tri-n-pentylamine and tri-n-octylamine are particularly desirable.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine) can be used.

Specific examples of the aliphatic monocyclic amine include piperidine, and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine, and 1,4-diazabicyclo[2.2.2]octane.

Examples of other aliphatic amines include tris(2-methoxymethoxyethyl)amine, tris{2-(2-methoxyethoxy)ethyl}amine, tris{2-(2-methoxyethoxymethoxy)ethyl}amine, tris {2-(1-methoxyethoxy)ethyl}amine, tris {2-(1-ethoxyethoxy)ethyl}amine, tris{2-(1-ethoxypropoxy)ethyl}amine, tris[2-{2-(2-hydroxyethoxy)ethoxy}ethyl] amine and triethanolamine triacetate.

Examples of aromatic amines include aniline, pyridine, 4-dimethylaminopyridine, pyrrole, indole, pyrazole, imidazole and derivatives thereof, diphenylamine, triphenylamine, tribenzylamine, 2,6-diisopropylaniline and N-tert-butoxycarbonylpyrrolidine.

As the component (D), one type of may be used alone, or two or more types may be used in combination.

When the resist composition of the present invention includes the component (D), the component (D) is used in an amount within a range from 0.01 to 5.0 parts by weight, relative to 100 parts by weight of the component (A). When the amount of the component (D) is within the above-mentioned range, the shape of the resist pattern and the post exposure stability of the latent image formed by the patternwise exposure of the resist layer are improved.

[Component (F)]

The resist composition may further include a fluorine additive (hereafter, referred to as "component (F)") for imparting water repellency to the resist film. As the component (F), for example, a fluorine-containing polymeric compound described in Japanese Unexamined Patent Application, First Publication No. 2010-002870 can be given.

As the component (F), a polymer having a structural unit (f1) represented by general formula (f1-1) shown below can be used. The polymer is preferably a polymer (homopolymer) consisting of a structural unit (f1) represented by formula (f1-1) shown below; a copolymer of a structural unit represented by formula (f1-1) shown below and the aforementioned structural unit (a1); or a copolymer of a structural unit represented by formula (f1-1) shown below, a structural unit derived from acrylic acid or methacrylic acid and the aforementioned structural unit (a1). As the structural unit (a1) to be copolymerized with a structural unit represented by the formula (f1-1) shown below, the structural unit (a11) is preferable, the structural unit represented by the formula (a1-1) is more preferable, and the structural unit represented by the formula (a1-1-02) is particularly preferable.

[Chemical Formula 80]

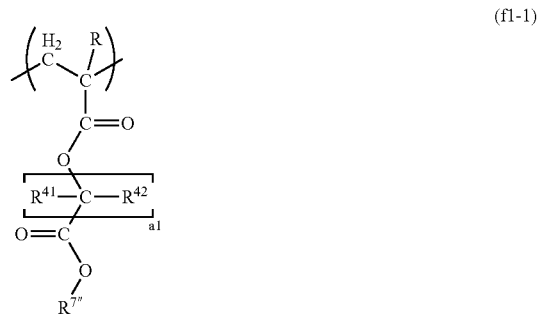

(f1-1)

In the formula, R is the same as defined above; each of $R^{41}$ and $R^{42}$ independently represents a hydrogen atom, a halogen atom, an alkyl group of 1 to 5 carbon atoms or a halogenated alkyl group of 1 to 5 carbon atoms, provided that the plurality of $R^{41}$ to $R^{42}$ may be the same or different from each other; a1 represents an integer of 1 to 5; and $R^{7\prime\prime}$ represents an organic group containing a fluorine atom.

In formula (f1-1), R is the same as defined above. As R, a hydrogen atom or a methyl group is preferable.

In formula (f1-1), examples of the halogen atom for $R^{41}$ and $R^{42}$ include a fluorine atom, a chlorine atom, a bromine atom and an iodine atom, and a fluorine atom is particularly desirable. Examples of the alkyl group of 1 to 5 carbon atoms for $R^{41}$ and $R^{42}$ include the same alkyl group of 1 to 5 carbon atoms as those defined above for R defined above, and a methyl group or an ethyl group is preferable. Specific examples of the halogenated alkyl group of 1 to 5 carbon atoms represented by $R^{41}$ or $R^{42}$ include groups in which part or all of the hydrogen atoms of the aforementioned alkyl groups of 1 to 5 carbon atoms have been substituted with halogen atoms. Examples of the halogen atom include a fluorine atom, a chlorine atom, a bromine atom and an iodine atom, and a fluorine atom is particularly preferred. Among these, $R^{41}$ and $R^{42}$ are preferably a hydrogen atom, a fluorine atom or an alkyl group of 1 to 5 carbon atoms, and more preferably a hydrogen atom, a fluorine atom, a methyl group or an ethyl group.

In formula (f1-1), a1 represents an integer of 1 to 5, preferably an integer of 1 to 3, and more preferably 1 or 2.

In formula (f1-1), $R^{7\prime\prime}$ represents an organic group containing a fluorine atom, and is preferably a hydrocarbon group containing a fluorine atom.

The hydrocarbon group containing a fluorine atom may be linear, branched or cyclic, and preferably has 1 to 20 carbon atoms, more preferably 1 to 15 carbon atoms, and particularly preferably 1 to 10 carbon atoms.

The hydrocarbon group having a fluorine atom preferably has 25% or more of the hydrogen atoms within the hydrocarbon group fluorinated, more preferably 50% or more, and most preferably 60% or more, because the hydrophobicity of the resist film during immersion exposure is enhanced.

As $R^{7\prime\prime}$, a fluorinated hydrocarbon group of 1 to 5 carbon atoms is particularly preferable, and most preferably methyl group, —$CH_2$—$CF_3$, —$CH_2$—$CF_2$—$CF_3$, —$CH(CF_3)_2$, —$CH_2$—$CH_2$—$CF_3$ and —$CH_2$—$CH_2$—$CF_2$—$CF_2$—$CF_2$—$CF_3$.

The weight average molecular weight (Mw) (the polystyrene equivalent value determined by gel permeation chromatography) of the component (F) is preferably 1,000 to 50,000, more preferably 5,000 to 40,000, and most preferably 10,000 to 30,000. When the weight average molecular weight of the component (F) is no more than the upper limit of the above-mentioned range, the resist composition exhibits a satisfactory solubility in a resist solvent. On the other hand, when the weight average molecular weight is at least as large as the lower limit of the above-mentioned range, the dry etching resistance and the cross-sectional shape of the resist pattern becomes satisfactory.

Further, the dispersity (Mw/Mn) of the component (F) is preferably 1.0 to 5.0, more preferably 1.0 to 3.0, and most preferably 1.2 to 2.5.

The component (F) can be produced by a conventional radical polymerization or the like of the monomers corresponding with each of the structural units, using a radical polymerization initiator such as dimethyl 2,2'-azobis(isobutyrate) (V-601) or azobisisobutyronitrile (AIBN). By using a chain transfer agent such as HS—$CH_2$—$CH_2$—$CH_2$—$C(CF_3)_2$—OH, a —$C(CF_3)_2$—OH group can be introduced at the terminals. Such a copolymer having introduced a hydroxyalkyl group in which some of the hydrogen atoms of the alkyl group are substituted with fluorine atoms is effective in reducing defects and LER (line edge roughness: unevenness of the side walls of a line pattern).

As the monomers which yield the corresponding structural units, commercially available monomers may be used, or the monomers may be synthesized by a conventional method.

As the component (F), one type may be used alone, or two or more types may be used in combination.

When the resist composition of the present invention includes the component (F), the component (F) is used in an amount within a range from 0.5 to 10 parts by weight, relative to 100 parts by weight of the component (A).

If desired, other miscible additives can also be added to the resist composition of the present invention. Examples of such miscible additives include additive resins for improving the performance of the resist film, surfactants for improving the applicability, dissolution inhibitors, plasticizers, stabilizers, colorants, halation prevention agents, and dyes.

The resist composition for immersion exposure according to the present invention can be prepared by dissolving the materials for the resist composition in an organic solvent (hereafter, frequently referred to as "component (S)").

The component (S) may be any organic solvent which can dissolve the respective components to give a uniform solution, and any one or more kinds of organic solvents can be appropriately selected from those which have been conventionally known as solvents for a chemically amplified resist.

Examples thereof include lactones such as γ-butyrolactone;

ketones such as acetone, methyl ethyl ketone, cyclohexanone, methyl-n-pentyl ketone, methyl isopentyl ketone, and 2-heptanone;

polyhydric alcohols, such as ethylene glycol, diethylene glycol, propylene glycol and dipropylene glycol;

compounds having an ester bond, such as ethylene glycol monoacetate, diethylene glycol monoacetate, propylene glycol monoacetate, and dipropylene glycol monoacetate; polyhydric alcohol derivatives including compounds having an ether bond, such as a monoalkylether (e.g., monomethylether, monoethylether, monopropylether or monobutylether) or monophenylether of any of these polyhydric alcohols or compounds having an ester bond (among these, propylene glycol monomethyl ether acetate (PGMEA) and propylene glycol monomethyl ether (PGME) are preferable);

cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate;

and aromatic organic solvents such as anisole, ethylbenzylether, cresylmethylether, diphenylether, dibenzylether, phenetole, butylphenylether, ethylbenzene, diethylbenzene, pentylbenzene, isopropylbenzene, toluene, xylene, cymene and mesitylene.

These solvents can be used individually, or in combination as a mixed solvent.

Among these, propylene glycol monomethyl ether acetate (PGMEA), propylene glycol monomethyl ether (PGME) and ethyl lactate (EL) are preferable.

Further, among the mixed solvents, a mixed solvent obtained by mixing PGMEA with a polar solvent is preferable. The mixing ratio (weight ratio) of the mixed solvent can be appropriately determined, taking into consideration the compatibility of the PGMEA with the polar solvent, but is preferably in the range of 1:9 to 9:1, more preferably from 2:8 to 8:2. For example, when EL is mixed as the polar solvent, the PGMEA:EL weight ratio is preferably from 1:9 to 9:1, and more preferably from 2:8 to 8:2. Alternatively, when PGME is mixed as the polar solvent, the PGMEA:PGME is preferably from 1:9 to 9:1, more preferably from 2:8 to 8:2, and still more preferably 3:7 to 7:3. Alternatively, when PGME and cyclohexanone is mixed as the polar solvent, the PGMEA:(PGME+cyclohexanone) weight ratio is preferably from 1:9 to 9:1, more preferably from 2:8 to 8:2, and still more preferably 3:7 to 7:3.

Further, as the component (S), a mixed solvent of PGMEA, EL, or PGMEA with a polar solvent and a mixed solvent of PGMEA, EL, or PGMEA with γ-butyrolactone are also preferable. The mixing ratio (former:latter) of such a mixed solvent is preferably from 70:30 to 95:5.

The amount of the organic solvent is not particularly limited, and is appropriately adjusted to a concentration which enables coating of a coating solution to a substrate, depending on the thickness of the coating film. In general, the organic solvent is used in an amount such that the solid content of the resist composition becomes within the range from 1 to 20% by weight, and preferably from 2 to 15% by weight.

Since the resist composition according to the present invention contains a component (C), various lithography properties such as resolution, depth of focus, mask reproducibility, in-plane uniformity of the pattern dimensions, pattern shape (e.g., rectangularity of the cross-sectional shape and circularity of hole patterns) and the like can be improved.

Further, the resist composition according to the present invention contains a component (C1) having an anion moiety which has a specific structure as a component (C) is superior in storage stability to the conventional resist composition, and less likely to deteriorate in the properties thereof due to the change in a storage temperature and a storage period.

For example, when the resist composition contains a resin component having the structural unit (f1) as a component (F), the surface of the resist film to be formed has a high hydrophobicity (for example, receding angle of 65° or more). The high hydrophobicity is desirable in immersion exposure. However, there is a problem that in the case where a conventional photoreactive quencher is used as a component (C), the hydrophobicity after storage is reduced (i.e., receding angle is reduced), in particular, when a storage temperature is high. When the component (C1) is used as a component (C), reducing angle can be suppressed.

The aforementioned improvement in storage stability is particularly significant when the acid (G) is included as well as the component (C1).

It is presumed that the reason that improvement in storage stability obtained by using the component (C1) as a component (C) is because the component (C1) has an anion moiety which has a low electron density and a high acidity having a pKa value of 4 or less as a counteranion. That is, the anion moiety constituting the component (C1) has X adjacent to the carbon atom having —COO⁻ bonded thereto (i.e., β-position), and therefore, the component (C1) has a pKa value of 4 or less and a lower electron density than the photoreactive quencher which does not have X adjacent to the carbon atom on the β-position. It is presumed that, when the counteranion in the component (C1) has a high acidity, the nucleophilic attack by the component (C1) onto the other component having a structure that is likely to be decomposed by a nucleophilic attack, such as ester bond (e.g., a resin component having a structural unit derived from an acrylate ester) is less likely to occur, and the decomposition of the other component caused by the nucleophilic attack can be suppressed.

In order to indicate the influence of the presence or absence of X and the influence of the position of X on acidity of the carboxylate anion, acetic acid and acetic acid derivatives having a substituent bonded to the carbon atom on the α-position are illustrated below together with the pKa value thereof. Further, examples of the cyclic carboxylic acid having an oxygen atom on the carbon atom on the β-position are illustrated below together with the pKa value thereof.

As shown below, when the carboxylic acid has an oxygen atom or a sulfur atom bonded to the β-position, a pKa value is significantly reduced. On the other hand, when the carboxylic acid has an oxygen atom or a sulfur atom bonded to γ-position, a pKa value is scarcely reduced.

In the formulas shown below, the compound marked with a character (*) has a pKa value of 4 or less, which is equivalent to a pKa value of two compounds illustrated on the upper side of the compounds marked with the character (*).

It is noted that a pKa value of the carboxylic acid is the same as a pKa value of the anion moiety of the carboxylic acid.

[Chemical Formula 81]

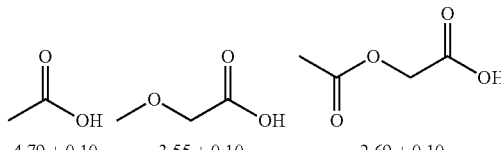

4.79 ± 0.10    3.55 ± 0.10    2.69 ± 0.10

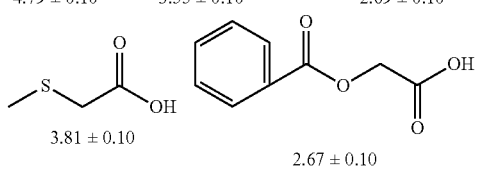

3.81 ± 0.10    2.67 ± 0.10

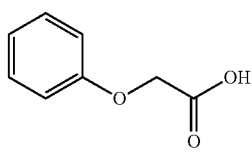

3.17 ± 0.10

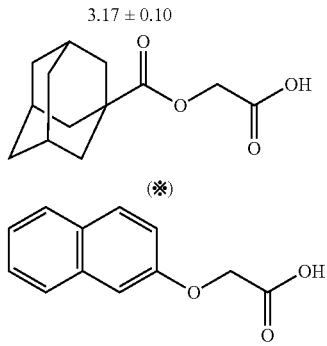

3.18 ± 0.30

1.95 ± 0.10

3.66 ± 0.10    3.99 ± 0.20

-continued

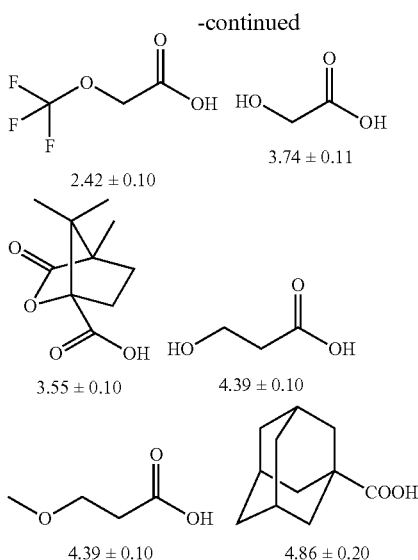

<<Method of Forming a Resist Pattern>>

The method of forming a resist pattern according to the present invention includes: forming a resist film on a substrate using a resist composition of the present invention; conducting exposure of the resist film; and developing the resist film to form a resist pattern.

The method for forming a resist pattern according to the present invention can be performed, for example, as follows.

Firstly, a resist composition of the present invention is applied to a substrate using a spinner or the like, and a bake treatment (post applied bake (PAB)) is conducted at a temperature of 80 to 150° C. for 40 to 120 seconds, preferably 60 to 90 seconds, to form a resist film.

Following selective exposure of the thus formed resist film, either by exposure through a mask having a predetermined pattern formed thereon (mask pattern) using an exposure apparatus such as an ArF exposure apparatus, a KrF exposure apparatus, an electron beam lithography apparatus or an EUV exposure apparatus, or by patterning via direct irradiation with an electron beam without using a mask pattern, baking treatment (post exposure baking (PEB)) is conducted under temperature conditions of 80 to 150° C. for 40 to 120 seconds, and preferably 60 to 90 seconds.

Next, the resist film is subjected to a developing treatment.

The developing treatment is conducted using an alkali developing solution in the case of an alkali developing process, whereas the developing treatment is conducted using a developing solution containing an organic solvent (organic developing solution) in the case of a solvent developing process.

After the developing treatment, it is preferable to conduct a rinse treatment. The rinse treatment is preferably conducted using pure water in the case of an alkali developing process, whereas the rinse treatment is preferably conducted using a rinse solution containing an organic solvent in the case of a solvent developing process.

In the case of a solvent developing process, after the developing treatment or the rinsing, the developing solution or the rinse liquid remaining on the pattern can be removed by a treatment using a supercritical fluid.

After the developing treatment or the rinse treatment, drying is conducted. If desired, bake treatment (post bake) can be conducted following the developing. In this manner, a resist pattern can be obtained.

The substrate is not specifically limited and a conventionally known substrate can be used. For example, substrates for electronic components, and such substrates having wiring patterns formed thereon can be used. Specific examples of the material of the substrate include metals such as silicon wafer, copper, chromium, iron and aluminum; and glass. Suitable materials for the wiring pattern include copper, aluminum, nickel, and gold.

Further, as the substrate, any one of the above-mentioned substrates provided with an inorganic and/or organic film on the surface thereof may be used. As the inorganic film, an inorganic antireflection film (inorganic BARC) can be used. As the organic film, an organic antireflection film (organic BARC) and an organic film such as a lower-layer organic film used in a multilayer resist method can be used.

Here, a "multilayer resist method" is method in which at least one layer of an organic film (lower-layer organic film) and at least one layer of a resist film (upper resist film) are provided on a substrate, and a resist pattern formed on the upper resist film is used as a mask to conduct patterning of the lower-layer organic film. This method is considered as being capable of forming a pattern with a high aspect ratio. More specifically, in the multilayer resist method, a desired thickness can be ensured by the lower-layer organic film, and as a result, the thickness of the resist film can be reduced, and an extremely fine pattern with a high aspect ratio can be formed.

The multilayer resist method is broadly classified into a method in which a double-layer structure consisting of an upper-layer resist film and a lower-layer organic film is formed (double-layer resist method), and a method in which a multilayer structure having at least three layers consisting of an upper-layer resist film, a lower-layer organic film and at least one intermediate layer (thin metal film or the like) provided between the upper-layer resist film and the lower-layer organic film (triple-layer resist method).

The wavelength to be used for exposure is not particularly limited and the exposure can be conducted using radiations such as ArF excimer laser, KrF excimer laser, $F_2$ excimer laser, extreme ultraviolet rays (EUV), vacuum ultraviolet rays (VUV), electron beam (EB), X-rays, and soft X-rays. The resist composition of the present invention is effective to KrF excimer laser, ArF excimer laser, EB and EUV.

The exposure of the resist film can be either a general exposure (dry exposure) conducted in air or an inert gas such as nitrogen, or immersion exposure (liquid immersion lithography).

In immersion lithography, the region between the resist film and the lens at the lowermost point of the exposure apparatus is pre-filled with a solvent (immersion medium) that has a larger refractive index than the refractive index of air, and the exposure (immersion exposure) is conducted in this state.

The immersion medium preferably exhibits a refractive index larger than the refractive index of air but smaller than the refractive index of the resist film to be exposed. The refractive index of the immersion medium is not particularly limited as long at it satisfies the above-mentioned requirements.

Examples of this immersion medium which exhibits a refractive index that is larger than the refractive index of air but smaller than the refractive index of the resist film include water, fluorine-based inert liquids, silicon-based solvents and hydrocarbon-based solvents.

Specific examples of the fluorine-based inert liquids include liquids containing a fluorine-based compound such as $C_3HCl_2F_5$, $C_4F_9OCH_3$, $C_4F_9OC_2H_5$ or $C_5H_3F_7$ as the main component, which have a boiling point within a range from 70 to 180° C. and preferably from 80 to 160° C. A fluorine-based inert liquid having a boiling point within the above-mentioned range is advantageous in that the removal of the immersion medium after the exposure can be conducted by a simple method.

As a fluorine-based inert liquid, a perfluoroalkyl compound in which all of the hydrogen atoms of the alkyl group are substituted with fluorine atoms is particularly desirable. Examples of these perfluoroalkyl compounds include perfluoroalkylether compounds and perfluoroalkylamine compounds.

Specifically, one example of a suitable perfluoroalkylether compound is perfluoro(2-butyl-tetrahydrofuran) (boiling point 102° C.), and an example of a suitable perfluoroalkylamine compound is perfluorotributylamine (boiling point 174° C.).

As the immersion medium, water is preferable in terms of cost, safety, environment and versatility.

As an example of the alkali developing solution used in an alkali developing process, a 0.1 to 10% by weight aqueous solution of tetramethylammonium hydroxide (TMAH) can be given.

As the organic solvent contained in the organic developing solution used in a solvent developing process, any of the conventional organic solvents can be used which are capable of dissolving the component (A) (prior to exposure). Specific examples of the organic solvent include polar solvents such as ketone-based solvents, ester-based solvents, alcohol-based solvents, amide-based solvents and ether-based solvents, and hydrocarbon solvents.

If desired, the organic developing solution may have a conventional additive blended. Examples of the additive include surfactants. The surfactant is not particularly limited, and for example, an ionic or non-ionic fluorine surfactant and/or silicon surfactant can be used.

When a surfactant is added, the amount thereof based on the total amount of the organic developing solution is generally 0.001 to 5% by weight, preferably 0.005 to 2% by weight, and more preferably 0.01 to 0.5% by weight.

The developing treatment can be performed by a conventional developing method. Examples thereof include a method in which the substrate is immersed in the developing solution for a predetermined time (a dip method), a method in which the developing solution is cast up on the surface of the substrate by surface tension and maintained for a predetermined period (a puddle method), a method in which the developing solution is sprayed onto the surface of the substrate (spray method), and a method in which the developing solution is continuously ejected from a developing solution ejecting nozzle while scanning at a constant rate to apply the developing solution to the substrate while rotating the substrate at a constant rate (dynamic dispense method).

As the organic solvent contained in the rinse liquid used in the rinse treatment after the developing treatment in the case of a solvent developing process, any of the aforementioned organic solvents contained in the organic developing solution can be used which hardly dissolves the resist pattern. In general, at least one solvent selected from the group consisting of hydrocarbon solvents, ketone-based solvents, ester-based solvents, alcohol-based solvents, amide-based solvents and ether-based solvents is used. Among these, at least one solvent selected from the group consisting of hydrocarbon-based solvents, ketone-based solvents, ester-based solvents, alcohol-based solvents and amide-based solvents is preferable, more preferably at least one solvent selected from the group consisting of alcohol-based solvents and ester-based solvents, and an alcohol-based solvent is particularly desirable.

The rinse treatment (washing treatment) using the rinse liquid can be performed by a conventional rinse method. Examples thereof include a method in which the rinse liquid is continuously applied to the substrate while rotating it at a constant rate (rotational coating method), a method in which the substrate is immersed in the rinse liquid for a predetermined time (dip method), and a method in which the rinse liquid is sprayed onto the surface of the substrate (spray method).

<<Compound>>

The compound of the present invention is represented by general formula (c1) shown below.

[Chemical Formula 82]

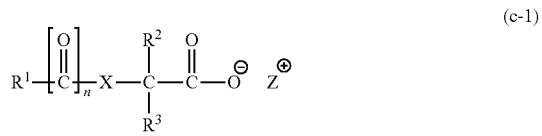

In the formula, $R^1$ represents a hydrogen atom or a hydrocarbon group of 1 to 20 carbon atoms which may have a substituent; each of $R^2$ and $R^3$ independently represents a hydrogen atom or a hydrocarbon group of 1 to 20 carbon atoms which may have a substituent; at least two of $R^1$ to $R^3$ may be mutually bonded to form a ring; X represents an oxygen atom or a sulfur atom; n represents 0 or 1; and $Z^+$ represents an organic cation.

The compound according to the present invention is the same compound as those described above for the component (C1) in the resist composition of the present invention.

The composition according to the present invention is a new compound useful as a photoreactive quencher, and can be blended in a chemically amplified resist composition.

EXAMPLES

As follows is a description of examples of the present invention, although the scope of the present invention is by no way limited by these examples.

In the following examples, a compound represented by a chemical formula (1) is designated as "compound (1)", and the same applies for compounds represented by other formulas.

In the NMR analysis, the internal standard for $^1$H-NMR and $^{13}$C-NMR was tetramethylsilane (TMS). The internal standard for $^{19}$F-NMR was hexafluorobenzene (provided that the peak of hexafluorobenzene was regarded as −160 ppm).

Synthesis Example 0-1

Synthesis Example of Acid (G4)

Under a nitrogen atmosphere, 50 g of dichloromethane was added to 5 g of hydroxyacetic acid, and then stirred to obtain a reaction solution. The obtained reaction solution was cooled to 10° C. or lower, and then, 26 g of a $CH_2Cl_2$ solution dissolving 13 g of 1-adamantanecarbonyl chloride was added thereto in a dropwise manner while maintaining the temperature. The reaction solution was stirred at 10° C. or lower for 30 minutes, followed by elevating the temperature to 25° C. and stirring for 15 hours to obtain a reaction solution. Next, the obtained reaction solution was cooled to 10° C. or lower, and 50 g of 1% HCl was added thereto, followed by stirring for 10 minutes to wash the organic phase and washing with 50 g of pure water at 25° C. three times. The obtained solution was added to 500 g of hexane in a dropwise manner over 30 minutes, and then the resultant was matured for 30 minutes, followed by filtration to obtain precipitated powders. The resulting powders were dried in a vacuum pressure at 40° C. for 12 hours, thereby obtaining 12.2 g of powders. The obtained compound was analyzed by NMR, and it was confirmed that obtained compound was an objective compound.

$^1$H-NMR (400 MHz, DMSO-d6): δ(ppm)=4.42 (s, 2H, $CH_2$), 1.58-1.93 (m, 15H, Ad)

[Chemical Formula 83]

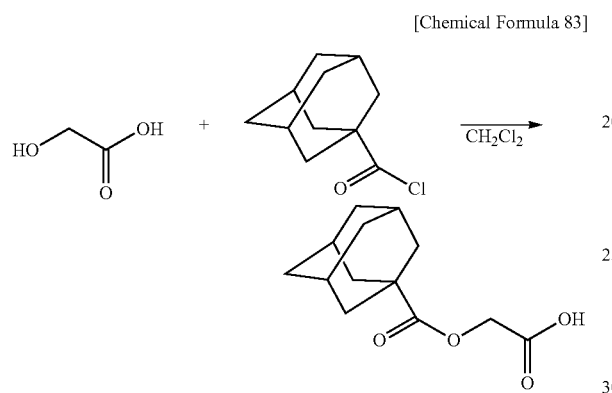

Synthesis Example 0-2

Synthesis Example of Acid (G5)>

The same procedure as in Synthesis Example 0-1 was performed, except that the compound shown below was used instead of 1-adamantanecarbonyl chloride, thereby obtaining an acid (G5).

[Chemical Formula 84]

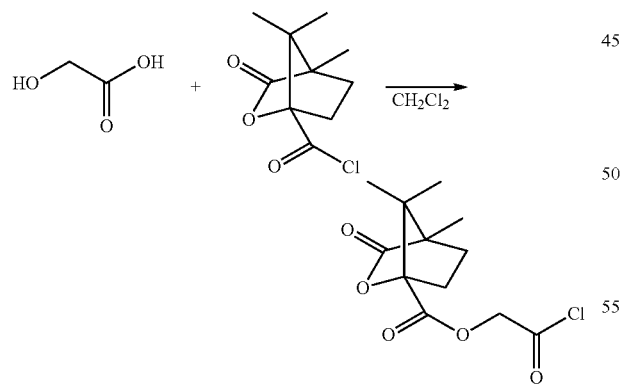

Synthesis Example of Component (C)

In the following manner, a variety of salts consisting of any one of anion moieties an-1 to an-5 shown below and any one of cation moieties ca-1 to ca-60 shown below (that is, compounds 1-1 to 1-60, 2-1 to 2-60, 3-1 to 3-60, 4-1 to 4-60 and 5-1 to 5-60) was obtained.

A reaction (salt-exchange reaction) between an acid corresponding to an anion moiety of an objective compound and a salt containing a predetermined cation moiety was performed, so as to change the anion moiety of the salt to the anion moiety corresponding to the acid, thereby obtaining an objective compound. An anion moiety an-4 shown below corresponds to the acid (G4) obtained in the aforementioned Synthesis Example 0-1, an anion moiety an-5 shown below corresponds to the acid (G5) obtained in the aforementioned Synthesis Example 0-2, and the other anion moieties an-3, an-4 and an-5 shown below correspond to commercially available acids.

[Chemical Formula 85]

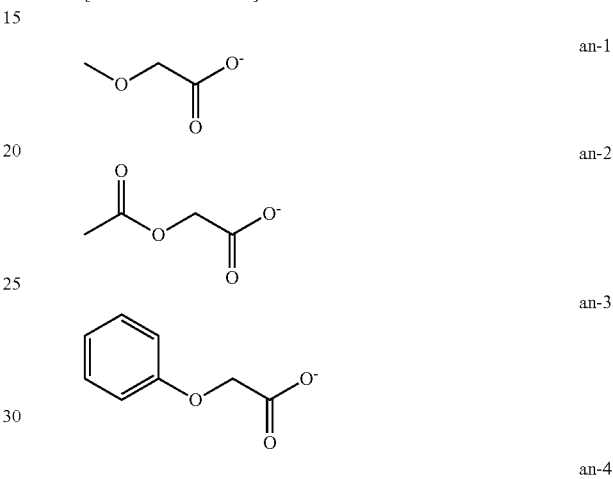

[Chemical Formula 86]

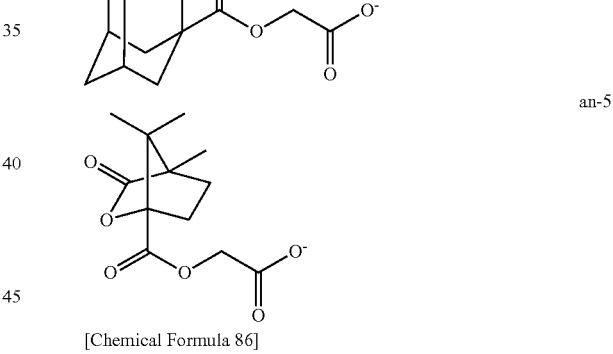

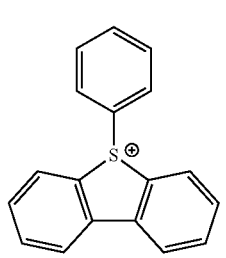

-continued
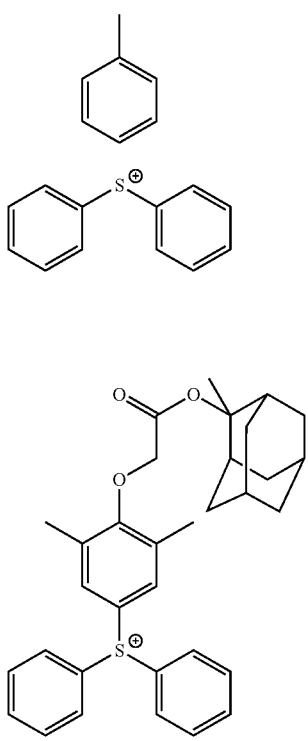
ca-3
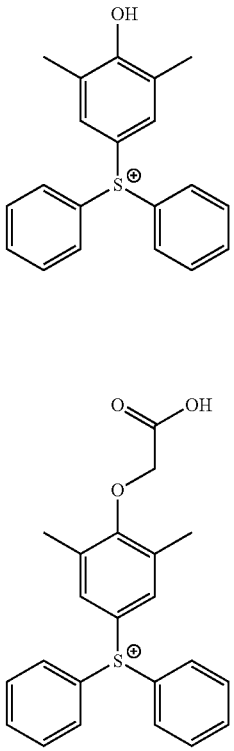
ca-7
ca-4
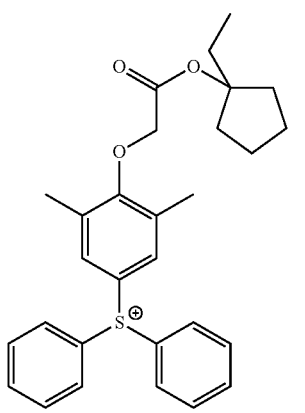
ca-5
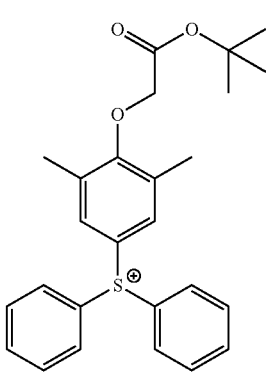
ca-8
ca-9
ca-6
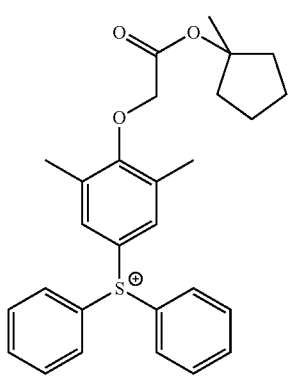
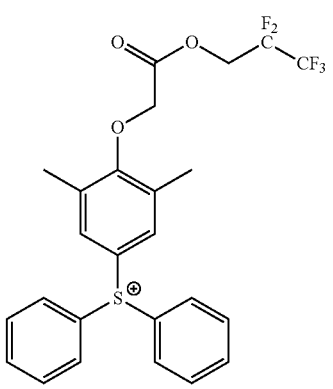
ca-10

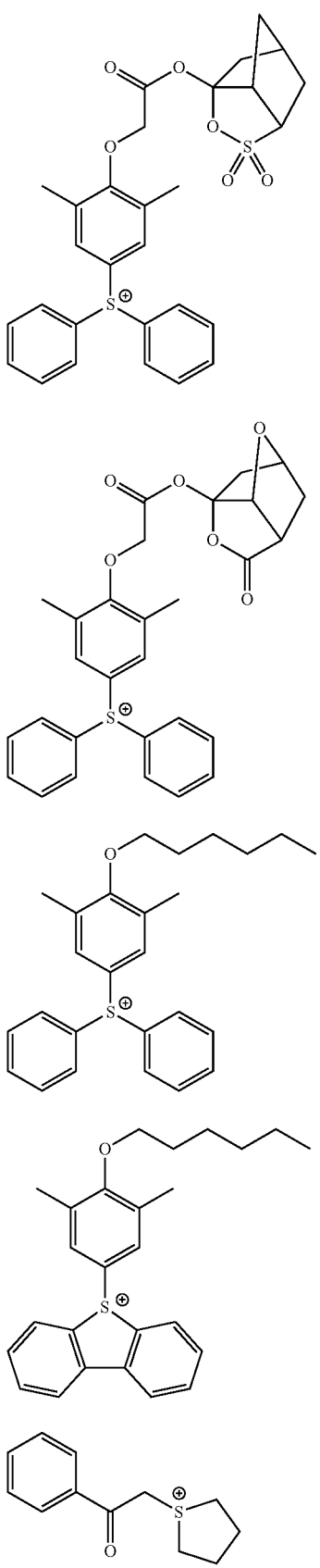
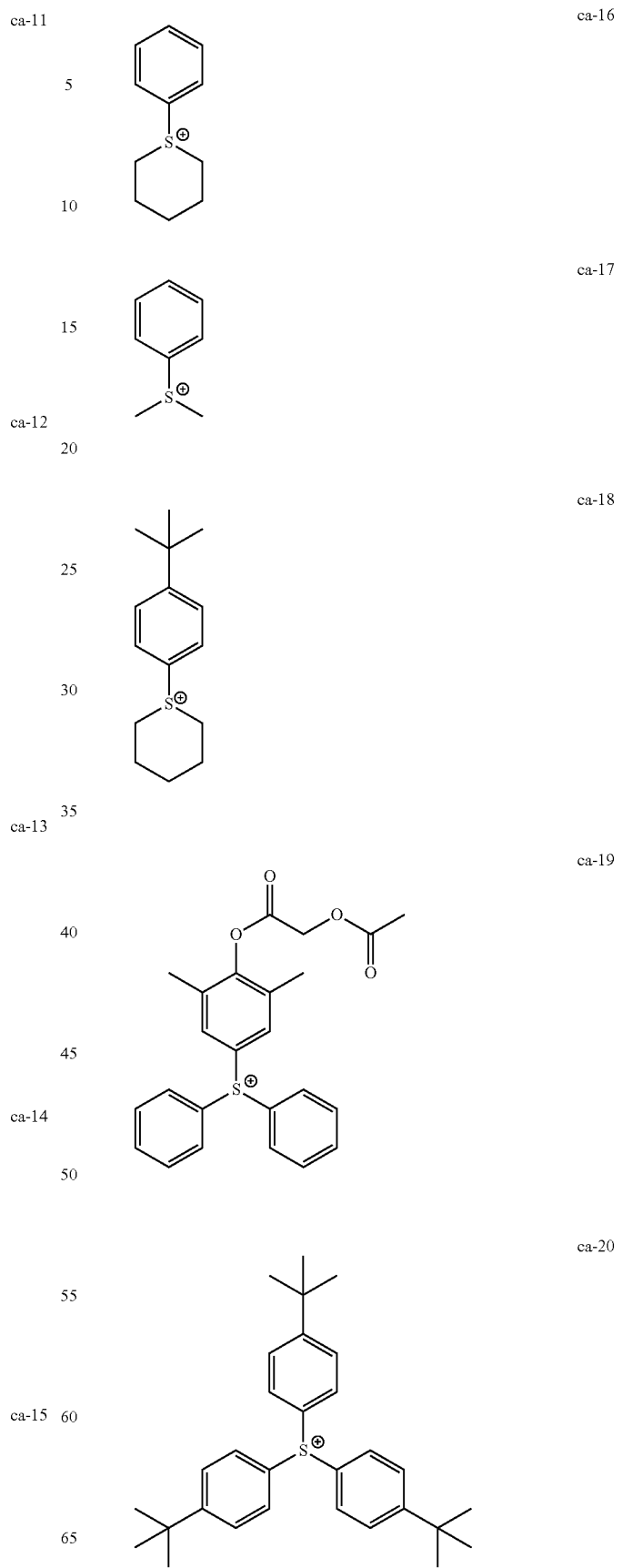

-continued
[Chemical Formula 87]
ca-21
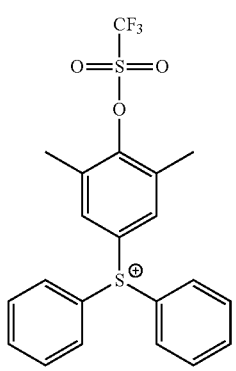
ca-22
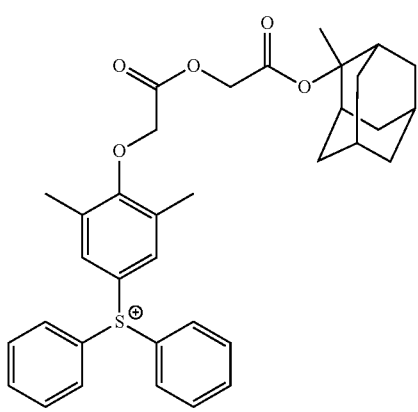
ca-23
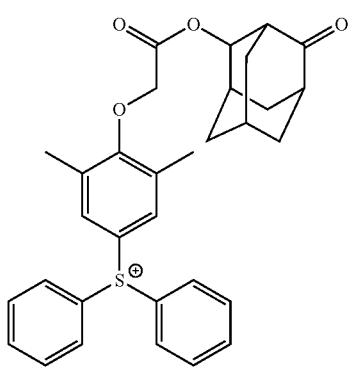
ca-24
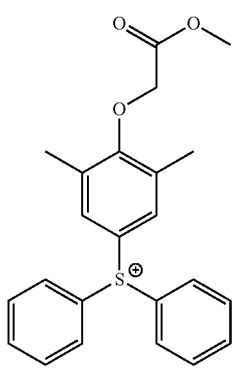
-continued
ca-25
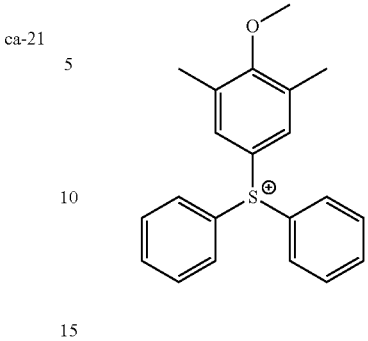
ca-26
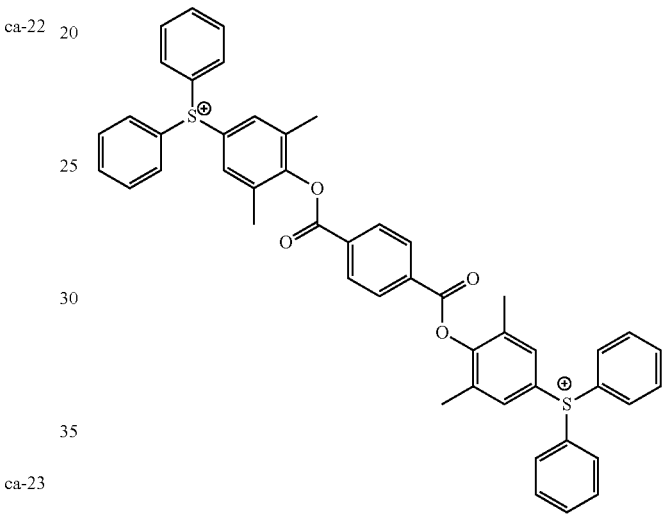
ca-27
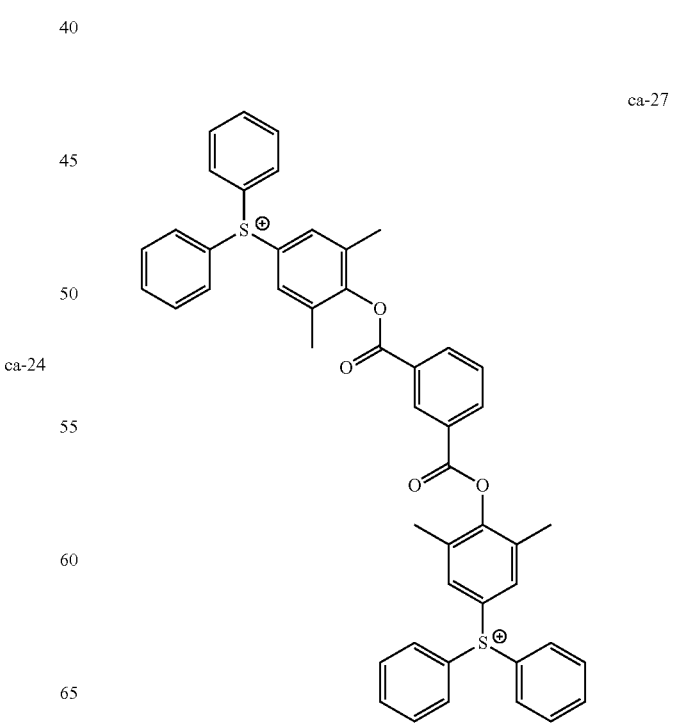

-continued
ca-28
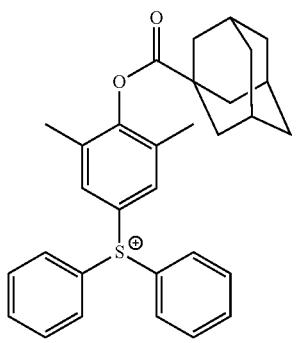
ca-29
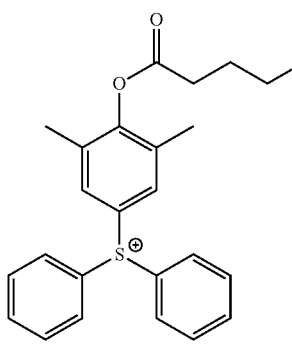
ca-30
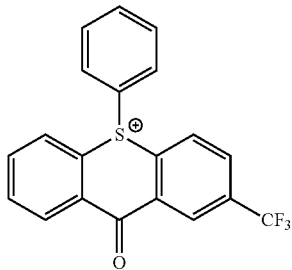
ca-32
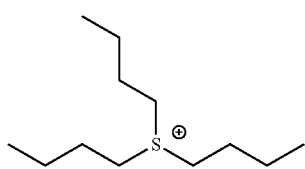
ca-33
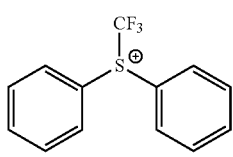
ca-34
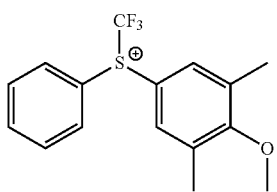
-continued
ca-36
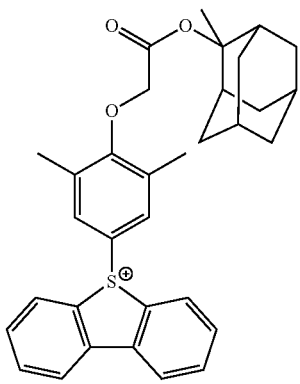
ca-37
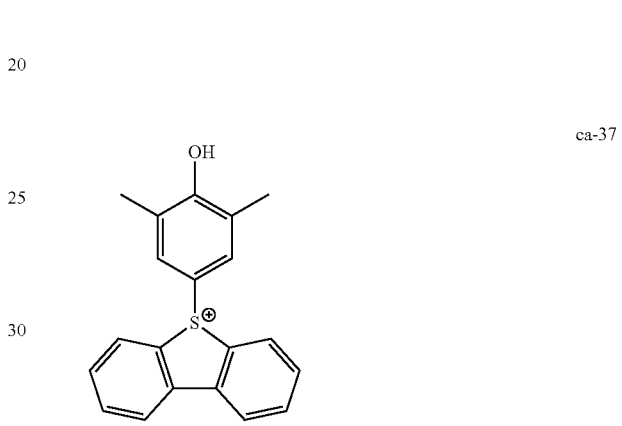
ca-38
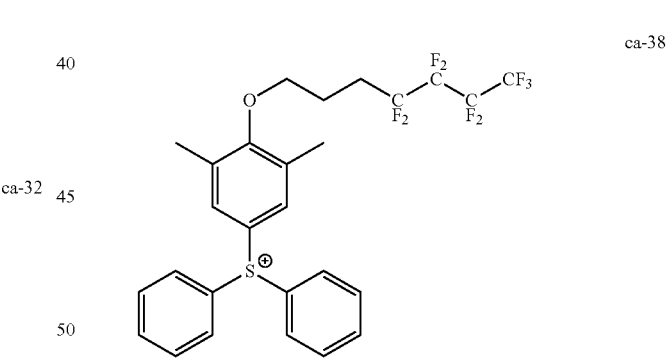
[Chemical Formula 88]
ca-39
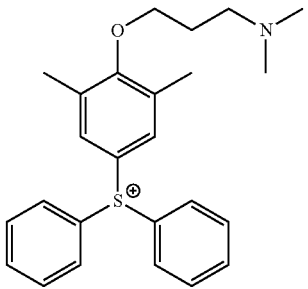

ca-40
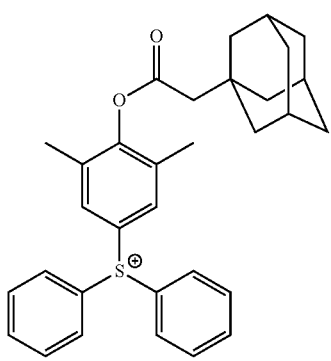
ca-41
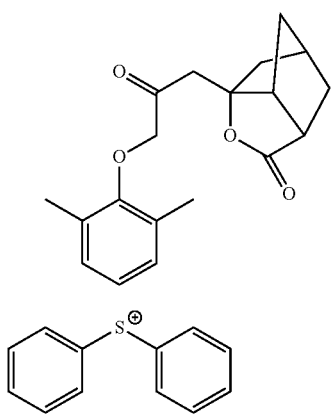
ca-42
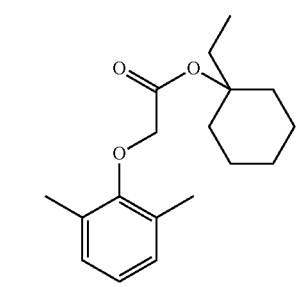
ca-43
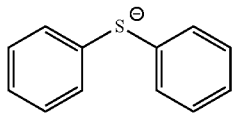
ca-44
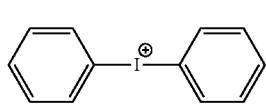
ca-45
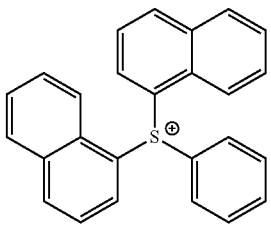
ca-47
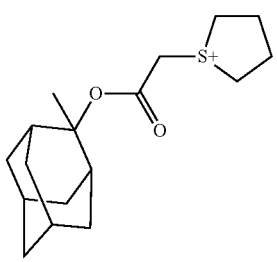
ca-48
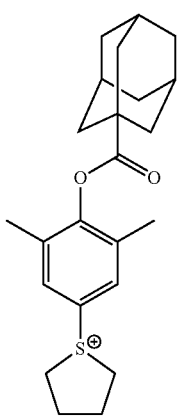
ca-49
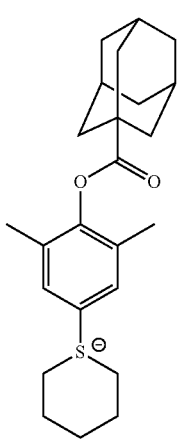
ca-50
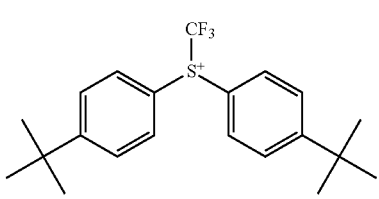

-continued
ca-51
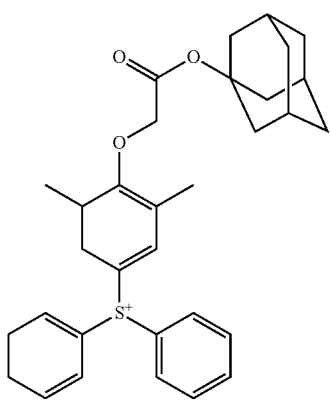
ca-52
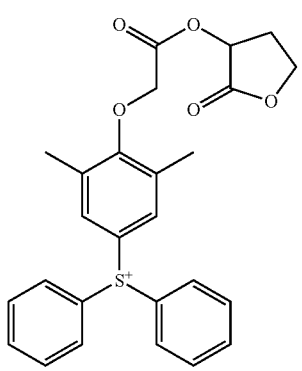
ca-53
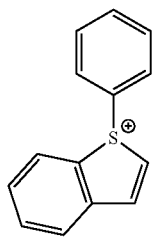
ca-54
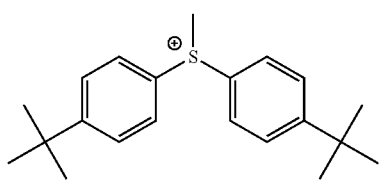
ca-55
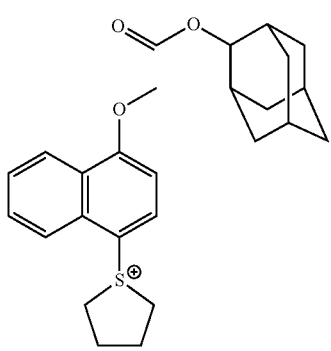
-continued
ca-56
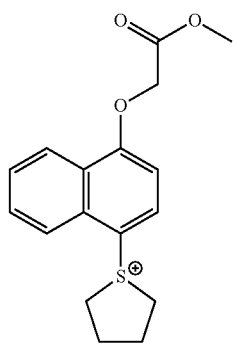
ca-57
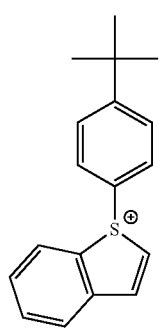
ca-58
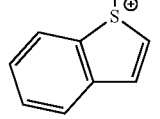
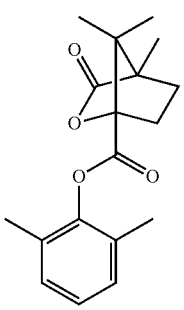
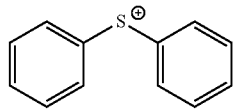
ca-59
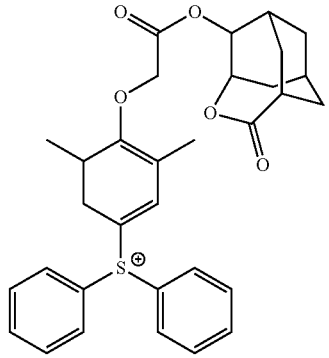

ca-60

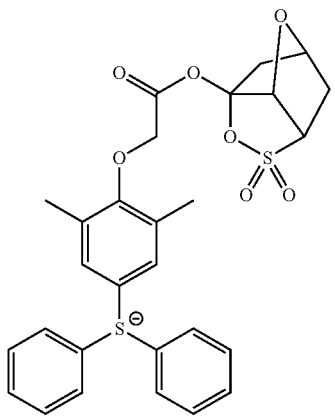

The obtained compounds were analyzed by $^1$H-NMR (400 MHz, DMSO-d6), and the obtained compounds containing a fluorine atom were further analyzed by $^{19}$F-NMR (376 MHz, DMSO-d6), and the structures thereof were determined.

The anion moiety and cation moiety of the obtained compound and the results of NMR analysis thereof are shown below in Tables 1 to 21.

TABLE 1

| Compound | Anion | Cation | NMR analysis |
|---|---|---|---|
| 1-1 | an-1 | ca-1 | $^1$H-NMR: δ (ppm) = 7.74-7.90 (m, 15H, ArH), 4.01(s, 2H, CH2), 3.23(s, 3H, CH3) |
| 1-2 | an-1 | ca-2 | $^1$H-NMR: δ (ppm) = 8.50(d, 2H, ArH), 8.37(d, 2H, ArH), 7.93(t, 2H, ArH), 7.55-7.75(m, 7H, ArH) 4.01(s, 2H, CH2), 3.23(s, 3H, CH3) |
| 1-3 | an-1 | ca-3 | $^1$H-NMR: δ (ppm) = 7.72-7.84(m, 12H, ArH), 7.56(d, 2H, ArH), 4.01(s, 2H, CH2), 3.23(d, 6H, CH3) |
| 1-4 | an-1 | ca-4 | $^1$H-NMR: δ (ppm) = 7.75-7.86 (m, 10H, ArH), 7.61 (s, 2H, ArH), 4.62 (s, 2H, CH2), 4.01(s, 2H, CH2), 3.23(s, 3H, CH3)2.31 (s, 6H, CH3), 1.49-1.97 (m, 17H, Adamantane) |
| 1-5 | an-1 | ca-5 | $^1$H-NMR: δ (ppm) = 7.76-7.82(m, 10H, ArH), 7.59(s, 2H, ArH), 4.55(s, 2H, CH2), 4.01(s, 2H, CH2), 3.23(s, 3H, CH3), 2.29(m, 6H, CH3), 1.90-1.93(m, 4H, CH2, cyclopentyl), 1.48-1.75(m, 6H, cyclopentyl), 0.77-0.81(t, 3H, CH3) |
| 1-6 | an-1 | ca-6 | $^1$H-NMR: δ (ppm) = 7.76-7.82(m, 10H, ArH), 7.59(s, 2H, ArH), 4.55(s, 2H, CH2), 4.01(s, 2H, CH2), 3.23(s, 3H, CH3), 2.29(m, 6H, CH3), 1.90-2.08(m, 2H, cyclopentyl), 1.48-1.75(m, 9H, CH3, cyclopentyl) |
| 1-7 | an-1 | ca-7 | $^1$H-NMR: δ (ppm) = 10.05 (s, 1H, OH), 7.64.-7.87 (m, 10H, ArH), 7.56 (s, 2H, ArH), 4.01(s, 2H, CH2), 3.23(s, 3H, CH3), 2.22 (m, 6H, CH3). |
| 1-8 | an-1 | ca-8 | $^1$H-NMR: δ (ppm) = 7.71-7.89 (m, 10H, ArH), 7.59 (s, 2H, ArH), 4.53 (s, 2H, CH2), 4.01(s, 2H, CH2), 3.23(s, 3H, CH3)2.30 (s, 6H, ArCH3) |
| 1-9 | an-1 | ca-9 | $^1$H-NMR: δ (ppm) = 7.75-7.86 (m, 10H, ArH), 7.63(s, 2H, ArH), 4.55(s, 2H, CH2), 4.01(s, 2H, CH2), 3.23(s, 3H, CH3), 2.30 (s, 6H, ArCH3), 1.43 (s, 9H, t-Butyl) |
| 1-10 | an-1 | ca-10 | $^1$H-NMR: δ (ppm) = 7.75-7.87(m, 10H, ArH), 7.63(s, 2H, ArH), 4.94(t, 2H, OCH2CF2), 4.84(s, 2H, OCH2), 4.01(s, 2H, CH2), 3.23(s, 3H, CH3), 2.37(s, 6H, CH3) $^{19}$F-NMR: δ (ppm) = −80.4, −119.7 |
| 1-11 | an-1 | ca-11 | $^1$H-NMR: δ (ppm) = 7.72-7.83(m, 10H, ArH), 7.59(s, 2H, ArH), 4.90(m, 1H, sultone), 4.62-4.68(m, 3H, CH2O + sultone), 4.01(m, 3H, sultone + CH2), 3.23(m, 4H, CH3 + sultone), 1.75-2.49(m, 11H, sultone + Ar—CH3) |
| 1-12 | an-1 | ca-12 | $^1$H-NMR: δ (ppm) = 7.74-7.84(m, 10H, ArH), 7.61(s, 2H, ArH), 5.42(t, 1H, oxo-norbornane), 4.97(s, 1H, oxo-norbornane), 4.67-4.71(m, 4H, CH2 + oxo-norbornane), 4.01(s, 2H, CH2), 3.23(s, 3H, CH3), 2.69-2.73(m, 1H, oxo-norbornane), 2.32 (s, 6H, Ar—CH3), 2.06-2.16(m, 2H, oxo-norbornane) |
| 1-13 | an-1 | ca-13 | $^1$H-NMR: δ (ppm) = 7.73-7.85(m, 10H, ArH), 7.59(S, 2H, ArH), 4.01(m, 4H, CH2 + OCH2), 3.23(s, 3H, CH3), 2.33(s, 6H, CH3), 1.45(m, 4H, CH2), 1.29(m, 4H, CH2), 0.87(t, 3H, CH3) |
| 1-14 | an-1 | ca-14 | $^1$H-NMR: δ (ppm) = 8.53 (d, 2H, ArH), 8.27(d, 2H, ArH), 7.95(t, 2H, ArH), 7.74 (t, 2H, ArH), 7.20(s, 1H, ArH), 6.38(s, 1H, ArH), 4.05(t, 2H, cation-OCH2), 4.01(s, 2H, CH2), 3.23(s, 3H, CH3), 2.86(s, 3H, ArCH3), 1.84(s, 3H, ArCH3), 1.69(quin, 2H, CH2), 1.37(quin, 2H, CH2), 1.24-1.26(m, 4H, CH2), 0.82(t, 3H, CH3) |
| 1-15 | an-1 | ca-15 | $^1$H-NMR: δ (ppm) = 7.99-8.01(d, 2H, Ar), 7.73-7.76(t, 1H, Ar), 7.58-7.61(t, 2H, Ar), 5.31 (s, 2H, SCH2C=O), 3.49-4.17(m, 6H, CH2), 3.23(s, 3H, CH3), 2.18-2.49(m, 4H, CH2S) |

TABLE 2

| Compound | Anion | Cation | NMR analysis |
|---|---|---|---|
| 1-16 | an-1 | ca-16 | $^1$H-NMR: δ (ppm) = 8.02-8.05(m, 2H, Phenyl), 7.61-7.73(m, 3H, Phenyl), 4.01(m, 6H, SCH2 + CH2), 3.23(s, 3H, CH3), 2.09-2.12(m, 2H, CH2), 1.84-1.93(m, 2H, CH2), 1.61-1.70 (m, 2H, CH2) |
| 1-17 | an-1 | ca-17 | $^1$H-NMR: δ (ppm) = 8.04-8.09(m, 2H, Phenyl), 7.69-7.79(m, 3H, Phenyl), 4.01(s, 2H, CH2), 3.23(d, 9H, CH3) |
| 1-18 | an-1 | ca-18 | $^1$H-NMR: δ (ppm) = 8.07(d, 2H, Phenyl), 7.81(d, 2H, Phenyl), 4.01(m, 4H, CH2), 3.59(d, 2H, CH2), 3.23(s, 3H, CH3)2.20(d, 2H, CH2), 1.71-2.19 (m, 4H, CH2), 1.23(s, 9H, t-Bu). |
| 1-19 | an-1 | ca-19 | $^1$H-NMR: δ (ppm) = 7.77-7.89(m, 10H, ArH), 7.70(s, 2H, ArH), 5.10(s, 2H, OCOCH2O), 4.01(s, 2H, CH2), 3.23(s, 3H, CH3), 2.07-2.19(m, 9H, CH3) |
| 1-20 | an-1 | ca-20 | $^1$H-NMR: δ (ppm) = 7.84(d, 6H, ArH), 7.78(d, 6H, ArH), 4.01(s, 2H, CH2), 3.23(s, 3H, CH3), 1.33(s, 27H, tBu—CH3) |
| 1-21 | an-1 | ca-21 | $^1$H-NMR: δ (ppm) = 7.73-7.89(m, 12H, ArH), 4.01(s, 2H, CH2), 3.23(s, 3H, CH3), 2.38(s, 6H, CH3) $^{19}$F-NMR: δ (ppm) = −70.2 |
| 1-22 | an-1 | ca-22 | $^1$H-NMR: δ (ppm) = 7.69-7.85(m, 10H, ArH), 7.56(s, 2H, ArH), 4.75(s, 4H, CH2), 4.01(s, 2H, CH2), 3.23(s, 3H, CH3), 2.31(s, 6H, ArCH3), 2.19(m, 2H, Adamantane), 1.47-1.98(m, 15H, Adamantane) |
| 1-23 | an-1 | ca-23 | $^1$H-NMR: δ (ppm) = 7.72-7.84 (m, 10H, ArH), 7.59 (s, 2H, ArH), 4.56 (s, 2H, CH2), 4.01(s, 2H, CH2), 3.23(s, 3H, CH3), 2.49 (m, 2H, Adamantane), 2.27-2.34 (m, 13H, CH3, Adamantane), 1.94-1.97 (m, 2H, Adamantane), 1.72-1.79 (m, 2H, Adamantane) |
| 1-24 | an-1 | ca-24 | $^1$H-NMR: δ (ppm) = 7.72-7.84 (m, 10H, ArH), 7.59 (s, 2H, ArH), 4.64 (s, 2H, CH2), 4.01 (d, 5H, CH2 + OCH3), 3.23(s, 3H, CH3), 2.29 (s, 6H, CH3). |
| 1-25 | an-1 | ca-25 | $^1$H-NMR: δ (ppm) = 7.78-7.89 (m, 10H, ArH), 7.64 (s, 2H, ArH), 4.01(d, 5H, CH2 + OCH3), 3.23(s, 3H, CH3), 2.32 (s, 6H, CH3). |
| 1-26 | an-1 | ca-26 | $^1$H-NMR: δ (ppm) = 8.44 (s, 4H, ArH in ArC=O), 7.78-7.90 (m, 24H, ArH), 4.01(s, 2H, CH2), 3.23(s, 3H, CH3), 2.23 (s, 12H, CH3), |
| 1-27 | an-1 | ca-27 | $^1$H-NMR: δ (ppm) = 8.90 (s, 1H, ArH in ArC=O), 8.60 (dd, 2H, ArH in ArC=O), 7.77-7.96 (m, 25H, ArH in cation + ArH in ArC=O), 4.01(s, 2H, CH2), 3.23(s, 3H, CH3), 2.24 (s, 12H, CH3) |
| 1-28 | an-1 | ca-28 | $^1$H-NMR: δ (ppm) = 7.76-7.87 (m, 10H, ArH), 7.69 (s, 2H, ArH), 4.01(s, 2H, CH2), 3.23(s, 3H, CH3), 2.13 (s, 6H, CH3), 1.66-2.03 (m, 15H, Adamantane). |
| 1-29 | an-1 | ca-29 | $^1$H-NMR: δ (ppm) = 7.79-7.93(m, 12H, ArH), 4.01(s, 2H, CH2), 3.23(s, 3H, CH3), 2.73(t, 2H, CO—CH2), 2.19(s, 6H, ArCH3), 1.65-1.72(m, 2H, CH2).1.25-1.38(m, 14H, CH2), 0.85(t, 3H, CH3) |
| 1-30 | an-1 | ca-30 | $^1$H-NMR: δ (ppm) = 8.76 (s, 1H, ArH), 8.59-8.64 (m, 1H, ArH), 8.42 (t, 2H, ArH), 8.03-8.19 (m, 5H, ArH), 7.81 (t, 1H, ArH), 7.69 (t, 2H, ArH), 4.01(s, 2H, CH2), 3.23(s, 3H, CH3) $^{19}$F-NMR: δ (ppm) = −62.1 |

TABLE 3

| Compound | Anion | Cation | NMR analysis |
|---|---|---|---|
| 1-32 | an-1 | ca-32 | $^1$H-NMR: δ (ppm) = 4.01(m, 8H, CH2), 3.23(s, 3H, CH3), 1.68 (quintet, 6H, CH2), 1.35-1.44 (m, 6H, CH2), 0.81-0.93 (m, 9H, CH3). |
| 1-33 | an-1 | ca-33 | $^1$H-NMR: δ (ppm) = 8.29 (d, 4H, ArH), 7.93-8.09 (m, 6H, ArH), 4.01(s, 2H, CH2), 3.23(s, 3H, CH3) $^{19}$F-NMR: δ (ppm) = −47.9 |
| 1-34 | an-1 | ca-34 | $^1$H-NMR: δ (ppm) = 7.90-8.24 (m, 7H, ArH), 4.01(d, 5H, CH2 + OCH3), 3.23(s, 3H, CH3), 2.40 (s, 6H, ArCH3) $^{19}$F-NMR: δ (ppm) = −48.8 |
| 1-36 | an-1 | ca-36 | $^1$H-NMR: δ (ppm) = 8.49 (d, 2H, ArH), 8.30 (d, 2H, ArH), 7.93 (t, 2H, ArH), 7.73 (t, 2H, ArH), 7.30 (s, 2H, ArH), 4.52 (s, 2H, OCH2), 4.01(s, 2H, CH2), 3.23(s, 3H, CH3), 2.16-2.24 (m, 8H, Ar—CH3 + Adamantane), 1.44-1.92 (m, 15H, Adamantane + CH3) |
| 1-37 | an-1 | ca-37 | $^1$H-NMR: δ (ppm) = 9.73 (br s, 1H, OH), 8.47 (d, 2H, ArH), 8.24 (d, 2H, ArH), 7.91 (t, 2H, ArH), 7.71 (t, 2H, ArH), 7.18 (s, 2H, ArH), 4.01(s, 2H, CH2), 3.23(s, 3H, CH3), 2.10 (s, 6H, ArCH3). |
| 1-38 | an-1 | ca-38 | $^1$H-NMR: δ (ppm) = 7.75-7.87(m, 10H, ArH), 7.62(s, 2H, ArH), 4.01(m, 4H, CH2), 3.23(s, 3H, CH3), 2.03-2.56(m, 10H, CH2, CH2) $^{19}$F-NMR: δ (ppm) = −123.5, −121.8, −111.6, −78.3 |
| 1-39 | an-1 | ca-39 | $^1$H-NMR: δ (ppm) = 7.75-7.86(m, 10H, ArH), 7.60(s, 2H, ArH), 4.01(m, 4H, CH2), 3.23(s, 3H, CH3), 2.40(m, 2H, CH2), 2.24-2.35(m, 6H, CH2), 2.12(m, 6H, N—CH3), 1.86(t, 2H, CH2) |
| 1-40 | an-1 | ca-40 | $^1$H-NMR: δ (ppm) = 7.77-7.89 (m, 10H, ArH), 7.71 (s, 2H, ArH), 4.01(s, 2H, CH2), 3.23(s, 3H, CH3), 2.51(s, 2H, CH2), 2.20 (s, 6H, CH3), 1.97 (s, 3H, Adamantane), 1.62-1.73 (m, 12H, Adamantane) |
| 1-41 | an-1 | ca-41 | $^1$H-NMR: δ (ppm) = 7.74-7.84(m, 10H, ArH), 7.61(s, 2H, ArH), 4.49-4.66(m, 4H, norbornane + OCH2), 4.01(s, 2H, CH2), 3.23(m, 4H, CH3 + norbornane), 2.44-2.54(m, 2H, norbornane), 2.37 (s, 6H, ArCH3), 1.91-2.06(m, 2H, norbornane), 1.57-1.67(m, 2H, norbornane) |
| 1-42 | an-1 | ca-42 | $^1$H-NMR: δ (ppm) = 7.80-7.92 (m, 10H, ArH), 7.67 (s, 2H, ArH), 4.66 (s, 2H, CH2), 4.01(s, 2H, CH2), 3.23(s, 3H, CH3)2.37 (s, 6H, ArCH3), 2.13-2.16 (m, 2H, cyclohexyl), 1.93 (q, 2H, CH2), 1.14-1.57 (m, 8H, cyclohexyl), 0.84 (t, 3H, CH3) |
| 1-43 | an-1 | ca-43 | $^1$H-NMR: δ (ppm) = 8.44 (d, 1H, ArH), 8.22 (m, 2H, ArH), 7.73-7.89 (m, 13H, ArH), 7.50 (d, 1H, ArH), 4.01(s, 2H, CH2), 3.23(s, 3H, CH3) |
| 1-44 | an-1 | ca-44 | $^1$H-NMR: δ (ppm) = 8.24 (d, 4H, ArH), 7.59 (t, 2H, ArH), 7.47 (t, 4H, ArH), 4.01(s, 2H, CH2), 3.23(s, 3H, CH3) |
| 1-45 | an-1 | ca-45 | $^1$H-NMR: δ (ppm) = 8.55 (d, 2H, ArH), 8.38 (d, 2H, ArH), 8.32 (d, 2H, ArH), 8.03 (d, 2H, ArH), 7.93-7.97 (m, 1H, ArH), 7.82-7.88 (m, 8H, ArH), 7.55 (d, 2H, ArH), 4.01(s, 2H, CH2), 3.23(s, 3H, CH3) |
| 1-47 | an-1 | ca-47 | $^1$H-NMR: δ (ppm) = 4.46 (s, 2H, CH2(C=O)), 4.01(s, 2H, CH2), 3.05-3.58(m, 7H, CH3 + CH2SCH2), 1.56-2.33 (m, 21H, Ad + CH2CH2). |

TABLE 4

| Compound | Anion | Cation | NMR analysis |
|---|---|---|---|
| 1-48 | an-1 | ca-48 | $^1$H-NMR: δ (ppm) = 7.75 (s, 2H, Ar), 3.91-3.96 (m, 2H, CH2), 4.01(m, 4H, CH2), 3.23(s, 3H, CH3), 2.29-2.41(m, 4H, CH2), 1.75-2.19(m, 21H, Ar—CH3 + Adamantane). |
| 1-49 | an-1 | ca-49 | $^1$H-NMR: δ (ppm) = 7.82 (m, 2H, Ar), 4.01(m, 6H, CH2), 3.23(s, 3H, CH3), 1.56-2.43(m, 27H, Ar—CH3 + CH2 + adamantane) |
| 1-50 | an-1 | ca-50 | $^1$H-NMR: δ (ppm) = 8.23 (d, 4H, ArH), 7.98 (d, 4H, ArH), 4.01(s, 2H, CH2), 3.23(s, 3H, CH3), 1.37 (s, 18H, CH3 of tert-butyl)<br>$^{19}$F-NMR: δ (ppm) = −48.5 |
| 1-51 | an-1 | ca-51 | $^1$H-NMR: δ (ppm) = 7.77-7.98 (m, 10H, ArH), 7.64 (s, 2H, ArH), 4.57(s, 2H, CH2O), 4.01(s, 2H, CH2), 3.23(s, 3H, CH3), 2.40 (s, 6H, CH3), 2.02-2.26 (m, 9H, Adamantane), 1.76 (br s, 6H, Adamantane) |
| 1-52 | an-1 | ca-52 | $^1$H-NMR: δ (ppm) = 7.77-7.89 (m, 10H, ArH), 7.64 (s, 2H, ArH), 5.70(t, 1H, OCHC=O), 4.82 (s, 2H, ArOCH2), 4.46-4.30 (m, 2H, OCOCH2), 4.01(s, 2H, CH2), 3.23(s, 3H, CH3), 2.71-2.64 (m, 1H, OCH2CH2), 2.33-2.24 (m, 7H, CH3 + OCH2CH2) |
| 1-53 | an-1 | ca-53 | $^1$H-NMR: δ (ppm) = 8.28 (d, 2H, ArH), 8.11(d, 1H, ArH), 7.86(t, 1H, ArH), 7.63-7.81(m, 7H, ArH), 4.01(s, 2H, CH2), 3.23(s, 3H, CH3) |
| 1-54 | an-1 | ca-54 | $^1$H-NMR: δ (ppm) = 8.05 (d, 2H, ArH), 7.74 (d, 2H, ArH), 4.01(d, 5H, CH2 + SCH3), 3.23(s, 3H, CH3), 1.30(s, 18H, t-Bu) |
| 1-55 | an-1 | ca-55 | $^1$H-NMR: δ (ppm) = 8.41(m, 2H ArH), 8.12(d, 1H, ArH), 7.73-7.93(m, 2H, ArH), 7.19(d, 1H, ArH), 5.23(s, 2H, CH2), 4.95(m, 1H, Adamantane), 4.01(m, 6H, CH2 + CH2S), 3.23(s, 3H, CH3), 2.27-2.43(m, 4H, SCH2CH2), 1.42-1.99(m, 14H, Adamantane) |
| 1-56 | an-1 | ca-56 | $^1$H-NMR: δ (ppm) = 8.42(m, 2H ArH), 8.17(d, 1H, ArH), 7.78-7.91(m, 2H, ArH), 7.23(d, 1H, ArH), 5.26(s, 2H, CH2), 3.67-4.19(m, 9H, CH2 + SCH2 + CH3), 3.23(s, 3H, CH3), 2.29-2.60(m, 4H, SCH2CH2) |
| 1-57 | an-1 | ca-57 | $^1$H-NMR: δ (ppm) = 8.28 (d, 2H, ArH), 8.12 (d, 1H, ArH), 7.88 (t, 1H, ArH), 7.80 (d, 1H, ArH), 7.62-7.74 (m, 5H, ArH), 4.01(s, 2H, CH2), 3.23(s, 3H, CH3), 1.27 (s, 9H, CH3) |
| 1-58 | an-1 | ca-58 | $^1$H-NMR: δ (ppm) = 7.76-7.90 (m, 12H, ArH), 4.01(s, 2H, CH2), 3.23(s, 3H, CH3), 2.62-2.69 (m, 1H, camphane), 2.08-2.26 (m, 8H, Ar—CH3 + camphane), 1.65-1.72 (m, 1H, camphane), 1.19 (s, 3H, CH3), 1.09 (s, 3H, CH3), 1.04 (s, 3H, CH3). |
| 1-59 | an-1 | ca-59 | $^1$H-NMR: δ (ppm) = 7.76-7.90 (m, 12H, ArH), 5.00 (s, 1H, Hyper-lactone), 4.77 (s, 2H, Hyper-lactone), 4.27 (s, 1H, Hyper-lactone), 4.01(s, 2H, CH2), 3.23(s, 3H, CH3), 2.94 (s, 1H, Hyper-lactone), 2.13 (d, 6H, CH3), 2.11-1.73 (m, 9H, Hyper-lactone), 1.53 (d, 1H, Hyper-lactone). |
| 1-60 | an-1 | ca-60 | $^1$H-NMR: δ (ppm) = 7.72-7.83(m, 10H, ArH), 7.59(s, 2H, ArH), 5.90(d, 1H, CH), 4.87-5.05(m, 3H, CH), 4.62-4.68(m, 2H, CH2), 4.23(m, 1H, CH), 4.01(s, 2H, CH2), 3.23(s, 3H, CH3), 1.75-2.48(m, 8H, CH3 + oxosultone) |

TABLE 5

| Compound | Anion | Cation | NMR analysis |
|---|---|---|---|
| 2-1 | an-2 | ca-1 | $^1$H-NMR: δ (ppm) = 7.74-7.90 (m, 15H, ArH), 4.43(s, 2H, CH2), 2.01(s, 3H, CH3). |
| 2-2 | an-2 | ca-2 | $^1$H-NMR: δ (ppm) = 8.50(d, 2H, ArH), 8.37(d, 2H, ArH), 7.93(t, 2H, ArH), 7.55-7.75(m, 7H, ArH), 4.43(s, 2H, CH2), 2.01(s, 3H, CH3). |
| 2-3 | an-2 | ca-3 | $^1$H-NMR: δ (ppm) = 7.72-7.84(m, 12H, ArH), 7.56(d, 2H, ArH), 4.43(s, 2H, CH2), 3.35(s, 3H, CH3), 2.01(s, 3H, CH3) |
| 2-4 | an-2 | ca-4 | $^1$H-NMR: δ (ppm) = 7.75-7.86 (m, 10H, ArH), 7.61 (s, 2H, ArH), 4.62 (s, 2H, CH2), 4.43(s, 2H, CH2), 2.31 (s, 6H, CH3), 1.49-2.01 (m, 20H, Adamantyl + CH3) |
| 2-5 | an-2 | ca-5 | $^1$H-NMR: δ (ppm) = 7.76-7.82(m, 10H, ArH), 7.59(s, 2H, ArH), 4.55(s, 2H, CH2), 4.43(s, 2H, CH2), 2.29(m, 6H, CH3), 2.01(s, 3H, CH3), 1.90-1.93(m, 4H, CH2, cyclopentyl), 1.48-1.75(m, 6H, cyclopentyl), 0.77-0.81(t, 3H, CH3) |
| 2-6 | an-2 | ca-6 | $^1$H-NMR: δ (ppm) = 7.76-7.82(m, 10H, ArH), 7.59(s, 2H, ArH), 4.55(s, 2H, CH2), 4.43(s, 2H, CH2), 2.29(m, 6H, CH3), 1.90-2.08(m, 5H, cyclopentyl + CH3), 1.48-1.75(m, 9H, CH3, cyclopentyl) |
| 2-7 | an-2 | ca-7 | $^1$H-NMR: δ (ppm) = 10.05 (s, 1H, OH), 7.64.-7.87 (m, 10H, ArH), 7.56 (s, 2H, ArH), 4.43(s, 2H, CH2), 2.22 (m, 6H, CH3), 2.01(s, 3H, CH3) |
| 2-8 | an-2 | ca-8 | $^1$H-NMR: δ (ppm) = 7.71-7.89 (m, 10H, ArH), 7.59 (s, 2H, ArH), 4.53 (s, 2H, CH2), 4.43(s, 2H, CH2), 2.30 (s, 6H, ArCH3), 2.01(s, 3H, CH3) |
| 2-9 | an-2 | ca-9 | $^1$H-NMR: δ (ppm) = 7.75-7.86 (m, 10H, ArH), 7.63 (s, 2H, ArH), 4.55 (s, 2H, CH2), 4.43(s, 2H, CH2), 2.30 (s, 6H, ArCH3), 2.01(s, 3H, CH3), 1.43 (s, 9H, t-Butyl) |
| 2-10 | an-2 | ca-10 | $^1$H-NMR: δ (ppm) = 7.75-7.87(m, 10H, ArH), 7.63 (s, 2H, ArH), 4.94(t 2H, OCH2CF2), 4.84(s, 2H, OCH2), 4.43(s, 2H, CH2), 2.37(s, 6H, CH3), 2.01(s, 3H, CH3)<br>$^{19}$F-NMR: δ (ppm) = −80.4, −119.7 |
| 2-11 | an-2 | ca-11 | $^1$H-NMR: δ (ppm) = 7.72-7.83(m, 10H, ArH), 7.59(s, 2H, ArH), 4.90(m, 1H, sultone), 4.62-4.68(m, 3H, CH2O + sultone), 4.43(s, 2H, CH2), 3.83-3.89(m, 1H, sultone), 3.43(m, 1H, sultone), 1.75-2.49(m, 14H, sultone + Ar—CH3 + CH3) |
| 2-12 | an-2 | ca-12 | $^1$H-NMR: δ (ppm) = 7.74-7.84(m, 10H, ArH), 7.61 (s, 2H, ArH), 5.42(t, 1H, oxo-norbornane), 4.97(s, 1H, oxo-norbornane), 4.67-4.71(m, 4H, CH2 + oxo-norbornane), 4.43(s, 2H, CH2), 2.69-2.73(m, 1H, oxo-norbornane), 2.32 (s, 6H, Ar—CH3), 2.01-2.16(m, 5H, oxo-norbornane + CH3) |
| 2-13 | an-2 | ca-13 | $^1$H-NMR: δ (ppm) = 7.73-7.85(m, 10H, ArH), 7.59(S, 2H, ArH), 4.43(s, 2H, CH2), 3.83(t, 2H, OCH2), 2.33(s, 6H, CH3), 2.01(s, 3H, CH3), 1.45(m, 4H, CH2), 1.29(m, 4H, CH2), 0.87(t, 3H, CH3) |

TABLE 6

| Compound | Anion | Cation | NMR analysis |
|---|---|---|---|
| 2-14 | an-2 | ca-14 | ¹H-NMR: δ (ppm) = 8.53 (d, 2H, ArH), 8.27(d, 2H, ArH), 7.95(t, 2H, ArH), 7.74(t, 2H, ArH), 7.20(s, 1H, ArH), 6.38(s, 1H, ArH), 4.05(t, 2H, cation-OCH2), 4.01(s, 2H, CH2), 3.23(s, 3H, CH3), 2.86(s, 3H, ArCH3), 1.84(s, 3H, ArCH3), 1.69(quin, 2H, CH2), 1.37(quin, 2H, CH2), 1.24-1.26(m, 4H, CH2), 0.82(t, 3H, CH3) |
| 2-15 | an-2 | ca-15 | ¹H-NMR: δ (ppm) = 7.99-8.01(d, 2H, Ar), 7.73-7.76(t, 1H, Ar), 7.58-7.61(t, 2H, Ar), 5.31 (s, 2H, SCH2C=O), 4.43(s, 2H, CH2), 3.49-3.62(m, 4H, CH2), 2.18-2.49(m, 4H, CH2S), 2.01(s, 3H, CH3) |
| 2-16 | an-2 | ca-16 | ¹H-NMR: δ (ppm) = 8.02-8.05(m, 2H, Phenyl), 7.61-7.73(m, 3H, Phenyl), 4.43(s, 2H, CH2), 3.76-3.86(m, 4H, SCH2), 2.01-2.12(m, 5H, CH2 + CH3), 1.84-1.93(m, 2H, CH2).1.61-1.70 (m, 2H, CH2) |
| 2-17 | an-2 | ca-17 | ¹H-NMR: δ (ppm) = 8.04-8.09(m, 2H, Phenyl), 7.69-7.79(m, 3H, Phenyl), 4.43(s, 2H, CH2), 3.29 (s, 6H, CH3), 2.01(s, 3H, CH3) |
| 2-18 | an-2 | ca-18 | ¹H-NMR: δ (ppm) = 8.07(d, 2H, Phenyl), 7.81(d.2H, Phenyl), 4.43(s, 2H, CH2), 4.10(t, 2H, CH2), 3.59(d, 2H, CH2), 2.20(d, 2H, CH2), 1.71-2.19 (m, 7H, CH2 + CH3), 1.23(s, 9H, t-Bu). |
| 2-19 | an-2 | ca-19 | ¹H-NMR: δ (ppm) = 7.77-7.89(m, 10H, ArH), 7.70(s, 2H, ArH), 5.10(s, 2H, OCOCH2O), 4.43(s, 2H, CH2), 2.01-2.19(m, 12H, CH3 + CH3) |
| 2-20 | an-2 | ca-20 | ¹H-NMR: δ (ppm) = 7.84(d, 6H, ArH), 7.78(d, 6H, ArH), 4.43(s, 2H, CH2), 2.01(s, 3H, CH3), 1.33(s, 27H, tBu—CH3) |
| 2-21 | an-2 | ca-21 | ¹H-NMR: δ (ppm) = 7.73-7.89(m, 12H, ArH), 4.43(s, 2H, CH2), 2.38(s, 6H, CH3), 2.01(s, 3H, CH3)<br>¹⁹F-NMR: δ (ppm) = −70.2 |
| 2-22 | an-2 | ca-22 | ¹H-NMR: δ (ppm) = 7.69-7.85(m, 10H, ArH), 7.56(s, 2H, ArH), 4.75(s, 4H, CH2), 4.43(s, 2H, CH2), 2.31(s, 6H, ArCH3), 2.19(m, 2H, Adamantane), 1.47-2.01(m, 15H, Adamantane + CH3) |
| 2-23 | an-2 | ca-23 | ¹H-NMR: δ (ppm) = 7.72-7.84 (m, 10H, ArH), 7.59 (s, 2H, ArH), 4.56 (s, 2H, CH2), 4.43 (s, 2H, CH2), 2.49 (m, 2H, Adamantane), 2.27-2.34 (m, 13H, CH3, Adamantane), 1.94-2.01 (m, 2H, Adamantane + CH3), 1.72 1.79 (m, 2H, Adamantane) |
| 2-24 | an-2 | ca-24 | ¹H-NMR: δ (ppm) = 7.72-7.84 (m, 10H, ArH), 7.59 (s, 2H, ArH), 4.64 (s, 2H, CH2), 4.43 (s, 2H, CH2), 3.70 (s, 3H, OCH3), 2.29 (s, 6H, CH3), 2.01(s, 3H, CH3) |
| 2-25 | an-2 | ca-25 | ¹H-NMR: δ (ppm) = 7.78-7.89 (m, 10H, ArH), 7.64 (s, 2H, ArH), 4.43 (s, 2H, CH2), 3.79 (s, 3H, OCH3), 2.32 (s, 6H, CH3), 2.01(s, 3H, CH3) |
| 2-26 | an-2 | ca-26 | ¹H-NMR: δ (ppm) = 8.44 (s, 4H, ArH in ArC=O), 7.78-7.90 (m, 24H, ArH), 4.43 (s, 2H, CH2), 2.23 (s, 12H, CH3), 2.01(s, 3H, CH3) |
| 2-27 | an-2 | ca-27 | ¹H-NMR: δ (ppm) = 8.90 (s, 1H, ArH in ArC=O), 8.60 (dd, 2H, ArH in ArC=O), 7.77-7.96 (m, 25H, ArH in cation + ArH in ArC=O), 4.43 (s, 2H, CH2), 2.24 (s, 12H, CH3), 2.01(s, 3H, CH3) |
| 2-28 | an-2 | ca-28 | ¹H-NMR: δ (ppm) = 7.76-7.87 (m, 10H, ArH), 7.69 (s, 2H, ArH), 4.43 (s, 2H, CH2), 2.13 (s, 6H, CH3), 1.66-2.03 (m, 18H, Adamantane + CH3). |

TABLE 7

| Compound | Anion | Cation | NMR analysis |
|---|---|---|---|
| 2-29 | an-2 | ca-29 | ¹H-NMR: δ (ppm) = 7.79-7.93(m, 12H, ArH), 4.43(s, 2H, CH2), 2.73(t, 2H, CO—CH2), 2.19(s, 6H, ArCH3), 2.01(s, 3H, CH3), 1.65-1.72(m, 2H, CH2), 1.25-1.38(m, 14H, CH2), 0.85(t, 3H, CH3) |
| 2-30 | an-2 | ca-30 | ¹H-NMR: δ (ppm) = 8.76 (s, 1H, ArH), 8.59-8.64 (m, 1H, ArH), 8.42 (t, 2H, ArH), 8.03-8.19 (m, 5H, ArH), 7.81 (t, 1H, ArH), 7.69 (t, 2H, ArH), 4.43 (s, 2H, CH2), 2.01(s, 3H, CH3)<br>¹⁹F-NMR: δ (ppm) = −62.1 |
| 2-32 | an-2 | ca-32 | ¹H-NMR: δ (ppm) = 4.43(s, 2H, CH2), 3.36 (t, 6H, CH2), 2.01(s, 3H, CH3), 1.68 (quintet, 6H, CH2), 1.35-1.44 (m, 6H, CH2), 0.81-0.93 (m, 9H, CH3). |
| 2-33 | an-2 | ca-33 | ¹H-NMR: δ (ppm) = 8.29 (d, 4H, ArH), 7.93-8.09 (m, 6H, ArH), 4.43 (s, 2H, CH2), 2.01(s, 3H, CH3)<br>¹⁹F-NMR: δ (ppm) = −47.9 |
| 2-34 | an-2 | ca-34 | ¹H-NMR: δ(ppm) = 7.90-8.24 (m, 7H, ArH), 4.43(s, 2H, CH2), 3.85 (s, 3H, OCH3), 2.40 (s, 6H, ArCH3), 2.01(s, 3H, CH3)<br>¹⁹F-NMR: δ (ppm) = −48.8 |
| 2-37 | an-2 | ca-37 | ¹H-NMR: δ (ppm) = 9.73 (br s, 1H, OH), 8.47 (d, 2H, ArH), 8.24 (d, 2H, ArH), 7.91 (t, 2H, ArH), 7.71 (t, 2H, ArH), 7.18 (s, 2H, ArH), 4.43 (s, 2H, CH2), 2.10 (s, 6H, ArCH3), 2.01(s, 3H, CH3). |
| 2-38 | an-2 | ca-38 | ¹H-NMR: δ (ppm) = 7.75-7.87(m, 10H, ArH), 7.62(s, 2H, ArH), 4.43(s, 2H, CH2), 3.97(t, 2H, CH2), 2.03-2.56(m, 10H, CH2, CH3), 2.01(s, 3H, CH3)<br>¹⁹F-NMR: δ (ppm) = −123.5, −121.8, −111.6, −78.3 |
| 2-39 | an-2 | ca-39 | ¹H-NMR: δ (ppm) = 7.75-7.86(m, 10H, ArH), 7.60(s, 2H, ArH), 4.43(s, 2H, CH2), 3.87(t, 2H, CH2), 2.40(m, 2H, CH2), 2.24-2.35(m, 6H, CH2), 2.12(m, 6H, CH2), 2.01(s, 3H, CH3), 1.86(t, 3H, CH2) |
| 2-40 | an-2 | ca-40 | ¹H-NMR: δ (ppm) = 7.77-7.89 (m, 10H, ArH), 7.71 (s, 2H, ArH), 4.43(s, 2H, CH2), 2.51(s, 2H, CH2), 2.20 (s, 6H, CH3), 2.01(s, 3H, CH3), 1.97 (s, 3H, Adamantane), 1.62-1.73 (m, 12H, Adamantane) |
| 2-41 | an-2 | ca-41 | ¹H-NMR: δ (ppm) = 7.74-7.84(m, 10H, ArH), 7.61(s, 2H, ArH), 4.49-4.66(m, 4H, norbornane + OCH2), 4.43(s, 2H, CH2), 3.24(m, 1H, norbornane), 2.44-2.54(m, 2H, norbornane), 2.37 (s, 6H, ArCH3), 1.91-2.06(m, 5H, norbornane + CH3), 1.57-1.67(m, 2H, norbornane) |
| 2-42 | an-2 | ca-42 | ¹H-NMR: δ (ppm) = 7.80-7.92 (m, 10H, ArH), 7.67 (s, 2H, ArH), 4.66 (s, 2H, CH2), 4.43 (s, 2H, CH2), 2.37 (s, 6H, ArCH3), 2.13-2.16 (m, 2H, cyclohexyl), 2.01 (s, 3H, CH3), 1.93 (q, 2H, CH2), 1.14-1.57 (m, 8H, cyclohexyl), 0.84 (t, 3H, CH3) |
| 2-43 | an-2 | ca-43 | ¹H-NMR: δ (ppm) = 8.44 (d, 1H, ArH), 8.22 (m, 2H, ArH), 7.73-7.89 (m, 13H, ArH), 7.50 (d, 1H, ArH), 4.43 (s, 2H, CH2), 2.01(s, 3H, CH3) |
| 2-44 | an-2 | ca-44 | ¹H-NMR: δ (ppm) = 8.24 (d, 4H, ArH), 7.59 (t, 2H, ArH), 7.47 (t, 4H, ArH), 4.43 (s, 2H, CH2), 2.01(s, 3H, CH3) |

TABLE 8

| Compound | Anion | Cation | NMR analysis |
|---|---|---|---|
| 2-45 | an-2 | ca-45 | ¹H-NMR: δ (ppm) = 8.55 (d, 2H, ArH), 8.38 (d, 2H, ArH), 8.32 (d, 2H, ArH), 8.03 (d, 2H, ArH), 7.93-7.97 (m, 1H, ArH), 7.82-7.88 (m, 8H, ArH), 7.55 (d, 2H, ArH), 4.43(s, 2H, CH2), 2.01(s, 3H, CH3) |
| 2-47 | an-2 | ca-47 | ¹H-NMR: δ (ppm) = 4.46 (s, 2H, CH2(C=O)), 4.43(s, 2H, CH2), 3.38-3.58 (m, 4H, CH2SCH2), 1.56-2.33 (m, 24H, Ad + CH2 + CH3). |
| 2-48 | an-2 | ca-48 | ¹H-NMR: δ (ppm) = 7.75 (s, 2H, Ar), 4.43(s, 2H, CH2), 3.91-3.96 (m, 2H, CH2), 3.72-3.79 (m, 2H, CH2), 2.29-2.41(m, 4H, CH2), 1.75-2.19(m, 24H, Ar—CH3 + Adamantane). |
| 2-49 | an-2 | ca-49 | ¹H-NMR: δ (ppm) = 7.82 (m, 2H, Ar), 4.43(s, 2H, CH2), 3.73-3.91(m, 4H CH2), 1.56-2.43(m, 30H, Ar—CH3 + CH2 + adamantane) |
| 2-50 | an-2 | ca-50 | ¹H-NMR: δ (ppm) = 8.23 (d, 4H, ArH), 7.98 (d, 4H, ArH), 4.43(s, 2H, CH2), 2.01(s, 3H, CH3), 1.37 (s, 18H, CH3 of tert-butyl)<br>¹⁹F-NMR: δ (ppm) = −48.5 |
| 2-51 | an-2 | ca-51 | ¹H-NMR: δ (ppm) = 7.77-7.98 (m, 10H, ArH), 7.64 (s, 2H, ArH), 4.57(s, 2H, CH2O), 4.43(s, 2H, CH2), 2.40 (s, 6H, CH3), 2.02-2.26 (m, 12H, Adamantane + CH3), 1.76 (br s, 6H, Adamantane) |
| 2-53 | an-2 | ca-53 | ¹H-NMR: δ (ppm) = 8.28 (d, 2H, ArH), 8.11 (d, 1H, ArH), 7.86(t, 1H, ArH), 7.63-7.81(m, 7H, ArH), 4.43(s, 2H, CH2), 2.01(s, 3H, CH3) |
| 2-54 | an-2 | ca-54 | ¹H-NMR: δ (ppm) = 8.05 (d, 2H, ArH), 7.74 (d, 2H, ArH), 4.43(s, 2H, CH2), 3.85(s, 3H, S—CH3), 2.01(s, 3H, CH3), 1.30(s, 18H, t-Bu) |
| 2-55 | an-2 | ca-55 | ¹H-NMR: δ (ppm) = 8.41(m, 2H ArH), 8.12(d, 1H, ArH), 7.73-7.93(m, 2H, ArH), 7.19(d, 1H, ArH), 5.23(s, 2H, CH2), 4.95(m, 1H, Adamantane), 4.43(s, 2H, CH2), 4.03(m, 2H, CH2S), 3.75(m, 2H, CH2S), 2.27-2.43(m, 4H, SCH2CH2), 1.42-2.01(m, 17H, Adamantane + CH3) |
| 2-56 | an-2 | ca-56 | ¹H-NMR: δ (ppm) = 8.42(m, 2H ArH), 8.17(d, 1H, ArH), 7.78-7.91(m, 2H, ArH), 7.23(d, 1H, ArH), 5.26(s, 2H, CH2), 4.43(s, 2H, CH2), 3.75-4.19(m, 7H, SCH2 + CH3), 2.29-2.60(m, 4H, SCH2CH2), 2.01(s, 3H, CH3) |
| 2-57 | an-2 | ca-57 | ¹H-NMR: δ (ppm) = 8.28 (d, 2H, ArH), 8.12 (d, 1H, ArH), 7.88 (t, 1H, ArH), 7.80 (d, 1H, ArH), 7.62-7.74 (m, 5H, ArH), 4.43(s, 2H, CH2), 2.01(s, 3H, CH3), 1.27 (s, 9H, CH3) |
| 2-58 | an-2 | ca-58 | ¹H-NMR: δ (ppm) = 7.76-7.90 (m, 12H, ArH), 4.43(s, 2H, CH2), 2.62-2.69 (m, 1H, camphane), 2.08-2.26 (m, 8H, Ar—CH3 + camphane), 2.01(s, 3H, CH3), 1.65-1.72 (m, 1H, camphane), 1.19 (s, 3H, CH3), 1.09 (s, 3H, CH3), 1.04 (s, 3H, CH3) . |
| 2-59 | an-2 | ca-59 | ¹H-NMR: δ (ppm) = 7.76-7.90 (m, 12H, ArH), 5.00 (s, 1H, Hyper-lactone), 4.77 (s, 2H, Hyper-lactone), 4.43(s, 2H, CH2), 4.27 (s, 1H, Hyper-lactone), 2.94 (s, 1H, Hyper-lactone), 2.13 (d, 6H, CH3), 2.11-1.73 (m, 9H, Hyper-lactone), 2.01(s, 3H, CH3), 1.53 (d, 1H, Hyper-lactone). |
| 2-60 | an-2 | ca-60 | ¹H-NMR: δ (ppm) = 7.72-7.83(m, 10H, ArH), 7.59(s, 2H, ArH), 5.90(d, 1H, CH), 4.87-5.05(m, 3H, CH), 4.62-4.68(m, 2H, CH2), 4.43(s, 2H, CH2), 4.23(m, 1H, CH), 2.01(s, 3H, CH3), 1.75-2.48(m, 8H, CH3 + oxosultone) |

TABLE 9

| Compound | Anion | Cation | NMR analysis |
|---|---|---|---|
| 3-1 | an-3 | ca-1 | ¹H-NMR: δ (ppm) = 7.74-7.90 (m, 15H, ArH), 6.80-7.30(m, 5H, phenyl), 4.62(s, 2H, CH2) |
| 3-2 | an-3 | ca-2 | ¹H-NMR: δ (ppm) = 8.50(d, 2H, ArH), 8.37(d, 2H, ArH), 7.93(t, 2H, ArH), 7.55-7.75(m, 7H, ArH) 6.80-7.30(m, 5H, phenyl), 4.62(s, 2H, CH2) |
| 3-3 | an-3 | ca-3 | ¹H-NMR: δ (ppm) = 7.72-7.84(m, 12H, ArH), 7.56(d, 2H, ArH), 6.80-7.30(m, 5H, phenyl), 4.62(s, 2H, CH2), 3.35(s, 3H, CH3) |
| 3-4 | an-3 | ca-4 | ¹H-NMR: δ (ppm) = 7.75-7.86 (m, 10H, ArH), 7.61 (s, 2H, ArH), 6.80-7.30(m, 5H, phenyl), 4.62 (m, 4H, CH2 + CH2), 2.31 (s, 6H, CH3), 1.49-1.97 (m, 17H, Adamantane) |
| 3-5 | an-3 | ca-5 | ¹H-NMR: δ (ppm) = 7.76-7.82(m, 10H, ArH), 7.59(s, 2H, ArH), 6.80-7.30(m, 5H, phenyl), 4.62(s, 2H, CH2), 4.55(s, 2H, CH2), 2.29(m, 6H, CH3), 1.90-1.93(m, 4H, CH2, cyclopentyl), 1.48-1.75(m, 6H, oyclopentyl), 0.77-0.81(t, 3H, CH3) |
| 3-6 | an-3 | ca-6 | ¹H-NMR: δ (ppm) = 7.76-7.82(m, 10H, ArH), 7.59(s, 2H, ArH), 6.80-7.30(m, 5H, phenyl), 4.62(s, 2H, CH2), 4.55(s, 2H, CH2), 2.29(m, 6H, CH3), 1.90-2.08(m, 2H, cyclopentyl), 1.48-1.75(m, 9H, CH3, cyclopentyl) |
| 3-7 | an-3 | ca-7 | ¹H-NMR: δ (ppm) = 10.05 (s, 1H, OH), 7.64-7.87 (m, 10H, ArH), 7.56 (s, 2H, ArH), 6.80-7.30(m, 5H, phenyl), 4.62(s, 2H, CH2), 2.22 (m, 6H, CH3). |
| 3-8 | an-3 | ca-8 | ¹H-NMR: δ (ppm) = 7.71-7.89 (m, 10H, ArH), 7.59 (s, 2H, ArH), 6.80-7.30(m, 5H, phenyl), 4.62(s, 2H, CH2), 4.53 (s, 2H, CH2), 2.30 (s, 6H, ArCH3) |
| 3-9 | an-3 | ca-9 | ¹H-NMR: δ (ppm) = 7.75-7.86 (m, 10H, ArH), 7.63(s, 2H, ArH), 6.80-7.30(m, 5H, phenyl), 4.62(s, 2H, CH2), 4.55(s, 2H, CH2), 2.30 (s, 6H, ArCH3), 1.43 (s, 9H, t-Butyl) |
| 3-10 | an-3 | ca-10 | ¹H-NMR: δ (ppm) = 7.75-7.87(m, 10H, ArH), 7.63(s, 2H, ArH), 6.80-7.30(m, 5H, phenyl), 4.94(t, 2H, OCH2CF2), 4.84(s, 2H, OCH2), 4.62(s, 2H, CH2), 2.37(s, 6H, CH3)<br>¹⁹F-NMR: δ (ppm) = −80.4, −119.7 |
| 3-11 | an-3 | ca-11 | ¹H-NMR: δ (ppm) = 7.72-7.83(m, 10H, ArH), 7.59(s, 2H, ArH), 6.80-7.30(m, 5H, phenyl), 4.90(m, 1H, sultone), 4.62-4.68(m, 5H, CH2O + sultone + CH2), 3.83-3.89(m, 1H, sultone), 3.43(m, 1H, sultone), 1.75-2.49(m, 11H, sultone + Ar—CH3) |
| 3-12 | an-3 | ca-12 | ¹H-NMR: δ (ppm) = 7.74-7.84(m, 10H, ArH), 7.61(s, 2H, ArH), 6.80-7.30(m, 5H, phenyl), 5.42(t, 1H, oxo-norbornane), 4.97(s, 1H, oxo-norbornane), 4.67-4.71(m, 4H, CH2 + oxo-norbornane), 4.62(s, 2H, CH2), 2.69-2.73(m, 1H, oxo-norbornane), 2.32 (s, 6H, Ar—CH3), 2.06-2.16(m, 2H, oxo-norbornane) |
| 3-13 | an-3 | ca-13 | ¹H-NMR: δ (ppm) = 7.73-7.85(m, 10H, ArH), 7.59(S, 2H, ArH), 6.80-7.30(m, 5H, phenyl), 4.62(s, 2H, CH2), 3.83(t, 2H, OCH2), 2.33(s, 6H, CH3), 1.45(m, 4H, CH2), 1.29(m, 4H, CH2), 0.87(t, 3H, CH3) |
| 3-14 | an-3 | ca-14 | ¹H-NMR: δ (ppm) = 8.53 (d, 2H, ArH), 8.27(d, 2H, ArH), 7.95(t, 2H, ArH), 7.74(t, 2H, ArH), 7.20(s, 1H, ArH), 6.38 (s, 1H, ArH), 4.05(t, 2H, cation-OCH2), 4.01(s, 2H, CH2), 3.23(s, 3H, CH3), 2.86(s, 3H, ArCH3), 1.84(s, 3H, ArCH3), 1.69(quin, 2H, CH2), 1.37 (quin, 2H, CH2), 1.24-1.26(m, 4H, CH2), 0.82(t, 3H, CH3) |

TABLE 10

| Compound | Anion | Cation | NMR analysis |
|---|---|---|---|
| 3-15 | an-3 | ca-15 | $^1$H-NMR: δ (ppm) = 7.99-8.01(d, 2H, Ar), 7.73-7.76(t, 1H, Ar), 7.58-7.61(t, 2H, Ar), 6.80-7.30(m, 5H, phenyl), 5.31 (s, 2H, SCH2C=O), 4.62(s, 2H, CH2), 3.49-3.62(m, 4H, CH2), 2.18-2.49(m, 4H, CH2S) |
| 3-16 | an-3 | ca-16 | $^1$H-NMR: δ (ppm) = 8.02-8.05(m, 2H, Phenyl), 7.61-7.73(m, 3H, Phenyl), 6.80-7.30(m, 5H, phenyl), 4.62(s, 2H, CH2), 3.76-3.86(m, 4H, SCH2), 2.09-2.12(m, 2H, CH2), 1.84-1.93(m, 2H, CH2), 1.61-1.70 (m, 2H, CH2) |
| 3-17 | an-3 | ca-17 | $^1$H-NMR: δ (ppm) = 8.04-8.09(m, 2H, Phenyl), 7.69-7.79(m, 3H, Phenyl), 6.80-7.30(m, 5H, phenyl), 4.62(s, 2H, CH2), 3.29 (s, 6H, CH3) |
| 3-18 | an-3 | ca-18 | $^1$H-NMR: δ (ppm) = 8.07(d, 2H, Phenyl), 7.81(d, 2H, Phenyl), 6.80-7.30(m, 5H, phenyl), 4.62(s, 2H, CH2), 4.10(t, 2H, CH2), 3.59(d, 2H, CH2), 2.20(d, 2H, CH2), 1.71-2.19 (m, 4H, CH2), 1.23(s, 9H, t-Bu). |
| 3-19 | an-3 | ca-19 | $^1$H-NMR: δ (ppm) = 7.77-7.89(m, 10H, ArH), 7.70(s, 2H, ArH), 6.80-7.30(m, 5H, phenyl), 5.10(s, 2H, OCOCH2O), 4.62(s, 2H, CH2), 2.07-2.19(m, 9H, CH3) |
| 3-20 | an-3 | ca-20 | $^1$H-NMR: δ (ppm) = 7.84(d, 6H, ArH), 7.78(d, 6H, ArH), 6.80-7.30(m, 5H, phenyl), 4.62(s, 2H, CH2), 1.33(s, 27H, tBu—CH3) |
| 3-21 | an-3 | ca-21 | $^1$H-NMR: δ (ppm) = 7.73-7.89(m, 12H, ArH), 6.80-7.30(m, 5H, phenyl), 4.62(s, 2H, CH2), 2.38(s, 6H, CH3) $^{19}$F-NMR: δ (ppm) = −70.2 |
| 3-22 | an-3 | ca-22 | $^1$H-NMR: δ (ppm) = 7.69-7.85(m, 10H, ArH), 7.56(s, 2H, ArH), 6.80-7.30(m, 5H, phenyl), 4.75(s, 4H, CH2), 4.62(s, 2H, CH2), 2.31(s, 6H, ArCH3), 2.19(m, 2H, Adamantane), 1.47-1.98(m, 15H, Adamantane) |
| 3-23 | an-3 | ca-23 | $^1$H-NMR: δ (ppm) = 7.72-7.84 (m, 10H, ArH), 7.59 (s, 2H, ArH), 6.80-7.30(m, 5H, phenyl), 4.62(s, 2H, CH2), 4.56 (s, 2H, CH2), 2.49 (m, 2H, Adamantane), 2.27-2.34 (m, 13H, CH3, Adamantane), 1.94-1.97 (m, 2H, Adamantane), 1.72-1.79 (m, 2H, Adamantane) |
| 3-24 | an-3 | ca-24 | $^1$H-NMR: δ (ppm) = 7.72-7.84 (m, 10H, ArH), 7.59 (s, 2H, ArH), 6.80-7.30(m, 5H, phenyl), 4.64 (m, 4H, CH2 + CH2), 3.70 (s, 3H, OCH3), 2.29 (s, 6H, CH3). |
| 3-25 | an-3 | ca-25 | $^1$H-NMR: δ (ppm) = 7.78-7.89 (m, 10H, ArH), 7.64 (s, 2H, ArH), 6.80-7.30(m, 5H, phenyl), 4.62(s, 2H, CH2), 3.79 (s, 3H, OCH3), 2.32 (s, 6H, CH3). |
| 3-26 | an-3 | ca-26 | $^1$H-NMR: δ (ppm) = 8.44 (s, 4H, ArH in ArC=O), 7.78-7.90 (m, 24H, ArH), 6.80-7.30(m, 5H, phenyl), 4.62(s, 2H, CH2), 2.23 (s, 12H, CH3), |
| 3-27 | an-3 | ca-27 | $^1$H-NMR: δ (ppm) = 8.90 (s, 1H, ArH in ArC=O), 8.60 (dd, 2H, ArH in ArC=O), 7.77-7.96 (m, 25H, ArH in cation + ArH in ArC=O), 6.80-7.30(m, 5H, phenyl), 4.62(s, 2H, CH2), 2.24 (s, 12H, CH3) |
| 3-28 | an-3 | ca-28 | $^1$H-NMR: δ (ppm) = 7.76-7.87(m, 10H, ArH), 7.69 (s, 2H, ArH), 6.80-7.30(m, 5H, phenyl), 4.62(s, 2H, CH2), 2.13 (s, 6H, CH3), 1.66-2.03 (m, 15H, Adamantane). |
| 3-29 | an-3 | ca-29 | $^1$H-NMR: δ (ppm) = 7.79-7.93(m, 12H, ArH), 6.80-7.30(m, 5H, phenyl), 4.62(s, 2H, CH2), 2.73(t, 2H, CO—CH2), 2.19(s, 6H, ArCH3), 1.65-1.72(m, 2H, CH2), 1.25-1.38(m, 14H, CH2), 0.85(t, 3H, CH3) |

TABLE 11

| Compound | Anton | Cation | NMR analysis |
|---|---|---|---|
| 3-30 | an-3 | ca-30 | $^1$H-NMR: δ (ppm) = 8.76 (s, 1H, ArH), 8.59-8.64 (m, 1H, ArH), 8.42 (t, 2H, ArH), 8.03-8.19 (m, 5H, ArH), 7.81 (t, 1H, ArH), 7.69 (t, 2H, ArH), 6.80-7.30(m, 5H, phenyl), 4.62(s, 2H, CH2) $^{19}$F-NMR: δ (ppm) = −62.1 |
| 3-32 | an-3 | ca-32 | $^1$H-NMR: δ (ppm) = 6.80-7.30(m, 5H, phenyl), 4.62(s, 2H, CH2), 3.36 (t, 6H, CH2), 1.68 (quintet, 6H, CH2), 1.35-1.44 (m, 6H, CH2), 0.81-0.93 (m, 9H, CH3). |
| 3-33 | an-3 | ca-33 | $^1$H-NMR: δ (ppm) = 8.29 (d, 4H, ArH), 7.93-8.09 (m, 6H, ArH), 6.80-7.30(m, 5H, phenyl), 4.62(s, 2H, CH2) $^{19}$F-NMR: δ (ppm) = −47.9 |
| 3-34 | an-3 | ca-34 | $^1$H-NMR: δ (ppm) = 7.90-8.24 (m, 7H, ArH), 6.80-7.30(m, 5H, phenyl), 4.62(s, 2H, CH2), 3.85 (s, 3H, OCH3), 2.40 (s, 6H, ArCH3) $^{19}$F-NMR: δ (ppm) = −48.8 |
| 3-38 | an-3 | ca-38 | $^1$H-NMR: δ (ppm) = 7.75-7.87(m, 10H, ArH), 7.62(s, 2H, ArH), 6.80-7.30(m, 5H, phenyl), 4.62(s, 2H, CH2), 3.97(t, 2H, CH2), 2.03-2.56(m, 10H, CH2, CH3) $^{19}$F-NMR: δ (ppm) = −123.5, −121.8, −111.6, −78.3 |
| 3-39 | an-3 | ca-39 | $^1$H-NMR: δ (ppm) = 7.75-7.86(m, 10H, ArH), 7.60(s, 2H, ArH), 6.80-7.30(m, 5H, phenyl), 4.62(s, 2H, CH2), 3.87(t, 2H, CH2), 2.40(m, 2H, CH2), 2.24-2.35(m, 6H, CH2), 2.12(m, 6H, N—CH3), 1.86(t, 2H, CH2) |
| 3-40 | an-3 | ca-40 | $^1$H-NMR: δ (ppm) = 7.77-7.89 (m, 10H, ArH), 7.71 (s, 2H, ArH), 6.80-7.30(m, 5H, phenyl), 2.51(s, 2H, CH2), 4.62(s, 2H, CH2), 2.20 (s, 6H, CH3), 1.97 (s, 2H, Adamantane), 1.62-1.73 (m, 12H, Adamantane) |
| 3-41 | an-3 | ca-41 | $^1$H-NMR: δ (ppm) = 7.74-7.84(m, 10H, ArH), 7.61(s, 2H, ArH), 6.80-7.30(m, 5H, phenyl), 4.49-4.66(m, 6H, norbornane + OCH2 + CH2), 3.24(m, 1H, norbornane), 2.44-2.54(m, 2H, norbornane), 2.37 (s, 6H, ArCH3), 1.91-2.06(m, 2H, norbornane), 1.57-1.67(m, 2H, norbornane) |
| 3-42 | an-3 | ca-42 | $^1$H-NMR: δ (ppm) = 7.80-7.92 (m, 10H, ArH), 7.67 (s, 2H, ArH), 6.80-7.30(m, 5H, phenyl), 4.62-4.66 (m, 4H, CH2 + CH2), 2.37 (s, 6H, ArCH3), 2.13-2.16 (m, 2H, cyclohexyl), 1.93 (q, 2H, CH2), 1.14-1.57 (m, 8H, cyclohexyl), 0.84 (t, 3H, CH3) |
| 3-43 | an-3 | ca-43 | $^1$H-NMR: δ (ppm) = 8.44 (d, 1H, ArH), 8.22 (m, 2H, ArH), 7.73-7.89 (m, 13H, ArH), 7.50 (d, 1H, ArH), 6.80-7.30(m, 5H, phenyl), 4.62(s, 2H, CH2) |
| 3-44 | an-3 | ca-44 | $^1$H-NMR: δ (ppm) = 8.24 (d, 4H, ArH), 7.59 (t, 2H, ArH), 7.47 (t, 4H, ArH), 6.80-7.30(m, 5H, phenyl), 4.62(s, 2H, CH2) |
| 3-45 | an-3 | ca-45 | $^1$H-NMR: δ (ppm) = 8.55 (d, 2H, ArH), 8.38 (d, 2H, ArH), 8.32 (d, 2H, ArH), 8.03 (d, 2H, ArH), 7.93-7.97 (m, 1H, ArH), 7.82-7.88 (m, 8H, ArH), 7.55 (d, 2H, ArH), 6.80-7.30(m, 5H, phenyl), 4.62(s, 2H, CH2) |
| 3-47 | an-3 | ca-47 | $^1$H-NMR: δ (ppm) = 6.80-7.30(m, 5H, phenyl), 4.62(s, 2H, CH2), 4.46 (s, 2H, CH2(C=O)), 3.38-3.58 (m, 4H, CH2SCH2), 1.56-2.33 (m, 21H, Ad + CH2CH2). |

TABLE 12

| Compound | Anion | Cation | NMR analysis |
|---|---|---|---|
| 3-48 | an-3 | ca-48 | $^1$H-NMR: δ (ppm) = 7.75 (s, 2H, Ar), 6.80-7.30(m, 5H, phenyl), 4.62(s, 2H, CH2), 3.91-3.96 (m, 2H, CH2), 3.72-3.79 (m, 2H, CH2), 2.29-2.41(m, 4H, CH2), 1.75-2.19(m, 21H, Ar—CH3 + Adamantane). |
| 3-49 | an-3 | ca-49 | $^1$H-NMR: δ (ppm) = 7.82 (m, 2H, Ar), 6.80-7.30(m, 5H, phenyl), 4.62(s, 2H, CH2), 3.73-3.91(m, 4H CH2), 1.56-2.43(m, 27H, Ar—CH3 + CH2 + adamantane) |
| 3-50 | an-3 | ca-50 | $^1$H-NMR: δ (ppm) = 8.23 (d, 4H, ArH), 7.98 (d, 4H, ArH), 6.80-7.30(m, 5H, phenyl), 4.62(s, 2H, CH2), 1.37 (s, 18H, CH3 of tert-butyl)<br>$^{19}$F-NMR: δ (ppm) = −48.5 |
| 3-51 | an-3 | ca-51 | $^1$H-NMR: δ (ppm) = 7.77-7.98 (m, 10H, ArH), 7.64 (s, 2H, ArH), 6.80-7.30(m, 5H, phenyl), 4.57-4.62(m, 2H, CH2O + CH2), 2.40 (s, 6H, CH3), 2.02-2.26 (m, 9H, Adamantane), 1.76 (br s, 6H, Adamantane) |
| 3-52 | an-3 | ca-52 | $^1$H-NMR: δ (ppm) = 7.77-7.89 (m, 10H, ArH), 7.64 (s, 2H, ArH), 6.80-7.30(m, 5H, phenyl), 5.70(t, 1H, OCHC=O), 4.82 (s, 2H, ArOCH2), 4.62(s, 2H, CH2), 4.46-4.30 (m, 2H, OCOCH2), 2.71-2.64 (m, 1H, OCH2CH2), 2.33-2.24 (m, 7H, CH3 + OCH2CH2) |
| 3-53 | an-3 | ca-53 | $^1$H-NMR: δ (ppm) = 8.28 (d, 2H, ArH), 8.11 (d, 1H, ArH), 7.86(t, 1H, ArH), 7.63-7.81(m, 7H, ArH), 6.80-7.30(m, 5H, phenyl), 4.62(s, 2H, CH2) |
| 3-54 | an-3 | ca-54 | $^1$H NMR: δ (ppm) = 8.05 (d, 2H, ArH), 7.74 (d, 2H, ArH), 6.80-7.30(m, 5H, phenyl), 4.62(s, 2H, CH2), 3.85(s, 3H, S—CH3), 1.30(s, 18H, t-Bu) |
| 3-55 | an-3 | ca-55 | $^1$H-NMR: δ (ppm) = 8.41(m, 2H ArH), 8.12(d, 1H, ArH), 7.73-7.93(m, 2H, ArH), 6.80-7.30(m, 6H, ArH), 5.23(s, 2H, CH2), 4.95(m, 1H, Adamantane), 4.62(s, 2H, CH2), 4.03(m, 2H, CH2S), 3.75(m, 2H, CH2S), 2.27-2.43(m, 4H, SCH2CH2), 1.42-1.99(m, 14H, Adamantane) |
| 3-56 | an-3 | ca-56 | $^1$H-NMR: δ (ppm) = 8.42(m, 2H ArH), 8.17(d, 1H, ArH), 7.78-7.91(m, 2H, ArH), 6.80-7.30(m, 6H, ArH), 5.26(s, 2H, CH2), 4.62(s, 2H, CH2), 3.75-4.19(m, 7H, SCH2 + CH3), 2.29-2.60(m, 4H, SCH2CH2) |
| 3-57 | an-3 | ca-57 | $^1$H-NMR: δ (ppm) = 8.28 (d, 2H, ArH), 8.12 (d, 1H, ArH), 7.88 (t, 1H, ArH), 7.80 (d, 1H, ArH), 7.62-7.74 (m, 5H, ArH), 6.80-7.30(m, 5H, phenyl), 4.62(s, 2H, CH2), 1.27 (s, 9H, CH3) |
| 3-58 | an-3 | ca-58 | $^1$H-NMR: δ (ppm) = 7.76-7.90 (m, 12H, ArH), 6.80-7.30(m, 5H, phenyl), 4.62(s, 2H, CH2), 2.62-2.69 (m, 1H, camphane), 2.08-2.26 (m, 8H, Ar—CH3 + camphane), 1.65-1.72 (m, 1H, camphane), 1.19 (s, 3H, CH3), 1.09 (s, 3H, CH3), 1.04 (s, 3H, CH3). |
| 3-59 | an-3 | ca-59 | $^1$H-NMR: δ (ppm) = 7.76-7.90 (m, 12H, ArH), 6.80-7.30(m, 5H, phenyl), 5.00 (s, 1H, Hyper-lactone), 4.77 (s, 2H, Hyper-lactone), 4.62(s, 2H, CH2), 4.27 (s, 1H, Hyper-lactone), 2.94 (s, 1H, Hyper-lactone), 2.13 (d, 6H, CH3), 2.11-1.73 (m, 9H, Hyper-lactone), 1.53 (d, 1H, Hyper-lactone). |
| 3-60 | an-3 | ca-60 | $^1$H-NMR: δ (ppm) = 7.72-7.83(m, 10H, ArH), 7.59(s, 2H, ArH), 6.80-7.30(m, 5H, phenyl), 5.90(d, 1H, CH), 4.87-5.05(m, 3H, CH), 4.62-4.68(s, 4H, CH2 + CH2), 4.23(m, 1H, CH), 1.75-2.48(m, 8H, CH3 + oxosultone) |

TABLE 13

| Compound | Anion | Cation | NMR analysis |
|---|---|---|---|
| 4-1 | an-4 | ca-1 | $^1$H-NMR: δ (ppm) = 7.74-7.90 (m, 15H, ArH), 4.55(s, 2H, CH2), 1.68-1.98(m, 15H, Ad) |
| 4-2 | an-4 | ca-2 | $^1$H-NMR: δ (ppm) = 8.50(d, 2H, ArH), 8.37(d, 2H, ArH), 7.93(t, 2H, ArH), 7.55-7.75(m, 7H, ArH), 4.55(s, 2H, CH2), 1.68-1.98(m, 15H, Ad) |
| 4-3 | an-4 | ca-3 | $^1$H-NMR: δ (ppm) = 7.72-7.84(m, 12H, ArH), 7.56 (s, 2H, ArH), 4.55 (s, 2H, CH2), 3.35(s, 3H, CH3), 1.68-1.98(m, 15H, Ad) |
| 4-4 | an-4 | ca-4 | $^1$H-NMR: δ (ppm) = 7.75-7.86 (m, 10H, ArH), 7.61 (s, 2H, ArH), 4.62 (s, 2H, CH2), 4.55(s, 2H, CH2), 2.31 (s, 6H, CH3), 1.49-1.97 (m, 32H, Adamantane) |
| 4-5 | an-4 | ca-5 | $^1$H-NMR: δ (ppm) = 7.76-7.82(m, 10H, ArH), 7.59(s, 2H, ArH), 4.55(m, 4H, CH2 + CH2), 2.29(m, 6H, CH3), 1.90-1.93(m, 4H, CH2, cyclopentyl), 1.48-1.98(m, 21H, cyclopentyl + Adamantan), 0.77-0.81(t, 3H, CH3) |
| 4-6 | an-4 | ca-6 | $^1$H-NMR: δ (ppm) = 7.76-7.82(m, 10H, ArH), 7.59(s, 2H, ArH), 4.55(m, 4H, CH2 + CH2), 2.29(m, 6H, CH3), 1.90-2.08(m, 2H, cyclopentyl), 1.48-1.98(m, 24H, CH3 + cyclopentyl + Adamantan) |
| 4-7 | an-4 | ca-7 | $^1$H-NMR: δ (ppm) = 10.05 (s, 1H, OH), 7.64.-7.87 (m, 10H, ArH), 7.56 (m, 2H, ArH), 2.22 (m, 6H, CH3), 4.55(s, 2H, CH2), 1.68-1.98(m, 15H, Ad) |
| 4-8 | an-4 | ca-8 | $^1$H-NMR: δ (ppm) = 7.71-7.89 (m, 10H, ArH), 7.59 (s, 2H, ArH), 4.53 (m, 4H, CH2 + CH2), 2.30 (s, 6H, ArCH3), 1.68-1.98(m, 15H, Ad) |
| 4-9 | an-4 | ca-9 | $^1$H-NMR: δ (ppm) = 7.75-7.86 (m, 10H, ArH), 7.63(s, 2H, ArH), 4.55(m, 4H, CH2 + CH2), 2.30 (s, 6H, ArCH3), 1.68-1.98(m, 15H, Ad), 1.43 (s, 9H, t-Butyl) |
| 4-10 | an-4 | ca-10 | $^1$H-NMR: δ (ppm) = 7.75-7.87(m, 10H, ArH), 7.63(s, 2H, ArH), 4.94(t, 2H, OCH2CF2), 4.84(s, 2H, OCH2), 2.37(s, 6H, CH3), 4.55(s, 2H, CH2), 1.68-1.98(m, 15H, Ad)<br>$^{19}$F-NMR: δ (ppm) = −80.4, −119.7 |
| 4-11 | an-4 | ca-11 | $^1$H-NMR: δ (ppm) = 7.72-7.83(m, 10H, ArH), 7.59(s, 2H, ArH), 4.90(m, 1H, sultone), 4.62-4.68(m, 3H, CH2O + sultone), 4.55(s, 2H, CH2), 3.83-3.89(m, 1H, sultone), 3.43(m, 1H, sultone), 1.68-2.49(m, 26H, sultone + Ar—CH3 + Adamantan) |
| 4-12 | an-4 | ca-12 | $^1$H-NMR: δ (ppm) = 7.74-7.84(m, 10H, ArH), 7.61(s, 2H, ArH), 5.42(t, 1H, oxo-norbornane), 4.97(s, 1H, oxo-norbornane), 4.67-4.71(m, 4H, CH2 + oxo-norbornane), 4.55(s, 2H, CH2), 2.69-2.73(m, 1H, oxo-norbornane), 2.32 (s, 6H, Ar—CH3), 2.06-2.16(m, 2H, oxo-norbornane), 1.68-1.98(m, 15H, Ad) |
| 4-13 | an-4 | ca-13 | $^1$H-NMR: δ (ppm) = 7.73-7.85(m, 10H, ArH), 7.59(S, 2H, ArH), 4.55(s, 2H, CH2), 3.83(t, 2H, OCH2), 2.33(s, 6H, CH3), 1.68-1.98(m, 15H, Ad), 1.45(m, 4H, CH2), 1.29(m, 4H, CH2), 0.87(t, 3H, CH3) |
| 4-14 | an-4 | ca-14 | $^1$H-NMR: δ (ppm) = 8.53 (d, 2H, ArH), 8.27(d, 2H, ArH), 7.95(t, 2H, ArH), 7.74 (t, 2H, ArH), 7.20(s, 1H, ArH), 6.38(s, 1H, ArH), 4.05(t, 2H, cation-OCH2), 4.01(s, 2H, CH2), 3.23(s, 3H, CH3), 2.86(s, 3H, ArCH3), 1.84(s, 3H, ArCH3), 1.69(quin, 2H, CH2), 1.37(quin, 2H, CH2), 1.24-1.26(m, 4H, CH2), 0.82(t, 3H, CH3) |

TABLE 14

| Compound | Anion | Cation | NMR analysis |
|---|---|---|---|
| 4-15 | an-4 | ca-15 | $^1$H-NMR: δ (ppm) = 7.99-8.01(d, 2H, Ar), 7.73-7.76(t, 1H, Ar), 7.58-7.61(t, 2H, Ar), 5.31 (s, 2H, SCH2C=O), 4.55(s, 2H, CH2), 3.49-3.62(m, 4H, CH2), 2.18-2.49(m, 4H, CH2S), 1.68-1.98(m, 15H, Ad) |
| 4-16 | an-4 | ca-16 | $^1$H-NMR: δ (ppm) = 8.02-8.05(m, 2H, Phenyl), 7.61-7.73(m, 3H, Phenyl), 4.55(s, 2H, CH2), 3.76-3.86(m, 4H, SCH2), 2.09-2.12(m, 2H, CH2), 1.84-1.93(m, 2H, CH2), 1.61-1.98 (m, 17H, CH2 + adamantan) |
| 4-17 | an-4 | ca-17 | $^1$H-NMR: δ (ppm) = 8.04-8.09(m, 2H, Phenyl), 7.69-7.79(m, 3H, Phenyl), 4.55(s, 2H, CH2), 3.29 (s, 6H, CH3), 1.68-1.98(m, 15H, Ad) |
| 4-18 | an-4 | ca-18 | $^1$H-NMR: δ (ppm) = 8.07(d, 2H, Phenyl), 7.81(d, 2H, Phenyl), 4.55(s, 2H, CH2), 4.10(t, 2H, CH2), 3.59(d, 2H, CH2), 2.20(d, 2H, CH2), 1.68-2.19 (m, 19H, CH2 + adamantan), 1.23(s, 9H, t-Bu). |
| 4-19 | an-4 | ca-19 | $^1$H-NMR: δ (ppm) = 7.77-7.89(m, 10H, ArH), 7.70(s, 2H, ArH), 5.10(s, 2H, OCOCH2O), 4.55(s, 2H, CH2), 1.68-2.19(m, 24H, CH3 + adamantan) |
| 4-20 | an-4 | ca-20 | $^1$H-NMR: δ (ppm) = 7.84(d, 6H, ArH), 7.78(d, 6H, ArH), 4.55(s, 2H, CH2), 1.68-1.98(m, 15H, Ad), 1.33(s, 27H, tBu—CH3) |
| 4-21 | an-4 | ca-21 | $^1$H-NMR: δ (ppm) = 7.73-7.89(m, 12H, ArH), 4.55(s, 2H, CH2), 2.38(s, 6H, CH3), 1.68-1.98(m, 15H, Ad) $^{19}$F-NMR: δ (ppm) = −70.2 |
| 4-22 | an-4 | ca-22 | $^1$H-NMR: δ (ppm) = 7.69-7.85(m, 10H, ArH), 7.56(s, 2H, ArH), 4.75(s, 4H, CH2), 4.55(s, 2H, CH2), 2.31(s, 6H, ArCH3), 2.19(m, 2H, Adamantane), 1.47-1.98(m, 30H, Adamantane) |
| 4-23 | an-4 | ca-23 | $^1$H-NMR: δ (ppm) = 7.72-7.84 (m, 10H, ArH), 7.59 (s, 2H, ArH), 4.56 (m, 4H, CH2 + CH2), 2.49 (m, 2H, Adamantane), 2.27-2.34 (m, 13H, CH3, Adamantane), 1.68-1.97 (m, 19H, Adamantane) |
| 4-24 | an-4 | ca-24 | $^1$H-NMR: δ (ppm) = 7.72-7.84 (m, 10H, ArH), 7.59 (s, 2H, ArH), 4.64 (s, 2H, CH2), 4.55(s, 2H, CH2), 3.70 (s, 3H, OCH3), 2.29 (s, 6H, CH3), 1.68-1.98(m, 15H, Ad) |
| 4-25 | an-4 | ca-25 | $^1$H-NMR: δ (ppm) = 7.78-7.89 (m, 10H, ArH), 7.64 (s, 2H, ArH), 4.55(s, 2H, CH2), 3.79 (s, 3H, OCH3), 2.32 (s, 6H, CH3), 1.68-1.98(m, 15H, Ad) |
| 4-26 | an-4 | ca-26 | $^1$H-NMR: δ (ppm) = 8.44 (s, 4H, ArH in ArC=O), 7.78-7.90 (m, 24H, ArH), 4.55(s, 2H, CH2), 2.23 (s, 12H, CH3), 1.68-1.98(m, 15H, Ad) |
| 4-27 | an-4 | ca-27 | $^1$H-NMR: δ (ppm) = 8.90 (s, 1H, ArH in ArC=O), 8.60 (dd, 2H, ArH in ArC=O), 7.77-7.96 (m, 25H, ArH in cation + ArH in ArC=O), 4.55(s, 2H, CH2), 2.24 (s, 12H, CH3), 1.68-1.98(m, 15H, Ad) |
| 4-28 | an-4 | ca-28 | $^1$H-NMR: δ (ppm) = 7.76-7.87 (m, 10H, ArH), 7.69 (s, 2H, ArH), 4.55(s, 2H, CH2), 2.13 (s, 6H, CH3), 1.66-2.03 (m, 15H, Adamantyl), 1.68-1.98(m, 15H, Adamantyl) |
| 4-29 | an-4 | ca-29 | $^1$H-NMR: δ (ppm) = 7.79-7.93(m, 12H, ArH), 4.55(s, 2H, CH2), 2.73(t, 2H, CO—CH2), 2.19(s, 6H, ArCH3), 1.68-1.98(m, 2H, CH2 + adamantyl), 1.25-1.38(m, 14H, CH2), 0.85(t, 3H, CH3) |

TABLE 15

| Compound | Anion | Cation | NMR analysis |
|---|---|---|---|
| 4-30 | an-4 | ca-30 | $^1$H-NMR: δ (ppm) = 8.76 (s, 1H, ArH), 8.59-8.64 (m, 1H, ArH), 8.42 (t, 2H, ArH), 8.03-8.19 (m, 5H, ArH), 7.81 (t, 1H, ArH), 7.69 (t, 2H, ArH), 4.55 (s, 2H, CH2), 1.68-1.98(m, 15H, Adamantyl) $^{19}$F-NMR: δ (ppm) = −62.1 |
| 4-32 | an-4 | ca-32 | $^1$H-NMR: δ (ppm) = 4.55(s, 2H, CH2), 3.36 (t, 6H, CH2), 1.68-1.98 (m, 21H, CH2 + Adamantyl), 1.35-1.44 (m, 6H, CH2), 0.81-0.93 (m, 9H, CH3). |
| 4-33 | an-4 | ca-33 | $^1$H-NMR: δ (ppm) = 8.29 (d, 4H, ArH), 7.93-8.09 (m, 6H, ArH), 4.55 (s, 2H, CH2), 1.68-1.98(m, 15H, Adamantyl) $^{19}$F-NMR: δ (ppm) = −47.9 |
| 4-34 | an-4 | ca-34 | $^1$H-NMR: δ (ppm) = 7.90-8.24 (m, 7H, ArH), 4.55(s, 2H, CH2), 3.85 (s, 3H, OCH3), 2.40 (s, 6H, ArCH3), 1.68-1.98(m, 15H, Adamantyl) $^{19}$F-NMR: δ (ppm) = −48.8 |
| 4-37 | an-4 | ca-37 | $^1$H-NMR: δ (ppm) = 9.73 (br s, 1H, OH), 8.47 (d, 2H, ArH), 8.24 (d, 2H, ArH), 7.91 (t, 2H, ArH), 7.71 (t, 2H, ArH), 7.18 (s, 2H, ArH), 4.55 (s, 2H, CH2), 2.10 (s, 6H, ArCH3), 1.68-1.98(m, 15H, Adamantyl) |
| 4-38 | an-4 | ca-38 | $^1$H-NMR: δ (ppm) = 7.75-7.87(m, 10H, ArH), 7.62(s, 2H, ArH), 4.55(s, 2H, CH2), 3.97(t, 2H, CH2), 2.03-2.56(m, 10H, CH2, CH3), 1.68-1.98(m, 15H, Adamantyl) $^{19}$F-NMR: δ (ppm) = −123.5, −121.8, −111.6, −78.3 |
| 4-40 | an-4 | ca-40 | $^1$H-NMR: δ (ppm) = 7.77-7.89 (m, 10H, ArH), 7.71 (s, 2H, ArH), 4.55(s, 2H, CH2), 2.51(s, 2H, CH2), 2.20 (s, 6H, CH3), 1.62-1.98 (m, 30H, Adamantane) |
| 4-42 | an-4 | ca-42 | $^1$H-NMR: δ (ppm) = 7.80-7.92 (m, 10H, ArH), 7.67 (s, 2H, ArH), 4.66 (s, 2H, CH2), 4.55(s, 2H, CH2), 2.37 (s, 6H, ArCH3), 2.13-2.16 (m, 2H, cyclohexyl), 1.68-1.93 (m, 17H, CH2 + Adamantyl), 1.14-1.57 (m, 8H, cyclohexyl), 0.84 (t, 3H, CH3) |
| 4-43 | an-4 | ca-43 | $^1$H-NMR: δ (ppm) = 8.44 (d, 1H, ArH), 8.22 (m, 2H, ArH), 7.73-7.89 (m, 13H, ArH), 7.50 (d, 1H, ArH), 4.55 (s, 2H, CH2), 1.68-1.98(m, 15H, Adamantyl) |
| 4-44 | an-4 | ca-44 | $^1$H-NMR: δ (ppm) = 8.24 (d, 4H, ArH), 7.59 (t, 2H, ArH), 7.47 (t, 4H, ArH), 4.55 (s, 2H, CH2), 1.68-1.98(m, 15H, Adamantyl) |
| 4-45 | an-4 | ca-45 | $^1$H-NMR: δ (ppm) = 8.55 (d, 2H, ArH), 8.38 (d, 2H, ArH), 8.32 (d, 2H, ArH), 8.03 (d, 2H, ArH), 7.93-7.97 (m, 1H, ArH), 7.82-7.88 (m, 8H, ArH), 7.55 (d, 2H, ArH), 4.55 (s, 2H, CH2), 1.68-1.98(m, 15H, Adamantyl) |
| 4-47 | an-4 | ca-47 | $^1$H-NMR: δ (ppm) = 4.46 (s, 2H, CH2(C=O)), 4.55(s, 2H, CH2), 3.38-3.58 (m, 4H, CH2SCH2), 1.56-2.33 (m, 36H, Adamantyl + CH2CH2). |
| 4-48 | an-4 | ca-48 | $^1$H-NMR: δ (ppm) = 7.75 (s, 2H, Ar), 4.55(s, 2H, CH2), 3.91-3.96 (m, 2H, CH2), 3.72-3.79 (m, 2H, CH2), 2.29-2.41(m, 4H, CH2), 1.68-2.19(m, 36H, Ar—CH3 + Adamantyl). |

TABLE 16

| Compound | Anion | Cation | NMR analysis |
|---|---|---|---|
| 4-49 | an-4 | ca-49 | $^1$H-NMR: δ (ppm) = 7.82 (m, 2H, Ar), 4.55(s, 2H, CH2), 3.73-3.91(m, 4H CH2), 1.56-2.43(m, 42H, Ar—CH3 + CH2 + adamantyl) |

TABLE 16-continued

| Compound | Anion | Cation | NMR analysis |
|---|---|---|---|
| 4-50 | an-4 | ca-50 | ¹H-NMR: δ (ppm) = 8.23 (d, 4H, ArH), 7.98 (d, 4H, ArH), 4.55(s, 2H, CH2), 1.68-1.98(m, 15H, Adamantyl), 1.37 (s, 18H, CH3 of tert-butyl)<br>¹⁹F-NMR: δ (ppm) = −48.5 |
| 4-51 | an-4 | ca-51 | ¹H-NMR: δ (ppm) = 7.77-7.98 (m, 10H, ArH), 7.64 (s, 2H, ArH), 4.55-4.577(m, 2H, CH2O + CH2), 2.40 (s, 6H, CH3), 2.02-2.26 (m, 9H, Adamantane), 1.68-1.98 (m, 21H, Adamantyl) |
| 4-52 | an-4 | ca-52 | ¹H-NMR: δ (ppm) = 7.77-7.89 (m, 10H, ArH), 7.64 (s, 2H, ArH), 5.70(t, 1H, OCHC=O), 4.82 (s, 2H, ArOCH2), 4.55(s, 2H, CH2), 4.46-4.30 (m, 2H, OCOCH2), 2.71-2.64 (m, 1H, OCH2CH2), 2.33-2.24 (m, 7H, CH3 + OCH2CH2), 1.68-1.98(m, 15H, Adamantyl) |
| 4-53 | an-4 | ca-53 | ¹H-NMR: δ (ppm) = 8.28 (d, 2H, ArH), 8.11 (d, 1H, ArH), 7.86(t, 1H, ArH), 7.63-7.81(m, 7H, ArH), 4.55(s, 2H, CH2), 1.68-1.98(m, 15H, Adamantyl) |
| 4-54 | an-4 | ca-54 | ¹H-NMR: δ (ppm) = 8.05 (d, 2H, ArH), 7.74 (d, 2H, ArH), 4.55(s, 2H, CH2), 3.85(s, 3H, S—CH3), 1.68-1.98(m, 15H, Adamantyl), 1.30(s, 18H, t-Bu) |
| 4-55 | an-4 | ca-55 | ¹H-NMR: δ (ppm) = 8.41(m, 2H ArH), 8.12(d, 1H, ArH), 7.73-7.93(m, 2H, ArH), 7.19(d, 1H, ArH), 5.23(s, 2H, CH2), 4.95(m, 1H, Adamantane), 4.55(s, 2H, CH2), 4.03(m, 2H, CH2S), 3.75(m, 2H, CH2S), 2.27-2.43(m, 4H, SCH2CH2), 1.42-1.99(m, 29H, Adamantyl) |
| 4-56 | an-4 | ca-56 | ¹H-NMR: δ (ppm) = 8.42(m, 2H ArH), 8.17(d, 1H, ArH), 7.78-7.91(m, 2H, ArH), 7.23(d, 1H, ArH), 5.26(s, 2H, CH2), 4.55(s, 2H, CH2), 3.75-4.19(m, 7H, SCH2 + CH3), 2.29-2.60(m, 4H, SCH2CH2), 1.68-1.98(m, 15H, Adamantyl) |
| 4-57 | an-4 | ca-57 | ¹H-NMR: δ (ppm) = 8.28 (d, 2H, ArH), 8.12 (d, 1H, ArH), 7.88 (t, 1H, ArH), 7.80 (d, 1H, ArH), 7.62-7.74 (m, 5H, ArH), 4.55 (s, 2H, CH2), 1.68-1.98(m, 15H, Adamantyl), 1.27 (s, 9H, CH3) |
| 4-58 | an-4 | ca-58 | ¹H-NMR: δ (ppm) = 7.76-7.90 (m, 12H, ArH), 4.55 (s, 2H, CH2), 2.62-2.69 (m, 1H, camphane), 2.08-2.26 (m, 8H, Ar—CH3 + camphane), 1.65-1.98 (m, 16H, camphane + Adamantyl), 1.19 (s, 3H, CH3), 1.09 (s, 3H, CH3), 1.04 (s, 3H, CH3). |
| 4-59 | an-4 | ca-59 | ¹H-NMR: δ (ppm) = 7.76-7.90 (m, 12H, ArH), 5.00 (s, 1H, Hyper-lactone), 4.77 (s, 2H, Hyper-lactone), 4.55(s, 2H, CH2), 4.27 (s, 1H, Hyper-lactone), 2.94 (s, 1H, Hyper-lactone), 2.13 (d, 6H, CH3), 1.68-2.11 (m, 24H, Hyper-lactone + Adamantyl), 1.53 (d, 1H, Hyper-lactone). |
| 4-60 | an-4 | ca-60 | ¹H-NMR: δ (ppm) = 7.72-7.83(m, 10H, ArH), 7.59(s, 2H, ArH), 5.90(d, 1H, CH), 4.87-5.05(m, 3H, CH), 4.62-4.68(m, 2H, CH2), 4.55(s, 2H, CH2), 4.23(m, 1H, CH), 1.68-2.48(m, 23H, CH3 + oxosultone + Adamantyl) |

TABLE 17

| Compound | Anion | Cation | NMR analysis |
|---|---|---|---|
| 5-1 | an-5 | ca-1 | ¹H-NMR: δ (ppm) = 7.74-7.90 (m, 15H, ArH), 4.12(s, 2H, CH2), 2.31-2.43(m, 1H, CH), 1.87-2.02(m, 2H, CH2), 1.49-1.68(m, 1H, CH), 0.85-1.15(m, 9H, CH3 + CH3 + CH3) |
| 5-2 | an-5 | ca-2 | ¹H-NMR: δ (ppm) = 8.50(d, 2H, ArH), 8.37(d, 2H, ArH), 7.93(t, 2H, ArH), 7.55-7.75(m, 7H, ArH), 4.12(s, 2H, CH2), 2.31-2.43(m, 1H, CH), 1.87-2.02(m, 2H, CH2), 1.49-1.68(m, 1H, CH), 0.85-1.15(m, 9H, CH3 + CH3 + CH3) |
| 5-3 | an-5 | ca-3 | ¹H-NMR: δ (ppm) = 7.72-7.84(m, 12H, ArH), 7.56(d, 2H, ArH), 4.12(s, 2H, CH2), 3.35(s, 3H, CH3), 2.31-2.43(m, 1H, CH), 1.87-2.02(m, 2H, CH2), 1.49-1.68(m, 1H, CH), 0.85-1.15(m, 9H, CH3 + CH3 + CH3) |
| 5-4 | an-5 | ca-4 | ¹H-NMR: δ (ppm) = 7.75-7.86 (m, 10H, ArH), 7.61 (s, 2H, ArH), 4.62 (s, 2H, CH2), 4.12(s, 2H, CH2), 2.31-2.43 (m, 7H, CH3 + CH), 1.49-2.07 (m, 19H, Adamantyl + CH2), 0.85-1.15(m, 9H, CH3 + CH3 + CH3) |
| 5-5 | an-5 | ca-5 | ¹H-NMR: δ (ppm) = 7.76-7.82(m, 10H, ArH), 7.59(s, 2H, ArH), 4.55(s, 2H, CH2), 4.12(s, 2H, CH2), 2.31-2.43(m, 1H, CH), 2.29(m, 6H, CH3), 1.87-2.02(m, 6H, CH2 + CH2 + cyclopentyl), 1.48-1.75(m, 7H, cyclopentyl + CH), 0.85-1.15(m, 9H, CH3 + CH3 + CH3) 0.77-0.81(t, 3H, CH3) |
| 5-6 | an-5 | ca-6 | ¹H-NMR: δ (ppm) = 7.76-7.82(m, 10H, ArH), 7.59(s, 2H, ArH), 4.55(s, 2H, CH2), 4.12(s, 2H, CH2), 2.31-2.43(m, 1H, CH), 2.29(m, 6H, CH3), 1.87-2.08(m, 4H, cyclopentyl + CH2), 1.48-1.75(m, 10H, CH3 + cyclopentyl + CH), 0.85-1.15(m, 9H, CH3 + CH3 + CH3) |
| 5-8 | an-5 | ca-8 | ¹H-NMR: δ (ppm) = 7.71-7.89 (m, 10H, ArH), 7.59 (s, 2H, ArH), 4.53 (s, 2H, CH2), 4.12(s, 2H, CH2), 2.30-2.43 (m, 7H, ArCH3 + CH), 1.87-2.02(m, 2H, CH2), 1.49-1.68(m, 1H, CH), 0.85-1.15(m, 9H, CH3 + CH3 + CH3) |
| 5-9 | an-5 | ca-9 | ¹H-NMR: δ (ppm) = 7.75-7.86 (m, 10H, ArH), 7.63(s, 2H, ArH), 4.55 (s, 2H, CH2), 4.12(s, 2H, CH2), 2.30-2.43 (m, 7H, ArCH3 + CH), 1.87-2.02(m, 2H, CH2), 1.49-1.68(m, 1H, CH), 1.43 (s, 9H, t-Butyl), 0.85-1.15(m, 9H, CH3 + CH3 + CH3) |
| 5-10 | an-5 | ca-10 | ¹H-NMR: δ (ppm) = 7.75-7.87(m, 10H, ArH), 7.63(s, 2H, ArH), 4.94(t, 2H, OCH2CF2), 4.84(s, 2H, OCH2), 4.12(s, 2H, CH2), 2.31-2.43(m, 7H, CH3 + CH), 1.87-2.02(m, 2H, CH2), 1.49-1.68(m, 1H, CH), 0.85-1.15(m, 9H, CH3 + CH3 + CH3)<br>¹⁹F-NMR: δ (ppm) = −80.4, −119.7 |
| 5-11 | an-5 | ca-11 | ¹H-NMR: δ (ppm) = 7.72-7.83(m, 10H, ArH), 7.59(s, 2H, ArH), 4.90(m, 1H, sultone), 4.62-4.68(m, 3H, CH2O + sultone), 4.12(s, 2H, CH2), 3.83-3.89(m, 1H, sultone), 3.43(m, 1H, sultone), 1.75-2.49(m, 14H, sultone + Ar—CH3 + CH + CH2), 1.49-1.68(m, 1H, CH), 0.85-1.15(m, 9H, CH3 + CH3 + CH3) |
| 5-12 | an-5 | ca-12 | ¹H-NMR: δ (ppm) = 7.74-7.84(m, 10H, ArH), 7.61(s, 2H, ArH), 5.42(t, 1H, oxo-norbornane), 4.97(s, 1H, oxo-norbornane), 4.67-4.71(m, 4H, CH2 + oxo-norbornane), 4.12(s, 2H, CH2), 2.69-2.73(m, 1H, oxo-norbornane), 2.31-2.43(m, 7H, Ar—CH3 + CH), 2.06-2.16(m, 2H, oxo-norbornane), 1.87-2.02(m, 2H, CH2), 1.49-1.68(m, 1H, CH), 0.85-1.15(m, 9H, CH3 + CH3 + CH3) |

TABLE 18

| Compound | Anion | Cation | NMR analysis |
|---|---|---|---|
| 5-13 | an-5 | ca-13 | $^1$H-NMR: δ (ppm) = 7.73-7.85(m, 10H, ArH), 7.59(S, 2H, ArH), 4.12(s, 2H, CH2), 3.83(t, 2H, OCH2), 2.31-2.43(m, 7H, CH3 + CH), 1.87-2.02(m, 2H, CH2), 1.45-1.68(m, 5H, CH2 + CH), 0.85-1.29(m, 16H, CH3 + CH3 + CH3 + CH3 + CH2) |
| 5-14 | an-5 | ca-14 | $^1$H-NMR: δ (ppm) = 8.53 (d, 2H, ArH), 8.27(d, 2H, ArH), 7.95(t, 2H, ArH), 7.74(t, 2H, ArH), 7.20(s, 1H, ArH), 6.38(s, 1H, ArH), 4.05(t, 2H, cation-OCH2), 4.01(s, 2H, CH2), 3.23(s, 3H, CH3), 2.86(s, 3H, ArCH3), 1.84(s, 3H, ArCH3), 1.69(quin, 2H, CH2), 1.37(quin, 2H, CH2), 1.24-1.26(m, 4H, CH2), 0.82(t, 3H, CH3) |
| 5-15 | an-5 | ca-15 | $^1$H-NMR: δ (ppm) = 7.99-8.01(d, 2H, Ar), 7.73-7.76(t, 1H, Ar), 7.58-7.61(t, 2H, Ar), 5.31 (s, 2H, SCH2C=O), 4.12(s, 2H, CH2), 3.49-3.62(m, 4H, CH2), 2.18-2.49(m, 5H, CH2S + CH), 1.87-2.02(m, 2H, CH2), 1.49-1.68(m, 1H, CH), 0.85-1.15(m, 9H, CH3 + CH3 + CH3) |
| 5-16 | an-5 | ca-16 | $^1$H-NMR: δ (ppm) = 8.02-8.05(m, 2H, Phenyl), 7.61-7.73(m, 3H, Phenyl), 4.12(s, 2H, CH2), 3.76-3.86(m, 4H, SCH2), 2.31-2.43(m, 1H, CH), 1.87-2.12(m, 6H, CH2 + CH2CH2), 1.49-1.70 (m, 3H, CH2 + CH), 0.85-1.15(m, 9H, CH3 + CH3 + CH3) |
| 5-17 | an-5 | ca-17 | $^1$H-NMR: δ (ppm) = 8.04-8.09(m, 2H, Phenyl), 7.69-7.79(m, 3H, Phenyl), 4.12(s, 2H, CH2), 3.29 (s, 6H, CH3), 2.31-2.43(m, 1H, CH), 1.87-2.02(m, 2H, CH2), 1.49-1.68(m, 1H, CH), 0.85-1.15(m, 9H, CH3 + CH3 + CH3) |
| 5-18 | an-5 | ca-18 | $^1$H-NMR: δ (ppm) = 8.07(d, 2H, Phenyl), 7.81(d, 2H, Phenyl), 4.10-4.12(m, 4H, CH2 + CH2), 3.59(d, 2H, CH2), 2.31-2.43(m, 1H, CH), 2.20(d, 2H, CH2), 1.71-2.19 (m, 6H, CH2 + CH2), 1.49-1.68(m, 1H, CH), 1.23(s, 9H, t-Bu), 0.85-1.15(m, 9H, CH3 + CH3 + CH3) |
| 5-19 | an-5 | ca-19 | $^1$H-NMR: δ (ppm) = 7.77-7.89(m, 10H, ArH), 7.70(s, 2H, ArH), 5.10(s, 2H, OCOCH2O), 4.12(s, 2H, CH2), 2.31-2.43(m, 1H, CH), 2.07-2.19(m, 9H, CH3), 1.87-2.02(m, 2H, CH2), 1.49-1.68(m, 1H, CH), 0.85-1.15(m, 9H, CH3 + CH3 + CH3) |
| 5-20 | an-5 | ca-20 | $^1$H-NMR: δ (ppm) = 7.84(d, 6H, ArH), 7.78(d, 6H, ArH), 4.12(s, 2H, CH2), 2.31-2.43(m, 1H, CH), 1.87-2.02(m, 2H, CH2), 1.49-1.68(m, 1H, CH), 1.33(s, 27H, tBu—CH3), 0.85-1.15(m, 9H, CH3 + CH3 + CH3) |
| 5-21 | an-5 | ca-21 | $^1$H-NMR: δ (ppm) = 7.73-7.89(m, 12H, ArH), 4.12(s, 2H, CH2), 2.31-2.43(m, 7H, CH3 + CH), 1.87-2.02(m, 2H, CH2), 1.49-1.68(m, 1H, CH), 0.85-1.15(m, 9H, CH3 + CH3 + CH3)<br>$^{19}$F-NMR: δ (ppm) = −70.2 |
| 5-22 | an-5 | ca-22 | $^1$H-NMR: δ (ppm) = 7.69-7.85(m, 10H, ArH), 7.56(s, 2H, ArH), 4.75(s, 4H, CH2), 4.12(s, 2H, CH2), 2.31-2.43(m, 7H, ArCH3 + CH), 2.19(m, 2H, Adamantane), 1.47-2.02(m, 17H, Adatnantane + CH2), 1.49-1.68(m, 1H, CH), 0.85-1.15(m, 9H, CH3 + CH3 + CH3) |
| 5-23 | an-5 | ca-23 | $^1$H-NMR: δ (ppm) = 7.72-7.84 (m, 10H, ArH), 7.59 (s, 2H, ArH), 4.56 (s, 2H, CH2), 4.12(s, 2H, CH2), 1.49-2.49 (m, 21H, Adamantyl + CH + CH2 + CH3), 0.85-1.15(m, 9H, CH3 + CH3 + CH3) |

TABLE 19

| Compound | Anion | Cation | NMR analysis |
|---|---|---|---|
| 5-24 | an-5 | ca-24 | $^1$H-NMR: δ (ppm) = 7.72-7.84 (m, 10H, ArH), 7.59 (s, 2H, ArH), 4.64 (s, 2H, CH2), 4.12(s, 2H, CH2), 3.70 (s, 3H, OCH3), 2.31-2.43(m, 1H, CH), 2.29 (s, 6H, CH3), 1.87-2.02(m, 2H, CH2), 1.49-1.68(m, 1H, CH), 0.85-1.15(m, 9H, CH3 + CH3 + CH3) |
| 5-25 | an-5 | ca-25 | $^1$H-NMR: δ (ppm) = 7.78-7.89 (m, 10H, ArH), 7.64 (s, 2H, ArH), 4.12(s, 2H, CH2), 3.79 (s, 3H, OCH3), 2.31-2.43(m, 7H, CH + CH3), 1.87-2.02(m, 2H, CH2), 1.49-1.68(m, 1H, CH), 0.85-1.15(m, 9H, CH3 + CH3 + CH3) |
| 5-26 | an-5 | ca-26 | $^1$H-NMR: δ (ppm) = 8.44 (s, 4H, ArH in ArC=O), 7.78-7.90 (m, 24H, ArH), 4.12(s, 2H, CH2), 2.31-2.43(m, 1H, CH), 2.23 (s, 12H, CH3), 1.87-2.02(m, 2H, CH2), 1.49-1.68(m, 1H, CH), 0.85-1.15(m, 9H, CH3 + CH3 + CH3) |
| 5-27 | an-5 | ca-27 | $^1$H-NMR: δ (ppm) = 8.90 (s, 1H, ArH in ArC=O), 8.60 (dd, 2H, ArH in ArC=O), 7.77-7.96 (m, 25H, ArH in cation + ArH in ArC=O), 4.12(s, 2H, CH2), 2.31-2.43(m, 1H, CH), 2.24 (s, 12H, CH3), 1.87-2.02(m, 2H, CH2), 1.49-1.68(m, 1H, CH), 0.85-1.15(m, 9H, CH3 + CH3 + CH3) |
| 5-28 | an-5 | ca-28 | $^1$H-NMR: δ (ppm) = 7.76-7.87 (m, 10H, ArH), 7.69 (s, 2H, ArH), 4.12(s, 2H, CH2), 2.31-2.43(m, 1H, CH), 2.13 (s, 6H, CH3), 1.87-2.02(m, 2H, CH2), 1.49-2.03 (m, 16H, Adamantane + CH), 0.85-1.15(m, 9H, CH3 + CH3 + CH3) |
| 5-29 | an-5 | ca-29 | $^1$H-NMR: δ (ppm) = 7.79-7.93(m, 12H, ArH), 4.12(s, 2H, CH2), 2.73 (t, 2H, CO—CH2), 2.31-2.43(m, 1H, CH), 2.19(s, 6H, ArCH3), 1.87-2.02(m, 2H, CH2), 1.49-1.72(m, 3H, CH2 + CH), 1.25-1.38(m, 14H, CH2), 0.85(t, 3H, CH3), 0.85-1.15(m, 9H, CH3 + CH3 + CH3) |
| 5-30 | an-5 | ca-30 | $^1$H-NMR: δ (ppm) = 8.76 (s, 1H, ArH), 8.59-8.64 (m, 1H, ArH), 8.42 (t, 2H, ArH), 8.03-8.19 (m, 5H, ArH), 7.81 (t, 1H, ArH), 7.69 (t, 2H, ArH), 4.12(s, 2H, CH2), 2.31-2.43(m, 1H, CH), 1.87-2.02(m, 2H, CH2), 1.49-1.68(m, 1H, CH), 0.85-1.15(m, 9H, CH3 + CH3 + CH3)<br>$^{19}$F-NMR: δ (ppm) = −62.1 |
| 5-33 | an-5 | ca-33 | $^1$H-NMR: δ (ppm) = 8.29 (d, 4H, ArH), 7.93-8.09 (m, 6H, ArH), 4.12(s, 2H, CH2), 2.31-2.43(m, 1H, CH), 1.87-2.02(m, 2H, CH2), 1.49-1.68(m, 1H, CH), 0.85-1.15(m, 9H, CH3 + CH3 + CH3)<br>$^{19}$F-NMR: δ (ppm) = −47.9 |
| 5-34 | an-5 | ca-34 | $^1$H-NMR: δ (ppm) = 7.90-8.24 (m, 7H, ArH), 4.12(s, 2H, CH2), 3.85 (s, 3H, OCH3), 2.31-2.43(m, 7H, CH + ArCH3), 1.87-2.02(m, 2H, CH2), 1.49-1.68(m, 1H, CH), 0.85-1.15(m, 9H, CH3 + CH3 + CH3)<br>$^{19}$F-NMR: δ (ppm) = −48.8 |
| 5-38 | an-5 | ca-38 | $^1$H-NMR: δ (ppm) = 7.75-7.87(m, 10H, ArH), 7.62(s, 2H, ArH), 4.12(s, 2H, CH2), 3.97(t, 2H, CH2), 2.03-2.56(m, 11H, CH + CH2 + CH3), 1.87-2.02(m, 2H, CH2), 1.49-1.68(m, 1H, CH), 0.85-1.15(m, 9H, CH3 + CH3 + CH3)<br>$^{19}$F-NMR: δ (ppm) = −123.5, −121.8, −111.6, −78.3 |

TABLE 20

| Compound | Anion | Cation | NMR analysis |
|---|---|---|---|
| 5-40 | an-5 | ca-40 | $^1$H-NMR: δ (ppm) = 7.77-7.89 (m, 10H, ArH), 7.71 (s, 2H, ArH), 4.12(s, 2H, CH2), 2.51(s, 2H, CH2), 2.31-2.43(m, 1H, CH),, 2.20 (s, 6H, CH3), 0.85-2.02 (m, 27H, Adamantane + CH2 + CH3 + CH) |

TABLE 20-continued

| Compound | Anion | Cation | NMR analysis |
|---|---|---|---|
| 5-42 | an-5 | ca-42 | $^1$H-NMR: δ (ppm) = 7.80-7.92 (m, 10H, ArH), 7.67 (s, 2H, ArH), 4.66 (s, 2H, CH2), 4.12(s, 2H, CH2), 2.31-2.43 (m, 7H, ArCH3 + CH), 2.13-2.16 (m, 2H, cyclohexyl), 1.97-2.02 (m, 4H, CH2 + CH2), 1.14-1.68 (m, 9H, cyclohexyl + CH), 0.84-1.15 (t, 12H, CH3) |
| 5-43 | an-5 | ca-43 | $^1$H-NMR: δ (ppm) = 8.44 (d, 1H, ArH), 8.22 (m, 2H, ArH), 7.73-7.89 (m, 13H, ArH), 7.50 (d, 1H, ArH), 4.12(s, 2H, CH2), 2.31-2.43(m, 1H, CH), 1.87-2.02(m, 2H, CH2), 1.49-1.68(m, 1H, CH), 0.85-1.15(m, 9H, CH3 + CH3 + CH3) |
| 5-44 | an-5 | ca-44 | $^1$H-NMR: δ (ppm) = 8.24 (d, 4H, ArH), 7.59 (t, 2H, ArH), 7.47 (t, 4H, ArH), 4.12(s, 2H, CH2), 2.31-2.43(m, 1H, CH), 1.87-2.02(m, 2H, CH2), 1.49-1.68(m, 1H, CH), 0.85-1.15(m, 9H, CH3 + CH3 + CH3) |
| 5-45 | an-5 | ca-45 | $^1$H-NMR: δ (ppm) = 8.55 (d, 2H, ArH), 8.38 (d, 2H, ArH), 8.32 (d, 2H, ArH), 8.03 (d, 2H, ArH), 7.93-7.97 (m, 1H, ArH), 7.82-7.88 (m, 8H, ArH), 7.55 (d, 2H, ArH), 4.12(s, 2H, CH2), 2.31-2.43(m, 1H, CH), 1.87-2.02(m, 2H, CH2), 1.49-1.68(m, 1H, CH), 0.85-1.15(m, 9H, CH3 + CH3 + CH3) |
| 5-47 | an-5 | ca-47 | $^1$H-NMR: δ (ppm) = 4.46 (s, 2H, CH2(C=O)), 4.12(s, 2H, CH2), 3.38-3.58 (m, 4H, CH2SCH2), 1.49-2.43 (m, 25H, Adamantyl + CH2CH2 + CH + CH2), 0.85-1.15(m, 9H, CH3 + CH3 + CH3) |
| 5-48 | an-5 | ca-48 | $^1$H-NMR: δ (ppm) = 7.75 (s, 2H, Ar), 4.12(s, 2H, CH2), 3.91-3.96 (m, 2H, CH2), 3.72-3.79 (m, 2H, CH2), 2.29-2.43(m, 5H, CH2 + CH), 1.49-2.19(m, 24H, Ar—CH3 + Adamantane + CH2 + CH), 0.85-1.15(m, 9H, CH3 + CH3 + CH3) |
| 5-49 | an-5 | ca-49 | $^1$H-NMR: δ (ppm) = 7.82 (m, 2H, Ar), 4.12(s, 2H, CH2), 3.73-3.91(m, 4H CH2), 1.49-2.43(m, 31H, Ar—CH3 + CH2 + CH + adamantane), 0.85-1.15(m, 9H, CH3 + CH3 + CH3) |
| 5-50 | an-5 | ca-50 | $^1$H-NMR: δ (ppm) = 8.23 (d, 4H, ArH), 7.98 (d, 4H, ArH), 4.12(s, 2H, CH2), 2.31-2.43(m, 1H, CH), 1.87-2.02(m, 2H, CH2), 1.49-1.68(m, 1H, CH), 1.37 (s, 18H, CH3 of tert-butyl), 0.85-1.15(m, 9H, CH3 + CH3 + CH3) $^{19}$F-NMR: δ (ppm) = −48.5 |
| 5-51 | an-5 | ca-51 | $^1$H-NMR: δ (ppm) = 7.77-7.98 (m, 10H, ArH), 7.64 (s, 2H, ArH), 4.57(s, 2H, CH2O), 4.12(s, 2H, CH2), 2.40 (s, 6H, CH3), 2.02-2.26 (m, 9H, Adamantane), 1.76 (br s, 6H, Adamantane) |
| 5-52 | an-5 | ca-52 | $^1$H-NMR: δ (ppm) = 7.77-7.89 (m, 10H, ArH), 7.64 (s, 2H, ArH), 5.70(t, 1H, OCHC=O), 4.82 (s, 2H, ArOCH2), 4.12(s, 2H, CH2), 4.46-4.30 (m, 2H, OCOCH2), 2.71-2.64 (m, 1H, OCH2CH2), 2.24-2.43 (m, 8H, CH3 + OCH2CH2 + CH), 1.87-2.02(m, 2H, CH2), 1.49-1.68(m, 1H, CH), 0.85-1.15(m, 9H, CH3 + CH3 + CH3) |
| 5-53 | an-5 | ca-53 | $^1$H-NMR: δ (ppm) = 8.28 (d, 2H, ArH), 8.11 (d, 1H, ArH), 7.86 (t, 1H, ArH), 7.63-7.81(m, 7H, ArH), 4.12(s, 2H, CH2), 2.31-2.43(m, 1H, CH), 1.87-2.02(m, 2H, CH2), 1.49-1.68(m, 1H, CH), 0.85-1.15(m, 9H, CH3 + CH3 + CH3) |

TABLE 21

| Compound | Anion | Cation | NMR analysis |
|---|---|---|---|
| 5-54 | an-5 | ca-54 | $^1$H-NMR: δ (ppm) = 8.05 (d, 2H, ArH), 7.74 (d, 2H, ArH), 4.12(s, 2H, CH2), 3.85(s, 3H, S—CH3), 1.87-2.02(m, 2H, CH2), 1.49-1.68(m, 1H, CH), 1.30(s, 18H, t-Bu), 0.85-1.15(m, 9H, CH3 + CH3 + CH3) |
| 5-55 | an-5 | ca-55 | $^1$H-NMR: δ (ppm) = 8.41 (m, 2H ArH), 8.12(d, 1H, ArH), 7.73-7.93(m, 2H, ArH), 7.19(d, 1H, ArH), 5.23(s, 2H, CH2), 4.95(m, 1H, Adamantane), 4.03(m, 2H, CH2S), 4.12(s, 2H, CH2), 3.75(m, 2H, CH2S), 2.27-2.43(m, 5H, SCH2CH2 + CH), 1.42-2.02(m, 17H, Adamantyl + CH + CH2), 0.85-1.15(m, 9H, CH3 + CH3 + CH3) |
| 5-56 | an-5 | ca-56 | $^1$H-NMR: δ (ppm) = 8.42(m, 2H ArH), 8.17(d, 1H, ArH), 7.78-7.91(m, 2H, ArH), 7.23(d, 1H, ArH), 5.26(s, 2H, CH2), 3.75-4.19(m, 9H, SCH2 + CH3 + CH2), 2.29-2.60(m, 5H, SCH2CH2 + CH), 1.87-2.02(m, 2H, CH2), 1.49-1.68(m, 1H, CH), 0.85-1.15(m, 9H, CH3 + CH3 + CH3) |
| 5-57 | an-5 | ca-57 | $^1$H-NMR: δ (ppm) = 8.28 (d, 2H, ArH), 8.12 (d, 1H, ArH), 7.88 (t, 1H, ArH), 7.80 (d, 1H, ArH), 7.62-7.74 (m, 5H, ArH), 4.12(s, 2H, CH2), 2.31-2.43(m, 1H, CH), 1.87-2.02(m, 2H, CH2), 1.49-1.68(m, 1H, CH), 1.27 (s, 9H, CH3), 0.85-1.15(m, 9H, CH3 + CH3 + CH3) |
| 5-58 | an-5 | ca-58 | $^1$H-NMR: δ (ppm) = 7.76-7.90 (m, 12H, ArH), 4.12(s, 2H, CH2), 1.87-2.69 (m, 12H, camphane + Ar—CH3 + CH2 + CH), 1.49-1.72 (m, 2H, camphane + CH), 0.65-1.19 (m, 18H, CH3). |
| 5-59 | an-5 | ca-59 | $^1$H-NMR: δ (ppm) = 7.76-7.90 (m, 12H, ArH), 5.00 (s, 1H, Hyper-lactone), 4.77 (s, 2H, Hyper-lactone), 4.27 (s, 1H, Hyper-lactone), 4.12(s, 2H, CH2), 2.94 (s, 1H, Hyper-lactone), 2.31-2.43(m, 1H, CH), 1.49-2.13 (m, 19H, Hyper-lactone + CH3 + CH2 + CH), 0.85-1.15(m, 9H, CH3 + CH3 + CH3) |
| 5-60 | an-5 | ca-60 | $^1$H-NMR: δ (ppm) = 7.72-7.83(m, 10H, ArH), 7.59(s, 2H, ArH), 5.90(d, 1H, CH), 4.87-5.05(m, 3H, CH), 4.62-4.68(m, 2H, CH2), 4.23(m, 1H, CH), 4.12 (s, 2H, CH2), 1.49-2.48(m, 12H, CH3 + CH2 + CH + oxosultone), 0.85-1.15(m, 9H, CH3 + CH3 + CH3) |

Examples 1 to 25, Comparative Examples 1 to 12

The components shown in Tables 22 to 24 were mixed together and dissolved to obtain resist compositions.

TABLE 22

| | Component (A) | Component (B) | Component (C) | Component (G) | Component (F) | Component (S) | |
|---|---|---|---|---|---|---|---|
| Example 1 | (A)-1 [100] | (B)-1 [11.5] | (C)-1 [1.74] | — | (F)-1 [2.5] | (S)-1 [10.0] | (S)-2 [2900] |
| Example 2 | (A)-1 [100] | (B)-1 [11.5] | (C)-2 [1.87] | — | (F)-1 [2.5] | (S)-1 [10.0] | (S)-2 [2900] |
| Example 3 | (A)-1 [100] | (B)-1 [11.5] | (C)-3 [2.04] | — | (F)-1 [2.5] | (S)-1 [10.0] | (S)-2 [2900] |
| Example 4 | (A)-1 [100] | (B)-1 [11.5] | (C)-4 [2.47] | — | (F)-1 [2.5] | (S)-1 [10.0] | (S)-2 [2900] |

TABLE 22-continued

|  | Component (A) | Component (B) | Component (C) | Component (G) | Component (F) | Component (S) | |
|---|---|---|---|---|---|---|---|
| Example 5 | (A)-1 [100] | (B)-1 [11.5] | (C)-5 [2.56] | — | (F)-1 [2.5] | (S)-1 [10.0] | (S)-2 [2900] |
| Example 6 | (A)-1 [100] | (B)-1 [11.5] | (C)-6 [2.76] | — | (F)-1 [2.5] | (S)-1 [10.0] | (S)-2 [2900] |
| Example 7 | (A)-1 [100] | (B)-1 [11.5] | (C)-7 [2.88] | — | (F)-1 [2.5] | (S)-1 [10.0] | (S)-2 [2900] |
| Example 8 | (A)-1 [100] | (B)-1 [11.5] | (C)-8 [3.06] | — | (F)-1 [2.5] | (S)-1 [10.0] | (S)-2 [2900] |
| Example 9 | (A)-1 [100] | (B)-1 [11.5] | (C)-9 [3.49] | — | (F)-1 [2.5] | (S)-1 [10.0] | (S)-2 [2900] |
| Example 10 | (A)-1 [100] | (B)-1 [11.5] | (C)-10 [3.50] | — | (F)-1 [2.5] | (S)-1 [10.0] | (S)-2 [2900] |
| Example 11 | (A)-1 [100] | (B)-1 [11.5] | (C)-11 [2.72] | — | (F)-1 [2.5] | (S)-1 [10.0] | (S)-2 [2900] |
| Example 12 | (A)-1 [100] | (B)-1 [11.5] | (C)-12 [3.32] | — | (F)-1 [2.5] | (S)-1 [10.0] | (S)-2 [2900] |
| Example 13 | (A)-1 [100] | (B)-1 [11.5] | (C)-13 [3.46] | — | (F)-1 [2.5] | (S)-1 [10.0] | (S)-2 [2900] |
| Example 14 | (A)-1 [100] | (B)-1 [11.5] | (C)-14 [3.48] | — | (F)-1 [2.5] | (S)-1 [10.0] | (S)-2 [2900] |
| Example 15 | (A)-1 [100] | (B)-1 [11.5] | (C)-15 [3.17] | — | (F)-1 [2.5] | (S)-1 [10.0] | (S)-2 [2900] |

TABLE 23

|  | Component (A) | Component (B) | Component (C) | Component (G) | Component (F) | Component (S) | |
|---|---|---|---|---|---|---|---|
| Example 16 | (A)-1 [100] | (B)-1 [11.5] | (C)-1 [1.74] | (G)-1 [1.78] | (F)-1 [2.5] | (S)-1 [10.0] | (S)-2 [2900] |
| Example 17 | (A)-1 [100] | (B)-1 [11.5] | (C)-1 [1.74] | (G)-2 [0.89] | (F)-1 [2.5] | (S)-1 [10.0] | (S)-2 [2900] |
| Example 18 | (A)-1 [100] | (B)-1 [11.5] | (C)-1 [1.74] | (G)-3 [1.16] | (F)-1 [2.5] | (S)-1 [10.0] | (S)-2 [2900] |
| Example 19 | (A)-1 [100] | (B)-1 [11.5] | (C)-1 [1.74] | (G)-4 [2.35] | (F)-1 [2.5] | (S)-1 [10.0] | (S)-2 [2900] |
| Example 20 | (A)-1 [100] | (B)-1 [11.5] | (C)-1 [1.74] | (G)-5 [1.50] | (F)-1 [2.5] | (S)-1 [10.0] | (S)-2 [2900] |
| Example 21 | (A)-1 [100] | (B)-1 [11.5] | (C)-1 [1.74] | (G)-6 [0.59] | (F)-1 [2.5] | (S)-1 [10.0] | (S)-2 [2900] |
| Example 22 | (A)-1 [100] | (B)-1 [11.5] | (C)-1 [1.74] | (G)-7 [1.20] | (F)-1 [2.5] | (S)-1 [10.0] | (S)-2 [2900] |
| Example 23 | (A)-1 [100] | (B)-1 [11.5] | (C)-1 [1.74] | (G)-8 [1.02] | (F)-1 [2.5] | (S)-1 [10.0] | (S)-2 [2900] |
| Example 24 | (A)-1 [100] | (B)-1 [11.5] | (C)-1 [1.74] | (G)-9 [1.36] | (F)-1 [2.5] | (S)-1 [10.0] | (S)-2 [2900] |
| Example 25 | (A)-1 [100] | (B)-1 [11.5] | (C)-1 [1.74] | (G)-10 [1.26] | (F)-1 [2.5] | (S)-1 [10.0] | (S)-2 [2900] |

TABLE 24

|  | Component (A) | Component (B) | Component (C) | Component (G) | Component (F) | Component (S) | |
|---|---|---|---|---|---|---|---|
| Comparative Example 1 | (A)-1 [100] | (B)-1 [11.5] | (C)-16 [2.18] | — | (F)-1 [2.5] | (S)-1 [10.0] | (S)-2 [2900] |
| Comparative Example 2 | (A)-1 [100] | (B)-1 [11.5] | (C)-17 [1.64] | — | (F)-1 [2.5] | (S)-1 [10.0] | (S)-2 [2900] |
| Comparative Example 3 | (A)-1 [100] | (B)-1 [11.5] | (C)-18 [1.90] | — | (F)-1 [2.5] | (S)-1 [10.0] | (S)-2 [2900] |
| Comparative Example 4 | (A)-1 [100] | (B)-1 [11.5] | (C)-19 [3.20] | — | (F)-1 [2.5] | (S)-1 [10.0] | (S)-2 [2900] |
| Comparative Example 5 | (A)-1 [100] | (B)-1 [11.5] | (C)-20 [2.61] | — | (F)-1 [2.5] | (S)-1 [10.0] | (S)-2 [2900] |
| Comparative Example 6 | (A)-1 [100] | (B)-1 [11.5] | (C)-21 [2.91] | — | (F)-1 [2.5] | (S)-1 [10.0] | (S)-2 [2900] |
| Comparative Example 7 | (A)-1 [100] | (B)-1 [11.5] | (C)-22 [3.16] | — | (F)-1 [2.5] | (S)-1 [10.0] | (S)-2 [2900] |
| Comparative Example 8 | (A)-1 [100] | (B)-1 [11.5] | (C)-23 [2.57] | — | (F)-1 [2.5] | (S)-1 [10.0] | (S)-2 [2900] |

TABLE 24-continued

| | Component (A) | Component (B) | Component (C) | Component (G) | Component (F) | Component (S) | |
|---|---|---|---|---|---|---|---|
| Comparative Example 9 | (A)-1 [100] | (B)-1 [11.5] | (C)-24 [2.87] | — | (F)-1 [2.5] | (S)-1 [10.0] | (S)-2 [2900] |
| Comparative Example 10 | (A)-1 [100] | (B)-1 [11.5] | (C)-16 [2.18] | (G)-1 [1.78] | (F)-1 [2.5] | (S)-1 [10.0] | (S)-2 [2900] |
| Comparative Example 11 | (A)-1 [100] | (B)-1 [11.5] | (C)-16 [2.18] | (G)-6 [0.59] | (F)-1 [2.5] | (S)-1 [10.0] | (S)-2 [2900] |
| Comparative Example 12 | (A)-1 [100] | (B)-1 [11.5] | (C)-16 [2.18] | (G)-7 [1.20] | (F)-1 [2.5] | (S)-1 [10.0] | (S)-2 [2900] |

In Tables 22 to 24, the values in brackets [ ] indicate the amount (in terms of parts by weight) of the component added, and the reference characters indicate the following.

(A)-1: a polymeric compound represented by chemical formula (A)-1 shown below [Mw=5,500, Mw/Mn=1.42, compositional ratio (molar ratio): l/m/n/o=45/40/5/10]

(B)-1: a compound represented by chemical formula (B)-1 shown below (F)-1: a polymeric compound represented by chemical formula (F)-1 shown below [Mw=24,000, Mw/Mn=1.38, compositional ratio (molar ratio): 1=100]

(C)-1 to (C)-15: compounds having a structure represented by chemical formulas (each compound is a combination of a cation moiety and an anion moiety) shown in Table 25; each compounds was synthesized in the aforementioned <Synthesis Example of Component (C)>.

(C)-16 to (C)-24: compounds represented by chemical formulas (C)-16 to (C)-24 shown below, respectively (G)-1 to (G)-10: compounds represented by chemical formulas (G)-1 to (G)-10 shown below, respectively (S)-1: γ-butyrolactone (S)-2: a mixed solvent of PGMEA/PGME=6/4 (weight ratio)

[Chemical Formula 89]

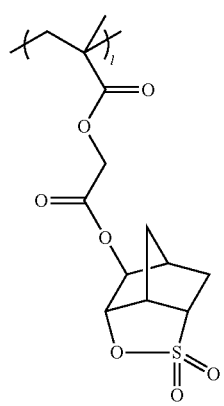
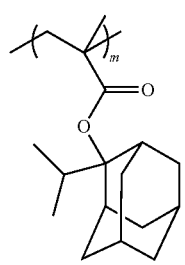
(A)-1

-continued

[Chemical Formula 90]

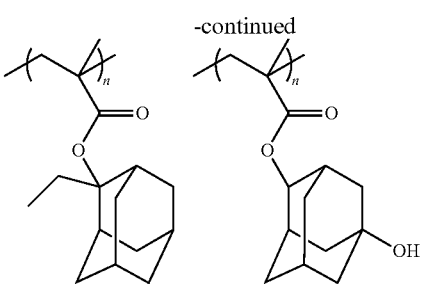
(B)-1

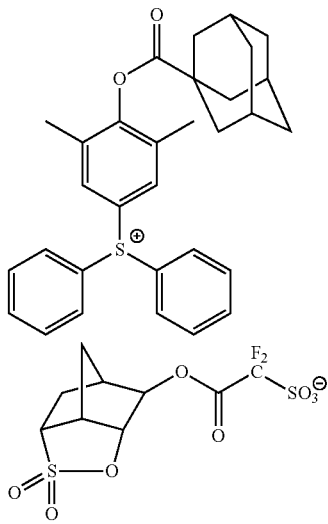

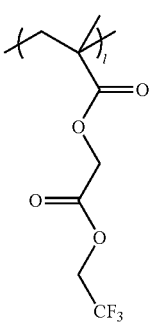
(F)-1

TABLE 25

| | (C)-1 | (C)-2 | (C)-3 | (C)-4 | (C)-5 |
|---|---|---|---|---|---|
| Anion | methoxyacetate | acetoxyacetate | phenoxyacetate | adamantanecarbonyloxyacetate | camphorsulfonyloxyacetate |
| Cation | | | triphenylsulfonium | | |

| | (C)-6 | (C)-7 | (C)-8 | (C)-9 | (C)-10 |
|---|---|---|---|---|---|
| Anion | methoxyacetate | acetoxyacetate | phenoxyacetate | adamantanecarbonyloxyacetate | camphorsulfonyloxyacetate |
| Cation | | | 4-(adamantanecarbonyloxy)-3,5-dimethylphenyl diphenylsulfonium | | |

TABLE 25-continued
| (C)-11 | (C)-12 | (C)-13 | (C)-14 | (C)-15 |
|---|---|---|---|---|
| Anion | | | | |
| Cation | | | | |
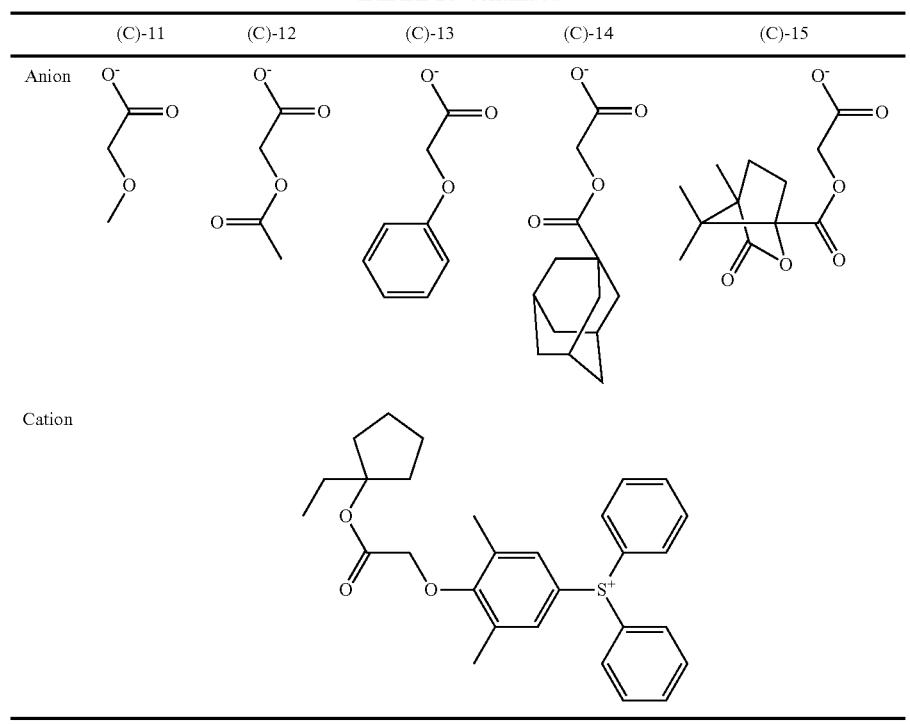
[Chemical Formula 91]
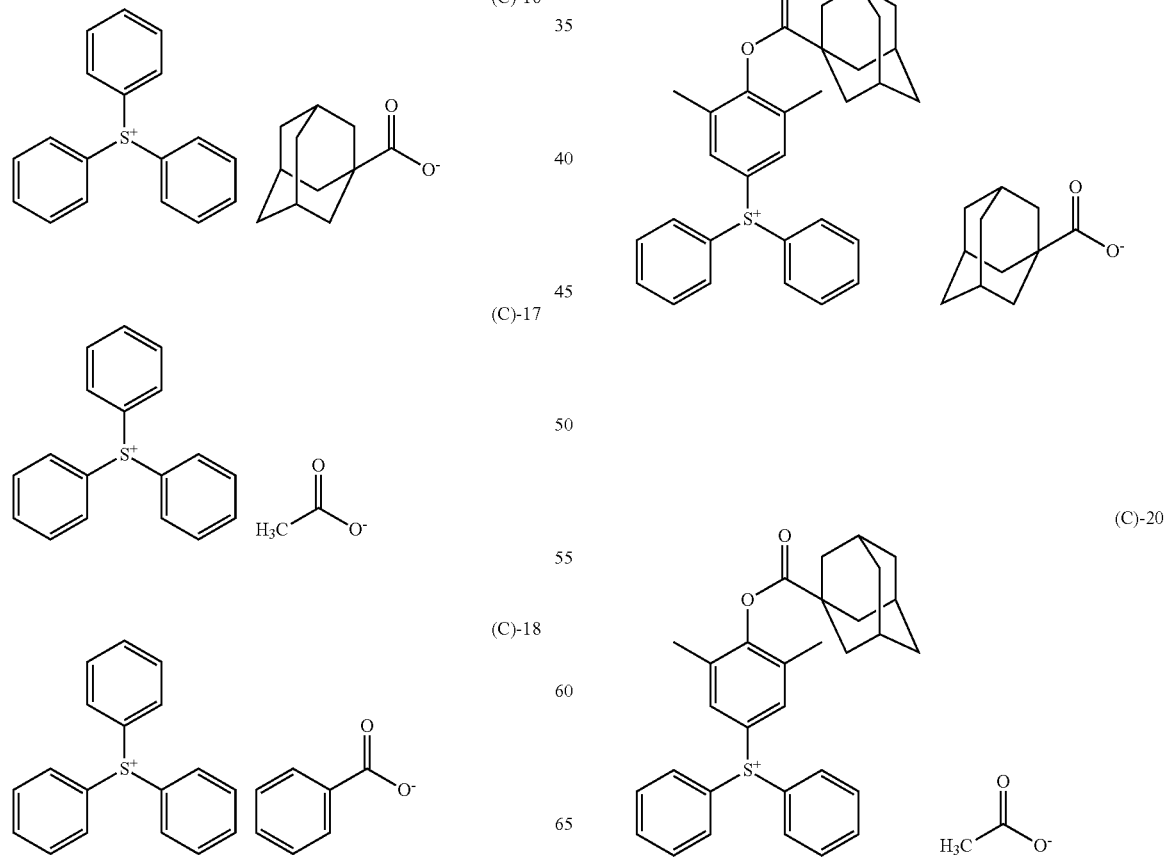

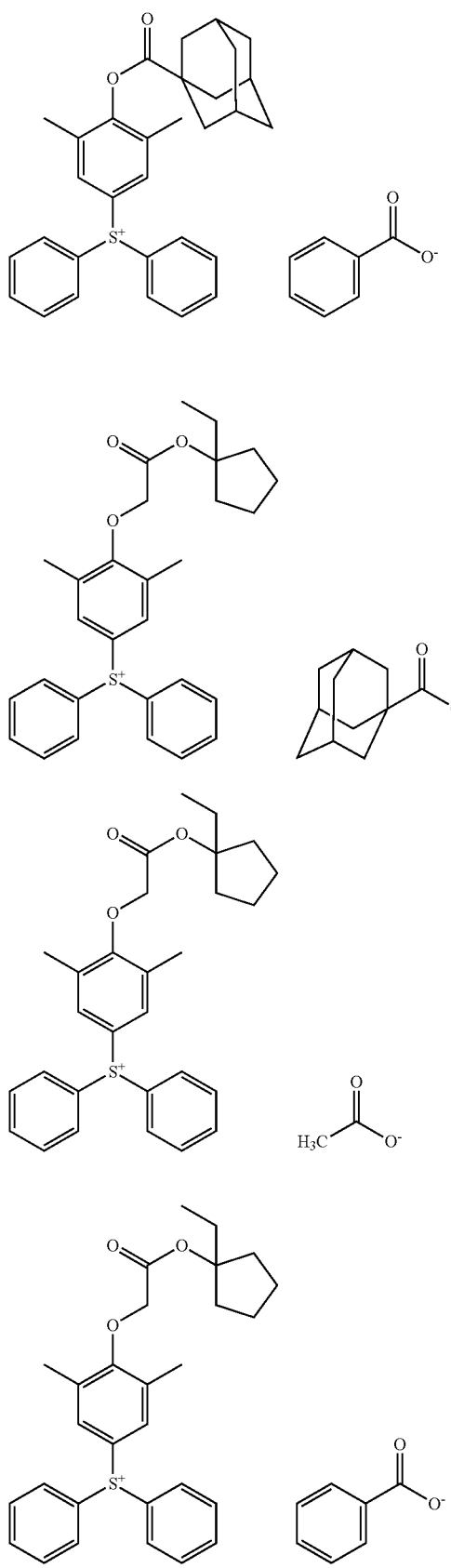

[Chemical Formula 92]

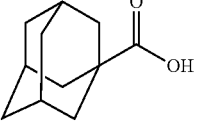 (G)-1

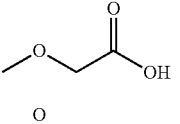 (G)-2

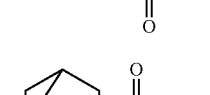 (G)-3

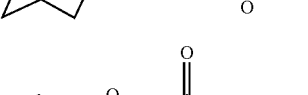 (G)-4

 (G)-5

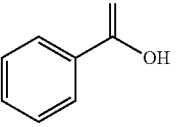 (G)-6

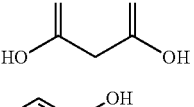 (G)-7

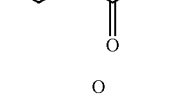 (G)-8

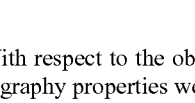 (C)-9

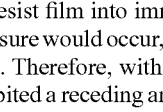 (C)-10

With respect to the obtained resist compositions, various lithography properties were evaluated.

However, when the receding angle was less than 65°, there was concern that elution of the component (B) or the like from the resist film into immersion medium during an immersion exposure would occur, thereby contaminating exposure apparatus. Therefore, with respect to a resist composition which exhibited a receding angle of less than 65° after storage at 40° C. as a result of the evaluation of storage stability, the present inventors did not conduct the evaluations of formation of resist pattern and various lithography properties (e.g., sensitivity, MEF, CDU, circularity and depth of focus) described later.

In these evaluations of formation of a resist pattern and various lithography properties in formation of a resist pattern, each resist composition was used after storage at 40° C. for 1 month.

[Evaluation of Storage Stability]

Each resist composition was stored at a temperature of −20° C. or 40° C. for 1 month. After storage, a resist film was formed using the resist composition in the following manner, and receding angle (°) thereof was measured. The results are shown in Table 26.

(Formation of Resist Film)

An organic anti-reflection film composition (product name: ARC29A, manufactured by Brewer Science Ltd.) was applied to an 12-inch silicon wafer using a spinner, and the composition was then baked at 205° C. for 60 seconds on a hotplate, thereby forming an organic anti-reflection film having a film thickness of 89 nm. Then, each resist composition was applied to the organic antireflection film using a spinner, and was then prebaked (PAB) on a hotplate at 80° C. for 60 seconds and dried, thereby forming a resist film having a film thickness of 100 nm.

(Measurement of Receding Angle)

A water droplet was dripped onto the surface of each resist film (resist film prior to exposure), and a DROP MASTER-700 (a product name, manufactured by Kyowa Interface Science Co. Ltd.) was used to measure a receding angle (receding angle measurement: water 50 μl).

Next, from the results of receding angle after storage at −20° C. and receding angle after storage at 40° C., a difference between these receding angles (%) was determined by the following formula. The results are indicated under "Angle difference" in Table 26.

Difference between receding angles={(receding angles after storage at −20° C.)−(receding angles after storage at 40° C.)/(receding angles after storage at −20° C.)}×100

[Formation of Resist Pattern]

An organic anti-reflection film composition (product name: ARC29A, manufactured by Brewer Science Ltd.) was applied to an 12-inch silicon wafer using a spinner, and the composition was then baked at 205° C. for 60 seconds on a hotplate, thereby forming an organic anti-reflection film having a film thickness of 89 nm.

Then, each resist composition was applied to the anti-reflection film using a spinner, and was then prebaked (PAB) on a hotplate at 80° C. for 60 seconds and dried, thereby forming a resist film having a film thickness of 100 nm.

Subsequently, the resist film was selectively irradiated with an ArF excimer laser (193 nm) through a photomask (binary), using an ArF exposure apparatus for immersion lithography (product name: NSR-S609B, manufactured by Nikon Corporation; NA (numerical aperture)=1.07, Annular(out-0.97/In-0.78)w/XY-Pol., immersion medium: water).

Next, a post exposure bake (PEB) treatment was conducted at 80° C. for 60 seconds, followed by development for 20 seconds at 23° C. in a 2.38% by weight aqueous solution of tetramethylammonium hydroxide (TMAH) (product name: NMD-W; manufactured by Tokyo Ohka Kogyo Co., Ltd.). Then, the resist film was rinsed for 30 seconds with pure water, followed by drying by shaking. Further, a post bake was conducted at 100° C. for 45 seconds on the hot plate.

As a result, in every examples, a contact hole pattern in which holes having a hole diameter of 70 nm and a pitch of 122.50 nm were equally spaced was formed (hereafter, this contact hole pattern is referred to as "CH pattern").

The optimum exposure dose Eop (mJ/cm$^2$) with which the CH pattern was formed was determined. The results are shown in Table 26.

[Evaluation of Mask Error Factor (MEF)]

With the above-mentioned Eop, CH patterns were formed in the same manner as in the aforementioned [Formation of resist pattern], except that a photomask having a different target size was used. Here, in the target size of the photomask, a hole diameter was changed within the range of 70 nm±5 nm at intervals of 1 nm while a pitch was fixed at 122.50 nm.

With respect to obtained 11 CH patterns, the hole diameter (nm) of the each of the holes was plotted on the vertical axis, and the hole diameter (nm) of the each of the target sizes was plotted on the horizontal axis. The gradient of the linear graph was determined as "MEF". The results are shown in Table 26.

A MEF value closer to 1 indicates that a resist pattern faithful to the mask pattern was formed.

[Evaluation of In-Plane Uniformity (CDU) of Pattern Size]

With respect to each of the contact hole patterns having the aforementioned target sizes obtained in the aforementioned [Formation of resist pattern], the hole diameter (nm) of 100 holes within the CH pattern were observed from above and measured by using a measuring scanning electron microscope (SEM) (product name: S-9380, manufactured by Hitachi High-Technologies Corporation, accelerating voltage: 300V). From the results, the value of 3 times the standard deviation σ (i.e., 3σ) was calculated. The results are indicated under "CDU" in Table 26.

The smaller this 3σ value is, the higher the level of the uniformity (CD uniformity) of size of the plurality of holes formed in the resist film.

[Evaluation of Circularity of Holes]

With respect to each of the contact hole patterns obtained in the aforementioned [Formation of resist pattern] having the aforementioned target sizes, 25 holes within the CH pattern were selected, and the distance from the center to the outer periphery in 24 directions of each hole was observed from above and measured by using a measuring scanning electron microscope (SEM) (product name: S-9380, manufactured by Hitachi High-Technologies Corporation, accelerating voltage: 300V). From the results, the value of 3 times the standard deviation σ (i.e., 3σ) was calculated. The results are shown in Table 26.

The smaller this 3σ value is, the higher the level of circularity of the holes.

[Evaluation of Depth of Focus]

With the above-mentioned Eop, CH patterns were formed in the same manner as in the aforementioned [Formation of resist pattern], except that focus was appropriately shifted up and down. The depth of focus (unit: μm) with which a contact hole pattern was formed within the range where the hole diameter (CD) was the target size (i.e., 70 nm)±5% (that is, within the range from 65 to 75 nm) was determined. The results are indicated under "DOF" in Table 26.

TABLE 26

| | Eop [mJ/cm$^2$] | MEF | CDU [3σ] | Circularity [3σ] | DOF [μm] | Receding angle [°] −20° C. | 40° C. | Angle difference |
|---|---|---|---|---|---|---|---|---|
| Example 1 | 25.7 | 4.55 | 6.11 | 3.98 | 0.44 | 70.1 | 68.7 | <2% |
| Example 2 | 25.5 | 4.61 | 6.15 | 3.98 | 0.45 | 69.8 | 68.5 | <2% |
| Example 3 | 25.9 | 4.59 | 6.14 | 3.99 | 0.46 | 69.5 | 68.4 | <2% |
| Example 4 | 25.5 | 4.55 | 6.15 | 4.09 | 0.44 | 69.3 | 68.1 | <2% |
| Example 5 | 25.4 | 4.49 | 6.11 | 4.07 | 0.45 | 70.2 | 70.3 | <2% |
| Example 6 | 25.8 | 4.59 | 6.18 | 4.11 | 0.41 | 69.7 | 69.0 | <2% |
| Example 7 | 25.6 | 4.57 | 6.22 | 3.99 | 0.46 | 69.8 | 68.5 | <2% |
| Example 8 | 25.6 | 4.61 | 6.23 | 3.97 | 0.47 | 69.5 | 68.2 | <2% |
| Example 9 | 25.3 | 4.39 | 6.21 | 3.99 | 0.44 | 70.4 | 69.6 | <2% |
| Example 10 | 26.2 | 4.38 | 6.19 | 4.05 | 0.45 | 70.3 | 70.1 | <2% |
| Example 11 | 26.5 | 4.44 | 6.18 | 4.06 | 0.48 | 69.0 | 68.5 | <2% |
| Example 12 | 25.5 | 4.56 | 6.16 | 4.12 | 0.45 | 70.1 | 68.7 | <2% |
| Example 13 | 25.9 | 4.50 | 6.26 | 4.07 | 0.41 | 69.7 | 68.5 | <2% |
| Example 14 | 25.7 | 4.62 | 6.21 | 4.05 | 0.45 | 70.1 | 68.9 | <2% |
| Example 15 | 25.4 | 4.63 | 6.44 | 4.12 | 0.43 | 69.6 | 68.7 | <2% |
| Example 16 | 25.8 | 4.61 | 6.09 | 4.01 | 0.43 | 68.9 | 67.6 | <2% |
| Example 17 | 26.3 | 4.65 | 6.11 | 4.02 | 0.42 | 69.9 | 70.1 | <2% |
| Example 18 | 26.1 | 4.63 | 6.12 | 4.06 | 0.41 | 69.7 | 69.9 | <2% |
| Example 19 | 26.4 | 4.67 | 6.11 | 4.10 | 0.42 | 68.8 | 69.0 | <2% |
| Example 20 | 25.9 | 4.66 | 6.08 | 4.11 | 0.43 | 69.1 | 68.8 | <2% |
| Example 21 | 26.1 | 4.67 | 6.08 | 4.08 | 0.43 | 69.5 | 68.9 | <2% |
| Example 22 | 26.1 | 4.69 | 6.09 | 4.07 | 0.46 | 69.7 | 69.2 | <2% |
| Example 23 | 26.3 | 4.68 | 6.09 | 4.10 | 0.41 | 69.8 | 69.1 | <2% |
| Example 24 | 26.2 | 4.61 | 6.11 | 4.08 | 0.42 | 69.4 | 68.7 | <2% |
| Example 25 | 26.1 | 4.66 | 6.10 | 4.07 | 0.41 | 69.7 | 69.2 | <2% |
| Comparative Example 1 | — | — | — | — | — | 68.9 | 55.5 | >10% |
| Comparative Example 2 | — | — | — | — | — | 68.8 | 60.1 | >10% |
| Comparative Example 3 | — | — | — | — | — | 69.5 | 60.9 | >10% |
| Comparative Example 4 | — | — | — | — | — | 69.8 | 54.8 | >10% |
| Comparative Example 5 | — | — | — | — | — | 68.9 | 57.5 | >10% |
| Comparative Example 6 | — | — | — | — | — | 68.4 | 60.0 | >10% |
| Comparative Example 7 | — | — | — | — | — | 68.7 | 60.0 | >10% |
| Comparative Example 8 | — | — | — | — | — | 69.2 | 59.8 | >10% |
| Comparative Example 9 | — | — | — | — | — | 69.4 | 57.9 | >10% |
| Comparative Example 10 | — | — | — | — | — | 68.5 | 55.1 | >10% |
| Comparative Example 11 | — | — | — | — | — | 69.9 | 60.1 | >10% |
| Comparative Example 12 | — | — | — | — | — | 68.4 | 59.2 | >10% |

As the aforementioned results, with respect to the resist compositions of Examples 1 to 25, the receding angle of a resist film formed using the resist composition after storage for 1 month at 40° C. was almost the same angle as that of a resist film formed using the resist composition after storage for 1 month at −20° C. The results indicated that the resist compositions have an excellent storage stability. Further, various lithography properties such as sensitivity MEF, CDU, circularity, depth of focus and the like were also excellent.

On the other hand, with respect to the resist compositions of Comparative Examples 1 to 12, the receding angle of a resist film formed using the resist composition after storage for 1 month at 40° C. was significantly reduced as compared to that of a resist film formed using the resist composition after storage for 1 month at −20° C. It was presumed that the component (F) was decomposed by the action of the component (C) during storage.

What is claimed is:

1. A resist composition comprising:
   a base component (A) that exhibits changed solubility in a developing solution by the action of acid;
   a photoreactive quencher (C); and
   an acid-generator component (B) that generates acid upon exposure, wherein
   the photoreactive quencher (C) contains a monomeric compound represented by general formula (c1) shown below:

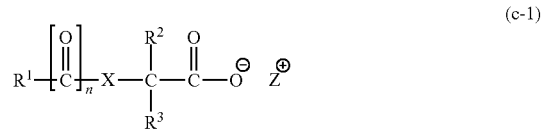

(c-1)

wherein R$^1$ represents a hydrocarbon group of 1 to 20 carbon atoms which may have a substituent; each of R$^2$ and $R^3$ represents a hydrogen atom; X represents an oxygen atom; n represents 0 or 1; and $Z^+$ represents an organic cation.

2. The resist composition according to claim 1, wherein $R^1$ represents a cyclic alkyl group of 3 to 20 carbon atoms which may have a substituent, and n represents 1 in the general formula (c1).

3. The resist composition according to claim 1, wherein the base component (A) is a base component (A0) that exhibits increased polarity by the action of acid.

4. The resist composition according to claim 1, wherein $Z^+$ is an organic cation represented by general formula (ca-1) shown below:

(ca-1)

wherein each of $R^{1''}$ to $R^{3''}$ independently represents an aryl group, alkyl group or alkenyl group, provided that two of $R^{1''}$ to $R^{3''}$ may be bonded to each other to form a ring with the sulfur atom, and at least one of $R^{1''}$ to $R^{3''}$ has a substituent represented by —C(=O)—O—$R^{6'}$ or —O—C(=O)—$R^{7'}$, wherein $R^{6'}$ and $R^{7'}$ independently represents a linear or branched saturated hydrocarbon group of 1 to 25 atoms, a cyclic saturated hydrocarbon group of 3 to 20 carbon atoms or a linear or branched, aliphatic unsaturated hydrocarbon group of 2 to 5 carbon atoms.

5. A method of forming a resist pattern, comprising: forming a resist film on a substrate using a resist composition of claim 1; conducting exposure of the resist film; and developing the resist film to form a resist pattern.

6. A monomeric compound represented by general formula (c1) shown below:

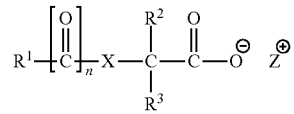
(c-1)

wherein $R^1$ represents a hydrocarbon group of 1 to 20 carbon atoms which may have a substituent; each of $R^2$ and $R^3$ independently represents a hydrogen atom; X represents an oxygen atom; n represents 0 or 1; and $Z^+$ represents an organic cation.

7. The compound according to claim 6, wherein $R^1$ represents a cyclic alkyl group of 3 to 20 carbon atoms which may have a substituent, and n represents 1 in the general formula (c1).

8. The monomeric compound according to claim 6, wherein $Z^+$ is an organic cation represented by general formula (ca-1) shown below:

(ca-1)

wherein each of $R^{1''}$ to $R^{3''}$ independently represents an aryl group, alkyl group or alkenyl group, provided that two of $R^{1''}$ to $R^{3''}$ may be bonded to each other to form a ring with the sulfur atom, and at least one of $R^{1''}$ to $R^{3''}$ has a substituent represented by —C(=O)—O—$R^{6'}$ or —O—C(=O)—$R^{7'}$, wherein $R^{6'}$ and $R^{7'}$ independently represents a linear or branched saturated hydrocarbon group of 1 to 25 atoms, a cyclic saturated hydrocarbon group of 3 to 20 carbon atoms or a linear or branched, aliphatic unsaturated hydrocarbon group of 2 to 5 carbon atoms.

* * * * *

UNITED STATES PATENT AND TRADEMARK OFFICE
CERTIFICATE OF CORRECTION

PATENT NO.         : 9,063,416 B2
APPLICATION NO.    : 13/706771
DATED              : June 23, 2015
INVENTOR(S)        : Yoshitaka Komuro et al.

It is certified that error appears in the above-identified patent and that said Letters Patent is hereby corrected as shown below:

Specification
Col. 5, line 25, "Resist Composition" should be --<<Resist Composition>>--.
Col. 7, line 7, "polycyclolefin" should be --polycycloolefin--.
Col. 9, line 46, "$R^7$" should be --$R^{71}$--.
Col. 13, line 39, "$R^1$" should be --$R^{1'}$--.
Col. 14, line 62, "cycloolefine" should be --cycloolefin--.
Col. 22, line 46, "and" should be --or--.
Col. 23, line 3, "$(CH_2)_n$" should be --$(CH_2)_{a'}$--.
Col. 23, line 18, "or$Y^{21}$" should be --or-$Y^{21}$--.
Col. 60, line 14, "genera" should be --general--.
Col. 61, line 28, "genera" should be --general--.
Col. 63, line 16, "a the" should be --the--.
Col. 63, line 25, "a the" should be --the--.
Col. 63, line 43, "pertluoroalkyl" should be --perfluoroalkyl--.
Col. 70, line 15, "β-propionolatone," should be --β-propiolactone,--.
Col. 70, line 60, "genera" should be --general--.
Col. 91, line 7, "$R^{00}$" should be --$R^m$--.
Col. 99, line 22, "alkoxyl" should be --alkoxy--.
Col. 101, line 67, "(a1))" should be --(a1)--.
Col. 103, line 49, "(1)" should be --(c1)--.
Col. 104, line 6, "substituent," should be --substituent.--.
Col. 118, line 9, "the of" should be --of the--.
Col. 119, line 24, "(ca-O)" should be --(ca-0)--.
Col. 119, line 56, "$^{13}$Examples" should be --Examples--.
Col. 133, line 61, "alkylsulfonyoxy" should be --alkylsulfonyloxy--.
Col. 134, line 21, "alkylsulfonyoxy" should be --alkylsulfonyloxy--.
Col. 135, line 59, "alkylsulfonyoxy" should be --alkylsulfonyloxy--.

Signed and Sealed this
Eighth Day of March, 2016

Michelle K. Lee
*Director of the United States Patent and Trademark Office*

Specification
Col. 139, line 20:
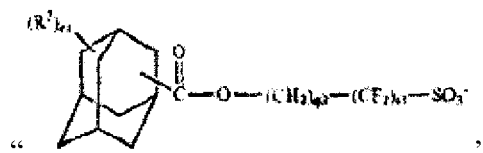 " should be
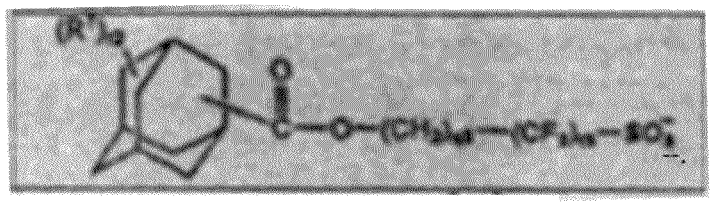
--        --.
Col. 140, lines 65-66, "pertluoroalkylene" should be --perfluoroalkylene--.
Col. 160, line 57, "as long at" should be --as long as--.
Col. 163, line 35, "Synthesis Example of Acid (G5)>" should be --<Synthesis Example of Acid (G5)>--.
Col. 163, lines 50-59:
"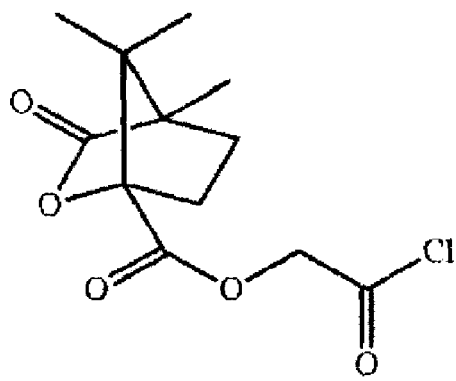 " should be -- 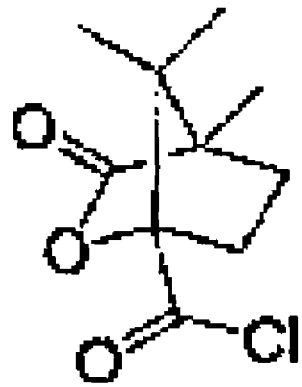 --.
Col. 163, line 61, "Synthesis Example of Component (C)" should be --<Synthesis Example of Component (C)>--.
Col. 165, lines 2-14:
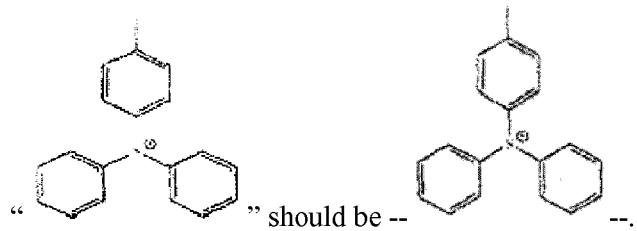

Specification
Col. 173, lines 17-34:
" 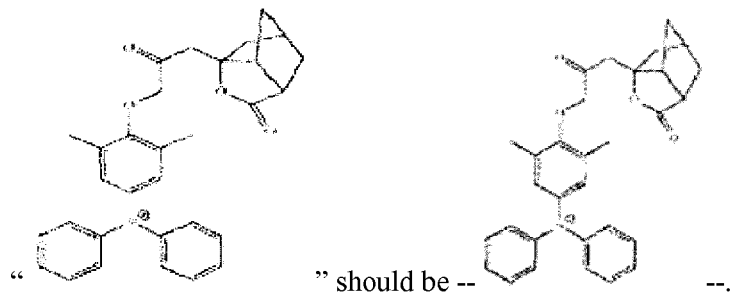 " should be -- --.
Col. 173, lines 35-51:
" 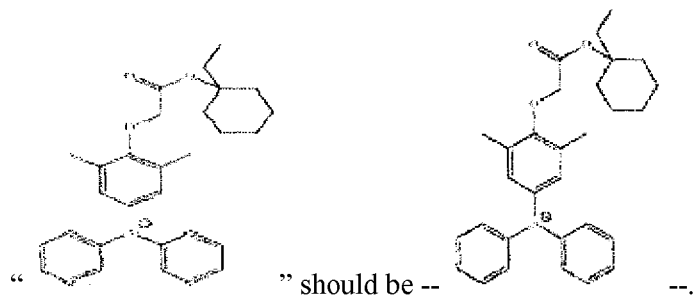 " should be -- --.
Col. 175, lines 55-65:
" 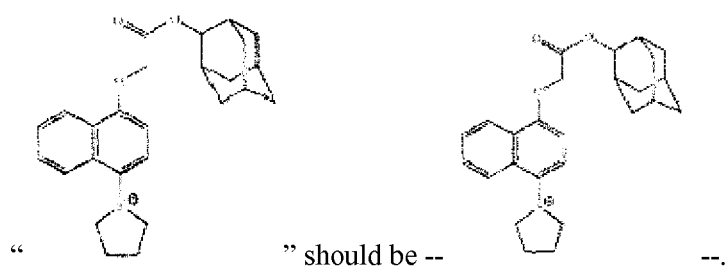 " should be -- --.
Col. 176, lines 33-50:
" 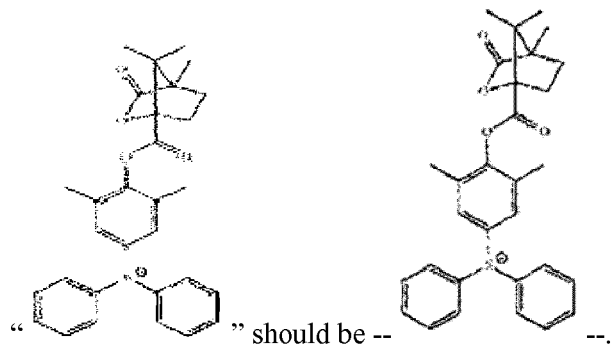 " should be -- --.
Col. 181-182, line 32 (Table 4), "oxosultone)" should be --oxosulfone)--.
Col. 185-186, line 33 (Table 8), "oxosultone)" should be --oxosulfone)--.
Col. 185-186, line 10 (Table 9), "oyclopentyl)," should be --cyclopentyl),--.
Col. 189-190, line 33 (Table 12), "oxosultone)" should be --oxosulfone)--.

CERTIFICATE OF CORRECTION (continued)
U.S. Pat. No. 9,063,416 B2

Specification
Col. 193-194, line 30 (Table 16), "oxosultone" should be --oxosulfone--.
Col. 195-196, line 28 (Table 18), "Adatnantane" should be --Adamantane--.
Col. 197-198, line 20 (Table 21), "oxosultone)," should be --oxosulfone),--.
Col. 209, line 42, "100" should be --100.--.